United States Patent [19]
Schneider et al.

[11] Patent Number: 5,867,402
[45] Date of Patent: Feb. 2, 1999

[54] COMPUTATIONAL ANALYSIS OF NUCLEIC ACID INFORMATION DEFINES BINDING SITES

[75] Inventors: Thomas D. Schneider, Frederick, Md.; Peter K. Rogan, Lebanon, Pa.

[73] Assignee: The United States of America as represented by the Department of Health and Human Services, Washington, D.C.

[21] Appl. No.: 494,115

[22] Filed: Jun. 23, 1995

[51] Int. Cl.⁶ .................................................. G06F 17/16
[52] U.S. Cl. ............................................ 364/496; 364/578
[58] Field of Search .................................. 364/496–500, 364/578; 395/144; 434/279

[56] References Cited

PUBLICATIONS

Stephens et al., "Features of Spliceosome Evolution and Function Inferred from Analysis of the Information at Human Splice Sites", *Journal of Medical Biology*, 1992, vol. 228, pp. 1124–1136.

Schneider et al., "Sequence logos: a new way to display consensus sequences", *Nucleic Acids Research*, 1990, vol. 18, pp. 6097–6100.

Staden, R., "Computer methods to locate signals in nucleic acid sequences", *Nucleic Acids Research*, 1984, vol. 12, pp. 505–519.

Schnider, T. "Poster on Information Theory and Individual Information," Web page at http://www–lmmb.ncifcrf.gov/~toms/just.say.no/index.html, Feb. 27, 1996—updated Oct. 18, 1996.

Thomas D. Schneider, "Sequence Logos, Machine/Channel Capacity, Maxwell's Demon, and Molecular Computers: A Review of the Theory of Molecular Machines," *Nanotechnology* vol. 5, pp. 1–8, 1994.

Nathan D. Herman, et al., "High Information Conservation Implies that at Least Three Proteins Bind Independently to F Plasmid incD Repeats," *Journal of Bacteriology*, pp. 3558–3560, Jun. 1992.

Thomas D. Schneider, et al., "Sequence Logos: A New Way to Display Consensus Sequences," *Nucleic Acids Research*, vol. 18, No. 20, pp. 6097–6100, Sep. 12, 1990.

Otto G. Berg, et al., "Selection of DNA Binding Sites by Regulatory Proteins: The Binding Specificity of Cyclic AMP Receptor Protein to Recognition Sites," *Journal of Molecular Biology*, No. vol. 200, No. 4, pp. 709–723, 1988.

Otto G. Berg, "Selection of DNA Binding Sites by Regulatory Proteins: The LexA Protein and the Arginine Repressor Use Different Strategies for Functional Specificity," *Nucleic Acids Research*, vol. 16, No. 11, pp. 5089–5105, Apr. 26, 1988.

Thomas D. Schneider, "Information and Entropy of Patterns in Genetic Switchs," *Maximum–Entropy and Bayesian Methods in Science and Engineering*, vol. 2, pp. 147–154, 1988.

Otto G. Berg, et al., "Selection of DNA Binding Sites by Regulatory Proteins: Statistical–Mechanical Theory and Application to Operators and Promoters," *Journal of Molecular Biology*, vol. 193, No. 4, pp. 723–750, Feb. 20, 1987.

Rodger Staden, "Computer Methods to Locate Signals in Nucleic Acid Sequences," *Nucleic Acids Research*, vol. 12, No. 1, pp. 505–519, 1984.

Gary D. Stormo, et al., "Use of the 'Perceptron' Algorithm to Distinguish Translational Initiation Sites in *E. coli*," *Nucleic Acids Research*, vol. 10., No. 9, pp. 2997–3011, 1982.

*Primary Examiner*—Ellis B. Ramirez
*Assistant Examiner*—M. Kemper
*Attorney, Agent, or Firm*—Morgan & Finnegan, L.L.P.

[57] ABSTRACT

In accordance with the present invention, binding sites are defined based upon the individual information content of a particular site of interest. Substitutions within the binding site sequences can be analyzed to determine whether the substitution will cause a deleterious mutation or a benign polymorphism. In addition, new binding sites can be identified using individual information content. Further a computer system is described for determining and displaying individual information content of a binding site sequence.

57 Claims, 22 Drawing Sheets the $j^{th}$ sequence matrix, $s(b, l, j)$

| base $b$ | position $l$ | | | | | | | | | |
|---|---|---|---|---|---|---|---|---|---|---|
| | C | A | G | G | T | C | T | G | C | A |
| | −3 | −2 | −1 | 0 | 1 | 2 | 3 | 4 | 5 | 6 |
| A | 0 | 1 | 0 | 0 | 0 | 0 | 0 | 0 | 0 | 1 |
| C | 1 | 0 | 0 | 0 | 0 | 1 | 0 | 0 | 1 | 0 |
| G | 0 | 0 | 1 | 1 | 0 | 0 | 0 | 1 | 0 | 0 |
| T | 0 | 0 | 0 | 0 | 1 | 0 | 1 | 0 | 0 | 0 |

FIG. 1A individual weight matrix, $R_i(b, l)$

| base $b$ | position $l$ | | | | | | | | | |
|---|---|---|---|---|---|---|---|---|---|---|
| | −3 | −2 | −1 | 0 | 1 | 2 | 3 | 4 | 5 | 6 |
| A | 0.42 | 1.25 | −1.41 | −∞ | −5.81 | 1.12 | 1.51 | −1.81 | −0.68 | 0.05 |
| C | 0.58 | −0.78 | −2.40 | −7.81 | −5.49 | −3.68 | −1.56 | −2.24 | −0.51 | −0.17 |
| G | −0.58 | −1.04 | 1.64 | 1.99 | −6.23 | 0.72 | −1.06 | 1.71 | −0.32 | 0.44 |
| T | −1.02 | −0.87 | −1.67 | −5.81 | 1.98 | −3.38 | −1.59 | −2.21 | 0.90 | −0.49 |

FIG. 1B

*E. coli* ribosome binding sites

| l | n(a,l) | n(c,l) | n(g,l) | n(t,l) | $R_i(a,l)$ | $R_i(c,l)$ | $R_i(g,l)$ | $R_i(t,l)$ |
|---|---|---|---|---|---|---|---|---|
| -10 | 28 | 7 | 18 | 23 | 0.530957 | -1.469043 | -0.106473 | 0.247164 |
| -9 | 19 | 14 | 11 | 32 | -0.028470 | -0.469043 | -0.816966 | 0.723602 |
| -8 | 16 | 20 | 11 | 29 | -0.276398 | 0.045531 | -0.816966 | 0.581583 |
| -7 | 2 | 0 | 70 | 4 | -3.276398 | -6.266787 | 1.852886 | -2.276398 |
| -6 | 21 | 17 | 20 | 18 | 0.115920 | -0.188935 | 0.045531 | -0.106473 |
| -5 | 18 | 13 | 12 | 33 | -0.106473 | -0.575958 | -0.691435 | 0.767997 |
| -4 | 3 | 35 | 7 | 31 | -2.691435 | 0.852886 | -1.469043 | 0.677799 |
| -3 | 58 | 2 | 14 | 2 | 1.581583 | -3.276398 | -0.469043 | -3.276398 |
| -2 | 44 | 9 | 8 | 15 | 1.183034 | -1.106473 | -1.276398 | -0.369507 |
| -1 | 35 | 6 | 9 | 26 | 0.852886 | -1.691435 | -1.106473 | 0.424042 |
| 0 | 35 | 3 | 3 | 35 | 0.852886 | -2.691435 | -2.691435 | 0.852886 |
| 1 | 26 | 9 | 6 | 35 | 0.424042 | -1.106473 | -1.691435 | 0.852886 |
| 2 | 15 | 8 | 9 | 44 | -0.369507 | -1.276398 | -1.106473 | 1.183034 |
| 3 | 2 | 14 | 2 | 58 | -3.276398 | -0.469043 | -3.276398 | 1.581583 |
| 4 | 31 | 7 | 35 | 3 | 0.677799 | -1.469043 | 0.852886 | -2.691435 |
| 5 | 33 | 12 | 13 | 18 | 0.767997 | -0.691435 | -0.575958 | -0.106473 |
| 6 | 18 | 20 | 17 | 21 | -0.106473 | 0.045531 | -0.188935 | 0.115920 |
| 7 | 4 | 70 | 0 | 2 | -2.276398 | 1.852886 | -6.266787 | -3.276398 |
| 8 | 29 | 11 | 20 | 16 | 0.581583 | -0.816966 | 0.045531 | -0.276398 |
| 9 | 32 | 11 | 14 | 19 | 0.723602 | -0.816966 | -0.469043 | -0.028470 |
| 10 | 23 | 18 | 7 | 28 | 0.247164 | -0.106473 | -1.469043 | 0.530957 |

FIG. 14

COMPUTATIONAL ANALYSIS OF NUCLEIC ACID INFORMATION DEFINES BINDING SITES

FIELD OF THE INVENTION

The present invention relates to information computational methods of defining binding sites.

BACKGROUND OF THE INVENTION

When studying molecular binding sites in DNA or RNA, it is conventional practice to align the sequences of several sites recognized by the same macromolecular recognizer and then to choose the most common bases at each position to create a consensus sequence (see Davidson et al., 1983. *Nature* (London), 301, 468–470). Consensus sequences are difficult to work with and are not reliable when searching for new sites (Sadler et al., 1983b. *Nucl. Acids Res.* 11:2221–2231; 26 Hawley & McClure, (1983) *Nuc. Acids Res.*; 11:2237–2255).

This is partly because information is lost when the relative frequency of specific bases at each position is ignored. For example, the first position of *Escherichia coli* translational initiation codons has 94% Adenine ("A"), 5% Guanine ("G"), 1% Uracil ("U") and 0% Cytosine ("C"), which is not represented precisely by the consensus "A". To avoid this problem, four histograms can be made that record the frequencies of each base at each position of the aligned sequences. Such histograms can be compressed into a single curve by the use of a $\chi^2$ function (Gold et al., 1981. *Annu. Rev. Microbiol.* 35, 365–403; Stormo et al., 1982. *Nuc. Acids Res.* 10, 2971–2996). Although these curves show where information lies in the site, they have several disadvantages: the $\chi^2$ scale is not easily understood in simple terms; it is difficult to compare the overall information content of two different kinds of sites, such as ribosome binding sites and restriction enzyme sites; and $\chi^2$ histograms are not directly useful in searching for new site sites (Stormo et al. 1982 *Nuc. Acids Res.* 10, 2997–3011).

Many general methods exists for identifying sequence changes which are deleterious. However, these methods require experimentation in the laboratory. The most common method is the identification of a disease state and a corresponding genetic mutation in a particular sequence element. This method is quite labor intensive and requires that the mutation produce an identifiable phenotype. Another method uses restriction fragment length polymorphisms to identify alterations within the genome. This method is also experimental, but can only detect alterations in the genome at restriction sites, whether or not a phenotype results.

The average information contained in a set of nucleic-acid binding sites can be calculated by using the methods of information theory, and this has been useful for understanding a number of genetic control systems (Schneider et al., 1986. *J. Mol. Biol.*, 188, 415–431; Schneider & Stormo, 1989. *Nuc. Acids. Res.*, 17, 659–674; Eiglmeier et al. 1989. *Mol. Microb.*, 3, 869–878; Penotti, 1990. *J. Mol. Biol.*, 213, 37–52; Penotti, 1991 *J. Theor. Biol.* 150, 385–420; Schneider & Stephens, 1990. *Nuc. Acids. Res.*, 18, 6097–6100; Herman & Schneider, 1992. *J. Bact.*, 174, 3558–3560; Gutell et al., 1992. *Nuc. Acids. Res.*, 20, 5785–5795; Papp et al., 1993. *J. Mol. Biol.*, 233, 219–230). However, thus far an effective method does not exist for working with information content of single sequences or for predicting the effect of changes in information content due to sequence alterations—be it through biological evolution or by genetic manipulation.

Information analysis of normal splice junctions reveals partially conserved nucleotide sequences that are not always reflected in the corresponding consensus sequence (Stephens & Schneider, 1992. *J. Mol. Biol.* 228:1124–1136). Information content may be represented by a sequence logo, which depicts the relative contribution of each position of the splice site and the relative frequencies of each nucleotide at every position (Schneider & Stephens, 1990. *Nucl. Acids Res.* 18:6097–6100). The logo illustrates the full range of normal variants in the splice junction.

The present invention is principally directed to binding sites on a sequence. In particular, the present "Walker" program enables a scientist or clinician to identify mutations within a nucleic acid binding site which are deleterious, without extensive experimentation. This method generates a model of the binding site which is called the $R_i(b,l)$ weight matrix, which can then be used to evaluate other individual sites for their information content. The present invention allows one to analyze the effect on the binding site of changing a base at a particular position within the site.

The weight matrices of the present invention are not found in the prior art in several respects. $R_i$ values, which represent the sum of all weights at each position within a site, are on an absolute scale, rather than the relative scale found in the prior art. $R_i=0$ is a cutoff point for functional sites within the present invention. This feature is lacking in both Staden's method (1984 *Nuc. Acids Res.*, 12:505–519) and Berg & von Hippel's method (1987 *J. Mol. Biol.*, 193:723–750; 1988 *J. Mol. Biol.*, 200:709–723; 1988 *Nuc. Acids Res.*, 16(11):5089–5105). Hence, these methods draw no distinction between polymorphisms and mutations.

Moreover, the Berg & von Hippel's method relies upon the consensus sequence as the ideal, i.e. the best binding sequence. Therefore, Berg & von Hippel had no way of distinguishing a polymorphism from a deleterious mutation.

In addition, unlike the prior art (Berg & von Hippel's statistical-mechanical theory, in particular), no assumption about the relationship between energy and information is required to obtain $R_i$ in the present invention. The statistical-mechanical approach assumes that the energy of binding, "discrimination energy", is equal to the information contained within a recognition sequence. This assumption does not allow for a situation where more than one protein could bind to a particular site and thus increase the apparent information contained within that site.

Further, the $R_i$ method described in the present invention is much more sensitive to sequence changes than the widely and almost universally used consensus sequence method. The consensus sequence destroys data by taking the most frequent base at every position as the base used in the consensus model, whereas the $R_i$ method does not alter the frequency data and so can be used to detect subtle effects.

One object of the present invention relates to the use of individual information content of the site and its comparison with the overall distribution of individual information in a set of binding sites, to determine whether a substitution is a polymorphism or a mutation.

Another object of the present invention relates to designing binding sites to adjust the activity of the site. The present invention further relates to a computer system capable of determining the individual information content of a binding sequence and identifying new binding sequences.

Yet another object of the present invention relates to the use of individual information content to determine the effect of a particular position change in a sequence acting as a binding site.

Another object of the invention is to use the "Ri" and "Walker" computer program to display the reaction of a binding macromolecule at every position in a sequence and to determine the change in information content when a particular position within a binding site is altered.

Objects and advantages of the invention set forth herein and will also be readily appreciated here from, or may be learned by practice with the invention. These objects and advantages are realized and obtained by means of instrumentalities and combinations pointed out in the specification and claims.

SUMMARY OF THE INVENTION

The present invention relates to identifying mutations and polymorphisms within a nucleic acid region acting as a macromolecule binding site. The invention further relates to analyzing protein regions acting as binding sites for macromolecules to identify mutations and polymorphisms within the site. In either case, the instant method relates to the identification of mutations/alterations in a sequence, either nucleic acid or amino acid, which will be deleterious to the system which it affects.

In accordance with the present invention, a computer system and computation method are described for processing sequence signals by a transformation into an information content weight matrix, as represented by $R_i(b,l)$. A second transformation follows which applies a particular sequence signal to the information content weight matrix, $R_i(b,l)$ thereby producing a value, Ri, which comprises the individual information content of said particular sequence signal. An alteration of a particular position within a binding sequence provides a third signal, transforming the individual information content of the binding sequence by the amount of information either lost or gained by the position change. The third transformation produces an output record, for example a graphical representation (an X-Y graph or a numerical value) of the information content of the sequence after the alteration and defines whether the alteration will be deleterious to the cell. Such a deleterious alteration is referred to as a mutation, whereas a non-deleterious alteration is a polymorphism. The invention also relates to computer programs embodied on a computer-readable medium.

The present invention also relates to the display of the product of the transformations of the present method in the form of a graphical image.

The present invention further relates to a method for identifying and manipulating the binding affinity of a particular position within and surrounding a binding site. The instant method allows comparison of the information on particular binding sites to the individual information content of other binding sites, to distances between features of the sequence, and to their measured binding energies. The present invention further allows adjustment of the binding affinity of a binding site by manipulating positions within the site to alter its individual information content.

The present invention further relates to a method of designing sequence elements which function as binding sites.

The invention also relates to a method of diagnosing a genetically-determined disease based upon the identification of a deleterious mutation, based upon a change in individual information content of the binding sequence. In addition, the invention relates to identification and use of cryptic binding sites on a particular sequence.

BRIEF DESCRIPTIONS OF THE DRAWINGS

The file of this patent contains at least one drawing executed in color. Copies of this patent with color drawing(s) will be provided by the Patent and Trademark Office upon request and payment of the necessary fee.

FIG. 1(*a*) is the sequence 5' CAGGTCTGCA 3' represented in matrix format.

FIG. 1(*b*) is the individual weight matrix for human donor splice junctions derived from data given in (Stephens & Schneider, 1992 *J. Mol. Biol.*, 228: 1124–1136). The weights of the matrix in (b) which are selected by the sequence in (a) are enclosed by boxes.

FIG. 2 is a histogram of individual information for 1055 *E. coli* ribosome binding sites. The mean and standard deviation of the $R_i$ values were fitted by a Gaussian distribution.

FIG. 3 is a histogram of individual information for 1799 human donor binding sites. Donor sites which lacked a complete sequence in the region 0 to +6 were not included.

FIG. 4 is a histogram of individual information for 1744 human acceptor binding sites. Acceptor sites which lacked a complete sequence in the region −25 to +2 were not included.

FIG. 5 is a graph illustrating the correlation between GCN4 sites and the log of their relative binding affinities.

FIG. 6 is a schematic diagram showing important landmarks on the individual information, $R_i$ scale. The consensus is the highest possible evaluation of the $R_i(b,l)$ matrix; the anti-consensus is the lowest. Sequences with $R_i=0$ separate sites ($R_i>0$) from nonsites ($R_i<0$). By definition, the mean of the distribution is $R_{sequence}$. The standard deviation of the distribution is $\sigma_{R_i}$. The standard deviation of $R_{sequence}$ is the standard error of the mean, SEM.

FIG. 7 is a flow diagram illustrating computer programs for individual information analysis in accordance with the present invention.

FIG. 8 is a graphic plot of the individual information of the Fis Promoter produced by the program Xyplo. The position of the zero base of the Fis weight matrix on the sequence is given on the abscissa, while the individual information for the sequence surrounding each position −10 to +10 is given on the ordinate. The 6 previously identified Fis sites are marked with a plus (+). Predicted sites are represented as squares above the zero line. Transcription begins at base 375 and proceeds to the right (arrow). The sequence is from GenBank accession X62399 (Ninnemann et al., 1992 *EMBO J.*, 11:1075–1083) (see also accession M95784 (Ball et al., 1992 *J. Bact.*, 174:8043–8056). Bottom: a larger region of sequence graphed by DNA plot shows clustering of potential fis sites around the promoter but not further downstream. The dashed line indicates the corresponding parts of the figure.

FIG. 9 is an example of a Walk Display.

FIG. 10 is an example showing the effect of mutations in a "Walk" display.

FIG. 11 is a sequence logo showing the location of the hMSH2 polymorphism in the human splice acceptor site. This sequence logo was created from 1744 wild-type acceptor sites. The height of each nucleotide is proportional to its frequency at that position, while the height of each entire stack of nucleotides corresponds to the information measure (in bits) or, equivalently, the sequence conservation at that position. When sequence conservation is measured in bits, the relative heights of the stacks can be compared to one another and the total sequence conservation in a region can be found by adding the heights of the stacks together (Shannon & Weaver, 1949, *The Mathematical Theory of Communication*, University of Illinois Press, Urbana, Ill.).

Coordinates in the splice site are defined along the abscissa. RNA strand cleavage during splicing occurs at the vertical line between positions 0 and 1. All positions except −3 in this logo are significantly above background ($p<8\times10^{-8}$). The arrow shows the position of the T→C substitution of the hMSH2 gene.

FIG. 12 is a set of graphs illustrating individual information scans of inversion regions. Symbols are the same as in FIG. 5. Previously identified Fis sites are marked with a plus inside a square and named as in (Finkel & Johnson, 1992 *Molec. Microb.*, 6:3257–3265; Finkel & Johnson, 1992 *Molec. Microb.*, 6:1023). The proposed Fis sites are marked with a circle inside a square. Spacing between sites is indicated by numerals surrounded by dashes. Note that the spacing between proximal and distal sites is always 48 bases.

FIG. 13 is the sequence for the *S. typhimurium* hin mutants. The wild-type sequence containing the proximal Fis site from the *S. typhimurium* hin region (HW) is given on the top, flanked by EcoRI and HindIII restriction sites. The known proximal site is indicated next to the predicted medial site. In the next sequence, the right anticonsensus (HR) was used to destroy the medial site, leaving the proximal site intact. In the third sequence, the left anticonsensus (HL) Fis site sequence was used to destroy the proximal site while leaving the medial site intact. In the fourth sequence both (HB) sites were destroyed.

FIG. 14 is a matrix table for the n(b,l) and the $R_i(b,l)$ weight matrix for 76 Fis binding sites. Column 1 is the position relative to the center of the Fis site. Columns n(a,l), n(c,l), n(g,l) and n(t,l) give the number of bases b at positions l (the n(b,l) table). The frequency table is defined as $f(b,l)=n(b,l)/\Sigma_b{}^T{}_{=A}\, n(b,l)$. The 4 columns for the $R_i(b,l)$ table give the individual information weights (in bits) for bases b at position l. This distribution of Fis sites has a mean of 8.24 bits and a standard deviation of 2.69 bits.

FIG. 15 is a sequence logo of Fis binding sites and DNA base pair structure with 38 experimentally defined Fis binding sequences and their complements. The total sequence conservation, found by adding the stack heights together, is $R_{sequence}=8.2\pm0.6$ bits per site. (this standard error of the mean=0.6 bits was calculated according to (Schneider et al., 1986 *J. Mol. Biol.* 188:415–431). See text for further description. Methylated guanines which interfere with Fis binding are indicated by filled circles (●) and methylated adenines which interfere with Fis binding are indicated by open circles (○) (Bruist et al., 1987 *Jones Dev.*, 1:762–772)

FIG. 16 are mobility shift experiments for hin and cin. Top: Gel shifts of DNA containing the hin proximal and medial Fis binding sites. Each lane contains increasing concentrations of Fis protein added, beginning with no Fis protein, Fis diluted 1 to 8, etc. The 1:1 ratio is 1000 nM Fis. Letter designations refer to the sequences given in FIG. 13. Bottom: Gel shifts of DNA containing the cin proximal and external Fis binding sites with the same conditions as above.

FIG. 17 is a Scattergram showing the relationship between $R_i$ and phenotype of mutations altering splice donor sequences. The clinical presentations of each inherited abnormality studied were categorized as mild, moderate or severely affected based on the descriptions of these patients. On the ordinate axis, individuals with a mild disorder are coded as 1, moderate as 2, and severely affected individuals as 3. The individual information content of the corresponding mutations is plotted on the abscissa.

FIG. 18 is a graph showing the relationship between mutant $R_i$ and splicing efficiency for mutant donor splice sites. The relationship between the logarithm (base 2) of the mRNA splicing efficiency with the change in $R_i$ for 21 splice donor site mutations (I) or 10 acceptor site mutations (II) associated with different inherited conditions. The change in $R_i$ due to the mutation (Δri) is expressed as the normalized absolute value of the difference between the mutant and cognate individual information content values (in bits). According to this definition, a non-functional mutation will have $\Delta R_i=1$; $\Delta R_i$ for a polymorphic substitution will be zero. The logarithm of the splice efficiency ranges from 10 (for 100% efficiency) to −27 (for negligible levels of splicing, this has been set at $1\times10^{-8}\%$, since the logarithm of 0 cannot be computed). Regression of the best linear fit of the data is shown as a line. the correlation coefficients of $\Delta R_i$ of donor and acceptor splice site mutations, respectively, are 0.45 and 0.68.

DETAILED DESCRIPTION OF THE INVENTION

Figure 2:
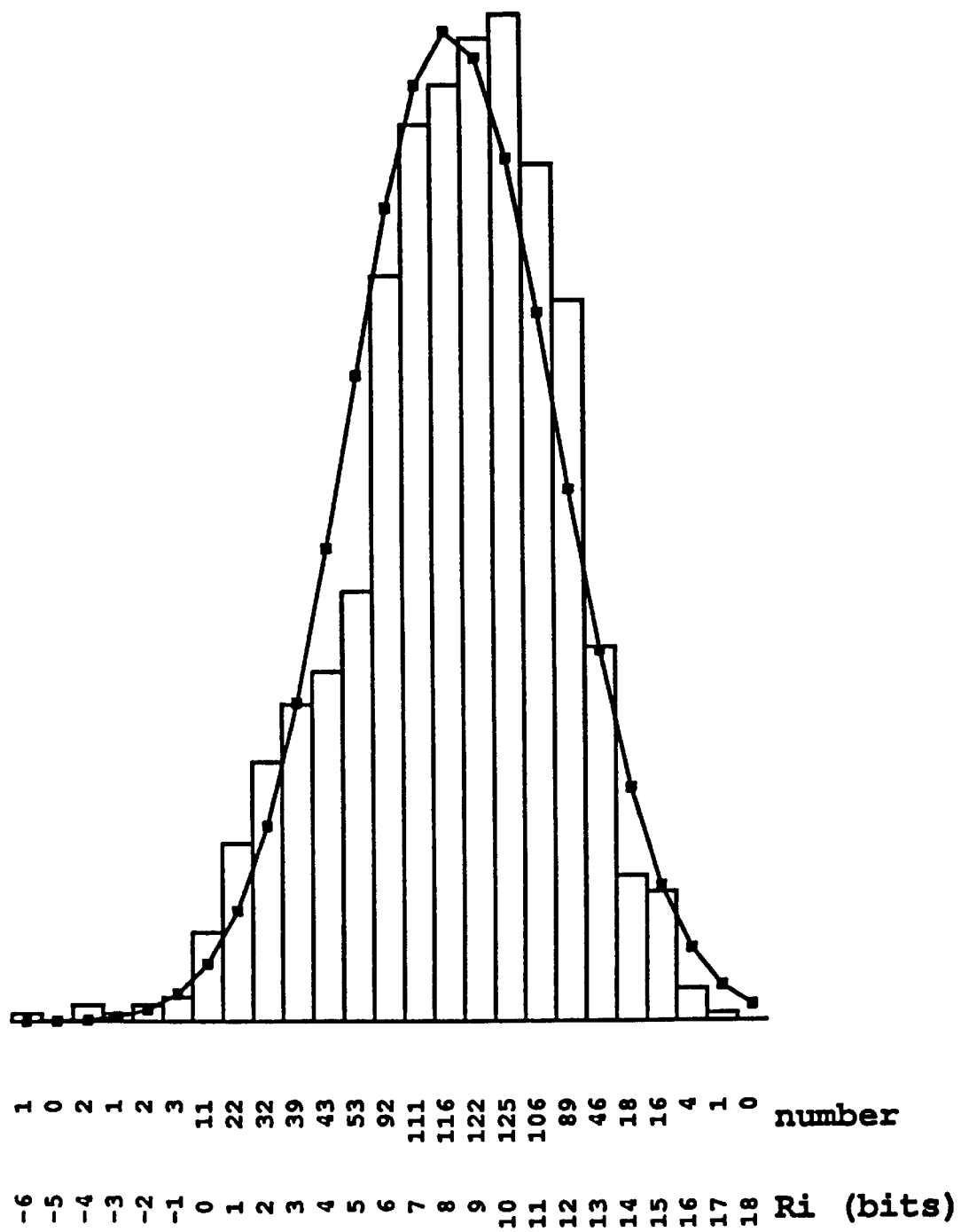

The present invention relates to a method of identifying and manipulating the affinity of macromolecule binding sites.

The present invention further provides a method for identifying mutations and polymorphisms within a nucleic acid region acting as a protein or—macromolecule—binding site. The method is also used on other binding sites, such as protein—protein sites or protein binding sites for other small molecules. In particular, these sites are analyzed to determine whether a particular amino acid substitution is deleterious or not. In either case, the method relates to the identification of alterations in a sequence, either nucleic acid or amino acid, which will be deleterious to the system.

Information as the term is used herein is defined as the number of choices made by a machine, given on a logarithmic scale in bits. Information content as the term is used herein is defined as the number of choices needed to describe a sequence pattern given on a logarithmic scale in bits. $R_{sequence}$ as the term used herein is defined as the information content of a nucleic-acid binding site or of a protein. A "binding site" as the term is used herein is defined as the region of macromolecule which binds to another molecule. A "cryptic site" as the term is used herein is defined as a weak nucleic-acid binding site that may be revealed by mutation of the sequence or by the destruction of a neighboring strong site. Splicing efficiency is defined as the proportion of normal mRNA produced by the mutant allele relative to the normal allele.

The individual information theory methods of the present invention can be applied to genetic engineering.

For example, polymorphisms are extremely useful tools in genetic engineering, one can use individual information analysis to introduce a polymorphism into splice sites or other types of motifs. For splice sites, one might introduce a substitution that does not impair splicing (at both the donor and acceptor sites flanking an exon) and which produces cleavable restriction sites at either end of the exon. This permits the investigator to "shuffle" the exon(s) in vitro to create a novel protein with additional functions. The only prerequisite for such an application of the instant invention is that the reading frame is preserved. A real benefit to this embodiment of the present invention is that it eliminates the necessity of flanking intron sequences to be carried along with the desired intron sequence. This is an important consideration, since not all introns consist of "junk" DNA. For example there are transcription factor binding sites, i.e. Oct 1 in the immunoglobulin V region introns, internal promoters, i.e. in the murine major histocompatibility complex genes, and even more important, cryptic splices sites in the flanking intron sequences, as shown below.

The same strategy is used to move promoters from one gene to another.

There is another way human geneticists may use the instant invention. A polymorphism may be introduced, without a loss of information or change in function, in order to track a transgene or a transfected gene in a cell type where other similar sequences may be present. An example of such a system is when the introduced gene is a member of a multigene family. Using Ri analysis to insure that the polymorphism does not have an effect on splicing or other aspects of gene or protein expression is an important consideration. Introducing transgenes in this way permits distinguishing maternally and paternally derived chromosomes, thus providing another tool for identification of imprinted genes.

Another embodiment of the present invention utilizes individual information techniques to allow design of binding sites. As genetic engineering advances, it is useful to have the capability to create more complex genetic structures. The strongest binding sites are not always the most desirable. For example, since a strong bacteriophage T7 promoter will kill a bacterial cell or tax the resources of the cell by using up the free ribonucleotides, it is at times not practical to have the strongest possible promoter. The tools of the present invention allow the design a promoter of the strength required for a particular application. In the case of T7 promoters, one may find an optimum at which a promoter strength is chosen which maximizes production of a gene product because cells are still healthy. These same tools allow not only the creation of "designer promoters" and "designer genetic control systems", but also the design of the active site in an enzyme, other motifs in proteins and drug binding sites.

Sometimes it is necessary to design two binding sites that overlap each other. To insure that each site has the required strength is impossible with the consensus methods, but the individual information technique of the present invention easily allows this. The present invention allows a user to select from many weight matrices which may be stored in a library. A computer may automatically evaluate the effect on binding for each recognizer and of any changes to the sequence that the user contemplates. This allows the user to modulate the strengths of the binding sites individually so that these binding sites work together for the desired genetic effect. This embodiment allows the fine-tuning of gene expression.

The term "recognizer" as it is used herein refers to a molecule which recognizes and binds to the binding site of interest. Recognizer is further defined to mean a macromolecule that locates specific sites on nucleic acids. These may include repressors, activators, polymerases, ribosomes and spliceosome.

The method uses individual information content to determine the effect of a particular mutation at a specific binding site. The information content for a particular binding site is derived from an analysis of nucleic acid sequence information from various data bases available for that information, which are used to determine the frequency of a particular nucleic acid base being present at a particular position within the sequence of interest. This analysis results in the development of a sequence logo, which is a graphical representation of the probability that a particular nucleic acid base will be present at a particular position within the sequence of interest. The height of each nucleotide within the sequence logo is proportional to its frequency at that position, while the height of each stack of nucleotides corresponds to the information measure (in bits) or, equivalently, the sequence conservation at that position. The area under the logo represents the information content in bits (referred to as $R_{sequence}$) of the binding site. The logo illustrates the full range of normal variants in the protein binding site of interest.

Preliminarily, a sequence logo may be produced. Each binding site, as represented in a sequence logo contains a specific amount of information, which is expressed as $R_{sequence}$, in "bits" of information. A bit, as the term is used herein, is the amount of information needed to choose one of two equally likely possible outcomes.

In accordance with the present method the gathered sequence information regarding a binding site is converted into a weight matrix, referred to as $R_i(b,l)$ which provides a model of the recognizer which binds to the binding sites. The information weight matrix is then applied to a particular sequence, generating an individual information content, Ri for that sequence. This sequence can be further analyzed for the effect of a specific mutation at any position within the sequence and the resulting change in Ri can be measured. A nucleic acid substitution may be analyzed for a change in the individual information content, which can be displayed in the sequence logo-type image (see FIGS. 9 and 10). True mutations are expected to reside in positions where the sequence conservation in bits significantly exceeds the background variation and where the base frequency decreases significantly.

It is noted that $R_i(b,l)$ is related to $R_{sequence}$, in that $R_{sequence}$ is the mean value generated from the $R_i(b,l)$ matrix, when that matrix is applied to the original site of binding sequences used to create the $R_i(b,l)$ matrix itself.

Practically, the invention is effectuated through the use a series of computer programs, which sequentially, retrieve selected nucleic acid information, and analyze the information content for the sequences retrieved by development of a weight matrix (in the Ri program). The weight matrix is applied to a specific sequence thereby producing an individual information content, Ri which is then loaded into a program called "Walker", which is capable of displaying the reaction of the binding protein to every base in a sequence and of determining the effect of a nucleic acid substitution at any position within the binding site, based on the information weight matrix. Where there is a change in the individual information content which deviates from the determined information content value by more than three standard deviations, or which makes the individual information content go below zero, these changes are considered mutations rather than polymorphisms. The Ri program, the Walker program and the related Scan program allow the user to investigate the effects of sequence changes in the regions around the binding site, so that the creation or destruction of binding sites nearby can be detected.

A preferred embodiment of the present invention relates to a method for assigning a sequence conservation to individual nucleic-acid binding site sequences based on a large collection of sample sites. In this method, the sample sequences bound by a particular protein or molecular complex (such as a ribosome or spliceosome) are aligned and the frequencies of bases at each position are determined. The base 2 logarithm of each frequency at every position is added to 2 and a sample size correction factor to obtain a weight matrix, $R_i(b,l)$, where b is one of the 4 bases and l is a position along the sequences. This "individual information" matrix represents the sequence conservation of the sites measured in bits of information and it can be used to rank-order the sites, to search for new sites, to compare binding sites of the same or of different kinds to one another, to compare binding sites to other quantitative data such as binding energy or distance between binding sites, and to detect errors in databases.

In accordance with the present invention the individual information matrix is:

$$R_i(b,l) = 2 - (-\log_2 f(b,l) + e(n(l))) \quad (1)$$
$$= E(H_n) + \log_2 f(b,l) \text{ (bits per base)}$$

where f(b,l) is the frequency of each base b at position l in the aligned binding site sequences and e(n(l)) is a sample size correction factor for the n sequences used to create f(b,l) (Schneider et al., 1986 *J. Mol. Biol.*, 188:415–31; Penotti, 1990 *J. Mol. Biol.*, 213:37–52). To simplify the notation, the factor e(n(l)) was separated from $\log_2$ f(b,l) and joined to "2" to create $E(H_n)$.

In a set of sequences the $j^{th}$ sequence by a matrix s(b,l,j) contains only 0's and 1's. For example, the sequence 5' CAGGTCTGCA 3' is represented as shown in FIG. 1a. Likewise, the $R_i(b,l)$ matrix for human donor splice junctions is shown in FIG. 1b.

The individual information of a sequence is the dot product between the sequence and the weight matrix:

$$R_i(j) = \sum_l \sum_{b=a}^{i} s(b,l,j) \times R_i(b,l). \quad (2)$$

For the donor splicing weight matrix given in the figure, the sequence 5' CAGGTCTGCA 3' is assigned 0.58+1.25+1.64+1.99+1.98+(−3.68)+(−1.59)+1.71+(−0.51)+0.05=3.42 bits. Essentially, each base of the sequence "picks out" a particular entry from a column of the $R_i(b,l)$ matrix, and these weights are added together to produce the total $R_i$.

The average information of the n individual sequences which were used to create the frequency matrix f(b,l) is the expectation (i.e. mean) of $R_i$:

$$E(R_i) = \frac{1}{n} \sum_{j=1}^{n} R_i(j). \quad (3)$$

We now substitute equation (1) into (2) and then substitute equation (2) into (3). By using the definition of the frequency matrix:

$$f(b,l) = \frac{1}{n} \sum_{j=1}^{n} s(b,l,j) \quad (4)$$

and the fact that the frequencies sum to 1:

$$\sum_{b=a}^{t} f(b,l) = 1 \quad (5)$$

we find with some manipulation that:

$$E(R_i) = \sum_l \left( E(H_n) - \left( -\sum_{b=a}^{t} f(b,l)\log_2 f(b,l) \right) \right). \quad (6)$$

The right hand side is exactly the definition of $R_{sequence}$ (Schneider et al., 1986 *J. Mol. Biol.*, 188:415–431), so we have demonstrated that the average of individual information contents is the average information content of the sites:

$$E(R_i)=R_{sequence} \quad (7)$$

By expressing the formula (6) as a subtraction, we emphasize that information is a state function defined as a difference of uncertainties (Schneider, 1994 *Nanotechnology*, 5(1):1–18). The $R_i(b,l)$ function is unique because it can be proven that $R_i(b,l)$ is the only function whose average is $R_{sequence}$, as described above.

Roots of information theory: surprisal of bases

The individual information method is consistent with early work on information theory. Selecting one symbol from a set of M symbols, requires $\log_2$ M binary decisions. For example, any corner of a cube may be specified by the answer to three yes-no questions of the form:

1. Is it on top?
2. Is it on the left side?
3. Is it in front?

That is, $\log_2$ 8=3 bits. The next step is to rearrange the formula:

$$\log_2 M = -\log_2 P \quad (8)$$

where P is the probability of the equally likely symbols. What can we do if the symbols are not equally likely, as is the case for frequencies of bases in binding sites? To handle this, Tribus (Tribus, 1961 *Thermostatics and Thermodynamics*, D. van Nostrand G., Inc., Princeton, N.J.) proposed the concept of "surprisal", $h_i$ as the negative logarithm of a symbol's probability in the midst of a stream of symbols:

$$h_i = -\log_2 p_i \quad (9)$$

where $p_i$ is the $i^{th}$ symbol's probability so that (9) is an extension of the form given in equations (8). For example, the less likely the ringing of a telephone is, the more startled we are to hear it. The advantage of using this definition becomes clear when we consider the average surprisal for the entire stream of symbols. To find this, we take the individual surprisals and weight them by their occurrence, $p_i$, and find the total:

$$H = \sum_i p_i h_i = -\sum_i p_i \log_2 p_i \text{ (bits per symbol)}. \quad (10)$$

This is the Shannon uncertainty measure, so we have demonstrated that H is an average of surprisals.

What change does an individual "finger" of a recognizer see when the recognizer goes from non-specific binding (the before state) to specific binding (the after state)? In the before state, the average surprisal may be 2 bits, since the recognizer is not making contact with the nucleic acid bases in that state, so the composition of the genome should not matter. It is noted that 2 in equation (1) represents 2 bits of information, that is the uncertainty before a recognizer binds to a binding site. However, it may alternatively be represented by a value $H_g$ which represents the uncertainty associated with binding anywhere in a particular genome. This value will vary from one genome to the next but will be a constant for all binding sites within one genome. Thus for the difference in surprisal we write:

$$R_i(b,l) = 2 - (-\log_2 f(b,l)) \text{ (bits per base)} \quad (11)$$

This is equation (1) except for the sampling correction.

We are now in a position to understand the individual information, which is the sum of $R_i(b,l)$ across a binding site, as the total surprisal decrease from the viewpoint of a particular recognizer binding to a particular sequence. This model allows a recognizer to have different responses to different sequences. Different recognizers have different surprisals for the same sequence because they have different molecular recognition surfaces.

A word of caution is in order. If the set of sequences contains gaps (as when sequence data are missing on one or both sides of a site) then the average of the individual information contents generally will not equal the $R_{sequence}$ as calculated from the frequencies of bases at each position. This is because the individual sequences can be strongly affected by missing data, but $R_{sequence}$ is not. For this reason calculation of $R_{sequence}$ should still be done by the original frequencies method, and individual information values taken from partial sequence data should be treated with care.

The model described above assumes that positions along the site are independent from one another. It should be possible to extend the method to cases where each base is correlated to the next, or even longer relationships. However, to do this requires many more sequences to avoid the severe effects of small sample size.

Individual Information Distribution

The $R_i(b,l)$ matrix can be applied to each sequence used to generate the $R_i(b,l)$ itself. This produces n numbers. A histogram of the number of sites with a given information versus the information displays the $R_i$ distribution (see FIG. 2 for an example). The expectation of this distribution is, by definition, $R_{sequence}$.

Variance of $R_i$

Analogous to the mean of the $R_i$ distribution is the spread or variance of the $R_i$ distribution, given by $$\text{var}(R_i) = \frac{1}{n} \sum_{j=1}^{n} (R_i(j) - E(R_i))^2. \quad (12)$$

For ease of calculation, this may be reexpressed as:

$$\text{var}(R_i) = \frac{1}{n} \sum_{j=1}^{n} R_i(j)^2 - R_{sequence}^2. \quad (13)$$

The standard deviation of the distribution is:

$$\sigma_{R_i} = \sqrt{\text{var}(R_i)} \text{ (bits per site)}. \quad (14)$$

This number measures how variable the binding sites are.

Standard Error of the Mean.

By definition, $R_{sequence}$ is the mean of the individual information distribution. By using the $R_i$ distribution, the standard deviation of this mean can be determined, and is known as the standard error of the mean (SEM). The SEM can be determined directly from the standard deviation of the $R_i$ distribution ($\sigma_{R_i}$) by $$SEM = \frac{\sigma_{R_i}}{\sqrt{n}} \quad (15)$$

where n is the number of examples (Taylor, 1982). The variation of $R_{sequence}$ can also be determined by a Monte Carlo method (program Rsim, as described in detail in Stephens & Schneider, 1992 *J. Mol. Biol.*, 228:1124–1136).

Individual information at each position in a binding site. $R_i(b,l)$ may also be used to determine the variance at each position l in the binding site. First we define the individual information at each position l of each sequence j:

$$R_i(l,j) = \sum_{b=a}^{t} s(b,l,j) \times R_i(b,l). \quad (16)$$

Since the mean at each position is:

$$R_{sequence}(l) = \frac{1}{n} \sum_{j=1}^{n} R_i(l,j) \quad (17)$$

we have for the variance $$\begin{aligned}\text{var}(R_i(l)) &= \frac{1}{n} \sum_{j=1}^{n} (R_i(l,j) - R_{sequence}(l))^2 \\ &= \frac{1}{n} \sum_{j=1}^{n} (R_i(l,j)^2 - R_{sequence}(l))^2.\end{aligned} \quad (18)$$

The standard deviation is:

$$\sigma_{R_i(l)} = \sqrt{\text{var}(R_i(l))} \quad (19)$$

Finally, the standard deviation of the mean is the variation of $R_{sequence}(l)$ at each position in the site:

$$SEM(l) = \frac{\sigma_{R_i(l)}}{\sqrt{n}}. \quad (20)$$

This measure may have practical application for producing error bars in the sequence logo display (Schneider & Stephens, 1990 *Nuc. Acid. Res.*, 18:6097–6100).

Searches using individual information

By applying the $R_i(b,l)$ matrix to sequences other than the sites from which it was derived, we create a search tool. Since the numerical value assigned to each position in a sequence by an $R_i(b,l)$ matrix is in bits per site, the evaluations can be directly compared to the average measures $R_{sequence}$ and $R_{frequency}$. Because information is the only measure which allows one to add together "scores" from each position in a binding site (Shannon, 1948 *Bell Systems Tech. I*, 27:379–423- 623–656), other proposed search methods (Mulligan et al., 1984 *Nuc. Acids Res.*, 12:789–800; Shapiro & Senapathy, 1987 *Nuc. Acids Res.*, 15:7155–7174; Goodrich et al., 1990 *Nuc. Acids Res.*, 18:4993–5000) cannot be justified.

When the $R_i(b,l)$ matrix is used for sequence searches, one must be aware that if a particular base does not appear in the data set used to create $f(b,l)$, then $f(b,l)=0$ and so $R_i(b,l)=-\infty$ at that position (see equation (1)). This expresses the fact that there are no known examples of a functioning site containing the base b at position l. That is, the simple-minded mathematics reacts as if it were very "surprised" that this is a site. This cannot happen if the matrix is only used to analyze the sequences that were used to make up the matrix itself because the infinite positions are never selected. Also, when using the dot product method, the fact that $$\lim_{f \to 0} f \log$$

$f=0$ assures that the infinite quantities are suppressed. Search programs can handle this situation by replacing $-\infty$ with a large negative value. Alternatively, the search may be relaxed by using a less severe penalty. Staden suggested replacing every $f(b,l)=0$ with $f(b,l)=1/n$ (Staden, 1984 *Nuc.*

*Acids Res.*, 12:505–519), which allows for the possibility that the base at the position is as rare as the number of sequences used to generate the matrix. Unfortunately both $-\infty$ and this proposed substitution will be erroneous in most cases because the true value of the frequency will usually lie somewhere between these two extremes. The computer program of the present invention therefore allows substitution with $1/(n+t)$, with $t \geq 0$. For example, using $t=1$ suggests that the missing base would be found if just one more binding site sequence were obtained.

The individual information method was applied to a series of situations.

Figure 3:
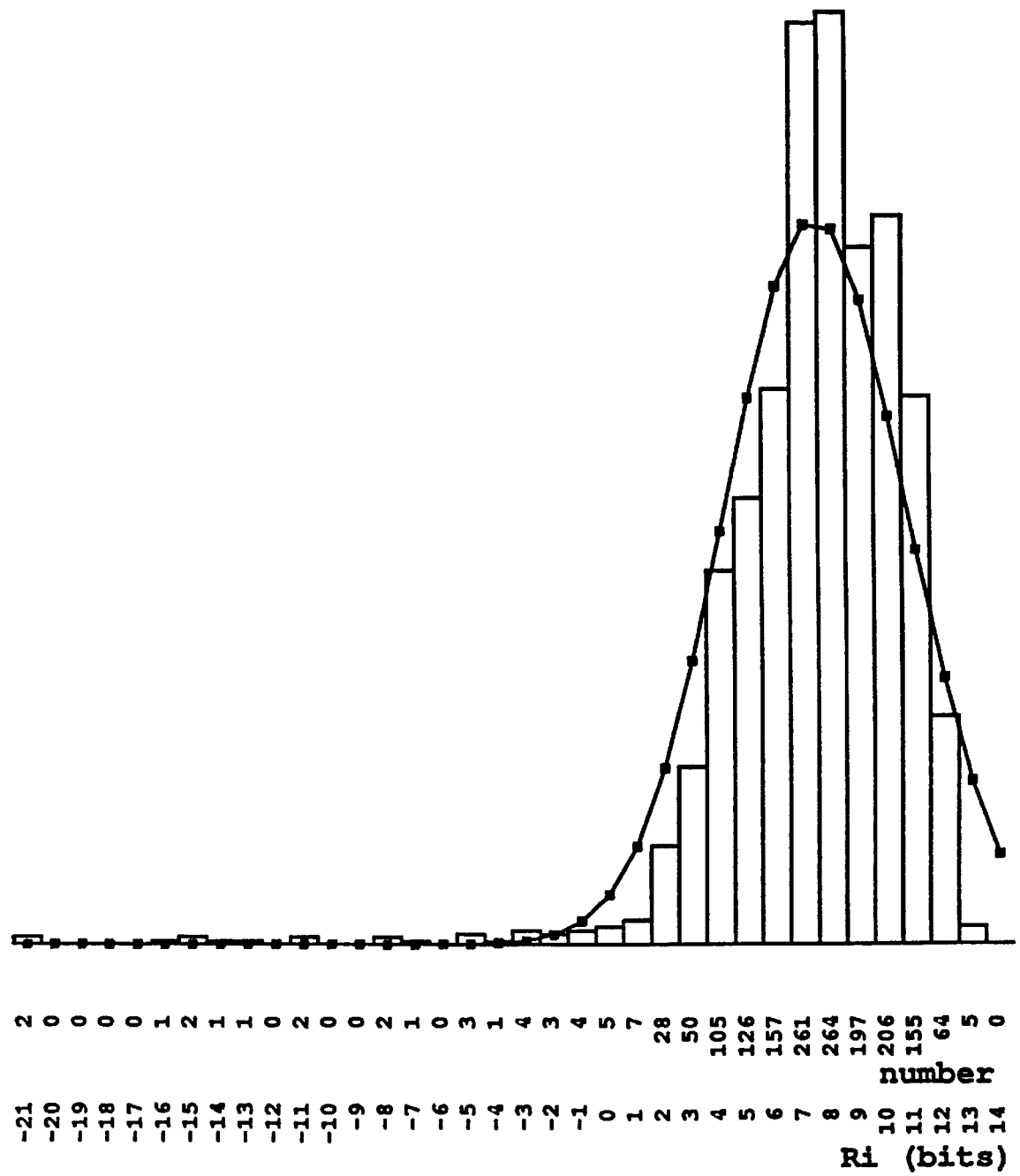
Figure 4:
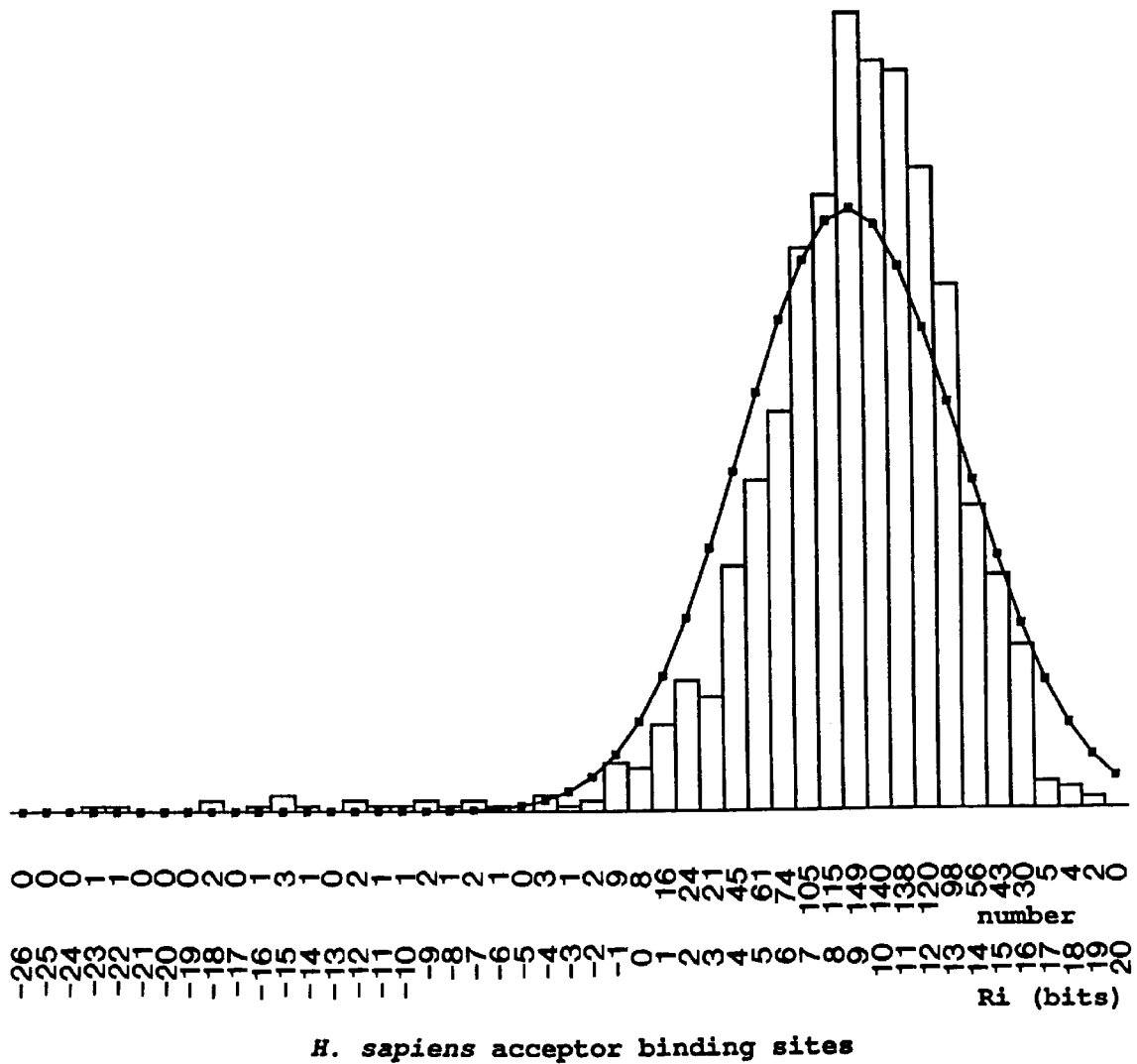

Single binding site conservation distributions. The individual conservation distribution for several binding sites are shown in FIGS. 2, 3, and 4. For the splice junctions, $R_i(b,l)$ was created from the data described in (Stephens & Schneider, 1992. *J. Mol. Biol.*, 228:1124–1136). Partially sequenced sites, which tend to make negative $R_i$ evaluations, were eliminated from the distributions shown.

Figure 5:
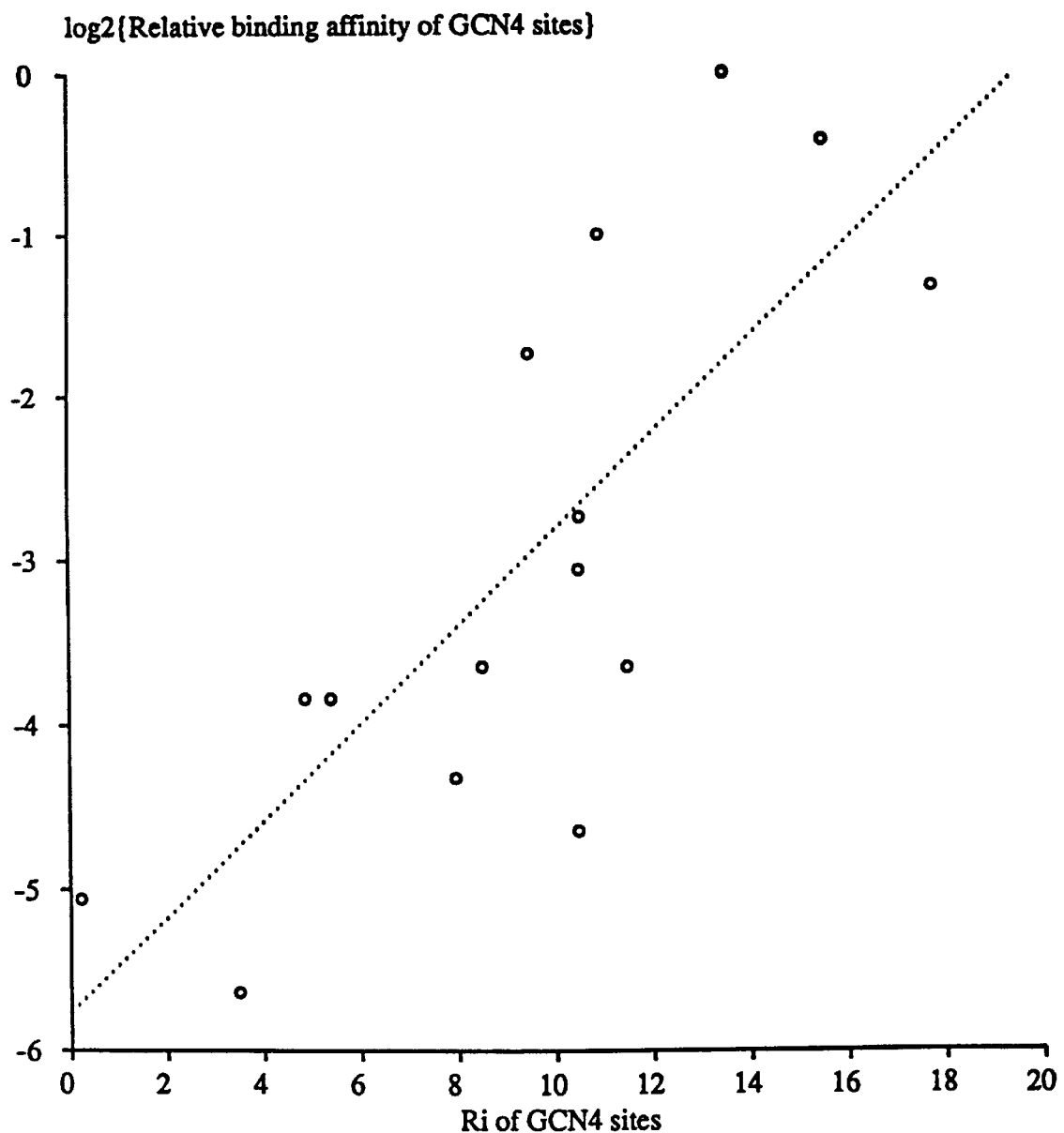

Correlation of a binding site conservations with a binding energy. As an example of the use of individual information to relate sequences to binding energy, the GCN4 affinity data of Arndt and Fink was chosen. (Arndt & Fink, 1986 *Proc. Natl. Acad. Sci. USA*, 83:8516–8520). 28 GCN4 sites were used to create the $R_i(b,l)$ matrix. When one plots affinity directly against the $R_i(j)$, the correlation coefficient is only 0.65. Although there is still a wide scatter, the GCN4 binding sites correlate better to the logarithm of the relative affinities, having a correlation coefficient of 0.78 (FIG. 5).

The present invention provides a method for evaluating the sequences of individual binding sites. It is important to realize that the method is performed in several steps. The first step is to gather a number of example sites. These are used to generate a model of the binding sites which is called the $R_i(b,l)$ weight matrix. Because this matrix can be created from a large numbers of sequences, it can give statistically significant evaluations of individual sequences. Thus there is no contradiction: the individual sites are always evaluated in the light of a model created from a large collection of sequences.

The $R_i$ evaluation is always relative to a particular nucleic-acid recognizer. For example, each position of a given nucleic-acid sequence can be searched with an $R_i$ matrix for donor splice sites and with a different $R_i$ matrix or acceptor splice sites. Each matrix provides a different evaluation as to what its respective recognizer's response should be at every position of the sequence.

The Scan program reports the evaluation of each position in three ways: the individual information ($R_i$), the standard deviation from the wild type distribution (Z) and the one tailed probability (p). The values of p are particularly curious because sequences with evaluations significantly higher than the mean (i.e. $R^{sequence}$) have low probabilities of being real sites. There is no denying this, as it is clear from the distributions (FIG. 2, FIG. 3, FIG. 4) but it is odd because we have been socially conditioned to think that stronger binding sites are always better. They may indeed be stronger, but they are less likely to appear in the set of natural sites. Evidently the sites evolve to what is required for their function (Schneider et al., 1986 *J. Mol. Biol.*, 188:415–431; Schneider, 1988 *Maximum-Entiopy and Bayesian Methods in Science & Engineering*, (Erickson, G. J. & Smith, C. R. eds) vol. 2, p.147–154, Kluver Academic Publishers Dordrecht, The Netherlands).

The computer system of the present invention comprises a processor and a memory storage device. In general, the computer system may be any IBM personal computer or compatible with operating system such a MS-DOS, PC-DOS, Windows, OS2, Unix, MacIntosh (i.e., system 7). A particularly preferred computer system is SPARCstation 20/61 with a Unix System 5 operating system (Sun Microsystems, Inc., Mountainview, Calif.). Additionally, as is readily apparent to those skilled in the art, the binding site defining system of the present invention can run effectively on currently available portable computers.

RAM: The walk program (produced from walker version 3.09) currently requires 4.2 megabytes of random access memory for a 1149 base sequence and a 21 base wide $R_i(b,l)$ weight matrix. This is within the range of many small modern computers.

DISK: The program source code sizes currently are:

walker.p 118463 bytes scan.p 40796 bytes ri.p 66021 bytes

Of the Delila programs, Delila is largest:

delila.p 164261 bytes

Thus a 1 gigabyte disk drive is sufficient to store the files.

Various types of database software can be used with the present invention. If it is preferred that output be produced as a printout, software exists for allowing many printers to print PostScript graphics. Any standard PostScript printer will suffice for printing the graphics from Walker.

The computer system of the present invention preferably is capable of reading a Postscript program from a file (the walk) and then switching to reading user-typed PostScript commands. One such program is the Ghostscript program, which is currently freely available from two sources. Ghostscript and Ghostview are freely available from "http://www.cs.wisc.edu/~ghost/index.html" and "http://155.198.1.40/gnu".

The programs are preferably compiled by a Pascal compiler such aspc, the Sun Microsystems Pascal Compiler. (See Jensen & Wirth, *Pascal User Manual and Report*, Springer-Verlag, New York, 1975). The source code in Appendix A through J is written in the Pascal and Postscript program languages to be portable and to avoid system dependent features. Other programming languages may be used as would be known to those skilled in the art, for example Fortran or C++.

If a Pascal compiler is not available, the Pascal code can be automatically converted to C using the p2c program. The p2c translator and library is freely available from David Gillespie (daveg@csvax.cs.caltech.edu). It can be obtained by anonymous ftp to csvax.caltech.edu in the pub directory.

The computer programs of the present invention may be stored on any computer-readable medium. Preferred types of computer-readable mediums include but are not limited to floppy diskettes, laser disks, tapes and cassettes.

COMPUTER PROGRAM DESCRIPTION

Figure 7:
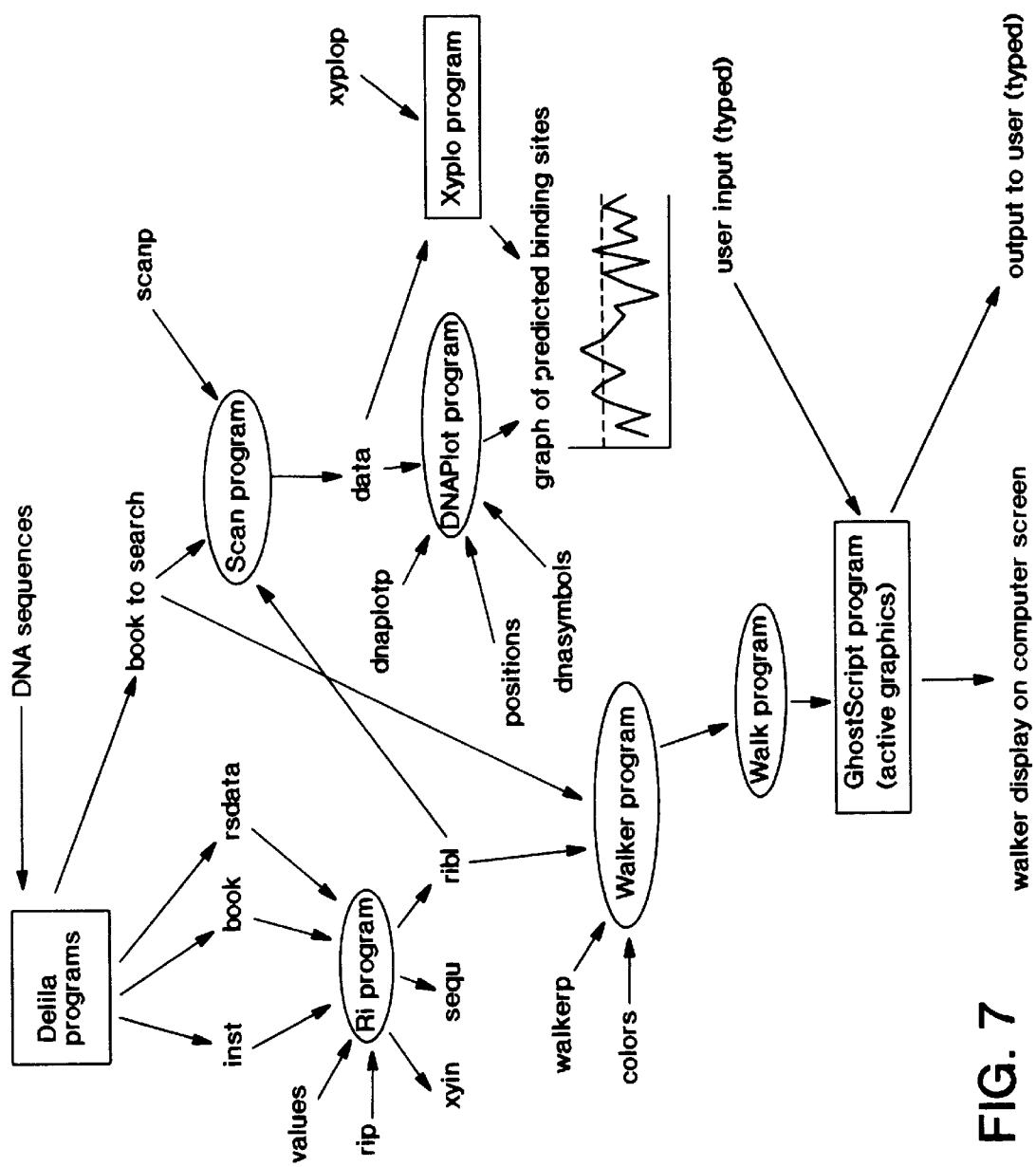

One embodiment of the present invention is a method for analyzing the binding sites of macromolecules on DNA or RNA. The way data flows through various programs is shown in FIG. 7. Rectangles surround the names of programs that have been described previously. Ellipses surround the names of programs of the present invention.

The Delila Program

The data flow begins with a set of DNA sequences to be analyzed. These sequences may be obtained from GenBank or from private sources and are called a "library". They are then analyzed by programs of the Delila system (Schneider, T. D., 1982 *Nuc. Acids Res.*, 10:3013–24; Schneider, T. D., 1984 *Nuc. Acids Res.*, 12:129–140 and in the Delila Library System: ftp://ftp.ncifcrf.gov/pub/delila/libdef ftp://ftp.ncifcrt.gov/pub/delila/delman.ps and http://www-lmmb.ncifcrf.gov/~toms/delila.html)). Four files are created. The inst (instruction) file, which can be created automatically or generated by band, defines the DNA fragments and coordinates on those fragments of the binding sites to be analyzed. This set of instructions is used by the Delila program to generate a subset of the library called a book. The book contains the sequences to be analyzed. Together the inst and book files define the binding sites. These files are used by several other programs (Encode and Rseq) to create the rsdata file, which contains the initial information analysis. The information analysis at this stage is for the average of the data set, not the individuals.

The Ri program

Analysis of the individual binding sites is accomplished with the Ri program. The program is controlled by a parameter file rip and it can be given quantitative experimental data about each binding site in the values file. The output of the Ri program is given in three files. The xyin file lists the individual information content values for every sequence in the inst and book files, and these data are joined to the data from the values file. The joined data can be plotted by the xyplo program (not shown in the diagram). The raw sequences of the sites are listed in the sequ file. The ribl file contains the individual information weight matrix. This is defined in equation (1) as:

$$R_i(b,l) = 2(-\log_2 f(b,l) + e(n(l))) \text{ (bits per base)} \quad (1)$$

where f(b,l) is the frequency of each base b at position l in the aligned binding site sequences and e(n(l)) is a sample size correction factor for the n sequences used to create f(b,l) at position l (Schneider, et al., 1986 *J. Mol. Biol.*, 188:415–431; Penotti, 1990 *J. Mol. Biol.*, 213:37–52). The mathematical reasoning behind this equation is given below. $R_i(b,l)$ defines how every "finger" (l) of a protein should react to every possible base (b).

The Scan program

The ribl file is used by the Scan program to search any sequences the user is interested in (book to search). The program is controlled by parameters in the scanp file, and the output is given as a data table. The table contains a list of coordinates evaluated and the evaluation of each position (in bits of information), the number of standard deviations of each evaluation from the mean $R_{sequence}$ (Z score) and one-tailed probability of that Z score.

The Xyplo and DNAPlot programs

The data table from Scan may be used as the input to many programs (not shown) or it may be graphed either by the general purpose Xyplo program (which is controlled with parameters in the xyplop file) or by the specific purpose DNAPlot program which is controlled with parameters in the dnaplotp file, a positions file that can define the ends of the graph and a dnasymbols file that defines symbols to put on the graph. The advantage of DNAPlot over Xyplo is that DNAPlot can handle many pages of graphs for many sequences, but Xyplo can only make one page and use one sequence. An example of graphs generated by Xyplo and DNAPlot is given in FIG. 8. An $R_i(b,l)$ model for the *E. coli* Fis protein was created as described above. The graph on the top of the figure was created by Xyplo. It shows the scan of the Fis model across the promoter region for the fis gene itself. At each step of the scan, the responses by each part of the weight matrix are added together to get the total response. This response is plotted against the position in the sequence. The plus symbols (+) indicate previously known Fis sites and the arrow shows the start and direction of transcription. The graph shows that there are several other Fis sites in this region. The lower graph, created by DNAPlot shows the scan for the entire fis gene, demonstrating that the newly predicted Fis sites cluster at the promoter.

The Walker program

The Walker program collects data from several sources. The individual information weight matrix model is read from the ribl file; colors to be used in the display are read from the colors file; parameters that define the initial display are read from the walkerp file; and the sequences to study are given in the book to search. The program manipulates these data and creates a PostScript graphics program called a walk. The walk can be shown on any PostScript device, but by using the public-domain GhostScript program it can be displayed on almost any computer system. The Walk program is carefully created so that a user can type commands (user input) in a window and receive results and help in the same window (output to user). At the same time, GhostScript displays the graphics in a second window.

Figure 9:
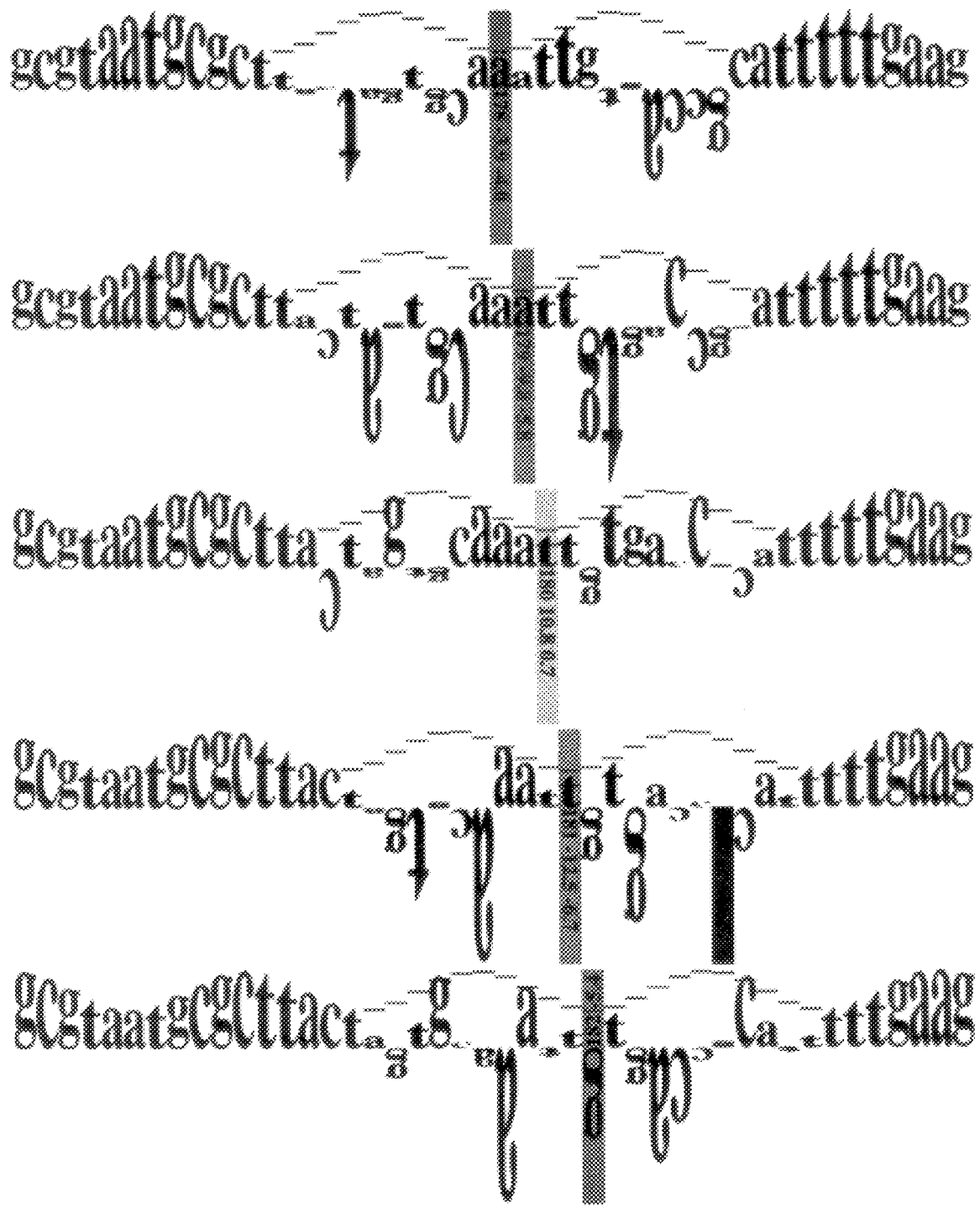

An example of this display is given in FIG. 9. There are 5 horizontal rows of characters. Each row represents the placement of the individual information weight matrix for the Fis protein at a particular position on the *S. typhimurium* hin sequence. The DNA sequence is the same in each row. As one proceeds down the figure, the walker is stepped one position to the right on the DNA sequence so that the figure shows the frames of a "movie". Normally this would be displayed on a computer screen and only one row would be needed since the user completely controls the display in real-time. The heights of the grey letters indicate the orientation of the DNA helix, with the high points of the sine wave representing the major groove facing the protein. Horizontal grey bars are used in the region of the Walker. Note that the DNA "turns" as the movie proceeds. A pink or light green vertical bar represents the 0 coordinate of the information weight matrix. This characterizes the position of the Fis protein on the DNA. The bar is a scale, with its lowest point at −4 bits and its upper point at +2 bits. The Walker itself is shown by colored letters. Letters that extend upwards represent energetically favorable DNA contacts, while those which are upside down and extend downward represent unfavorable contacts. If a contact is more unfavorable than −4 bits, the letter is surrounded by a purple box (an example is shown in the 4throw). If a contact has never been observed at a position in the weight matrix, it is given a black box.

Three numbers are reported in the vertical bar shown in FIG. 9. The first number is the position of the bar on the sequence. The second number is the $R_i$ evaluation of the entire binding site, given in bits. This is obtained by adding together the heights of all the letters in the Walker. The third number is the Z score for this evaluation. A Z score is calculated by subtracting the mean and dividing by the standard deviation of the individual information distribution. If the Z score is below a given threshold (that can be set by the user) and the $R_i$ evaluation is positive (or greater than some value set by the user) then the bar is green to indicate that a binding site has been located. Otherwise the bar is pink. Position 180 is a known Fis binding site.

Figure 10:
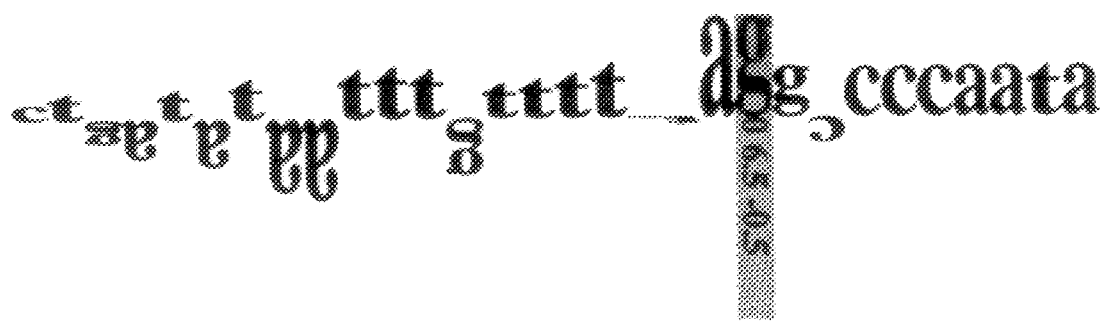
Figure 10:
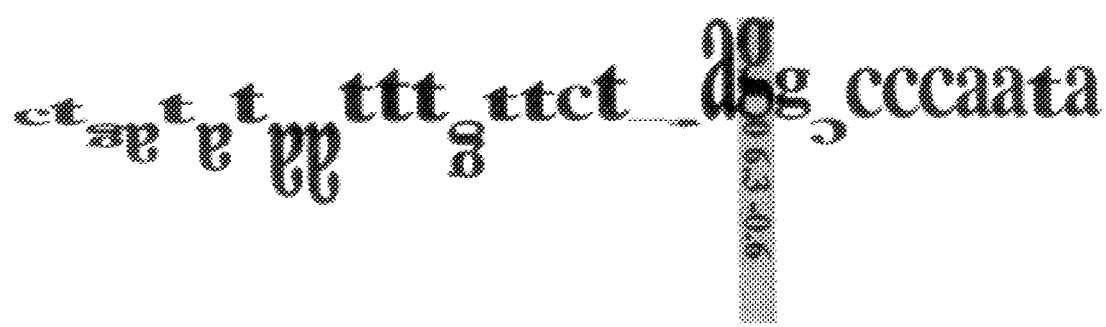
Figure 10:

FIG. 10 demonstrates the use of the mutation feature of the Walker program to distinguish mutations from polymorphic changes (see also, Example 1). The weight matrix in this case was created from human splice acceptor sites. (See Stephens & Schneider. 1992. *J. Mol. Biol.*, 228:1124–1136, for the details regarding how this data set was constructed). Three rows of sequence are given, but unlike the previous figure, these represent modifications of one sequence. The top sequence in FIG. 10 is the human splice acceptor site given in Fishel et al. (1993. Cell, 75:1027–1038). This is the DNA found in normal colon tissue. The middle sequence is an altered sequence found in a sporadic colorectal tumor. Fishel et al. (1993. Cell, 75:1027–1038) proposed that this T→C change at position −5 was the cause of the cancer, but inspection of the Walker immediately shows that this change is not significant since the $R_i$ only changes from 6.5 to 6.3 bits and the absolute value of the Z score is still below 1. Thus this change represents a polymorphism and not a mutation. The true mutation lies elsewhere or this mutation represents a change in the binding site for some molecule other than the spliceosome. The bottom row shows the effect of altering the sequence in the top row: when position −1 is changed to a cytosine ("C"), the $R_i$ becomes negative and the Z score approaches significance (p<0.02). Such an alteration would probably lead to colon cancer.

OVERVIEW OF PROGRAM ACTIONS

The specific actions of each of the programs are set forth in the Appendices A, C, E, G, and H. However, a brief overview of the activity flow is helpful for further understanding of the program's operation.

"Initialize"—gather information on a number of experimentally demonstrated example binding sites.

Align the binding sites to maximize their information content:
  chose an alignment of the sequences relative to a "zero" base. (Delila programs dbbk.p, catal.p, delila.p, alist.p).
  Tabulate the number of bases b at each position l, n(b,l). (Delila programs encode.p, rseq.p)
  sum the n(b,l) to find the number of bases at each position, n(l). (Delila program rseq.p)
  calculate from n(l) the small sampling correction factor e(n(l)) for each position. (Delila program rseq.p)
  calculate a frequency matrix, f(b,l) from n(b,l)/n(l). (Delila program rseq.p)
  calculate Rsequence from f(b,l) and e(n(l)). (Delila program rseq.p)
  repeat the previous steps with different alignments until Rsequence is maximized. (Delila program malign.p)
  generate the sequence logo. (Delila programs dalvec.p, makelogo.p)
  Generate the Ri(b,l) matrix from f(b,l) and e(n(l)) (program ri.p, Appendix A; file rip, Appendix B).
  if f(b,l)>0, use Ri(b,l)=2−(−log 2(f(b,l))+e(n(l))).
  if f(b,l)=0, use Ri(b,l)=2−(−log 2(F(l))+e(n(l))).
    where F(l)=1/(t+n(l)), with t>=0. Larger values of t are more stringent. Alternatively, the program can record "negative infinity" for the Ri(b,l) rather than stopping execution.
  Evaluation of a sequence:
  (program ri.p, Appendix A; file rip, Appendix B;
  program scan.p, Appendix C; file scanp, Appendix D;
  program walker.p, Appendix H; file walkerp, Appendix I;
  file walk, Appendix J)
    Obtain a sequence to be analyzed. (Delila programs: dbbk.p, catal.p, delila.p).
    set the zero of the Ri(b,l) matrix at a position on the sequence.
    Select the values of Ri(b,l) that correspond to the sequence.
    Add these values together to obtain the individual information, Ri.

Evaluation of mean:
  The mean is Rsequence determined above. (This is more reliable than the average of the Ri values unless there are no gaps in the sequence data.) (Delila program rseq.p)
Evaluation of Standard Deviation: (program ri.p, Appendix A; file rip, Appendix B)
  Set the Ri(b,l) matrix at the position of each sequence used to generate the n(b,l).
  Evaluate each sequence by the global Ri(b,l) matrix.
  Collect the distribution in a file and calculate the standard deviation for the distribution. Scan: (program scan.p, Appendix C; file scanp, Appendix D)
  Step base by base across a sequence to be analyzed. (program scan.p, Appendix C, procedure scansequence).
  For a particular step, evaluate the Ri at that position (program scan.p, Appendix C, procedure scansequence).
  Determine the Z score for the Ri by subtracting the mean and dividing by the standard deviation (program scan.p, Appendix C, procedure writeitout).
  Determine the probability of this or a higher Z score (program scan.p, Appendix C, procedure simpson).
  Record the coordinate, Ri evaluation, Z and probabilities in a data file (program scan.p, Appendix C, procedure writeitout).
  Plot the data file information in a graph. (programs xyplo.p or dnaplot.p, Appendix E; file dnaplotp, Appendix F; file dnasymbols, Appendix G)
Walker: (program walker.p, Appendix H; file walkerp, Appendix I; file walk, Appendix J)
  collect together information:
    the sequence to analyze (program walker.p, Appendix H procedure make sequence array).
    the Ri(b,l) matrix (program walker.p, Appendix H procedure makeribl).
    the color scheme to use (program walker.p, Appendix H procedure varchardefs).
    the overall form of the walker display (program walker.p, Appendix H procedure read parameters).
    specific instructions for generation of the display (program walker.p, Appendix H procedure themain).
    generate the walk graphic program described below (program walker.p, Appendix H procedure themain; file walk, Appendix J)
Running the walk program: (file walk, Appendix J) Note: commands in the walk program are implemented directly as GhostScript procedures. For example, "goto" is a procedure that the user knows about from the documentation, while "movesequence" is a procedure that the user generally does not know about.
  Draw the sequence using grey in one or more lines on a graphics device. The vertical scale is in bits running from some defined lower bound in bits to zero and to 2 bits. For DNA, the letters of sequence vary in height according to a cosine wave between 1 and 2 bits high with a periodicity of 10.6 letters to indicate the helical twist of the DNA. (file walk, Appendix J, procedure movesequence).
  Draw the walker either inside the sequence or next to it. When the walker is inside the DNA cosine wave is given by dashes. (file walk, Appendix J, procedure movesequence)

Evaluate each base of the sequence within the range of the walker by the Ri(b,l) matrix. These letters are colored, usually by the scheme A=green, C=blue, G=orange, T=red. When the walker is next to the sequence, the letters being evaluated are colored blue. (file walk, Appendix J, procedures evaluate, sumribl)

Draw the letters of the sequence upwards for positive Ri(b,l) evaluations. These are proportional to the evaluation and are between 0 and 2 bits (file walk, Appendix J, procedure anycolorletter)

Draw the letters for the sequence downwards for negative Ri(b,l) evaluations. These letters are drawn upside down, and range from 0 to the lower bound. Letters that extend below the lower bound are placed on a purple background. Letters for positions that have negative infinity for their evaluation are placed on a black background (file walk, Appendix J, procedure anycolorletter)

The aligning base is printed on top of a colored bar that extends from the lower to the upper bound. The bar is light green if the
program finds a binding site by the current criteria. The bar is light red (pink) if not.

The use of lighter colors is important because otherwise the letter on top of the bar would sometimes be invisible (file walk, Appendix J, procedure anycolorletter).

In the space of the colored bar opposite to the base (up or down) the coordinate, the Ri evaluation, the Z score and conceivably the probability are printed. (Evaluation of probability is currently too expensive.) (file walk, Appendix J, procedure display data)

Once the basic drawing has been made, relinquish control of the graph to the user who may then type commands. At every command the walker is redrawn as appropriate. At each step the evaluation is given not only on the walker itself but also in the window that the user uses to control the walker (file walk, Appendix J.

After all procedures have been read by the PostScript interpreter, the display is generated once by a call to toggleprinting. The user may call any procedure after that point.)

The user may move the walker or the sequence to the left or to the right by one base, by direct jumps or by a series of steps as in a movie (file walk, Appendix J, procedures h, l, jump, goto)

The user may move the walker complete lines up and down (file walk, Appendix J, procedures k, j)

The user may have the walker stay still while the sequence moves instead. (file walk, Appendix J, procedure w)

The user may move the walker in and out of the sequence. (file walk, Appendix J, procedures in, out)

The user may restructure the number of lines and bases per line on the page, the position of the entire graph on the page and
the size of the entire graph on the page. (file walk, Appendix J, procedures lines, bases, left, right, up, down, height, width)

The user may turn on and off the wave that represents DNA twist. (file walk, Appendix J, procedures waveon, waveoff)

The user may redefine the criteria for locating a binding site. (file walk, Appendix J, procedures setri, setz)

The user may instruct the program to run a search for the next or previous binding site. (file walk, Appendix J, procedures f, b)

The user may reverse the direction of the weight matrix or sequence (not yet but soon-to-be implemented).

The user may change the sequence either at an absolute coordinate or at a coordinate relative to the current position
of the walker Ri(b,l) matrix, and immediately see the effect.
(file walk, Appendix J, procedures a, c, g, t, A, C, G, T)

The user may define delays in the display (in seconds) so that
the individual steps of the walker motion can be observed on a
fast computer.
(file walk, Appendix J, procedures setwait, isasecond)

The user may turn on and off printing and erasing of the display so that several displays can be shown on one page. (file walk, Appendix J, procedures toggleprinting, tp, toggleerase, te)

User commands may be stored in the file that defines the initial graph configuration so that figures can be generated on a printer. (file walkerp, Appendix I)

The user may ask for help, refresh the current display, restart
GhostScript on the current walk file and quit the program.
(file walk, Appendix J, procedures help, ?, r, R, q, quit)

Evaluating the Effect of sequence changes
By scan:
(program scan.p, Appendix C; file scanp, Appendix D; xyplo.p or dnaplot.p, Appendix E;
file dnaplotp, Appendix F; file dnasymbols, Appendix G)
Scan the sequence and obtain the evaluation graph.
Modify the sequence.
Re-scan the sequence and generate another graph for the changes.
Compare the graphs to determine the effects of the changes.

By walker:
Set up the walker on the sequence of interest. (program walker.p, Appendix H; file walkerp, Appendix I; file walk, Appendix J)
Move the walker to the binding site. (file walk, Appendix J, procedures w, h, j, k, l, jump, goto)
Instruct the program to make the changes that generate the mutation. (file walk, Appendix J, procedures a, c, g, t, A, C, G, T)
Observe the change in the walker at the point of the mutation and observe the change in the evaluations that the mutations engender.

ANALYSIS

For mutation/polymorphism analysis, there are two preferred methods of analysis. With either method, a database is created containing the normal and the mutant sequence, each as a component of the same book (or separate books). In one preferred method, one may use Delila instructions to select sequences around the site of interest. The size of the region selected must be at least the size of the site defined by the $R_i(b,l)$ with the $R_i$ program but is generally larger. One can then run the Scan program on both sequences, and then may plot the normal (WT) and the mutant (MT) sites with the Dnaplot program. This will display the changes in information, including the appearance of novel binding sites or cryptic binding sites (which can be particularly important in splicing for example). This approach may be more intuitive than Walker for identification of novel or cryptic sites.

Alternatively, one can make mutations in a Postscript capable software program, such as Ghostscript, using the Walk file directly. This has the advantage of being faster particularly when there are several mutations at the same site that can be studied. A disadvantage is that it is not simple to examine mutations that result from deletions, insertions, or inversions with Walker unless a user changes many bases in the starting sequence or evaluates a book with this sequence in it. User-error is more likely when multiple sequence changes are introduced.

Figure 17A:
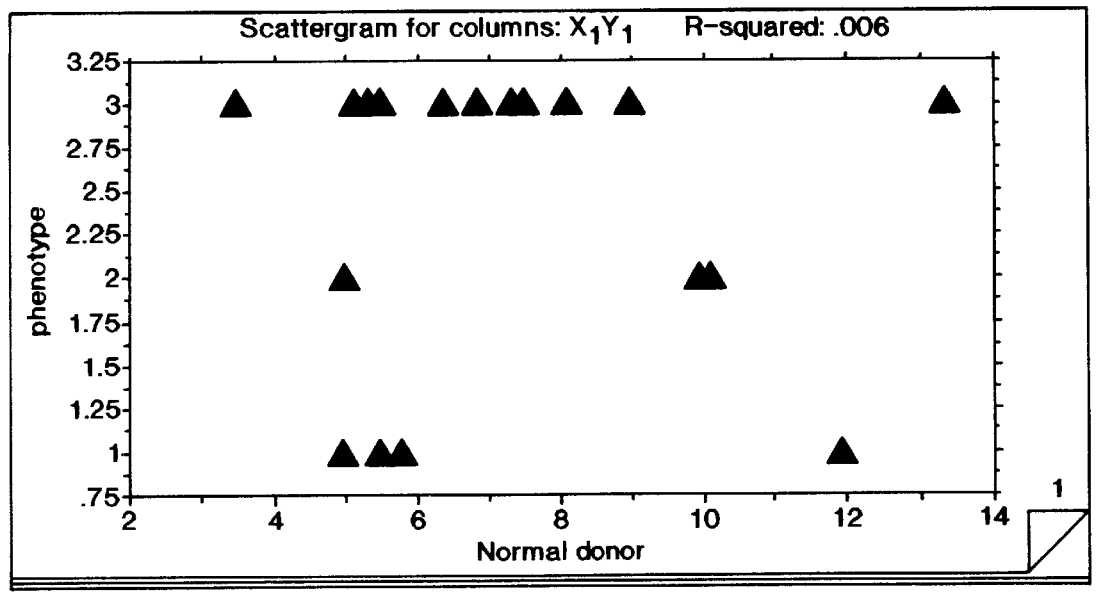
Figure 17B:
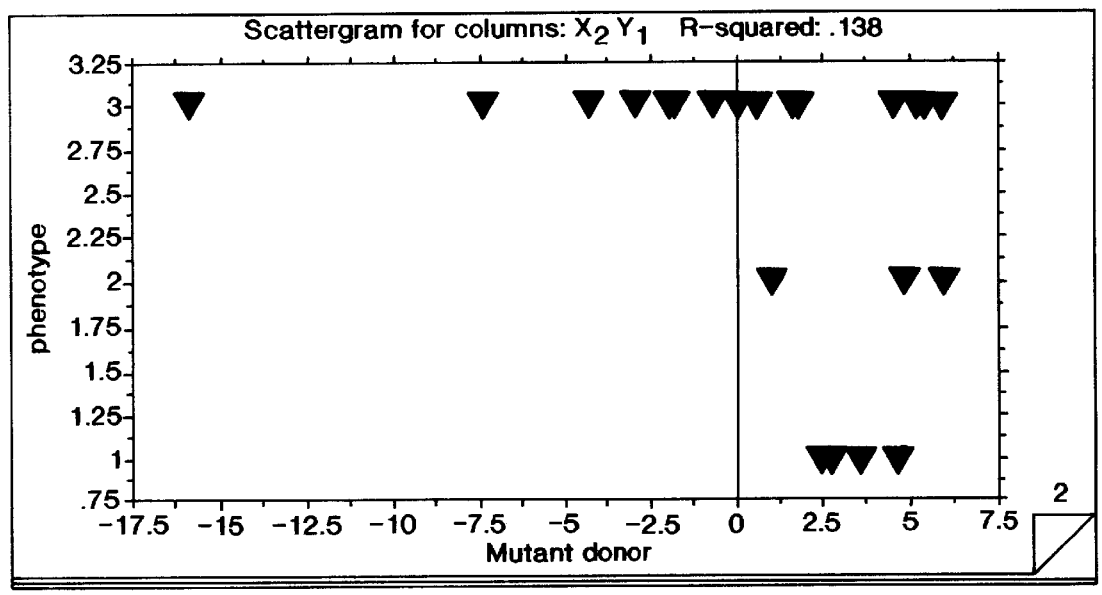

Polymorphic substitutions in splice recognition sites would be expected to have little or no effect on mRNA splicing, whereas true mutations reduce splicing efficiency or produce aberrant messages. Ri analysis can be used to distinguish between polymorphisms and mutations. The mean information content of 26 mutant donor splice junctions responsible for a wide variety of genetic disorders is significantly lower than the cognate wild type junctions (1.9±2.2 bits versus 7.0±2.4 bits; p=0.0001 by 2-tailed Student's t test). Similarly, the mean Ri for 10 mutant acceptor sites is also significantly lower (2.8±2.3 bits versus 9.4±3.4 bits; p=0.0001). More severe mutations involving either donor or acceptor sites tend towards lower Ri values, whereas those with a mild or moderate phenotype are likely to have information contents greater than zero, but these are still significantly less than normal sites (see FIG. 17) Mutations at normal sites with high Ri values (>12 bits) may produce non-functional sites with borderline Ri values (between 4 and 5). This observation supports the notion that while there is a minimum quantity of information needed to recognize a splice site, some sites have evolved specific requirements for nominal splicing that depend on the genic context in which they reside. For example, selection for particularly strong recognizer at the IVS2 acceptor in the human beta globin gene has been imposed by the presence of a potential cryptic acceptor sequence in the intron upstream of the normal site. A mutation at a strong splice recognition site in one context may splice appropriately in another context. Conversely, even subtle mutations at a weak splice site could make it exquisitely susceptible to loss of function regardless of genic context. In accordance with this hypothesis, it is possible to predict which genes will be affected by mutations in splice sites. Clinically, this may be useful in developing a strategy for efficient screening of various classes of mutations in particular genes, since it may permit diagnostic laboratories to determine which inherited conditions should be screened for substitutions in splice sites prior to examining other types of mutations.

Of the 49 nucleotide substitutions examined in this study, 5 polymorphic changes in splice acceptor sites were identified that were presumed in the original reports to be mutations that alter splice efficiency or the sequence of the mature mRNA. These included nucleotide changes in the familial non-polyposis colon cancer gene MSH2, the p53 gene which has been associated with some instances of bladder carcinoma, the gene encoding ornithine-transcarbamylase, and the gene encoding steroid 21-hydroxylase causing adrenal hyperplasia. To show that the change in Ri in these instances was not significantly different form the wild type sequence, splicing efficiency was categorized as either normal or severely impaired and analysis of variance on Ri was performed. Splicing was assumed to be normal if either mRNA studies demonstrated nominal splicing or levels of correct, mature message or protein were observed or the true mutation was demonstrated elsewhere in this or another gene. The Ri values for individuals with normal splicing were significantly different from those with a severe splicing defect (F test=8.85, p=0.01). This indicates that the change in Ri in the normal individuals is inconsequential, and therefore, these substitutions are genetic polymorphisms.

Figure 18:
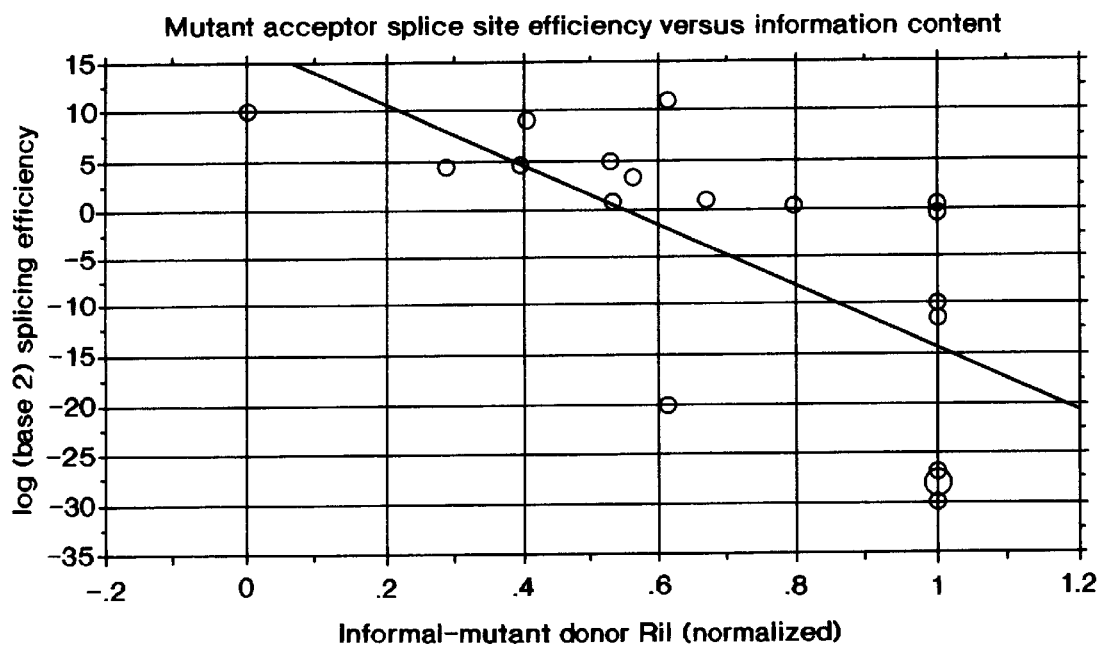
Figure 19:
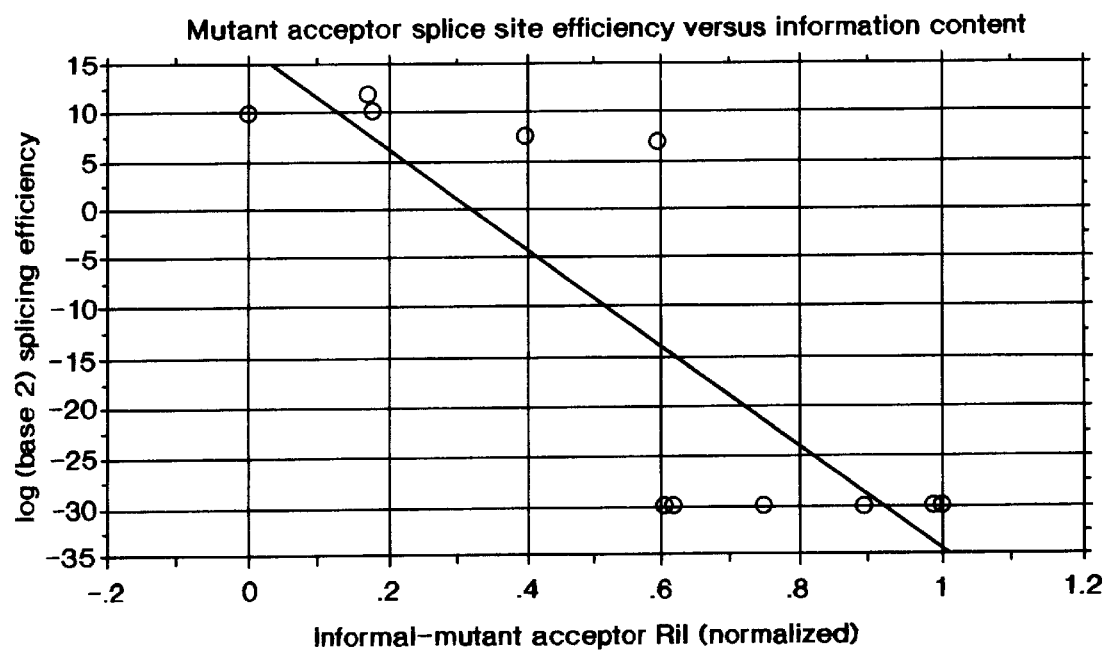
FIG. 19 is a graph showing the relationship between mutant $R_i$ and splicing efficiency for mutant acceptor splice sites. (See FIG. 18 above for details.)

Measuring the Ri of mutant splice sites may permit prediction of the severity of the splicing defect. According to level 2 information theory (Schneider, 1994 *Nanotechnology* 5(1):1–18), the Gibbs' free energy between bound and unbound recognisers is related to information at the binding site. We therefore can compare the Gibbs energy to the $R_i$ values. We substitute the logarithm of the splicing efficiency for the energy. This is plotted for those donor and acceptor sites where quantitative studies of mRNA splicing were available (FIG. 18 and 19). The relationship is approximately linear (Correlation coefficients: for 14 donor mutations, R squared=0.60; for 9 acceptor mutations, R squared=0.40). These results provide a consistent, quantifiable approach to measuring splice efficiency.

The following examples illustrate various aspects of the present invention and in no way are intended to limit the scope thereof. All books, articles, and patents referenced herein are incorporated herein, in toto, by reference. Other similar embodiments will be clear to the skilled artisan and are encompassed within the spirit and purview of the present invention.

EXAMPLE 1

ANALYZING A BINDING SITE.

Figure 11:
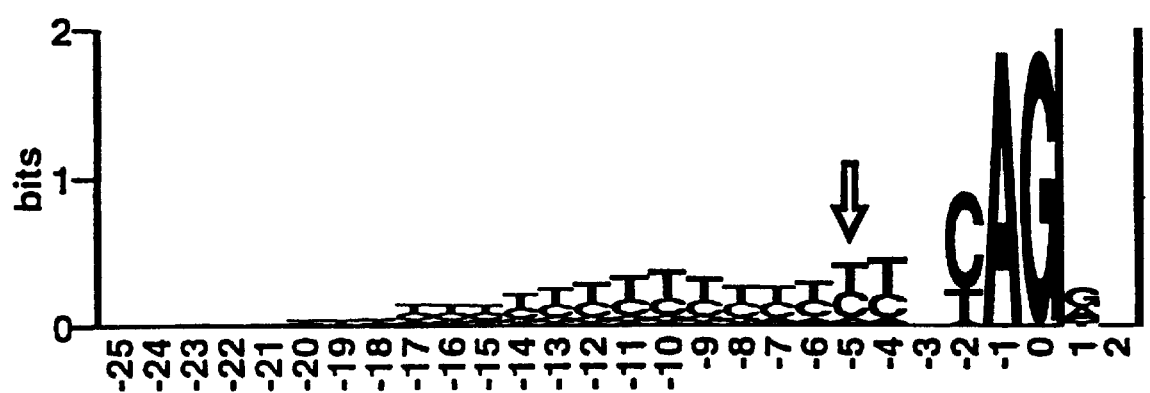

As an example of this method, a T→C transition found at position −5 of the intervening sequence of the hMSH2 gene from multiple, independent sporadic colon carcinomas and patients with Lynch syndrome (Fishel, et al., 1993. *Cell* 75:1027–1038) has been analyzed by the method of the present invention. Other mutations in the coding domain of this gene cause hereditary nonpolyposis colon cancer by disrupting the repair of somatic lesions that accumulate in genomic DNA (Leach et al., 1993. *Cell* 75:1215–1225). Although the substitution at position −5 of the splice site was proposed to cause aberrant splicing of hMSH2 mRNA (Fishel et al., 1993. *Cell* 75:1027–1038), our analysis using the method of the present invention indicated that such alteration was probably not deleterious to maturation of the hMSH2 message. First, upon inspection of the sequence logo, there is a nearly equal probability of observing C or T at position −5 in this set of splice acceptor sequences (FIG. 11; this corresponds to position −6 in Fishel et al. (1993. *Cell* 75:1027–1038)). Second, cytosine at this position does not impede the normal splicing of 691 of 1712 acceptor sites derived from numerous human genes (Stephens & Schneider, 1992. *J. Mol. Biol.* 228:1124–1136). Third, we find that the common allele contains 6.5 bits of information, and the substitution weakens it to 6.3 bits. The average of the distribution of sites is 9.3 bits, and the distribution has a standard deviation of 4.6 bits. Non-functional sites are predicted to be below zero on this scale. Indeed, 2 of 20 unrelated normal individuals displayed this variant, consistent with the suggestion that this change represents a polymorphism (Leach et al., 1993. *Cell* 75:1215–1225).

This change is unlikely to affect the recognition of other nucleotides in the same acceptor site, as mutational analysis of the polypyrimidine tract in which it resides suggests that these nucleotides are independently recognized by the spliceosome (Stephens & Schneider, 1992. *J. Mol. Biol.* 228:1124–1136; Roscigno et al., 1993. *J. Biol Chem.* 268:11222–11229). One hundred ninety six normal human sites were found having the same or lower information content as the hMSH2 acceptor containing this substitution. 51 of these contain cytosine at position −5. Either the true mutation lies elsewhere, in this or another gene (Leach et al., 1993. *Cell* 75:1215–1225; Bronner et al., 1994. *Nature*

362:258–261; Papadopoulos et al., 1994. *Science* 263:1625–1629), or the change indicates that this base is involved in a genetic control mechanism other than mRNA splicing (Amrein et al., 1994. *Cell* 76:735–746).

To summarize, inference of genetic mutations in splice junction recognition sites based on consensus sequences may be inaccurate, whereas information analysis of sequence variants can distinguish between polymorphic nucleotides and mutant sites. True mutations are expected to reside in positions where the sequence conservation in bits significantly exceeds the background variation and where the base frequency decreases significantly.

A similar approach may be applied to the analysis of other conserved transcriptional and translational signals or protein motifs in human sequences.

EXAMPLE 2

Figure 21:
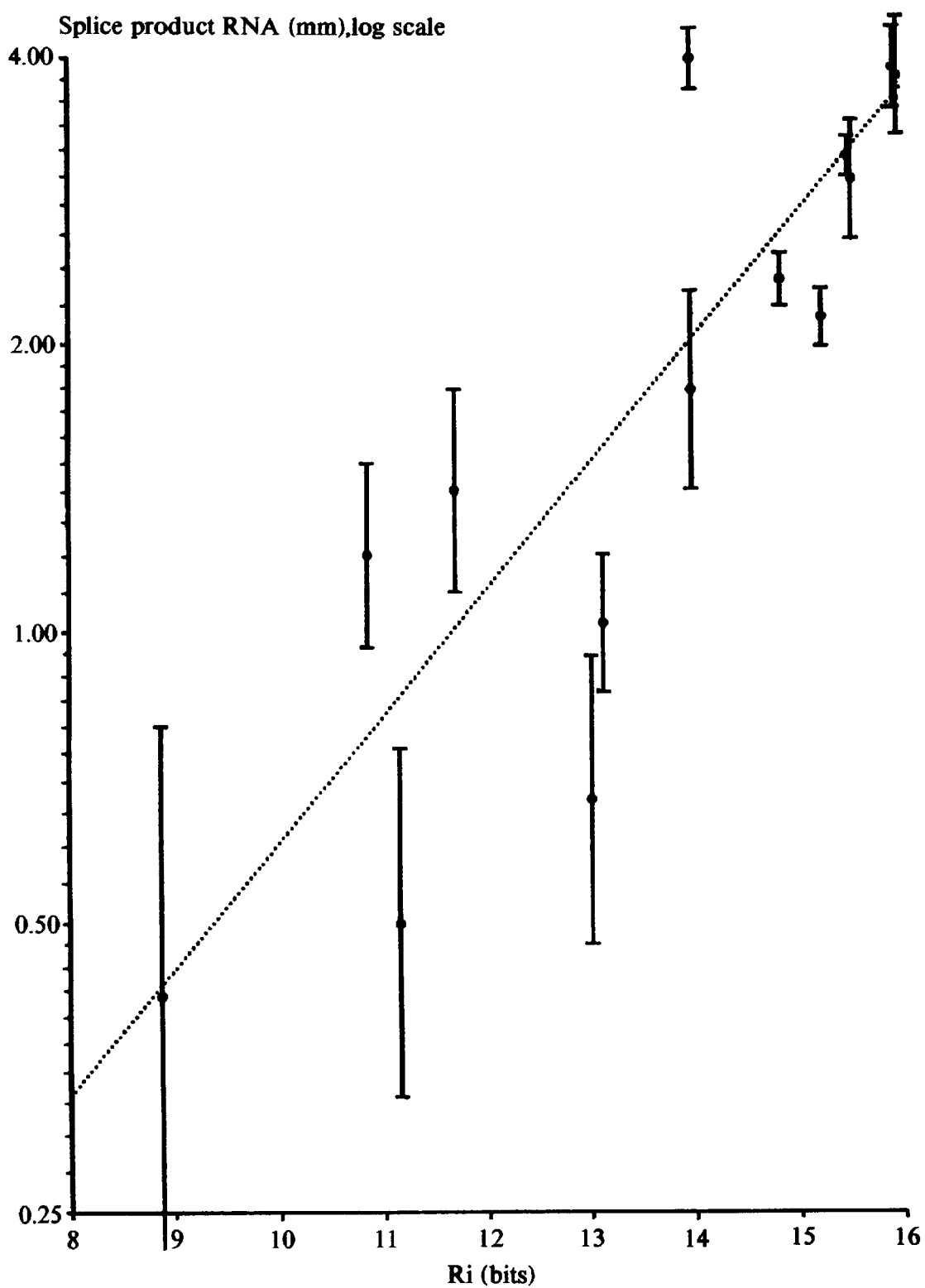
FIG. 21 is a graph showing measured splice product for variations in the polypyrimidine tract of the adenovirus 2 intron of the major late promoter Leader 1 and Leader 2 splicing unit versus individual information $R_i$ of the same sequences.

Roscigno et al. (1993 *J. Biol. Chem.*, 268:11222–11229) determined the effect of making changes in the polypyrimidine tract of adenovirus 2 intron of the major late promoter Leader 1 and Leader 2 splicing unit (GenBank accession J01917 coordinate 7100, Adenovirus type 2 DNA). They mutated this site and measured the splice product RNA divided by the wild-type product produced. These data and their standard deviations were measured from their graphs (See Roscigno FIGS. 3 and 4) in millimeters. The logarithm of these values were plotted against the predicted $R_i$ values (FIG. 21). One case of zero splicing was removed because the logarithm cannot be taken, and because small amounts of splicing may have occurred but were not reported. The correlation coefficient is 0.81. This case demonstrates that the $R_i$ analysis can predict the strength of a splice site within the experimental error.

EXAMPLE 3

This example demonstrates the use of the present invention as a tool for identifying binding sites and manipulating the affinity of a binding site by specific changes within positions of the sequence.

In this example, Fis binding sites are analyzed. Fis is a bacterial protein which functions by binding to specific binding sequences on DNA and bending DNA in sitespecific recombination systems. The resulting information content model is used to locate previously unidentified sites adjacent to known ones. DNA mobility shift experiments were then performed to determine if the predicted sites are bound by Fis in vitro.

Figure 8A:
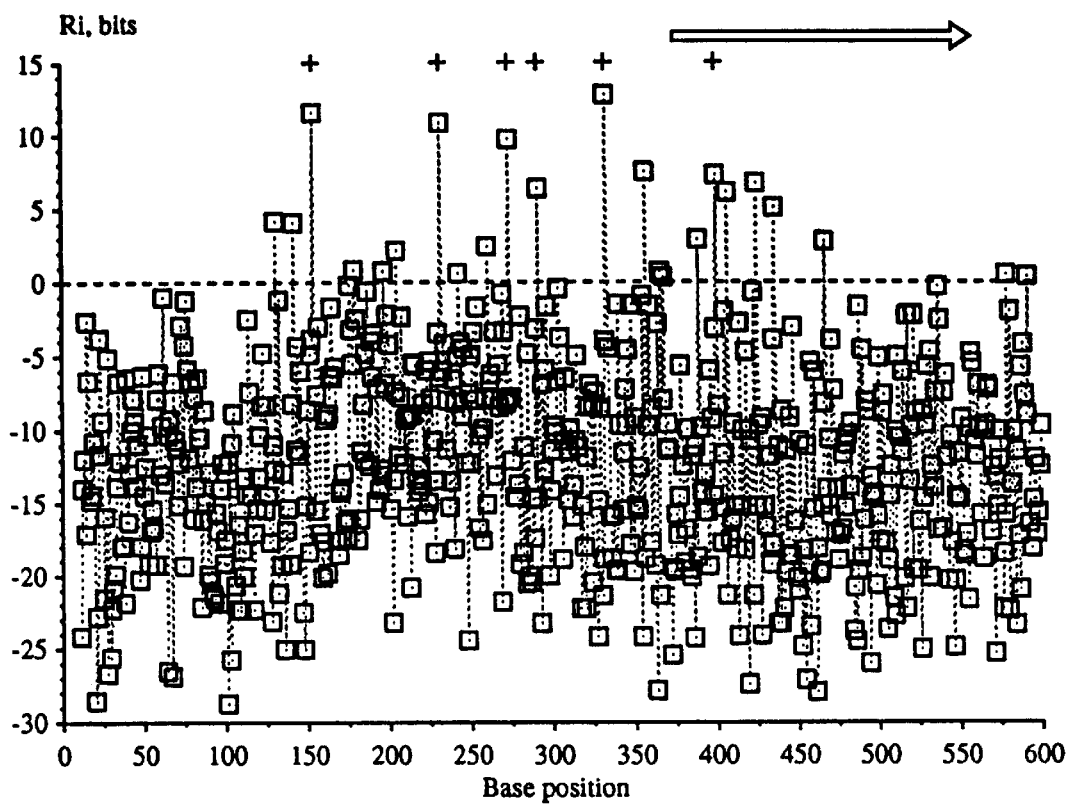
Figure 8B:
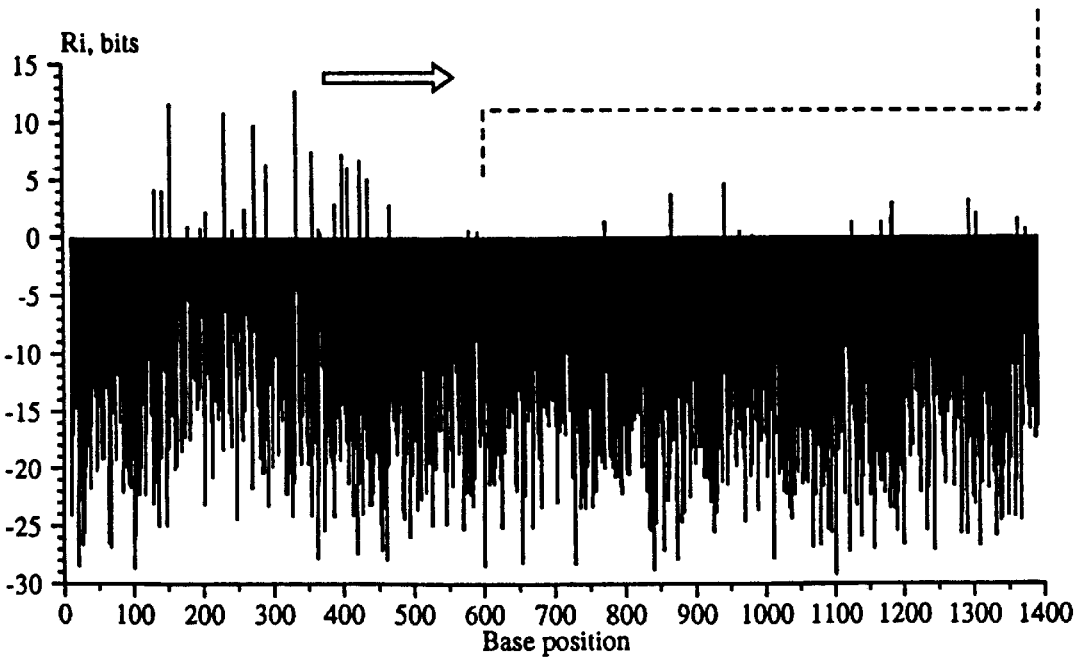

Searching sequences with the Fis individual information matrix model. The programs Scan, Xyplo and DNAplot were used to study Fis binding site on the fis promoter. At the transcription initiation site of the fis promoter, there are 6 strong Fis sites (Ball et al., 1992 *J. Bact.*, 17: 8043–8056; Ninnemann et al., 1992 *EMBO J.* 11: 1075–1083). The Scan results show up to 13 additional sites in the immediate region of the promoter, but few elsewhere on the gene (FIG. 8). Presumably these correspond to the weaker sites noted by Ball et al. (1992 *J. Bact.*, 174: 8043–8056).

Figures 12A, 12B:
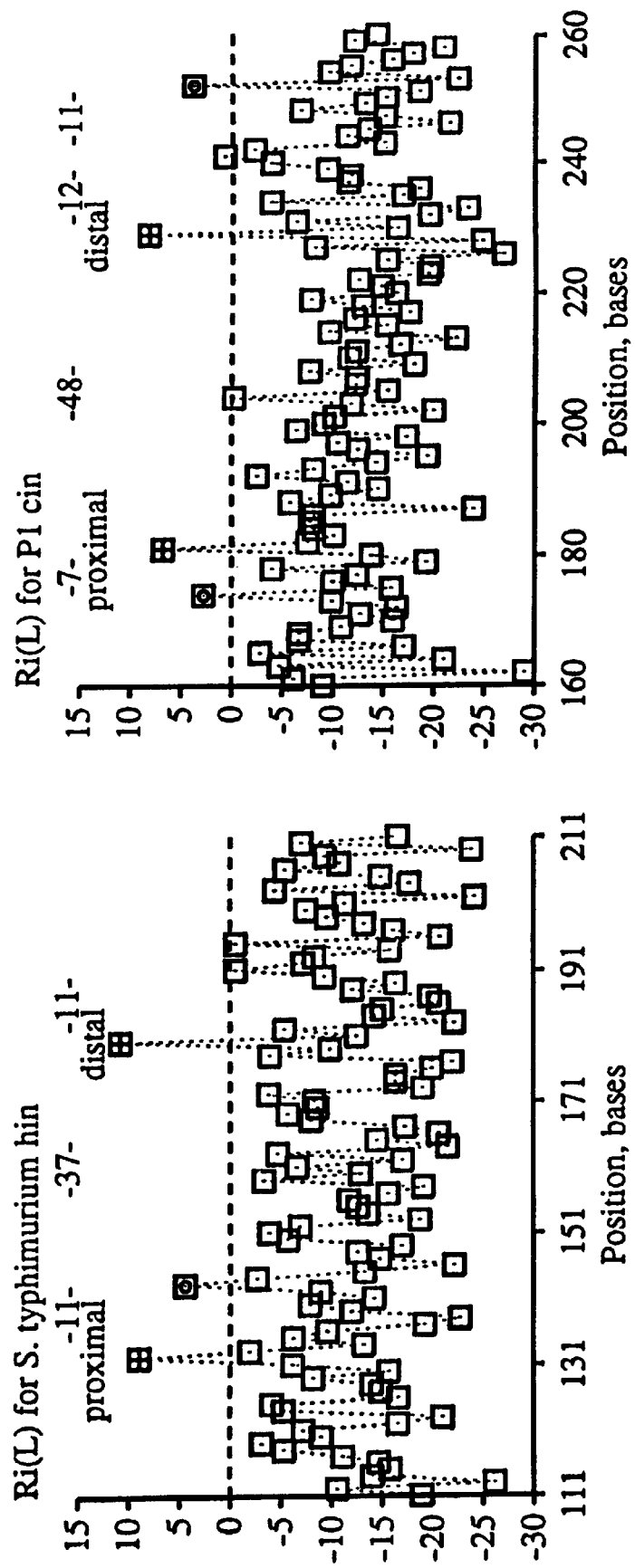
Figures 12C, 12D:
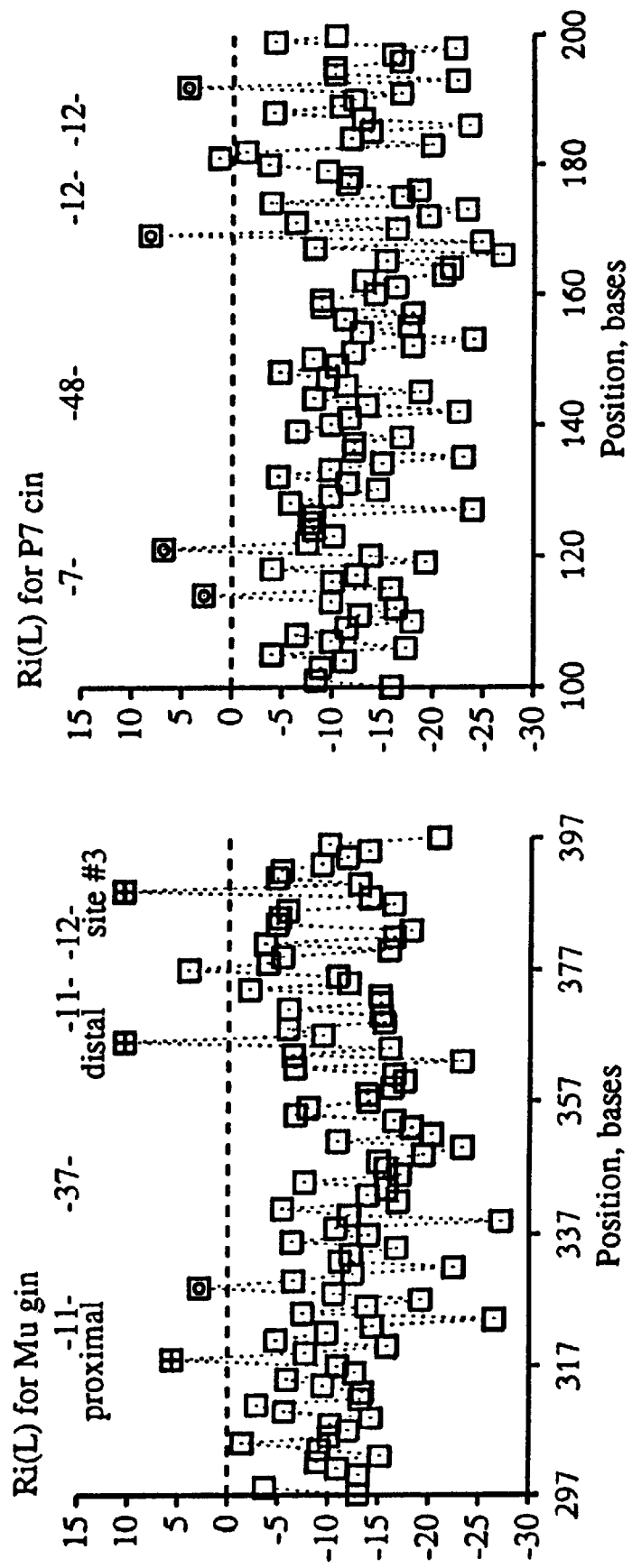
Figures 12E, 12F:
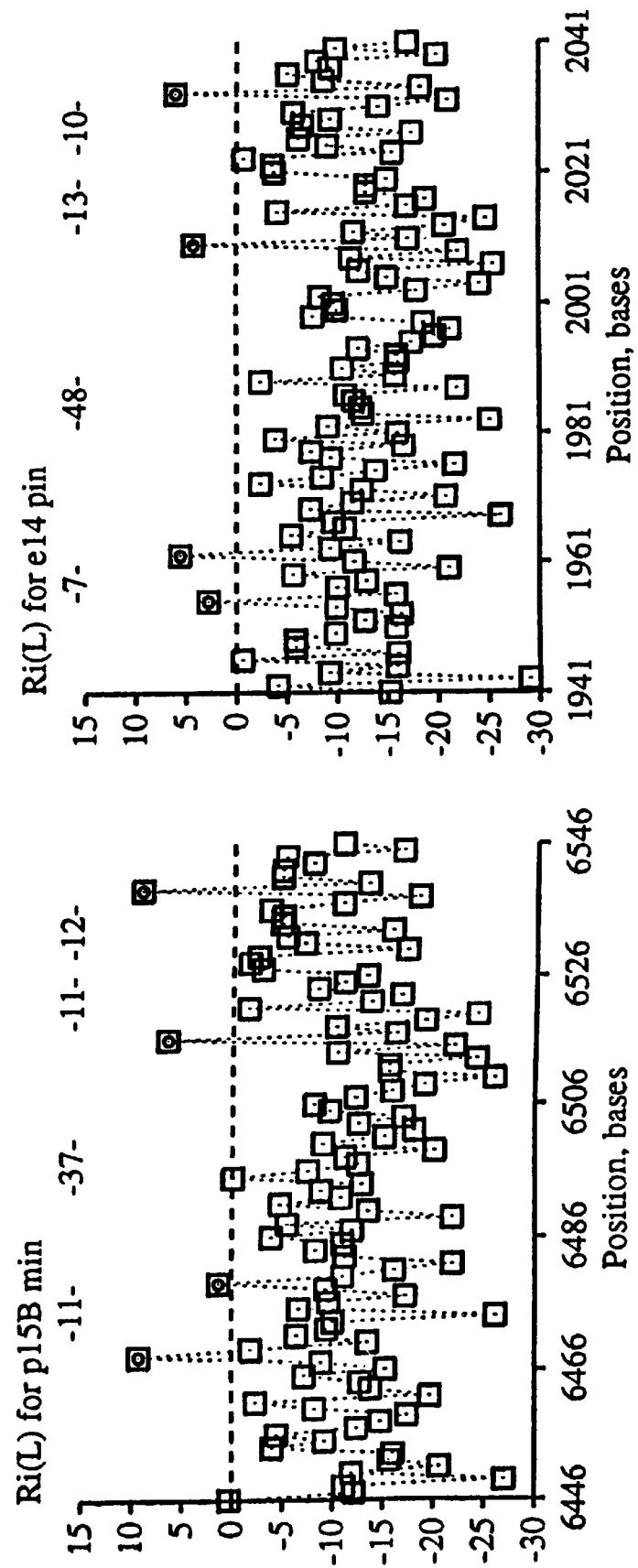

In the bacteriophage P1 cin, bacteriophage P7 cin, and *E. coli* e14 pin enhancers, a potential overlapping site occurs 7 base pairs (~½ helical turn) to the left of the previously identified proximal site. (FIG. 12, right three graphs). Since this potential site is outside the region between the proximal and distal sites, we named it the "external" site. When a new site is on the right, it is 11 bases from the previously identified site, while a new site on the left is 7 bases from the previously identified site. We do not know if this correlation is coincidental. We also observed that a pattern corresponding to site III in gin (Koch et al., 1991 *Nuc. Acids. Res.*, 19:5915–5922) appears in all other enhancers scanned except hin that in three cases a weaker potential site falls exactly between the distal site and that site with spacings of 10 to 13 base pairs (FIG. 12). Because the nomenclature for binding sites is already obscure, we decided not to name these sites.

Two Fis sites have been identified in the *E. coli* oriC locus at coordinates 202 (8.2 bits) and 283 (5.7 bits) (Filutowicz et al., 1992 *J. Bact.*, 174:398–407). There is another strong potential Fis site exactly 11 bases from the 202 site at coordinate 213 (8.0 bits). Footprinting data in Filutowicz (1992, FIG. 5b, c, site "I") shows DNase I protection that covers both sites.

Total sequence conservation at Fis sites. The total number of Fis sites in the *E. coli* genome is not known, so the information needed to locate those sites ($R_{frequency}$) cannot be calculated. However, the total sequence conservation at the binding sites is 8.5 bits, which suggests that there is one site every $2^{8.5}=362$ bases or an average of 4 sites at each of the 3239 genes of the 4,673,000 bp genome. It also implies that about 1300 Fis molecules would be needed to fill the Fis sites. When we searched Ecoseq7, which contains 60% of the known *E. coli* sequences (Rudd, et al. 1993, *ASM News*, 59: 335–341), for Fis sites with more than 1 bit of sequence conservation we found 36,000 sites, so there should be 60,000 possible Fis sites in the entire genome. These estimates are comparable to the number of Fis molecules per cell, which ranges from close to zero in stationary cells to between 50,000 and 100,000 molecules per cell during the transition to exponential growth or an increase in nutrients.

EXAMPLE 4

This example provides an illustration of designing binding sites with the method of the present invention.

Figure 13:
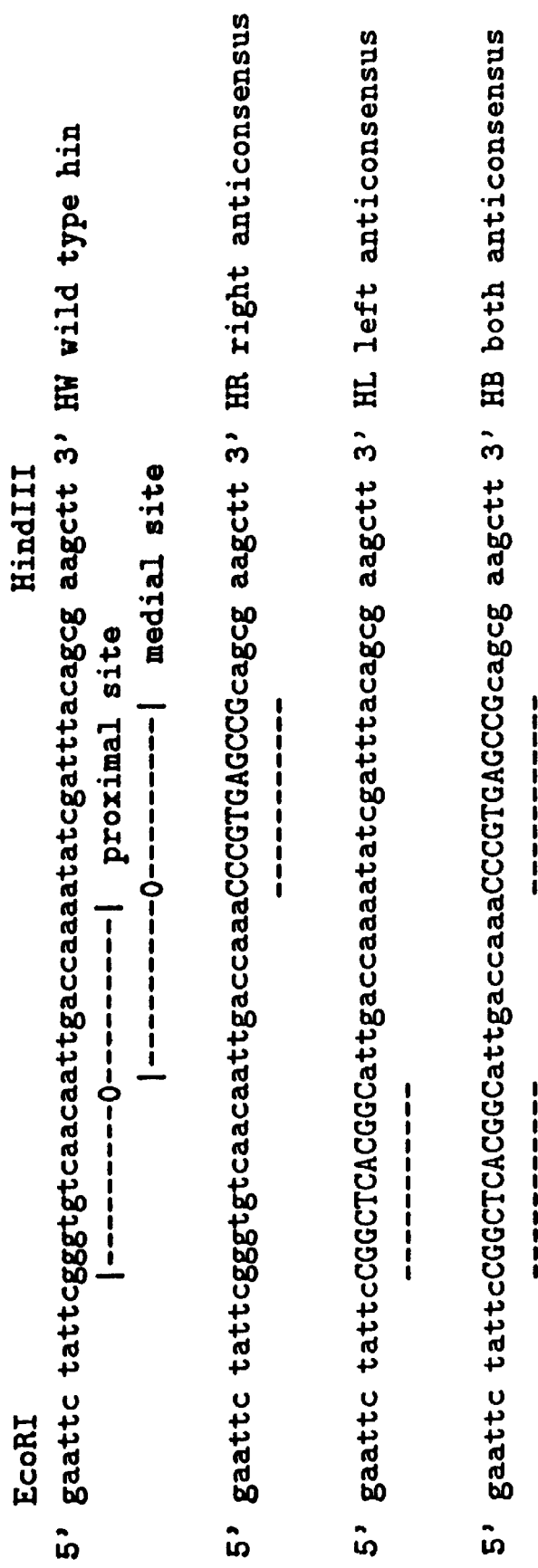
Figure 15:
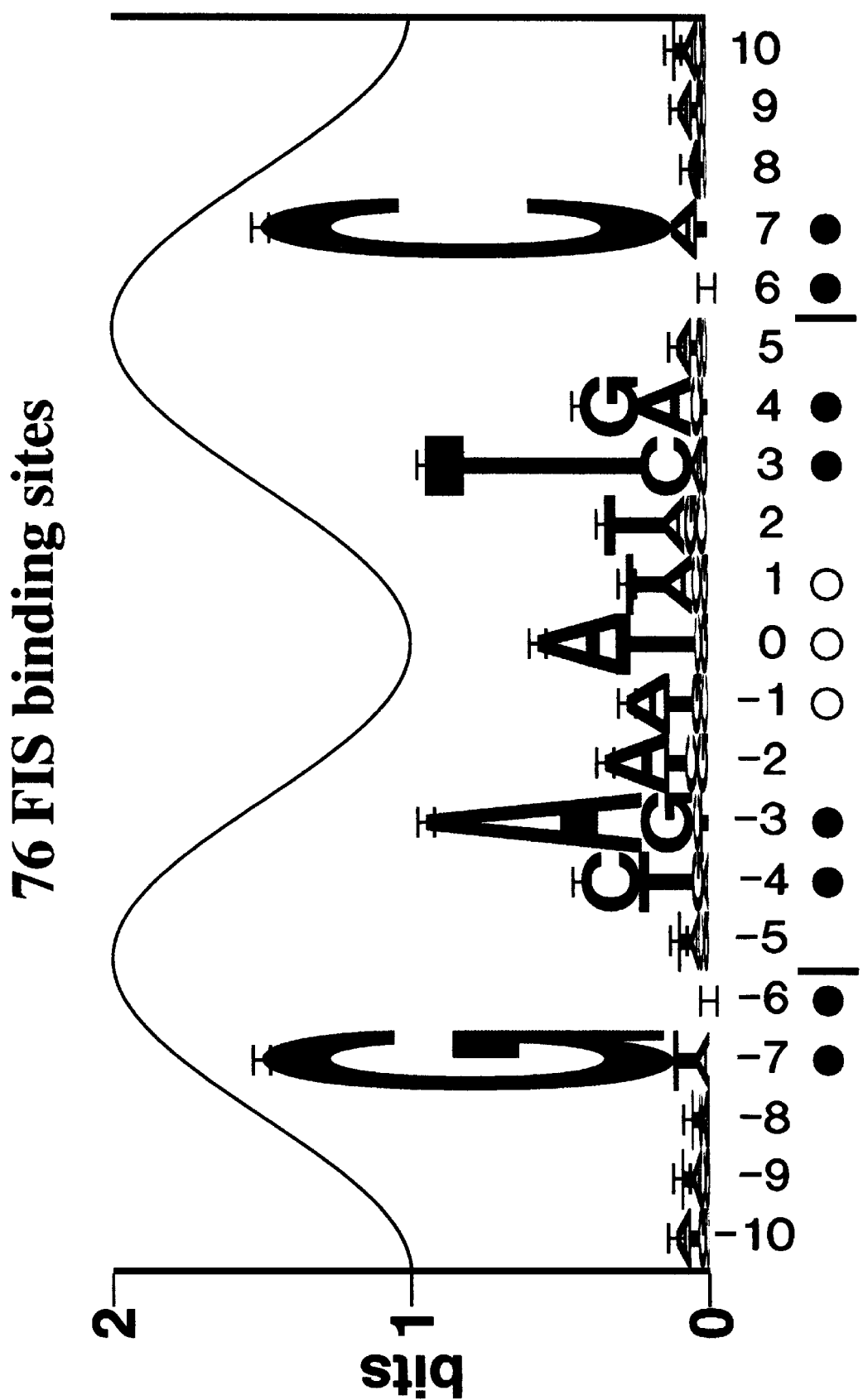

We chose 32 bases of the hin sequence because according to the information-theory based search this region contains two overlapping Fis sites, one of which is the Fis site proximal to the recombination junction hixL (Bruist et al., 1987 *Gens Dev.*, 1:762–772). We added 5 bases on each end—half a twist of DNA—to be sure we were not missing important components, although this region does not show up significantly in the sequence logo. Beyond these ends we added EcoRI and HindIII overhangs. We created three other sequences using the anticonsensus of the Fis sequence to destroy the proximal site, the newly identified "medial" site, or both sites (FIG. 13). The anticonsensus sequence is the sequence which should bind Fis the worst. It is predicted from the number of bases at each position (n(b, l) numbers matrix or the $R_i(b,l)$ weight matrix, FIG. 14) by noting which bases appear least frequently at each position of the site. In ambiguous cases we chose C or G when possible because these appear rarely in the logo (FIG. 15). We used the same rationale in designing the DNA from bacteriophage P1 cin.

These sequences and their complements were synthesized (Midland Oligos, Inc., Midland, Tex., USA) so that when annealed they provide sticky EcoRI and HindIII ends. Annealed oligos were ligated into plasmid pTS385 digested with EcoRI and HindIII and transformed into *E. coli* DH5α as previously described (Hengen & Iyer, 1992 *Biotechniques*, 13:57–62). Transformants were selected on LB media containing 50 μg/ml kanamycin and 50 μg/ml of ampicillin. When necessary, we transformed *E. coli* BL21/DE2 (Studier & Moffatt, 1986 *J. Mol. biol.*, 189:113–130)

and selected them on the same media containing 1 mM IPTG. We knew from previous experiments that the parental plasmid pTS385 is conditionally lethal to this strain because a strong T7 promoter is positioned between the EcoRI and HindIII sites. Induction of T7 RNA polymerase with IPTG thus provided a strong selection for recombinant plasmids containing the intended insert Fis DNA, eliminating all but a few wild-type pTS385 plasmids from the lot of transformants. The resultant plasmids were screened by restriction analysis and PCR amplified using primers flanking the inserted DNA pTS37fl 5' acatttcccgaaaagtgc 3' and pTS37rl 5' cggaacacgtagaaagcca 3'. When recombinants were identified, plasmid DNA was transformed into and maintained within $E.$ $coli$ DH5α. The sequence between the EcoRI and HindIII sites was then confirmed by dideoxy sequencing with an ABI model 373A automated sequencer (Hunkapiller et al., 1991 $Science$, 254:59–67).

For gel mobility shifts (Fried & Crothers, 1981 $Nuc.$ $Acids$ $Res.$ 9(23):6515–6525), we used Fis protein cloned and purified from $E.$ $coli$ obtained as a gift from R. Johnson 1986 $Cell$, 46:531–539). Plasmid DNA from the 8 clones was purified by the method of Birnboim and Doly (1979 $Nuc$ $Acids$ $Res.$ 7:1513–1523) or Hengen (1995 $Biotechniques$, 13:57–62), digested with EcoRI, end-filled with biotin-11-dUTP using the Klenow fragment of $E.$ $coli$ DNA polymerase I, and linearized with BglII, which cleaves 369 bp from the EcoRI site. The 369 bp DNA fragment was purified away from the larger plasmid fragment by electrophoresis through SeaPlaque GTG agarose (FMC, Rockland, Me., USA), sliced from the gel, and extracted using a freeze-and-spin method through Costar Spin-® centrifuge tubes containing 0.2 μm pore size nylon filters. Purified DNA was extracted with an equal volume of isoamyl alcohol to remove residual ethidium bromide, digested with HindIII, heated to 65° C. for 30 minutes to inactivate the HindIII enzyme, and cooled to room temperature.

Binding assays were accomplished by incubating DNA at approximately 1 nM with various concentrations of Fis protein ranging from 125 to 1000 nM at room temperature for 15 minutes in 25 mM Tris HCl (pH 7.6), 80 mM NaCl, 1 mM EDTA, 2 mM DTT 100 μg/ml acetylated bovine serum albumin, and 100 μg/ml calf thymus DNA. Gel shift analysis was done by separation of the different species on a 8.0% polyacrylamide gel in 1×TBE. The DNA was electrotransferred onto Tropilon-Plus™ nylon membrane (Tropix, Inc. Bedford, Mass., USA) with a Hoefer Semi-Phor Model TE70 semi-dry transfer unit for 30 minutes at 30 mA, and crosslinked by exposure to 254 nm UV light for 10 minutes on a UVP Model T5-15 transilluminator (Ultra-Violet Products, Inc., San Gabriel, Calif., USA). Biotinylated DNA was detected using a Southern-Light■ chemiluminescent kit using the CSPD® substrate (Tropix, Inc., Bedford, Mass., USA) and exposure to Kodak BioMax MR film.

Figure 6:
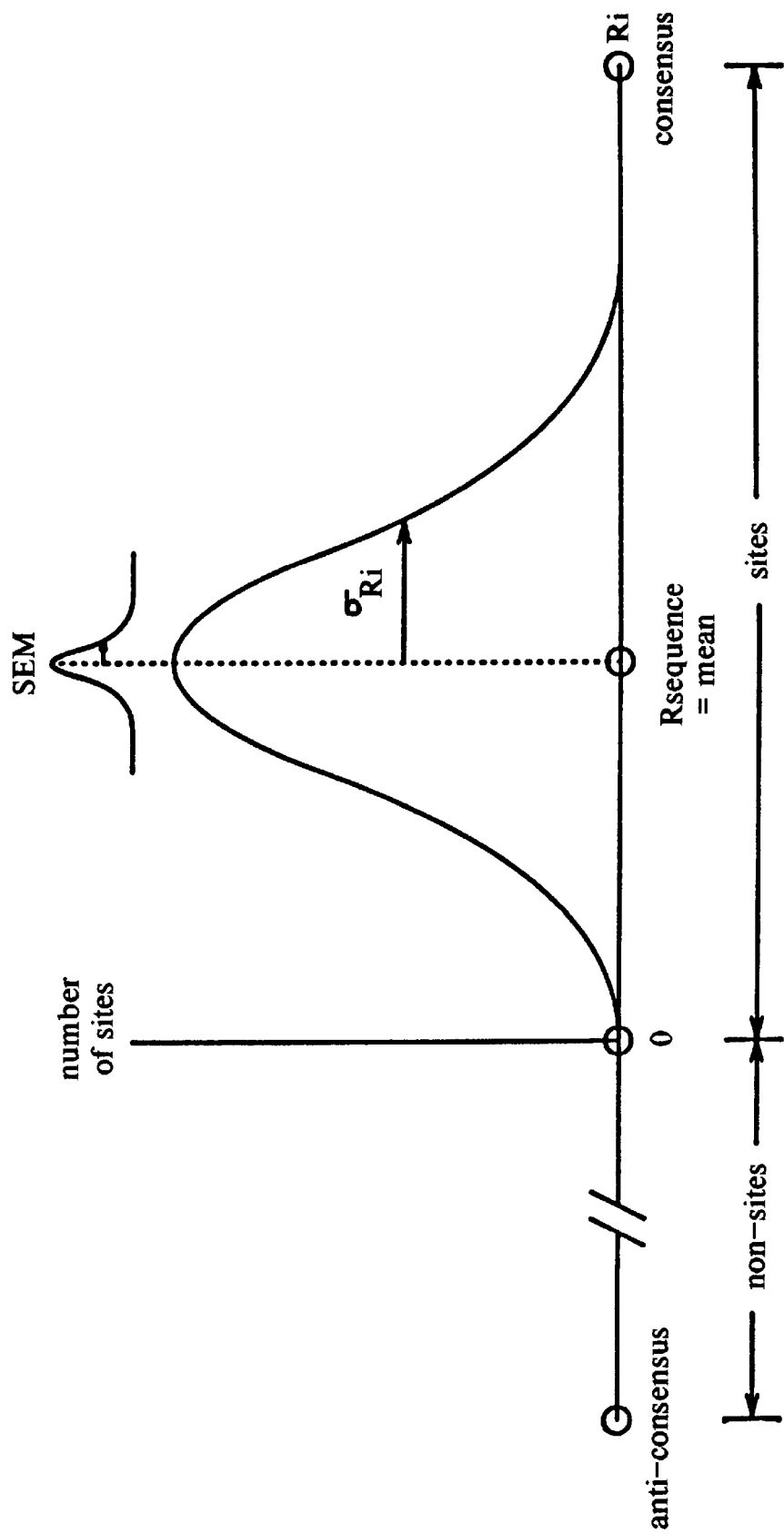

Strong Fis sites separated by 11 and 7 base pairs were designed by selecting the most frequent base at each position in the Fis sequence logo (FIG. 6, FIG. 9). These were then merged with the same sequence shifted by 11 or 7 base pairs. 5 extra bases were added to the ends and the DNAs were made self complementary (FIG. 8). They were synthesized with biotin on the 5' end and gel purified (Oligos Etc. Wilsonville, Oreg., USA). To insure complete annealing, they were heated, and slowly cooled to room temperature.

To determine whether overlapping Fis sites can be simultaneously bound by Fis, we synthesized strong Fis sites which overlap by 11 or 7 base pairs and tested their properties by gel shift. Fis protein shifts both DNAs, but the DNA with two Fis sites separated by 11 bases was shifted once, while the DNA with two Fis sites separated by 7 bases is shifted twice. This demonstrates that Fis molecules separated by 11 bases are on the same face of the DNA and collide with each other, while those separated by 7 bases are on different faces and do not collide. These results are consistent with many observations of Fis sites naturally separated by 7 or 11 bases, with molecular modelling and with a detailed analysis of the sequence logo structure which reveals that the Fis sites are internally redundant at spacings of 7 and 11 bases. We therefore propose that the collision and non-collision properties of Fis are used in genetic control systems as part of molecular flip-flops. Such flip-flops may be useful for constructing molecular computers.

EXAMPLE 5

This example demonstrates the relationship between information content and binding ability.

Fis sites at inversion regions. When we scanned our Fis $R_f(b,l)$ model across DNA inversion regions, we discovered that each known proximal site had an overlapping sequence with the same characteristics as a Fis site (FIG. 12). To test whether the new sites exist, we performed gel shift experiments on DNAs in which we presumably had knocked out neither, one, or both of the sites.

Figure 16A:
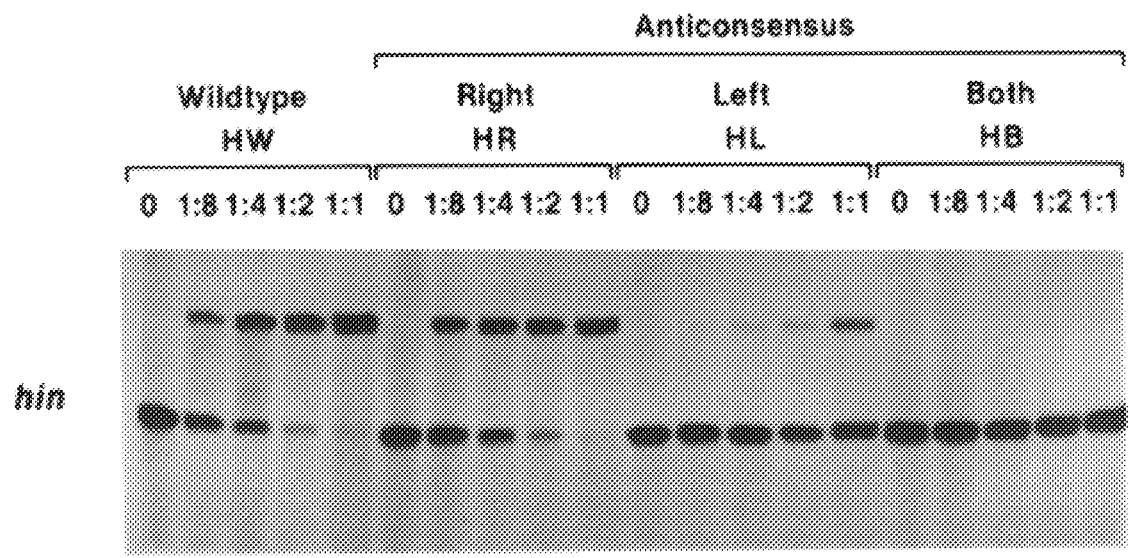
Figure 16B:
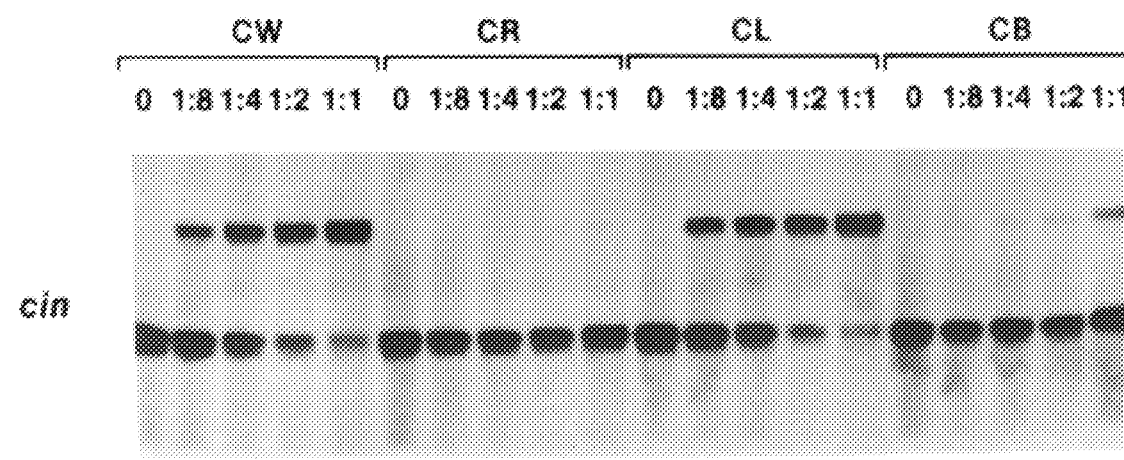

Under our experimental conditions hin does have a second site as predicted, since the knockout of the stronger proximal site still allowed the DNA to shift (FIG. 16). However, more Fis protein was required to shift an equivalent amount of DNA than for the wild-type proximal site, indicating that Fis binds weakly to the medial site. This is consistent with the weaker sequence conservation of the medial site (4.5 bits) compared to the proximal site (9.0 bits).

For the cin experiment, the stronger proximal site was confirmed, but the weaker external site showed a barely detectable shift (visible on the original X-ray film). To our surprise, when both cin sites were destroyed, we still detected a weak shift, which is stronger than that of the external site. In the process of destroying both the external and proximal sites, we inadvertently created a new Fis binding site shifted one base to the left of the original external site. The new site is only 1.3 bits, but it still gives a band shift.

EXAMPLE 6
EXAMPLE OF SPLICE MUTATIONS

Six donor site mutations have been examined, all of which cause beta+ thalassemia, i.e. there is some normal splicing.

Three of these mutations are in exon 1 of the beta globin gene and give a mild thalassemia phenotype. The normal intervening sequence 1 ("IVS1") donor at position 246 has 4.96 bits. There are two cryptic sites in the normal sequence that are apparently not used in vivo, but which are more likely to be used either if the position 246 site is mutated to become weaker or if mutations occur that make them stronger.

The cryptic sites are at positions 208 (7.69 bits) and 230 (8.73 bits), i.e. in exon 1. Mutations at position 228 (t→a) increases the site at 230 to 10.86 bits 232 (g→a) increases the site at 230 to 9.14 bits 235 (g→t) increases the site at 230 to 9.96 bits The difference in information content between the normal and mutant sequences appears to be rather small, as is the phenotypic affect.

Conversely, mutations in the donor site itself, even ones that are somewhat removed from the splice site result in preferential splicing at these cryptic sites. At position 251 (i.e. +5), G→C results in a reduction to 1.01 bits and G→T results in a reduction to 1.04 bits. Patients with these mutations have beta-plus thalassemia, but splicing at this site is severely reduced compared to normal. In contrast, T→C mutation at position 252 (i.e. +6) results in a reduction to 3.54 bits. This mutation is not a severe beta+ thalassemia, with splicing of the normal message occurring at 50–70% of the wild-type splice site.

It may be useful to use Scan to analyze for cryptic splice sites in the normal sequence close to the splice donors and acceptors that are normally used for all of the human genes in the database. Then, a correlation can be made to the disease database of splice mutations with that list to see whether those splice mutations are more severe than others where no such cryptic sites can be found.

Two mutations have been found in intron 1 which activate cryptic acceptors: g355a and t362g, upstream from the one normally used. The site created by g355a has 4.89 bits and has a beta+ thalassemia phenotype. In monkey kidney cells—not erythroid cells, the cryptic site is used 90% of the time, the normal site 10%. In erythroid cells the abnormal message is not detected, but processed mRNA levels are lower than normal. The site created by t362g has 5.08 bits and the normal site is not used in the heterologous expression system. This would be interpreted as a beta-0 thalassemia, except that the cell type in which splicing is analyzed appears to be important, so it may not be possible to draw the inference of beta-0 thalassemia. There appears to be a minimum threshold of information required for choice of the splice acceptor, but as long as the cryptic acceptor falls within the normal range it can and will be used.

An interesting cryptic acceptor site in intron 2 has been identified. The normal intron sequence contains a splice acceptor site at 1177 that is stronger than the one adjacent to exon 3 (position 1448). The site at 1177 has 14.779 bits and the one at 1448 has 13.33 bits. An A→G mutation at 1447 has been described which has a beta-0 (no mature globin mRNA) phenotype. This mutation reduces information content to 5.17 bits at the normal splice site (curiously, one is created at 1446 with 7.046 bits). Note that both of these are in the normal range. However, neither can compete with the cryptic site at 1177, so that essentially all of the spliced message is untranslatable and unstable. This site is so strong that mutations that create new donor sites between 1177 and 1448 create an untranslatable exon with the 1177 as 5' end (then, the IVS IVS2 donor splices to 1177 instead of 1448).

These two examples are paradoxical. In the first intron, the cryptic sites are weaker by Ri analysis than the normal acceptor but they are preferred. In the second intron, the cryptic acceptor is stronger than the "mutant" site in the normal acceptor and is preferred even though the "mutant" site has respectable information content. These results are reconciled in that the spliceosome processively reads the sequence until it finds an acceptable site (from 5'→13') and makes a lariat.

EXAMPLE 7

Mutations at the +3 position of the donor splice site in different genes were analyzed. Specifically, the sequence alterations were G→T in Von Willebrand Factor mRNA, A→G in Ornithine Transcarbamylase mRNA ("OTC") (exon 7), and G→C in CD18 (beta integrin). The first causes a form of hemophilia, the second—congenital hyperammonemia, mental retardation and usually infantile death, and the third, recurrent often fatal infections due to deficient expression of leukocyte adhesion glycoproteins. The severity of these different diseases is or appears to be correlated with the splice site mutation present.

In the Von Willebrand Factor mutation, there is exon skipping because the splice site is not recognized in some instances (and because there are no cryptic site in the neighborhood—which is confirmed by the scan). The normal site has 10.07 bits while the mutation has 5.97 bits. Experimentally it appears that the affected homozygote (by RT-PCR) makes similar amounts of mutant and normal transcripts. Clotting, however, is markedly reduced in the homozygote due to low levels of factor present. This may be related more to the turnover and stability of the factor (which is found in plasma).

In the OTC patient, the substitution does not change the information content of the site very significantly. The previous normal site has 6.954 bits, the "mutant" has 6.554. The Northern and Western blots do not demonstrate a reduced expression and sythesis of OTC in this patient. Also reported is a T→C substitution at the invariant +2 site which does abolish expression experimentally and has −11.138 bits of information. The OTC (+3) change, represents another polymorphism.

The last mutation, in CD18, was found in a set of related individuals with moderate deficiency phenotype. This mutation does not completely abolish splicing: however the level was measured to be 3% of that seen in normal individuals. The normal splice site has 9.179 bits and the mutant site has 4.78 bits, which appears to be towards the low end of the distribution.

EXAMPLE 8

Steroid 21-hydroxylase gene splice site substitutions in intron 2 (IVS21).

Mutations in the Cytochrome P450 (C21) (which encodes Steroid 21-hydroxylase), cause congenital adrenal hyperplasia ("CAH"), a recessive disorder. Patients with this disorder display a virilizing phenotype or a salt wasting phenotype. Virilization is more apparent in females, in males it can result in precocious puberty and hypersexualization. Most of the mutations characterized to date result form gene conversion of the B gene by the neighboring A gene, which is non-functional pseudogene. These two genes are very similar in sequence, there are numerous nucleotide substitutions in the A gene that when introduced into the B gene by gene conversion result in a non-functional P450(C21)B allele. Depending on the extent of the gene conversion event, the mutated sequences may affect the entire B gene or a subset of sequences in this gene.

Higashi et al. (*Proc. Nat Acad Sci. USA*, 85: 7486–90, 1988) described two patients with CAH that exhibited substitutions in the acceptor sequence of IVS2 of P450 (C21)B. Patient 10 was a virilized female with a C→G transversion at position −12 of the normal splice site (pos. 2333 of GenBank locus M12792). Patient 7 was a salt-wasting male with a C→A transversion at the same site. The substitutions in both of these individuals arose by gene conversion of the 5' or amino-terminal domain of the B gene by the A-pseudogene. The 3' terminal segment of the CAH gene was not involved in the gene conversion event. This led the investigators to suspect hat these amino-terminal nucleotide substitutions may have been responsible for inactivation of these CAH alleles. S1 nuclease protection studies show that the C→G substitution abolishes mRNA splicing at this acceptor and results in the exclusive use of 3 preexisting and new cryptic acceptor sites upstream of the normal site, and premature termination of translation.

Individual information analysis of these substitutions is consistent with the S1 nuclease protection experiments. The C→G substitution creates an adequate cryptic acceptor with 7.99 bits of information from a site with 0.70 bits. The normal acceptor decreases slightly from 12.1 to 10.5 bits, however it is within the range of functional sites. In order to explain the preference for using the cryptic acceptor over the normal site even though it has a lower $R_i$ value, it would appear that the cryptic site is detected by the spliceosome prior to seeing the normal site. This preference for a weaker, but adequate cryptic acceptor has been seen at similar mutations in several other genes that we have been examined and may be a consequence of processivity of the spliceosome in recognizing acceptor sites.

In contrast, the C→A allele does not create a new splice recognizer sequence at position −12 (there is a small decrease in the Ri at this site compared to the normal sequence to 0.41). It does not appreciably reduce the information content of the normal acceptor site either (form 12.1 to 10.0 bits), which is within the range of functional sites. This analysis indicates the C→A is a genetic polymorphism independent of the S1 nuclease digestion result. The prevalence of this substituter in patients with CAH is therefore unrelated to the diagnosis. We would predict that if a similar number of normal individuals without evidence of this disorder were examined, this substitution would also be detected frequently.

EXAMPLE 9

Fis sites at the nrd promoter demonstrate prediction of sites for which footprinting data exist.

Figure 20:
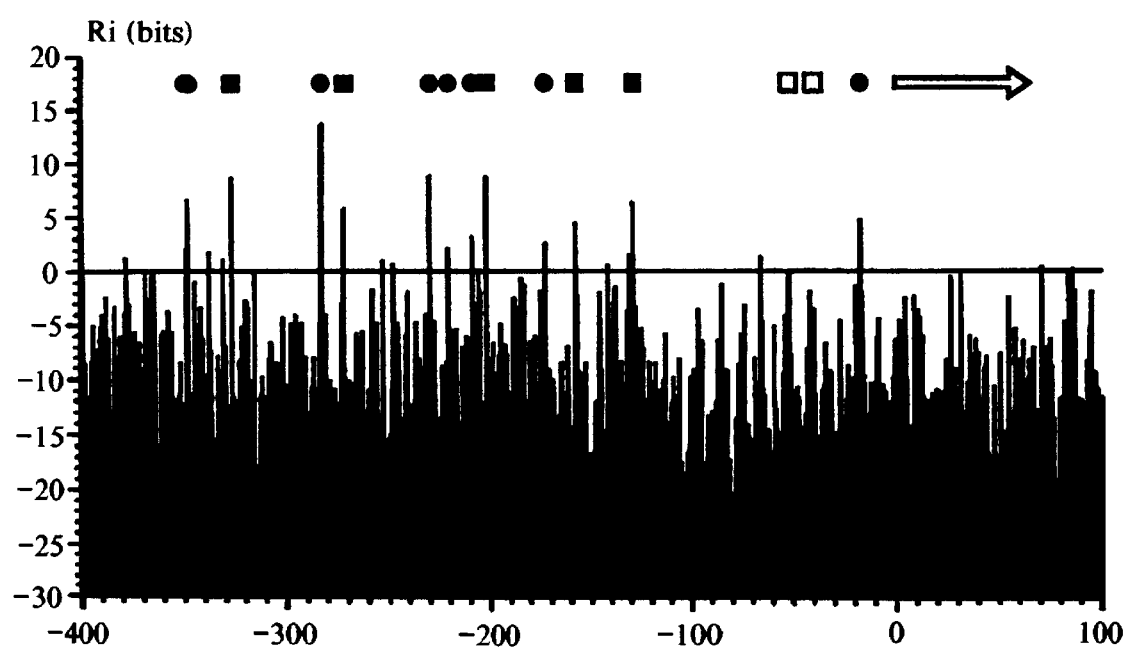
FIG. 20 is a Scan plot of nrd binding sites.

By using a degenerate consensus pattern, 5 Fis binding sites were found upstream of the transcriptional start site of the nrd operon of E. coli (Augustin, et al., 1994 J. Bact., 176:378–387). When we scanned for potential Fis binding sites, about 8 more sites were identified (FIG. 20).

These sites were easily confirmed to be true sites since Cu-phenantroline footprinting of this region had been carried out by (See Augustin et al., FIG. 3), corresponding well with our predictions even though none of these sites were used in the generation of the $R_i(b,l)$ weight matrix model used in this analysis.

The DNA sequence was from the GenBank; accession number K02672 (Carlson, et al., 1984, Prac. Natl. Acad. Sci. USA, 81:4294–4297).

Transcription begins at position 0 (GenBank coordinate 3395) and proceeds to the right. Potential Fis sites ($R_i \geq 2$ bits) relative to the start of transcription are at:

−349 (2.0 bits), 348 (6.6 bits), −327 (8.7 bits), −283 (13.8 bits), −272 (5.8 bits), 230 (8.9 bits), −221 (2.2 bits), 209 (3.2 bits), 202 (8.8 bits), −173 (2.6 bits), −158 (4.4 bits), −129 (6.4 bits) and −17 (4.8 bits).

Five Fis sites were identified by Augustin et al. to be in the ranges: −310 to −328 (probably site 327), −268 to −285 (site −272), −187 to −204 (probably site −202), −142 to −160 (probably site −158), and −122 to −139 (site −129) relative to the start of transcription. These are indicated by filled squares in FIG. 20.

Those sites which were located by the Scan program and visible on the footprinting data of Augustin et al. (Augustin, et al. FIG. 4, lanes 4 and 5) but not previously described, are indicated by filled circles.

The two DNA sites found by Augustin et al. are at −52 and −40 and indicated by open squares.

We extracted this sequence using a new feature of the Delila program which allows sequences to be renumbered by giving the command "default coordinate zero" followed by instructions of the form "get from 3395 −4000 to 3395 +4000;". Thus when this sequence was searched with the Scan program, the reported locations were relative to the transcriptional initiation point.

This plot also differs from those of FIG. 12 in that the individual information scores are drawn as lines from the bottom up, rather than from zero bits up or down. This is set by using a switch within the DNAplot parameter file.

It will thus be seen that the objects set forth above, among those made apparent from the preceding description, are effectively obtained. Since certain changes may be made above system and method without departing from the scope of the invention, it is intended that all matter contained in the above description and shown in the accompanying drawing shall be interpretive as illustrative and not limiting. It is also understood that the following claims are intended to cover all of the generic and specific features of the invention described herein, and all statements of the scope of the invention which, as a matter of a language might be said to fall between.

- 64 -

APPENDIX A

```
program Ri(inst, book, rsdata, values, rip, xyin, sequ,
ribl, output);
(* Ri: Rindividual is calculated for every site in the
aligned book
    by Thomas Schneider
module libraries required: delman, prgmods *)

label 1; (* end of program *)

const
(* begin module version *)
version = 2.12; (* of ri.p 1995 May 29
origin 1990 Aug 15 from Dalvec 1.05 *)
(* end module version *)

(* begin module describe.ri *)
(*
name
    ri: Rindividual is calculated for every site in the
aligned book synopsis
    Ri(inst: in, book: in, rsdata: in, values: in, rip: in,
      xyin: out, sequ: out, ribl: out, output: out)

files
    inst: delila instructions of the form 'get from 56 -5
to 56 +10;'
       (This file may be empty, in which case the sequences
will be
         aligned by their 5' ends.)
    book: the book generated by delila using inst
    rsdata: data file from rseq program
    values: a file containing the values of the objects to
which the Ri
```

- 65 - values are to be compared.  The file may be empty.
rip:  Parameters to control the program.
    On the FIRST LINE are the FROM and TO over which to do the Ri
    calculation.  These must not exceed either of those in the inst/book or
    the rsdata.

The SECOND LINE defines the column of the values file to use.

The THIRD LINE: two integers: the lowest and highest evaluation to report
    to xyin and sequ.  If the first character of the line is 'a' then all
    evaluations are reported.  Otherwise two real numbers are expected.

- 66 -

Sequences within this range are printed to xyin and to sequ depending
        also on the fifth parameter.

The FOURTH LINE: two integers: the lowest and highest evaluation to
        report to xyin and sequ.  If the first character of the line is 'a' then
        all evaluations are reported.  Otherwise two real numbers are expected.
    Sequences within this range are printed to xyin and to sequ depending
        also on the fifth parameter.

The FIFTH LINE determines whether or not to produce any raw sequences in
        the sequ file.  If the first character of the line is 'p', sequences
        selected according to the third and fouth parameters are printed to sequ
        file.  (This is a complete on-off switch for the sequ file.)

The SIXTH LINE determines whether or not to print the sequence of the
        site being analyzed.  If the first character is 'p' then the sequence is
        printed to the xyin file.

The SEVENTH LINE determines whether or not to print sequences which have
        a partial site.  The problem is that if there is part of a site, then the
        Ri value is questionable, depending on where the deletion was.  The best
        analysis would not use a partial site, as it messes up the statistics.

- 67 -

If the first character is:

n  Don't print the line at all.
     i  Keep the line, but force the Ri value to be -infinity.

This allows the lines of xyin to be correlated to the values
        still.
     -  (any other character): print as it is.

The EIGHTH LINE determines what to do when $f(b,l) = 0$. Positions for which $f(b,l) = 0$ will have negative infinity in the $Ri(b,l)$ table.

- 68 -

The letter 's' means to use Rodger Staden's method of giving 1/(n+t),
where t is a non-negative integer following the 's'. When t = 0, it
is Staden's method. Using t=1 may be the most logical choice. If
there is no 's', the program expects a number which the value for
negative infinity. It should be a value sufficiently below zero so
that sites that are being excluded from the definition according to
f(b,l) are separated from the true sites. -1000 is a useful value, as
it will always displace sites with exceptions far away from zero.

xyin: input to the xyplo program. The file contains these columns of data:
    1 piece number
    2 piece name
    3 sequence of region analyzed
    4 length of region analyzed on this piece
    5 aligning coordinate on the piece
    6 Rindividual for the piece
    7 value from the values file (or 0 if values is empty)

sequ: the raw sequences reported to xyin if any selection is made
(fourth line of rip file). These end in periods, so they can be
given to makebk to create a book.

ribl: weight matrix $Ri(b,l)$. The information content for each base b at
each position l, in bits. Lines that start with *

- 69 - are notes. The next
    line contains the matrix FROM and TO coordinates,
this is followed by the
    matrix in the order A, C, G, T from FROM to TO.
    Then real numbers on individual lines report:
       Ri mean (Rsequence of selected region)
       Ri standard deviation
       Ri of consensus sequence
       Ri of anticonsensus sequence
       Ri average for random (equiprobable) sequence
    These are all for the given range.
    (Note: Although the mean Ri for the sites is
Rsequence, to get a good
    estimate of this, it is better to use the value
calculated by the rseq

- 70 - program because that is less sensitive to missing sequence data.)

output: messages to the user description
The program determines the individual informations of the sites in the book
as aligned by the instructions, according to the frequency table given in
the rsdata file. The program calculates the Ri(b,l) table:

Ri(b,l) := 2 - (- log2( f(b,l)))

and sums this up for each sequence. Ri is defined so that the average of
the Ri's for a set of sequences is Rsequence. However, if the sequences are
incomplete, the average will probably be less than Rsequence. The xyin
output is ready to read into the xyplo program for plotting and linear
regression. The ribl matrix is ready to be used to scan sequences with the
scan program.

The program can be used in subtle ways. For example, one can analyze the
individual information of the left half of a binding site. This result can
then be used in the values file to compare against the analysis of the right
side of a binding site.

author
Thomas D. Schneider

- 71 - examples rip:

```
-10 +10        From-to range to do the evaluation
1              column of the values file to copy to xyin
a 0 1000       lowest to highest Ri to put in xyin and sequ
(a = any)
a -1000 +1000  lowest to highest Value to put in xyin and
sequ (a = any)
n              p means print sequence to the sequ file
p              p means print sequence to the xyin file
-              -: accept all sites; n: no partials; i:
partials -> -infinity
```

- 72 - s 1         s: use Staden's Method, f(b,l)=1/(n+t); else negative infinity documentation @article{Staden1984,
author = "R. Staden",
title = "Computer methods to locate signals in nucleic acid sequences",
journal = "Nucl. Acids Res.",
volume = "12",
pages = "505-519",
year = "1984"} and

@unpublished{SchneiderRi,
author = "T. D. Schneider",
title = "Measuring the Information of Individual Binding Sites
on Nucleotide Sequences",
comment = "indiv.tex",
note = "in preparation"} see also
   rseq.p, xyplo.p, scan.p bugs technical notes

*)
(* end module describe.ri *)

(* begin module Ri.const *)
   defnegativeinfinity = -1000; (* default for negative infinity

- 73 -

```
                               for the Ri(b,l) table
*)
   maxribl = 2000; (* maximum size of Ri(b,l) table *)

infofield = 12; (* size of field for printing
information in bits *)
   infodecim = 6; (* number of decimal places for printing
information *)
        (* these are used for conlist only *)
   nfield = 6; (* size of field for printing n, the number
of sites *)

(* end module Ri.const *)

(* begin module interact.const *)
      maxstring = 150; (* the maximum string *)
(* end module interact.const version = 4.75; (@ of rsgra.p
1990 Oct 2 *)
```

- 74 -

```
(* begin module Ri.filler.const *)
      fillermax = 21; (* the size of the filler array for
a string *)
(* end module Ri.filler.const *)

(* begin module my.book.const *)
(* constants needed for book manipulations *)

dnamax = 3000;  (* length of dna arrays *)
      namelength = 12; (* maximum key name length *)   (*
changed!!! *)
      linelength = 80; (* maximum line readable in book *)

(* end module my.book.const version = 'delmod 6.60 91 Jan
11 tds/gds' *)

type (* begin module rs.type *)
   rstype = record (* types of data in the data table from
rseq *)
      rstart, rstop: integer; (* range of the data *)
      l, (* position *)
      nal,ncl,ngl,ntl: integer; (* numbers of each base *)
      rsl, (* rsequence(l) *)
      rs,  (* running sum of rs *)
      varhnb, (* variance estimate for small sample
correction *)
      sumvar: (* sum of varhnb *)
         real;
      nl: integer; (* = a+c+g+t *)
      ehnb: real; (* hg-e(n) *)
      flag: char; (* e = exact, a = approximate sampling
statistics *)
   end;
(* end module rs.type version = 4.75; (@ of rsgra.p 1990
Oct 2 *)
```

- 75 -

```
(* begin module interact.type *)
      string = record (* a string of characters *)
         letters: array[1..maxstring] of char; (* the
letters in the string *)
         length: integer; (* the number of characters in
the string *)
         current: integer; (* the letter we are working on
*)
      end;
(* end module interact.type version = 4.75; (@ of rsgra.p
1990 Oct 2 *)

(* begin module trigger.type *)
      trigger = record (* an object to be searched for *)
         seek: string; (* the characters looked for *)
         state: integer; (* how close to triggering we are
*)
         skip: boolean; (* trigger not found- skip the
line *)
```

- 76 -

```
        found: boolean (* the trigger was found *)
     end;
(* end module trigger.type version = 4.75; (@ of rsgra.p
1990 Oct 2 *)

(* begin module filler.type *)
     (* the following is an array used to fill a string.
     it is convenient to have it much shorter than the
maxstring, so that
     it is easy to fill the string using procedure
fillstring.
     the user must declare the value of constant
fillermax. *)
     filler = packed array[1..fillermax] of char;
(* end module filler.type version = 4.75; (@ of rsgra.p
1990 Oct 2 *)

(* begin module book.type *)
(* types needed for book manipulations *)

chset = set of 'a'..'z';

(* types defined in book definition *)

alpha = packed array[1..namelength] of char; (* this
is not alfa *)

(* name is a left justified string with blanks
following the
          characters *)
     name = record
          letters: alpha;
          length: 0..namelength (* zero means an
unspecified structure *)
     end;

lineptr = ^line;
```

- 77 -

```
line = record (* a line of characters *)
   letters: packed array [1..linelength] of char;
   length: 0..linelength;
   next: lineptr
end;

direction = (plus, minus, dircomplement,
dirhomologous);
configuration = (linear, circular);
state = (on, off);

header = record (* header of key *)
   keynam: name; (* key name of structure *)
   fulnam: lineptr; (* full name of structure *)
   note:   lineptr (* note key *)
end;
```

- 78 -

```
(* base types *)
base = (a,c,g,t);
dnaptr = ^dnastring;
dnarange = 0..dnamax;
seq = packed array[1..dnamax] of base;
dnastring = record
    part: seq;
    length: dnarange;
    next: dnaptr
end;

orgkey = record (* organism key *)
    hea: header;
    mapunit: lineptr (* genetic map units *)
end;

chrkey = record (* chromosome key *)
    hea: header;
    mapbeg: real; (* number of genetic map beginning
*)
    mapend: real (* number of genetic map ending *)
end;

pieceptr = ^piece;
piekey = record (* piece key *)
    hea: header;
    mapbeg: real; (* genetic map beginning *)
    coocon: configuration; (* configruation
(circular/linear) *)
    coodir: direction; (* direction (+/-) relative to
genetic map *)
    coobeg: integer; (* beginning nucleotide *)
    cooend: integer; (* ending nucleotide *)
    piecon: configuration; (* configruation
(circular/linear) *)
    piedir: direction; (* direction (+/-) relative to
```

- 79 -

```
coordinates *)
        piebeg: integer; (* beginning nucleotide *)
        pieend: integer; (* ending nucleotide *)
      end;

piece = record
        key: piekey;
        dna: dnaptr
     end;

reference = record
        pienam : name;   (* name of piece referred to *)
        mapbeg : real;   (* genetic map beginning *)
        refdir : direction;  (* direction relative to
coordinates *)
```

- 80 -

```
      refbeg : integer;  (* beginning nucleotide *)
      refend : integer;  (* ending nucleotide *)
   end;

genkey = record  (* gene key *)
      hea : header;
      ref : reference;
   end;

trakey = record  (* transcript key *)
      hea : header;
      ref : reference;
   end;

markerptr = ^marker;
   markey = record (* marker key *)
      hea : header;
      ref : reference;
      sta : state;
      phenotype : lineptr;
      next : markerptr;
   end;

marker = record
      key : markey;
      dna : dnaptr;
   end;

(* end module book.type version = 'delmod 6.60 91 Jan 11
tds/gds' *)

(* begin module scan.type *)
   rblarray = array[a..t, 0..maxribl] of real; (*
real(B,L) *)
(* end module scan.type *)

var
```

- 81 -

```
(* begin module Ri.var *)
    inst, (* the delila instructions required by the align
procedures *)
    book, (* the book to be aligned *)
    rsdata, (* output of rseq program *)
    values, (* values of objects to correlate Ri with *)
    rip, (* parameters to control the program *)
    xyin, (* output of Ri, columns of Ri and length data *)
    sequ, (* raw sequences if selection is being done *)
    ribl: (* output of Ri, Ri(b,l) weight matrix *)
       text;
(* end module Ri.var *)

(* begin module book.var *)
```

- 82 -

```
(*
**************************************************************
************** *)
(* global variables needed for book manipulations *)

(* free storage: *)
      freeline: lineptr; (* unused lines *)
      freedna: dnaptr; (* unused dnas *)

readnumber: boolean; (* whether to read a number
from the notes, or
                              to read in the notes *)
      number: integer; (* the number of the item just read
*)
      numbered: boolean; (* true when the item just read
is numbered *)
      skipunnum: boolean; (* a control variable to allow
skipping of
                              un-numbered items in the book
*)

(*
**************************************************************
************** *)
(* end module book.var version = 'delmod 6.60 91 Jan 11
tds/gds' *)

(* begin module halt *)
procedure halt;
(* stop the program.  the procedure performs a goto to the
end of the
   program.  you must have a label:
       label 1;
   declared, and also the end of the program must have
this label:
       1: end.
   examples are in the module libraries.
```

- 83 -

```
   this is the only goto in the delila system. *)
begin
      writeln(output,' program halt.');
      goto 1
end;
(* end module halt version = 'delmod 6.60 91 Jan 11
tds/gds' *)

(* begin module interact.clearstring *)
procedure clearstring(var ribbon: string);
(* empty the string *)
var   index: integer; (* to the ribbon *)
begin (* clearstring *)
      with ribbon do begin
          for index := 1 to maxstring do letters[index] :=
' ';
          length := 0;
          current := 0;
      end
```

- 84 -

```
end; (* clearstring *)
(* end module interact.clearstring version = 4.75; (@ of
rsgra.p 1990 Oct 2 *)

(* begin module interact.writestring *)
procedure writestring(var tofile: text; var s: string);
(* write the string s to file tofile, no writeln *)
var   i: integer; (* index to s *)
begin (* writestring *)
      with s do for i := 1 to length do write(tofile,
letters[i])
end; (* writestring *)
(* end module interact.writestring version = 4.75; (@ of
rsgra.p 1990 Oct 2 *)

(* begin module trigger.proc *)
(* this module allows one to scan a series of characters,
as from
an array or a file, and to "trigger" or detect a simple
string
in the series.  the advantage of the trigger is that
several triggers
can "observe" a stream of characters at once, each looking
for a
different thing.
some other modules required: interact.const, interact.type
*)

procedure resettrigger(var t: trigger);
(* reset the trigger to ground state *)
begin (* resettrigger *)
      with t do begin
         state := 0;
         skip := false;
         found := false
      end
end; (* resettrigger *)
```

- 85 -

```
procedure testfortrigger(ch: char; var t: trigger);
(* look at the character ch.
   if it is part of the trigger (at the current trigger
state),
      then the trigger state goes higher.
   if it is not part of the trigger then the trigger state
is reset,
      skip is true and one should skip onward to find the
trigger.
   if the trigger is found, found is true. *)
begin (* testfortrigger *)
     with t do begin
        state := succ(state);
(*         if debugging then begin
             writestring(list,seek);
             writeln(list,'testfortrigger
seek.letters[',state:1,']:',
                              seek.letters[state],' ch:',ch);
```

- 86 -

```
        end;*)
        if seek.letters[state] = ch
        then begin
            skip := false;
            if state = seek.length then found := true
                                   else found := false
        end
        else begin (* reset trigger *)
            state := 0;
            skip := true;
            found := false
        end
      end
end; (* testfortrigger *)
(* end module trigger.proc version = 4.75; (@ of rsgra.p
1990 Oct 2 *)

(* begin module filler.fillstring *)
procedure fillstring(var s: string; a: filler);
(* this procedure makes it reasonably easy to fill the
string s with
characters.  one calls the procedure as: *)
(*                          1         2         3
4         5 *)
(*
123456789012345678901234567890123456789012345678 90 *)
(*   fillstring(s, 'this-is-the-string
             ');
the two comments make it easy to line the characters up.
also, for this
example, it was assumed that the length of filler as
defined by the
constant fillermax was 50. *)
var
      length: integer; (* of the string without trailing
blanks *)
      index: integer; (* of s *)
```

- 87 -

```
begin (* fillstring *)
      clearstring(s);
      length := fillermax;
      while (length > 1) and (a[length] = ' ') do length
:= pred(length);
      if (length = 1) and (a[length] = ' ') then begin
         writeln(output, 'fillstring: the string is
empty');
         halt
      end;

for index := 1 to length do s.letters[index] :=
a[index];
      s.length := length;
      s.current := 1
end; (* fillstring *)
```

- 88 -

```
(* end module filler.fillstring version = 4.75; (@ of
rsgra.p 1990 Oct 2 *)

(* begin module filler.filltrigger *)
procedure filltrigger(var t: trigger;
                      a: filler);
(* fill the trigger t *)
begin (* filltrigger *)
        fillstring(t.seek,a)
end; (* fillstring *)
(* end module filler.filltrigger version = 4.75; (@ of
rsgra.p 1990 Oct 2 *)

(* begin module copyaline *)
procedure copyaline(var fin, fout: text);
(* copy a line from file fin to file fout *)
begin (* copyaline *)
      while not eoln(fin) do begin
          fout^ := fin^;
          put(fout);
          get(fin)
      end;
      readln(fin);
      writeln(fout);
end; (* copyaline *)
(* end module copyaline version = 'delmod 6.60 91 Jan 11
tds/gds' *)

(*
***********************************************************
************ *)

(* begin module package.align *)
(*
***********************************************************
```

- 89 -

```
************** *)
(* begin module package.getpiece *)
(*
************************************************************
************** *)
(* begin module package.brpiece *)
(*
************************************************************
************** *)
(* begin module book.basis *)
(* procedures needed for book manipulations *)

(* get procedures should be used for all linked lists of
records *)
```

- 90 -

```
procedure getline(var l: lineptr);
(* obtain a line from the free line list or by making a
new one *)
begin
      if freeline<>nil
         then begin
            l:=freeline;
            freeline:=freeline^.next
         end
         else new(l);
      l^.length:=0;
      l^.next:=nil
end;

procedure getdna(var l: dnaptr);
begin
      if freedna<>nil
         then begin
            l:=freedna;
            freedna:=freedna^.next
         end
         else new(l);
      l^.length:=0;
      l^.next:=nil
end;

(* clear procedures should be called each time the records
are no longer needed
         failure to do this may result in a stack
overflow. *)

procedure clearline(var l: lineptr);
(* return a line to the free line list *)
var   lptr: lineptr;
begin
      if l<>nil then begin
         lptr:=l;
```

- 91 -

```
            l:=l^.next;
            lptr^.next:=freeline;
            freeline:=lptr
        end
end;

procedure cleardna(var l: dnaptr);
var     lptr: dnaptr;
begin
        if l<>nil then begin
            lptr:=l;
            l:=l^.next;
            lptr^.next:=freedna;
            freedna:=lptr
        end
end;
```

- 92 -

```
procedure clearheader(var h: header);
(* clear the header h (remove lines to free storage) *)
begin
      with h do begin
          clearline(fulnam);
          while note<>nil do clearline(note)
      end
end;

procedure clearpiece(var p: pieceptr);
(* clear the dna of the piece *)
begin
      while p^.dna<>nil do cleardna(p^.dna);
      clearheader(p^.key.hea)
end;

function chartobase(ch:char):base;
(* convert a character into a base *)
begin
      case ch of
          'a': chartobase:=a;
          'c': chartobase:=c;
          'g': chartobase:=g;
          't': chartobase:=t
      end
end;

function basetochar(ba:base):char;
(* convert a base into a character *)
begin
      case ba of
          a: basetochar:='a';
          c: basetochar:='c';
          g: basetochar:='g';
          t: basetochar:='t';
      end
end;
```

- 93 -

```
function complement(ba:base):base;
(* take the complement of ba *)
begin
      case ba of
          a: complement:=t;
          c: complement:=g;
          g: complement:=c;
          t: complement:=a;
      end
end;

function pietoint(p: integer; pie: pieceptr): integer;
(* p is a coordinate on the piece.
   we want to transform p into a number
```

```
                            - 94 -
   from 1 to n: an internal coordinate system for
   easy manipulation of piece coordinates *)
var   i: integer; (* an intermediate value *)
begin
      with pie^.key do begin
         case piedir of
            plus:  if p>=piebeg
                      then i:=p-piebeg+1
                      else i:=(p-coobeg)+(cooend-piebeg)+2;
            minus: if p<=piebeg
                      then i:=piebeg-p+1
                      else i:=(cooend-p)+(piebeg-coobeg)+2
         end;
         pietoint:=i
      end
end;

function inttopie(i: integer; pie: pieceptr):integer;
(* i is in the range 1 to some maximum.  it is an internal
coordinate
   system for the program.  we want to do a
   coordinate transformation to obtain
   a value in the range of the piece called pie:
   i=1 corresponds to piebeg and
   i=its maximum corresponds to pieend *)
var   p: integer; (* an intermediate value *)
begin
      with pie^.key do begin
         case piedir of
            plus: begin
               p:=piebeg+(i-1);
               if p>cooend
                  then if coocon=circular
                     then p:=p-(cooend-coobeg+1)
            end;
            minus: begin
               p:=piebeg-(i-1);
```

```
                        - 95 -
                if p<coobeg
                    then if coocon=circular
                        then p:=p+(cooend-coobeg+1)
                end
            end;
            inttopie:=p
        end
end;

function piecelength(pie: pieceptr): integer;
(* return the length of the dna in pie *)
begin
    piecelength:=pietoint(pie^.key.pieend,pie)
end;
```

- 96 -

```
(* end module book.basis version = 'delmod 6.60 91 Jan 11
tds/gds' *)

(* begin module book.getto *)
function getto(var thefile: text; ch: chset): char;
(* search the file for a character in the first line which
is a
   member of the set ch. *)
var achar: char;
begin
      achar:=' ';
      while (not(achar in ch)) and (not eof(thefile))
         do readln(thefile,achar);
      if (achar in ch) then getto:=achar
                       else getto:=' '
end;
(* end module book.getto version = 'delmod 6.60 91 Jan 11
tds/gds' *)

(* begin module book.skipstar *)
procedure skipstar(var thefile:text);
(* skip start of line (or star = '*'). *)
begin (* skipstar *)
      if thefile^ <> '*' then begin
         writeln(output,' procedure skipstar: bad book');
         writeln(output,' "*" expected as first character
on the line, but "',
                        thefile^,'" was found');
         halt
      end;
      get(thefile); (* skip the star *)

if thefile^ <> ' ' then begin
         writeln(output,' procedure skipstar: bad book');
         writeln(output,' "* " expected on a line but "*',
                        thefile^,'" was found');
         halt
```

- 97 -

```
      end;
      get(thefile) (* skip the blank *)
end; (* skipstar *)
(* end module book.skipstar version = 'delmod 6.60 91 Jan
11 tds/gds' *)

(* begin module book.brreanum *)
procedure brreanum(var thefile: text; var reanum: real);
(* read a real number from the file *)
begin
      skipstar(thefile);
      readln(thefile,reanum);
end;
(* end module book.brreanum version = 'delmod 6.60 91 Jan
11 tds/gds' *)
```

- 98 -

```
(* begin module book.brnumber *)
procedure brnumber(var thefile: text; var num: integer);
(* read a number from the file *)
begin
      skipstar(thefile);
      readln(thefile,num)
end;
(* end module book.brnumber version = 'delmod 6.60 91 Jan
11 tds/gds' *)

(* begin module book.brname *)
procedure brname(var thefile: text; var nam: name);
(* read a name from the file *)
var   i: integer; (* an index to the name *)
      c: char; (* a character read *)
begin (* brname *)
      skipstar(thefile);
      with nam do begin
         length:=0;
         repeat
            length:=succ(length);
            read(thefile,c);
            letters[length] := c
         until (eoln(thefile)) or
               (length>=namelength) or
               (letters[length]=' ');
         if letters[length]=' ' then length:=length-1;
         if length<namelength
            then for i:=length+1 to namelength do
letters[i]:=' '
      end;
      readln(thefile)
end; (* brname *)
(* end module book.brname version = 'delmod 6.60 91 Jan 11
tds/gds' *)

(* begin module book.brline *)
```

- 99 -

```
procedure brline(var thefile: text; var l: lineptr);
(* read a line from the file *)
var
      i,j: integer;
      acharacter: char;
begin
      skipstar(thefile);
      i:=0;
      while (not eoln(thefile)) do begin
         i:=succ(i);
         read(thefile,acharacter);
         l^.letters[i]:=acharacter
      end;
      if i<l^.length then for j:=i+1 to l^.length do
l^.letters[j]:=' ';
      l^.length:=i;
```

- 100 -

```
      l^.next:=nil;
      readln(thefile)
end;
(* end module book.brline version = 'delmod 6.60 91 Jan 11
tds/gds' *)

(* begin module book.brdirect *)
procedure brdirect(var thefile: text; var direct:
direction);
(* read a direction *)
var   ch: char;
begin
      skipstar(thefile);
      readln(thefile,ch);
      if ch='+' then direct:=plus
                else direct:=minus
end;
(* end module book.brdirect version = 'delmod 6.60 91 Jan
11 tds/gds' *)

(* begin module book.brconfig *)
procedure brconfig(var thefile: text; var config:
configuration);
(* read a configuration *)
var   ch: char;
begin
      skipstar(thefile);
      readln(thefile,ch);
      if ch='l' then config:=linear
                else config:=circular
end;
(* end module book.brconfig version = 'delmod 6.60 91 Jan
11 tds/gds' *)

(* begin module book.brnotenumber *)
procedure brnotenumber(var thefile: text; var note:
lineptr);
```

- 101 -

```
(* book note reading to obtain the number of the object.
the procedure returns the value of the number as a global.
(this is not such a good practice, but we are stuck with
it for now.) *)
begin (* brnotenumber *)
      note:=nil;
      numbered := false;
      number := 0; (* force number to zero if there
          is no number at all *)
      (* the next character is n or * depending on whether
there are notes *)
      if thefile^ = 'n' then begin
         readln(thefile);
         if thefile^ <> 'n' then begin
            skipstar(thefile);
            if not eoln(thefile) then begin
               if thefile^ = '#' then begin
                  numbered := true;
```

- 102 -

```
                get(thefile); (* move past the number
symbol *)
                read(thefile,number);
            end
        end;
        repeat
            readln(thefile)
        until thefile^ = 'n';
        readln(thefile)
        end
        else readln(thefile)
    end
end; (* brnotenumber *)
(* end module book.brnotenumber version = 'delmod 6.60 91
Jan 11 tds/gds' *)

(* begin module book.brnote *)
procedure brnote(var thefile: text; var note: lineptr);
(* read note key *)
var
    newnote: lineptr; (* the new note *)
    previousnote: lineptr; (* the last line of the notes
*)
begin (* brnote *)
    note:=nil;
    if thefile^ = 'n' then begin (* enter note *)
        readln(thefile);
        if thefile^ <> 'n' then begin (* abort null note
(n/n) *)
            getline(note);
            newnote:=note;
            while thefile^ <> 'n' do begin (* wait until
end of note *)
                brline(thefile,newnote);
                previousnote:=newnote;
                (* get next note *)
                getline(newnote^.next);
```

- 103 -

```
              newnote:=newnote^.next;
           end;
           (* last note was not used, so: *)
           clearline(newnote);
           previousnote^.next:=nil;
           readln(thefile)
        end
        else readln(thefile)
     end
end; (* brnote *)
(* end module book.brnote version = 'delmod 6.60 91 Jan 11
tds/gds' *)

(* begin module book.brheader *)
procedure brheader(var thefile: text; var hea: header);
(* read the header of a key. *)
begin
```

- 104 -

```
     with hea do begin
         (* read key name *)
         brname(thefile,keynam);

(* read full name *)
         getline(fulnam);
         brline(thefile,fulnam);

(* read note key *)
         if readnumber then brnotenumber(thefile,note)
                     else brnote(thefile,note)
     end
end;
(* end module book.brheader version = 'delmod 6.60 91 Jan
11 tds/gds' *)

(* begin module book.brpiekey *)
procedure brpiekey(var thefile: text; var pie: piekey);
(* read piece key *)
begin
     with pie do begin
         brheader(thefile,hea);
         brreanum(thefile,mapbeg);
         brconfig(thefile,coocon);
         brdirect(thefile,coodir);
         brnumber(thefile,coobeg);
         brnumber(thefile,cooend);
         brconfig(thefile,piecon);
         brdirect(thefile,piedir);
         brnumber(thefile,piebeg);
         brnumber(thefile,pieend);
     end
end;
(* end module book.brpiekey version = 'delmod 6.60 91 Jan
11 tds/gds' *)

(* begin module book.brdna *)
```

- 105 -

```
procedure brdna(var thefile: text; var dna: dnaptr);
(* read in dna from thefile *)
(* note: if the dna were circularized, by linking the last
dnastring
to the first, then the cleardna routine could not clear
properly,
and would loop forever... there is no reason to do that,
since a simple
mod function will allow one to access the circle. *)
var
      ch: char;
      workdna: dnaptr;
begin
      getdna(dna);
      workdna:=dna;
      ch:=getto(thefile,['d']);
```

- 106 -

```
      read(thefile,ch); (* skipstar *)
      while (ch = '*') do
      begin
          read(thefile,ch); (* skip blank *)
          repeat
             read(thefile,ch);
             if ch in ['a','c','g','t'] then begin
                if workdna^.length=dnamax then begin
                   getdna(workdna^.next);
                   workdna:=workdna^.next
                end;
                workdna^.length:=succ(workdna^.length);

workdna^.part[workdna^.length]:=chartobase(ch)
             end
          until eoln(thefile);
          readln(thefile); (* go to next line *)
          read(thefile,ch); (* ch is either '*' or 'd' *)
      end;
      readln(thefile)
end;
(* end module book.brdna version = 'delmod 6.60 91 Jan 11
tds/gds' *)

(* begin module book.brpiece *)
procedure brpiece(var thefile: text; var pie: pieceptr);
(* read in a piece *)
begin
       brpiekey(thefile,pie^.key);
       if numbered or (not skipunnum)
           then brdna(thefile,pie^.dna)
end;
(* end module book.brpiece version = 'delmod 6.60 91 Jan
11 tds/gds' *)

(* begin module book.brinit *)
procedure brinit(var book: text);
```

- 107 -

```
(* check that the book is ok to read, and
   set up the global variables for br routines *)
begin (* brinit *)
      (* halt if the book is bad (first word is 'halt') or
the first
         character is not * *)
      reset(book);
      if not eof(book) then begin
         (* check for the date line *)
         if book^ <> '*' then begin
            if book^ <> 'h'
            then writeln(output, ' this is not the first
line of a book:')
            else writeln(output, ' bad book:');
            write(output, ' ');
```

- 108 -

```
            while not (eoln(book) or eof(book)) do begin
               write(output, book^);
               get(book)
            end;
            writeln(output);
            halt
         end
      end
      else begin
         writeln(output, ' book is empty');
         halt
      end;

(* initialize free storage *)
      freeline:=nil;
      freedna:=nil;

readnumber:=true; (* usually we read in numbers for
items *)
      number:=0; (* arbitrary value *)
      numbered:=false; (* the piece has no number (none
yet read in) *)
      skipunnum:=false;
end; (* brinit *)
(* end module book.brinit version = 'delmod 6.60 91 Jan 11
tds/gds' *)

(*
************************************************************
************** *)
(* end module package.brpiece version = 'delmod 6.60 91
Jan 11 tds/gds' *)

(* begin module book.getpiece *)
procedure getpiece(var thefile: text; var pie: pieceptr);
(* move to and read in the next piece in the book *)
var   ch: char;
```

- 109 -

```
begin
      ch:=getto(thefile,['p']); (* get to the next p(iece)
in the book *)
      if ch<>' ' then begin
         brpiece(thefile,pie);
         ch:=getto(thefile,['p']); (* read past closing p
*)
      end
end;
(* end module book.getpiece version = 'delmod 6.60 91 Jan
11 tds/gds' *)

(*
***********************************************************
************** *)
```

- 110 -

```
(* end module package.getpiece version = 'delmod 6.60 91
Jan 11 tds/gds' *)

(* begin module findblank *)
procedure findblank(var afile: text);
(* read a file to find the next blank character *)
var   ch: char;
begin
      repeat read(afile,ch) until ch = ' '
end;
(* end module findblank version = 'delmod 6.60 91 Jan 11
tds/gds' *)

(* begin module findnonblank *)
procedure findnonblank(var afile: text; var ch: char);
(* find the next non blank character in a file, return it
in ch. *)
begin
      ch:=' ';
      while (not eof(afile)) and
            (ch = ' ')
      do begin
         read(afile,ch);
         if eoln(afile) then readln(afile)
      end
end;
(* end module findnonblank version = 'delmod 6.60 91 Jan
11 tds/gds' *)

(* begin module align.align *)
procedure align(var inst, book: text;
                var pie:  pieceptr;
                var length, alignedbase: integer);
(* documentation on align is in module info.align and
delman.use.aligned.books *)
const maximumrange = 2000; (* if the alignment point is
more than this
```

- 111 -

```
    distance from the piece ends, the program halts in an
attempt to catch
    the alignment bug... 1991 Jan 11 It appears that the
rewrite of the
    code has removed the bug, but the check will be kept.
*)
var
    ch: char; (* a character in inst *)
    comment: boolean; (* true means we are inside a comment
*)
    done: boolean; (* done finding an aligning get *)
    thebase: integer; (* the base read in *)
begin
    if not eof(book) then begin (* if there is still more
to the book ... *)
        getpiece(book,pie); (* read in the piece *)
        if not eof(book) then begin (* if we found a piece
... *)
```

- 112 -

```
        length:=pietoint(pie^.key.pieend,pie); (*
calculate piece length *)

(* now find inst the next occurance of 'get' *)
        done := false;
        while not done do begin
            if eof(inst) then begin (* no instructions? *)
                alignedbase := 1; (* simply align by the
first base *)
                done := true
            end
            else begin
                if inst^ = '(' then begin (* skip comment
*)
                    get(inst);
                    if inst^ = '*' then comment := true;
    {if comment then write(output,'COMMENT: (');}
                    while comment do begin
                        if eof(inst) then begin
                            writeln(output,' in procedure
align:');
                            writeln(output,' an instruction
comment does not end!');
                            halt
                        end;
    {write(output,inst^);}
                        get(inst);
                        if inst^ = '*' then begin
                            get(inst);
    {if inst^ = ')' then writeln(output,'*)');}
                            if inst^ = ')' then comment :=
false
                        end;
                    end;
                end;
                if inst^ = 'g' then begin
                    get(inst);
```

- 113 -

```
                if inst^ = 'e' then begin
                get(inst);
                    if inst^ = 't' then begin
                        get(inst);
                        if inst^ = ' ' then begin
                            findnonblank(inst,ch); (* get
to "from" *)
                            findblank(inst); (* get past
"from" *)
                            read(inst,thebase); (* read in
the alignedbase *)
    {writeln(output,'thebase=',thebase:1);} alignedbase:=pietoint(thebase,pie);
                            done := true
                        end;
                    end;
                end;
            end;
            get(inst); (* move along now *)
```

- 114 -

```
            end;
        end;

if (alignedbase <= -maximumrange) or
           (alignedbase > length + maximumrange) then
begin
            writeln(output,' in procedure align:');
            writeln(output,' read in base was
',thebase:1);
            writeln(output,' in internal coordinates:
',alignedbase:1);
            writeln(output,' maximum range was
',maximumrange:1);
            writeln(output,' piece length was ',length:1);
            with pie^.key.hea.keynam
                do writeln(output,' piece name:
',letters:length);
            writeln(output,' piece number: ',number:1);
            writeln(output,' aligned base is too far
away... see the code');
            halt
          end
      end
   end
end;
(* end module align.align version = 'delmod 6.60 91 Jan 11
tds/gds' *)

(*
***********************************************************
************** *)
(* end module package.align version = 'delmod 6.60 91 Jan
11 tds/gds' *)

(* begin module align.maxminalignment *)
procedure maxminalignment(var inst, book: text;
                          var fromparam, toparam:
```

- 115 -

```
integer);
(* prescan the book to find the range over which the pieces of the
   book are spread, relative to the aligned base.  the procedure uses
   the same variables that align does (so it can call align itself), and
   it returns the range in fromparam and toparam.
 *)
const
      maximumrange = 2000; (* the maximum size aligned piece;
                              this will presumably catch the alignment bug *)
var
      distance: integer; (* a distance to the aligned base *)
      pie: pieceptr;
      length, alignedbase: integer;
begin
      new(pie);
      (* set an initial range for the two bounds *)
```

- 116 -

```
    fromparam:=+maxint;
      toparam:=-maxint;

reset(book);
    reset(inst);
    while not eof(book) do begin
        align(inst,book,pie,length,alignedbase);
        if not eof(book) then begin
            distance:=1-alignedbase;
            if fromparam > distance then
fromparam:=distance;

distance:=length-alignedbase;
            if toparam < distance then toparam:=distance;
            clearpiece(pie)
        end
    end;

if toparam - fromparam > maximumrange then begin
        writeln(output,' in procedure maxminalignment:');
        writeln(output,' fromparameter = ',fromparam:1);
        writeln(output,' toparameter = ',toparam:1);
        writeln(output,' this exceeds the maximum range
allowed (',
                        maximumrange:1,')');
        writeln(output,' see notes in the procedure. ');
        halt
        (* notes:  if you desired this range, increase
'maximumrange'.
            otherwise, this may indicate a bug - either:
            1) locate the bug (and tell tom schneider,
please...)
            2) reduce the size of the fragments, from one
or the other end
                until the bombing is stopped. *)
    end;
```

- 117 -

```
      (* make the book readable again *)
      reset(book);
      reset(inst);
      dispose(pie)
end;
(* end module align.maxminalignment version = 'delmod 6.60
91 Jan 11 tds/gds' *)

(* begin module align.withinalignment *)
function withinalignment(alignedposition, alignedbase,
length: integer)
                        :boolean;
(* this function tells one if an aligned position,
relative to an aligned
   base in a piece of some length is within the piece. *)
var   p: integer;(* the position on the piece *)
begin
```

- 118 -

```
      p := alignedposition + alignedbase;
      withinalignment := (p>0) and (p<=length)
end;
(* end module align.withinalignment version = 'delmod 6.60
91 Jan 11 tds/gds' *)

(* begin module book.getbase *)
function getbase(position: integer; pie: pieceptr):base;
(* get a base from the nth position (internal coordinates)
of the
   piece.  no protection is made against positions outside
the piece *)
var
      workdna: dnaptr;
      p: integer; (* the last base of the dna part *)
begin
      workdna:=pie^.dna;
      p:=dnamax;
      while position>p do begin
         p:=p+dnamax;
         workdna:=workdna^.next
      end;
      getbase:=workdna^.part[position-(p-dnamax)]
end;
(* end module book.getbase version = 'delmod 6.60 91 Jan
11 tds/gds' *)

(*
*************************************************************
************ *)

(* begin module Ri.Riheader *)
procedure Riheader(var infile, book: text; c: char; var
outfile: text);
(* do the header of the plot, using c as the comment
character *)
var
```

- 119 -

```
      index: integer; (* to lines in the infile *)
begin
   reset(infile);
   rewrite(outfile);

writeln(outfile,c,' Ri ',version:4:2);

writeln(outfile,c);
   writeln(outfile,c,' Ri(b,l) table is from:');

(* copy header lines to outfile *)
   for index := 1 to 3 do begin
      write(outfile,c);
      copyaline(infile,outfile);
   end;

writeln(outfile,c);
```

- 120 -

```
   reset(book);
   writeln(outfile,c,' BOOK/INST sequences are from:');
   copyaline(book,outfile);
   write(outfile,c,' ');
   reset(inst);
   if not eof(inst) then copyaline(inst,outfile)
                    else writeln(outfile, '(no
instructions)');
   writeln(outfile,c);
end;
(* end module Ri.Riheader *)

(*
*************************************************************
************ *)
(*
*************************************************************
*********** *)

(* begin module rs.readrsrange *)
procedure readrsrange(var rsdata: text; var r: rstype);
(* read the range data from rsdata to r.  data is assumed
to
be the rsdata file from program rseq. *)
var
   index: integer; (* for counting lines of rsdata *)
   skip: char; (* a character to skip the '*' on the line
*)
begin
     for index := 1 to 11 do readln(rsdata);
     readln(rsdata, skip, r.rstart, r.rstop);
    (*  writeln(output, 'range: ',r.rstart:1,'
',r.rstop:1);*)
end;
(* end module rs.readrsrange version = 4.75; (@ of rsgra.p
1990 Oct 2 *)
```

- 121 -

```
(* begin module rs.getrsbegin *)
procedure getrsbegin(var infile: text);
(* skip to the beginning of the data in a data file from
the rseq program *)
var
      ch: char; (* a character read from infile *)
      begindata: trigger; (* a trigger to locate the
beginning of the data *)
begin
(*                                     1         2   *)
(*                            123456789012345678901 *)
filltrigger(begindata        ,'l    a    c    g    t');

resettrigger(begindata);

reset(infile);
      while not begindata.found do begin
         if eoln(infile) then readln(infile);
         if eof(infile) then begin
            writeln(output,'beginning of data not found');
```

- 122 -

```
            halt;
         end;
         read(infile,ch);
         testfortrigger(ch,begindata);
      end;
      readln(infile);
end;
(* end module rs.getrsbegin version = 4.75; (@ of rsgra.p
1990 Oct 2 *)

(* begin module rs.readrsdata *)
procedure readrsdata(var rsdata: text;.var rdata: rstype);
(* read data from the data file of program rseq into the
datatype *)
begin
   with rdata do begin read(rsdata,l,nal,ncl,ngl,ntl,rsl,rs,varhnb,sumvar,nl,ehnb
);
      (* skip spaces to find the flag: *)
      while rsdata^=' ' do get(rsdata);
      readln(rsdata,flag);
(* writeln(output,'readrsdata: l a c g t flag = ',
l:1,' ',nal:1,' ',ncl:1,' ',ngl:1,' ',ntl:1,' ',flag); *)
   end
end;
(* end module rs.readrsdata version = 4.75; (@ of rsgra.p
1990 Oct 2 *)

(*
*************************************************************
************ *)
(*
*************************************************************
************ *)

(* begin module ri.ricalc *)
```

- 123 -

```
function Ricalc(ehnb: real; nxl, nl: integer;
                niot: integer; Staden: boolean): real;
(* calculate the individual information Ri(b,l) for a base
x having nxl
numbers out of a total of nl numbers total.  Ehnb is 2 -
e(n), where
e(n) is the sampling correction. *)
begin
   if nl <= 0 then begin
      writeln(output,' Ricalc: a position in the data has
less than 1 example!',
                      ' ehnb = ',ehnb:8:5,
                      ' nxl = ',nxl:1,
                      ' nl = ',nl:1);
      halt
   end;
```

- 124 -

```
   if nxl < 1
   then if Staden
        then Ricalc := ln(1/(nl+niot))/ln(2)
        else Ricalc := niot
   else Ricalc := ehnb + ln(nxl/nl)/ln(2);
end;
(* end module ri.ricalc *)

(* begin module skipblanks *)
procedure skipblanks(var thefile: text);
(* skip over blanks until a non-blank, or end of line, is
found *)
begin
      while (thefile^ = ' ') and not eoln(thefile) do
get(thefile);
end;

procedure skipnonblanks(var thefile: text);
(* skip over nonblanks until a blank, or end of line, is
found *)
begin
      while (thefile^ <> ' ') and not eoln(thefile) do
get(thefile);
end;
(* end module skipblanks version = 4.75; (@ of rsgra.p
1990 Oct 2 *)

(* begin module min *)
function min(a, b: real): real;
(* return the minimum of a and b *)
begin
   if a < b then min := a
            else min := b
end;
(* end module min *)

(* begin module max *)
```

- 125 -

```
function max(a, b: real): real;
(* return the maximum of a and b *)
begin
   if a > b then max := a
            else max := b
end;
(* end module max *)

(* begin module ri.writeconsensus *)
procedure writeconsensus(var fout: text;
                             consensus; anticonsensus:
real;
                             thefrom, theto: integer);
(* write the consensus and anticonsensus to the file fout,
for the range from thefrom to theto. *)
begin
```

- 126 -

```
   writeln(fout,' ',consensus:infofield:infodecim,
                   ' bits = Ri of consensus sequence',
                   ' from ',thefrom:1,' to ',theto:1,'
*');
   writeln(fout,' ',anticonsensus:infofield:infodecim,
                   ' bits = Ri of anticonsensus sequence',
                   ' from ',thefrom:1,' to ',theto:1,'
*');
end;
(* end module ri.writeconsensus *)

(* begin module ri.writerandomav *)
procedure writerandomav(var fout: text;
                        data: rstype; Riblmatrix:
rblarray;
                        thefrom, theto: integer);
(* write the average of the response of the matrix to
equiprobable random
sequences to the file fout, for the range from thefrom to
theto. *)
var
   average: real; (* running average *)
   lindex: integer; (* index to Riblmatrix *)
   position: integer; (* a location in the aligned
sequence *)
   sum: real; (* running sum of Ribl for one position *)
   count: integer; (* the number of non-infinite ribl
values at the position *)
procedure addin(lindex: integer; b: base);
(* add the base b to the running sum and increment count
only if the Ri(b,l) value is not negative infinity. *)
begin
   if Riblmatrix[b,lindex] > defnegativeinfinity
   then begin
      count := succ(count);
      sum := sum + Riblmatrix[b,lindex]
   end;
```

- 127 -

```
end;
begin
   average := 0.0;
   for position := data.rstart to data.rstop do begin lindex := position - data.rstart + 1;

sum := 0.0;
      count := 0;
      addin(lindex,a);
      addin(lindex,c);
      addin(lindex,g);
      addin(lindex,t);

if count > 0 then average := average + sum/count
   end;

writeln(fout,' ',average:infofield:infodecim,
                  ' bits = average Ri for random
sequence',
```

- 128 -

```
                          ' from ',thefrom:1,' to ',theto:1,'
*');
end;
(* end module ri.writerandomav *)

(* begin module ri.readparameters *)
procedure readparameters(var rip: text;
                         var thefrom,theto,column:
integer;
                         var lowerRi: real;
                         var upperRi: real;
                         var lowerValue: real;
                         var upperValue: real;
                         var printsequ: boolean;
                         var printxyin: boolean;
                         var partials: char;
                         var niot: integer;
                         var Staden: boolean);
(* read the parameters *)
begin
   reset(rip);

if eof(rip) then begin
      writeln(output,'missing From-To parameters');
      halt
   end;

readln(rip, thefrom, theto);

if eof(rip) then begin
      writeln(output,'missing column parameter');
      halt
   end;

readln(rip, column);
   if column < 1 then begin
      writeln(output,'column parameter must be positive');
```

- 129 -

```
    halt
  end;

if eof(rip) then begin
      writeln(output,'You are missing the Ri bound
parameters');
      halt
  end;

if rip^='a' then begin
     lowerRi := -maxint;
     upperRi := +maxint;
     readln(rip)
  end
  else readln(rip, lowerRi, upperRi);

if eof(rip) then begin
```

- 130 -

```
      writeln(output,'You are missing the Value bound
parameters');
      halt
   end;

if rip^='a' then begin
      lowerValue := -maxint;
      upperValue := +maxint;
      readln(rip)
   end
   else readln(rip, lowerValue, upperValue);

if eof(rip) then begin
      writeln(output,'You are missing the selection
parameter');
      halt
   end;

if rip^ = 'p' then printsequ := true
                 else printsequ := false;
   readln(rip);

if rip^ = 'p' then printxyin := true
                 else printxyin := false;
   readln(rip);

readln(rip, partials);
   if (not (partials = 'n')) and (not (partials = 'i'))
   then partials := '-';

if not eof(rip) then begin
      if rip^ = 's'
      then begin (* Staden's method, read t for niot *)
         Staden := true;
         get(rip);
         readln(rip, niot);
         if niot < 0 then begin
```

- 131 -

```
            writeln(output,'t must be non-negative');
            halt
         end;
      end
      else begin (* read negative infinity for niot *)
         readln(rip, niot);
         Staden := false;
      end
   end
   else begin
      niot := defnegativeinfinity;
      Staden := false
   end;
end;
(* end module ri.readparameters *)
```

```
- 132 -
(* begin module ri.writeparameters *)
procedure writeparameters(var fout: text;
                              thefrom,theto,column: integer;
                              lowerRi: real;
                              upperRi: real;
                              lowerValue: real;
                              upperValue: real;
                              printsequ: boolean;
                              printxyin: boolean;
                              partials: char;
                              niot: integer;
                              Staden: boolean);
(* write the parameters to file fout *)
begin
   writeln(fout,'* PARAMETERS FOR Ri:');
   writeln(fout,'* ', thefrom:1,' ',theto:1,' From-To');
   writeln(fout,'* ',column:1,' column of value file');
   writeln(fout,'* ',lowerRi:infofield:infodecim,
                 ' ', upperRi:infofield:infodecim,
                 ' lowest to highest Ri selected');
   writeln(fout,'* ',lowerValue:infofield:infodecim,
                 ' ', upperValue:infofield:infodecim,
                 ' lowest to highest Value selected');
   write(fout,'* ');
   if not printsequ then write(fout,'not')
                    else write(fout,'   ');
   writeln(fout,' printing sequences to sequ');

write(fout,'* ');
   if not printxyin then write(fout,'not')
                    else write(fout,'   ');
   writeln(fout,' printing sequences to xyin');

write(fout,'* ');
   case partials of
      'n': writeln(fout,'n: no line printed when partial site');
```

- 133 -

```
    'i': writeln(fout,'i: keep line printed when partial
site,',
                       ' but force Ri = -infinity');
    '-': writeln(fout,'-: whole line printed when partial
site');
   end;

write(fout,'* ');
   if Staden then writeln(fout,' using Staden''s Method:
when f(b,l) = 0,',
                             ' replace with f(b,l) =
1/(n+t), t = ',niot:1)
         else writeln(fout,niot:infofield,
                             ' is the value of negative
infinity');

writeln(fout,'* ');
```

- 134 -

```
end;
(* end module ri.writeparameters *)

(* begin module ri.themain *)
procedure themain(var inst, book, rsdata, values, rip,
xyin, sequ, ribl: text);
(* the main procedure of the program *)
var
    anticonsensus: real; (* the value of the anticonsensus
sequence *)
    b: base; (* a base in one of the sites *)
    column: integer; (* column of values file to use *)
    character: char; (* a character of the sequence to
write out *)
    columnindex: integer; (* index for counting columns of
values file *)
    consensus: real; (* the value of the consensus sequence
*)
    data: rstype; (* data from rseq *)
    dontkillpartials: boolean; (* don't kill partial sites
when partials <> n *)
    lengthanalyzed: integer; (* length of region analyzed
by Value(b,l) *)
    lindex: integer; (* index to Riblmatrix, equivalent to
l *)
    ln2: real; (* ln(2) *)
    lowerRi: real; (* lowest Ri to report *)
    lowerValue: real; (* lowest Value to report *)
    mean: real; (* mean of Ritotal = Rsequence *)
    n: integer; (* Ritotal in the selected region *)
    niot: integer; (* negative infinity or t *)
    position: integer; (* a location in the aligned
sequence *)
    partials: char; (* n: no line, i: -infinity, - : keep
anyway *)
    fullsite: boolean; (* true if the site is complete (not
partial) *)
```

- 135 -

```
    printsequ: boolean; (* true if sequences are being
printed to sequ *)
    printxyin: boolean; (* true if sequences are being
printed to xyin *)
    Riblmatrix: rblarray; (* the Ri(b,l) table *)
    Ritotal: real; (* the total of Ri(b,l) for a site *)
    Staden: boolean; (* if true, use Staden's method *)
    stdev: real; (* standard deviation of Ritotal *)
    sumRi: real; (* running sum of Ritotal *)
    sumRi2: real; (* running sum of Ritotal squared *)
    thefrom: integer; (* the from base *)
    theto: integer; (* the to base *)
    upperRi: real; (* highest Ri to report *)
    upperValue: real; (* highest Value to report *)
    value: real; (* a value to compare to ri *)
    valuesfull: boolean; (* true if there are data in the
values file *)
```

- 136 -

```
(* variables used by the align routines: *)
apiece: pieceptr;
length, alignedbase: integer;
fromparam, toparam: integer;

begin
    writeln(output,'Ri ',version:4:2);
    rewrite(xyin);
    writeln(xyin,'* Ri ',version:4:2);
    ln2 := ln(2);
    new(apiece);

(* copy header stuff *)
    brinit(book);
    Riheader(rsdata,book,'*',xyin);
    Riheader(rsdata,book,'*',ribl);

readparameters(rip,thefrom,theto,column,
                   lowerRi,upperRi,
                   lowerValue,upperValue,
                   printsequ,printxyin,partials,
                   niot,staden);
    if printsequ then rewrite(sequ);
    dontkillpartials := (partials <> 'n');

writeparameters(output,thefrom,theto,column,
                    lowerRi,upperRi,
                    lowerValue,upperValue,
                    printsequ,printxyin,partials,
                    niot,staden);
    writeparameters(xyin,thefrom,theto,column,
                    lowerRi,upperRi,
                    lowerValue,upperValue,
                    printsequ,printxyin,partials,
                    niot,staden);
    writeparameters(ribl,thefrom,theto,column,
                    lowerRi,upperRi,
```

- 137 -

```
                lowerValue,upperValue,
                printsequ,printxyin,partials,
                niot,staden);

writeln(xyin,'* Lengths file:');
    reset(values);
    if eof(values)
    then begin
        writeln(xyin,'* empty');
        valuesfull := false;
        value := 0.0; (* this is the value that will be
written out *)
    end
    else begin
        while values^='*' do copyaline(values,xyin);
```

- 138 -

```
      valuesfull := true;
   end;
   writeln(xyin,'*');

(* Obtain the data for and create the Ri(b,l) table *)
   if eof(rsdata) then begin
      writeln(output,'empty rsdata file');
      halt
   end;

(* find the range of the graph in bases *)
   reset(rsdata);
   readrsrange(rsdata,data);
   if data.rstop - data.rstart + 1 > maxribl then begin
      writeln(output,' width of site ',data.rstop -
data.rstart + 1:1,
                     ' exceeds maxribl ',maxribl:1);
      halt
   end;
   getrsbegin(rsdata);

(* prepare the inst and book for reading *)
   maxminalignment(inst, book, fromparam, toparam);

with data do writeln(xyin, '* data are from ',
rstart:1, ' to ', rstop:1);
   writeln(xyin, '* book/inst alignment is from ',
                  fromparam:1, ' to ', toparam:1);
   writeln(xyin,'* Ri analysis is from ',thefrom:1,' to
',theto:1);

with data do begin
      if fromparam > thefrom then begin
         writeln(output, ' Aligned FROM = ',fromparam:1,
                         ' > requested FROM =
',thefrom:1);
         halt
```

- 139 -

```
    end;

if rstart > thefrom then begin
        writeln(output, ' In file rsdata the FROM =
',rstart:1,
                         ' > requested FROM =
',thefrom:1);
        halt
    end;

if toparam < theto then begin
        writeln(output, ' Aligned TO = ',toparam:1,
                         ' > requested TO = ',theto:1);
        halt
    end;

if rstop < theto then begin
        writeln(output, ' In file rsdata the TO =
',rstop:1,
```

- 140 -

```
                     ' > requested TO = ',theto:1);
        halt
      end;
  end;

(* prepare for reading the rsdata *)
  getrsbegin(rsdata);

(* create the Ri(b,l) *)

writeln(ribl,'*',
                  ' ','a':infofield,
                  ' ','c':infofield,
                  ' ','g':infofield,
                  ' ','t':infofield,
                  ' ','l':nfield);
  writeln(ribl,thefrom:nfield,' ',theto:nfield);

consensus := 0.0;
  anticonsensus := 0.0;
  for position := data.rstart to data.rstop do begin
      (* skip lines with an '*' *)
      if rsdata^ <> '*' then begin
          readrsdata(rsdata,data);
          with data do begin
              if position <> l
              then writeln(output, 'Warning: position should
be',
                              ' ',position:1,', but is
actually',
                              ' ',l:1);

if (position >= thefrom) and (position <=
theto) then begin lindex := l - data.rstart;
                  Riblmatrix[a, lindex] :=
```

- 141 -

```
Ricalc(ehnb,nal,nl,niot,Staden);
            Riblmatrix[c, lindex] :=
Ricalc(ehnb,ncl,nl,niot,Staden);
            Riblmatrix[g, lindex] :=
Ricalc(ehnb,ngl,nl,niot,Staden);
            Riblmatrix[t, lindex] :=
Ricalc(ehnb,ntl,nl,niot,Staden);

writeln(ribl,' ',
                           ' ',Riblmatrix[a,
lindex]:infofield:infodecim,
                           ' ',Riblmatrix[c,
lindex]:infofield:infodecim,
                           ' ',Riblmatrix[g,
lindex]:infofield:infodecim,
```

- 142 -

```
                             ' ',Riblmatrix[t,
lindex]:infofield:infodecim,
                             ' ',position:nfield);

consensus := max(
                              max(
                                max(Riblmatrix[a,
lindex],
                                    Riblmatrix[c,
lindex]),
                                Riblmatrix[g,
lindex]),
                              Riblmatrix[t, lindex])
                            + consensus;

anticonsensus := min(
                              min(
                                min(Riblmatrix[a,
lindex],
                                    Riblmatrix[c,
lindex]),
                                Riblmatrix[g,
lindex]),
                              Riblmatrix[t, lindex])
                            + anticonsensus;
            end;
          end;
        end;
    end;

(* Read the book using inst to align the pieces *)

writeln(xyin,'*');
    writeln(xyin,'* Columns:');
    writeln(xyin,'*  1 piece number');
    writeln(xyin,'*  2 piece name');
    writeln(xyin,'*  3 sequence region analyzed (if
```

- 143 -

```
printed, - if not)');
   writeln(xyin,'*  4 length of region analyzed on this
piece ');
   writeln(xyin,'*  5 aligning coordinate on piece');
   writeln(xyin,'*  6 Rindividual for the piece');
   writeln(xyin,'*  7 value from the values file');
   writeln(xyin,'*');

sumRi := 0.0;
   sumRi2 := 0.0;
   n := 0;
   while not eof(book) do begin
       align(inst, book, apiece, length, alignedbase);
       if not eof(book) then begin Ritotal := 0.0;
          fullsite := true; (* innocent till proven guilty!
*)
          for position:=thefrom to theto do begin
              if withinalignment(position, alignedbase,
length) then begin
```

- 144 -

```
            b := getbase(position+alignedbase, apiece);
            lindex := position - data.rstart;
            Ritotal := Ritotal + Riblmatrix[b, lindex];
         end
         else fullsite := false (* proven guilty! *)
      end;

(* obtain values from the values file *)
      if valuesfull then begin
         while values^='*' do readln(values);
         columnindex := 1;
         while columnindex < column do begin
            skipblanks(values);
            skipnonblanks(values);
            columnindex := columnindex + 1
         end;
         if eoln(values) then begin
            writeln(output,'Missing data column ',
                          column:1,' in values
file');
            halt
         end;
         readln(values, value);
      end;

(* primary selection *)
      if (Ritotal >= lowerRi) and (Ritotal <= upperRi)
         and (fullsite or dontkillpartials)
      then begin (* secondary selection *)
         if (value >= lowerValue) and (value <=
upperValue) then begin
            n := n + 1;
            sumRi := sumRI + Ritotal;
            sumRi2 := sumRi2 + Ritotal*Ritotal;
```

- 145 -

```
if numbered
   then write(xyin, ' ', number:6, ' ')
   else write(xyin, ' (no.#) ');

(* name of the piece *)
write(xyin, '
',apiece^.key.hea.keynam.letters);

(* print the sequence and determine length
of analyzed region *)
if printxyin then write(xyin, ' ')
             else write(xyin, ' -');

lengthanalyzed := 0;
for position := thefrom to theto do begin
    if withinalignment(position,
alignedbase, length) then begin
```

- 146 -

```
                character :=
basetochar(getbase(position+alignedbase, apiece));
                if printsequ then
write(sequ,character);
                if printxyin then
write(xyin,character);
                lengthanalyzed := lengthanalyzed + 1;
             end
             else if printxyin then write(xyin, '-');
          end;
          if printsequ then writeln(sequ,'.');

(* length of the sequence analyzed *)
          write(xyin, ' ', lengthanalyzed:nfield);

(* coordinate of aligning base *)
          write(xyin, ' ',
inttopie(alignedbase,apiece):nfield);

(* Ri *)
          if fullsite or (partials <> 'i')
          then write(xyin, '
',Ritotal:infofield:infodecim)
             (* I had niot here, but
defnegativeinifinity is better
             because it assures that partial sites
are removed: *)
             else write(xyin, '
',defnegativeinfinity:infofield);

write(xyin, ' ',
value:infofield:infodecim);

writeln(xyin);
          end;
```

- 147 -

```
    end;

clearpiece(apiece);
      end
    end;

if n = 1
    then writeln(output,'WARNING: ONLY ONE SEQUENCE FOUND
IN BOOK!');

mean := sumRi / n;
    stdev := sqrt(sumRi2/n - (mean*mean));

writeln(ribl,'*');
    write   (ribl,mean:infofield:infodecim);
    writeln(ribl,' bits = mean (Rsequence of selected
region) *');
    write   (ribl,stdev:infofield:infodecim);
    writeln(ribl,' bits = standard deviation *');

writeln(ribl,'*');
```

- 148 -

```
writeconsensus(ribl,consensus,anticonsensus,thefrom,theto)
;

writeln(ribl,'*');
   writerandomav(ribl,data,Riblmatrix,thefrom,theto);
end;
(* end module ri.themain *)

begin
   themain(inst, book, rsdata, values, rip, xyin, sequ, ribl);
1: end.
```

- 149 -

APPENDIX B

```
-10 +10      From-to range to do the evaluation
1            column of the values file to copy to xyin
a 0 1000     lowest to highest Ri to put in xyin and sequ
(a = any)
a -1000 +1000 lowest to highest Value to put in xyin and
sequ (a = any)
n            p means print sequence to the sequ file
p            p means print sequence to the xyin file
-            -: accept all sites; n: no partials; i:
partials -> -infinity
s 1          s: use Staden's Method, f(b,l)=1/(n+t); else
negative infinity rip: parameters for the Ri program, version >= 1.92
```

- 150 -

APPENDIX C

```
program scan(book, ribl, scanp, data, output);
(* scan: scan a book with a wmatrix and generate a vector
     Thomas Schneider
     Not copyrightable module libraries: delman, delmods
*)

label 1;   (* end of program *)

const
(* begin module version *)
version = 1.97; (* of scan.p 1995 May 24
reading ribl instead of histog for mean and st.dev: 1992
sep 8
reading mean and st.dev directly from ri 1992 Sep 6
reading histog for mean and st.dev: 1992 sep 3
Limit portion of the ribl desired for the scan: 1991 May
31
Scan both strands: 1991 March 22
generalize to calculate Berg and von Hippel measure: 1990
Nov 19
generalize to accept weight matrix from Ri: 1990 Sep 26
search T7: 1988 feb 24
origin: 1988 february 24 from parse *)
(* end module version *)

(* begin module describe.scan *)
(*
name
    scan: scan a book with a wmatrix and generate a vector synopsis
    scan(book: in, ribl: in, scanp: in, data: out, output:
```

- 151 - out)

files
   book: a book from the delila system
   ribl: a weight matrix from sites or ri programs.
      Lines that start with * are notes.  the next line contains the matrix
      FROM-TO coordinates, this is followed by the matrix in the order A, C, G,
      T from FROM to TO.
   scanp: parameters to control the program.
      seqs: One integer on the first line is the number of sequences to scan to
      produce the vector.  0 = none, positive = that number; negative = all.

Ri cutoff: One real on the second line is the information content at or
      above which to report in the data file.

Probability cutoff: One real on the third line is the lowest probability

- 152 - which to report in the data file. The probability of a site is determined
    from the mean and standard deviation of the Ri distribution.

range: two integers that define the FROM-TO range of the ribl matrix to
        use.

ways: One integer. 2 means scan both the sequence and its complement.
        1 means simply scan the sequence. 0 means to let the program figure
        it out. The program determines the symmetry of the matrix. If it is
        symmetrical, it will only scan one way. If it is asymmetrical, both
        scans are done.

data: The results. Comments are lines that begin with '*'. The columns are
        defined in comments in the file. The matrix is searched over both the
        sequence and its complement. Ri is reported, as is the Z and probability
        based on the mean and st.dev.
  output: messages to the user description
  The Ri(b,l) weight matrix is scanned across the sequences in the book to
    produce a vector.

examples documentation

- 153 - see also
   sites.p ri.p genhis.p author
   Thomas Dana Schneider bugs technical notes
   The mean and standard deviation of the Ri distribution are stored just
   after the Ri(b,l) table in the ribl file.  They are produced automatically
   by the ri program.

- 154 -

```
*)
(* end module describe.scan *)

(* constants continued *)
(* begin module scan.const *)
   maxribl = 2000; (* largest matrix allowed *)
   infofield = 12; (* size of field for printing
information in bits *)
   infodecim = 6; (* number of decimal places for printing
information *)
        (* these are used for conlist only *)
   nfield = 4; (* size of field for printing n, the number
of sites *)
   countmark = 50; (* how often to report the number of
sequences scanned *)
   bvshow = false; (* if bvshow is true, then the Berg and
von Hippel measure is
        calculated and reported.  It's not as useful as the
individual
        information, so I will keep it off *)
(* end module scan.const *)

(* begin module book.const *)
(* constants needed for book manipulations *)

dnamax = 3000;   (* length of dna arrays *)
        namelength = 20; (* maximum key name length *)
        linelength = 80; (* maximum line readable in book *)

(* end module book.const version = 'delmod 6.54 86 nov 12
tds/gds' *)

type (* begin module book.type *)
(* types needed for book manipulations *)
```

- 155 -

```
    chset = set of 'a'..'z';

(* types defined in book definition *)

alpha = packed array[1..namelength] of char;  (* this
is not alfa *)

(* name is a left justified string with blanks
following the
        characters *)
    name = record
        letters: alpha;
        length: 0..namelength  (* zero means an
unspecified structure *)
    end;
```

- 156 -

```
    lineptr = ^line;
    line = record (* a line of characters *)
       letters: packed array [1..linelength] of char;
       length: 0..linelength;
       next: lineptr
    end;

direction = (plus, minus, dircomplement,
dirhomologous);
    configuration = (linear, circular);
    state = (on, off);

header = record (* header of key *)
       keynam: name; (* key name of structure *)
       fulnam: lineptr; (* full name of structure *)
       note:   lineptr (* note key *)
    end;

(* base types *)
    base = (a,c,g,t);
    dnaptr = ^dnastring;
    dnarange = 0..dnamax;
    seq = packed array[1..dnamax] of base;
    dnastring = record
       part: seq;
       length: dnarange;
       next: dnaptr
    end;

orgkey = record (* organism key *)
       hea: header;
       mapunit: lineptr (* genetic map units *)
    end;
```

```
                         - 157 -
     chrkey = record (* chromosome key *)
        hea: header;
        mapbeg: real; (* number of genetic map beginning
*)
        mapend: real (* number of genetic map ending *)
     end;

pieceptr = ^piece;
     piekey = record (* piece key *)
        hea: header;
        mapbeg: real; (* genetic map beginning *)
        coocon: configuration; (* configruation
(circular/linear) *)
        coodir: direction; (* direction (+/-) relative to
genetic map *)
        coobeg: integer; (* beginning nucleotide *)
        cooend: integer; (* ending nucleotide *)
```

- 158 -

```
      piecon: configuration; (* configruation
(circular/linear) *)
      piedir: direction; (* direction (+/-) relative to
coordinates *)
      piebeg: integer; (* beginning nucleotide *)
      pieend: integer; (* ending nucleotide *)
    end;

piece = record
       key: piekey;
       dna: dnaptr
    end;

reference = record
       pienam : name;   (* name of piece referred to *)
       mapbeg : real;   (* genetic map beginning *)
       refdir : direction;  (* direction relative to
coordinates *)
       refbeg : integer;   (* beginning nucleotide *)
       refend : integer;   (* ending nucleotide *)
    end;

genkey = record   (* gene key *)
       hea : header;
       ref : reference;
    end;

trakey = record   (* transcript key *)
       hea : header;
       ref : reference;
    end;

markerptr = ^marker;
    markey = record (* marker key *)
       hea : header;
       ref : reference;
```

```
            sta : state;
            phenotype : lineptr;
            next : markerptr;
        end;

marker = record
            key : markey;
            dna : dnaptr;
        end;

(* end module book.type version = 2.11; (@ of ri.p 1995
May 24 *)

(* begin module scan.type *)
    rblarray = array[a..t, 0..maxribl] of real; (*
real(B,L) *)
(* end module scan.type version = 2.11; (@ of ri.p 1995
May 24 *)
```

- 160 -

```
var
(* begin module book.var *)
(*
***********************************************************
************** *)
(* global variables needed for book manipulations *)

(* free storage: *)
      freeline: lineptr; (* unused lines *)
      freedna: dnaptr; (* unused dnas *)

readnumber: boolean; (* whether to read a number
from the notes, or
                              to read in the notes *)
      number: integer; (* the number of the item just read
*)
      numbered: boolean; (* true when the item just read
is numbered *)
      skipunnum: boolean; (* a control variable to allow
skipping of
                              un-numbered items in the book
*)

(*
***********************************************************
************** *)
(* end module book.var version = 2.11; (@ of ri.p 1995 May
24 *)

book,  (* a book from the sequence library *)
      ribl,  (* weight matrix *)
      scanp, (* program parameters *)
      data: text;  (* result of the scan *)

(* begin module package.primitive *)
(*
***********************************************************
```

- 161 -

```
************** *)
(* begin module halt *)
procedure halt;
(* stop the program.  the procedure performs a goto to the end of the
   program.  you must have a label:
      label 1;
   declared, and also the end of the program must have this label:
      1: end.
   examples are in the module libraries.
   this is the only goto in the delila system. *)
begin
      writeln(output,' program halt.');
      goto 1
end;
(* end module halt version = 'delmod 6.54 86 nov 12 tds/gds' *)
```

- 162 -

```
(* begin module copyaline *)
procedure copyaline(var fin, fout: text);
(* copy a line from file fin to file fout *)
begin (* copyaline *)
      while not eoln(fin) do begin
         fout^ := fin^;
         put(fout);
         get(fin)
      end;
      readln(fin);
      writeln(fout);
end; (* copyaline *)
(* end module copyaline version = 'delmod 6.54 86 nov 12
tds/gds' *)

(* begin module copylines *)
function copylines(var fin, fout: text; n: integer):
integer;
(* copy n lines of file fin to file fout.
the actual number of lines copied is returned. *)
var
      index: integer; (* the current line number *)
begin (* copylines *)
      index := 0;
      while (not eof(fin)) and (index < n) do begin
         copyaline(fin, fout);
         index := succ(index)
      end;

copylines := index
end; (* copylines *)
(* end module copylines version = 'delmod 6.54 86 nov 12
tds/gds' *)

(*
***********************************************************
************** *)
```

- 163 -

```
(* end module package.primitive version = 'delmod 6.54 86
nov 12 tds/gds' *)

(* begin module missparam *)
procedure missparam(var param: text);
(* look at param to see if the next parameter is missing
this is useful when reading in a series of parameters.
use it
just before readln of each parameter.*)
begin (* missparam *)
      if eof(param) then begin
          writeln(output,' missing parameter');
          halt
      end
end; (* missparam *)
(* end module missparam version = 'delmod 6.54 86 nov 12
tds/gds' *)
```

- 164 -

```
(* begin module package.getpiece *)
(*
*************************************************************
************** *)
(* begin module package.brpiece *)
(*
*************************************************************
************** *)
(* begin module book.basis *)
(* procedures needed for book manipulations *)

(* get procedures should be used for all linked lists of
records *)

procedure getline(var l: lineptr);
(* obtain a line from the free line list or by making a
new one *)
begin
      if freeline<>nil
         then begin
              l:=freeline;
              freeline:=freeline^.next
           end
           else new(l);
      l^.length:=0;
      l^.next:=nil
end;

procedure getdna(var l: dnaptr);
begin
      if freedna<>nil
         then begin
              l:=freedna;
              freedna:=freedna^.next
           end
           else new(l);
      l^.length:=0;
```

- 165 -

```
      l^.next:=nil
end;

(* clear procedures should be called each time the records
are no longer needed
        failure to do this may result in a stack
overflow. *)

procedure clearline(var l: lineptr);
(* return a line to the free line list *)
var   lptr: lineptr;
begin
      if l<>nil then begin
          lptr:=l;
          l:=l^.next;
          lptr^.next:=freeline;
```

- 166 -

```
            freeline:=lptr
        end
end;

procedure cleardna(var l: dnaptr);
var    lptr: dnaptr;
begin
        if l<>nil then begin
            lptr:=l;
            l:=l^.next;
            lptr^.next:=freedna;
            freedna:=lptr
        end
end;

procedure clearheader(var h: header);
(* clear the header h (remove lines to free storage) *)
begin
        with h do begin
            clearline(fulnam);
            while note<>nil do clearline(note)
        end
end;

procedure clearpiece(var p: pieceptr);
(* clear the dna of the piece *)
begin
        while p^.dna<>nil do cleardna(p^.dna);
        clearheader(p^.key.hea)
end;

function chartobase(ch:char):base;
(* convert a character into a base *)
begin
        case ch of
            'a': chartobase:=a;
            'c': chartobase:=c;
```

- 167 -

```
            'g': chartobase:=g;
            't': chartobase:=t
        end
end;

function basetochar(ba:base):char;
(* convert a base into a character *)
begin
        case ba of
            a: basetochar:='a';
            c: basetochar:='c';
            g: basetochar:='g';
            t: basetochar:='t';
        end
end;
```

- 168 -

```
function complement(ba:base):base;
(* take the complement of ba *)
begin
      case ba of
          a: complement:=t;
          c: complement:=g;
          g: complement:=c;
          t: complement:=a;
      end
end;

function pietoint(p: integer; pie: pieceptr): integer;
(* p is a coordinate on the piece.
   we want to transform p into a number
   from 1 to n: an internal coordinate system for
   easy manipulation of piece coordinates *)
var   i: integer; (* an intermediate value *)
begin
      with pie^.key do begin
          case piedir of
              plus:  if p>=piebeg
                       then i:=p-piebeg+1
                       else i:=(p-coobeg)+(cooend-piebeg)+2;
              minus: if p<=piebeg
                       then i:=piebeg-p+1
                       else i:=(cooend-p)+(piebeg-coobeg)+2
          end;
          pietoint:=i
      end
end;

function inttopie(i: integer; pie: pieceptr):integer;
(* i is in the range 1 to some maximum.  it is an internal
coordinate
   system for the program.  we want to do a
   coordinate transformation to obtain
   a value in the range of the piece called pie:
```

- 169 -

```
    i=1 corresponds to piebeg and
    i=its maximum corresponds to pieend *)
var    p: integer; (* an intermediate value *)
begin
     with pie^.key do begin
        case piedir of
           plus: begin
              p:=piebeg+(i-1);
              if p>cooend
                 then if coocon=circular
                    then p:=p-(cooend-coobeg+1)
           end;
           minus: begin
              p:=piebeg-(i-1);
              if p<coobeg
```

- 170 -

```
                    then if coocon=circular
                        then p:=p+(cooend-coobeg+1)
              end
           end;
           inttopie:=p
      end
end;

function piecelength(pie: pieceptr): integer;
(* return the length of the dna in pie *)
begin
      piecelength:=pietoint(pie^.key.pieend,pie)
end;

(* end module book.basis version = 'delmod 6.54 86 nov 12
tds/gds' *)

(* begin module book.getto *)
function getto(var thefile: text; ch: chset): char;
(* search the file for a character in the first line which
is a
   member of the set ch. *)
var achar: char;
begin
      achar:=' ';
      while (not(achar in ch)) and (not eof(thefile))
          do readln(thefile,achar);
      if (achar in ch) then getto:=achar
                       else getto:=' '
end;
(* end module book.getto version = 'delmod 6.54 86 nov 12
tds/gds' *)

(* begin module book.skipstar *)
procedure skipstar(var thefile:text);
(* skip start of line (or star = '*'). *)
begin (* skipstar *)
```

- 171 -

```
    if thefile^ <> '*' then begin
        writeln(output,' procedure skipstar: bad book');
        writeln(output,' "*" expected as first character
on the line, but "',
                        thefile^,'" was found');
        halt
    end;
    get(thefile); (* skip the star *)

if thefile^ <> ' ' then begin
        writeln(output,' procedure skipstar: bad book');
        writeln(output,' "* " expected on a line but "*',
                        thefile^,'" was found');
        halt
    end;
    get(thefile) (* skip the blank *)
```

- 172 -

```
end; (* skipstar *)
(* end module book.skipstar version = 'delmod 6.54 86 nov
12 tds/gds' *)

(* begin module book.brreanum *)
procedure brreanum(var thefile: text; var reanum: real);
(* read a real number from the file *)
begin
      skipstar(thefile);
      readln(thefile,reanum);
end;
(* end module book.brreanum version = 'delmod 6.54 86 nov
12 tds/gds' *)

(* begin module book.brnumber *)
procedure brnumber(var thefile: text; var num: integer);
(* read a number from the file *)
begin
      skipstar(thefile);
      readln(thefile,num)
end;
(* end module book.brnumber version = 'delmod 6.54 86 nov
12 tds/gds' *)

(* begin module book.brname *)
procedure brname(var thefile: text; var nam: name);
(* read a name from the file *)
var   i: integer; (* an index to the name *)
      c: char; (* a character read *)
begin (* brname *)
      skipstar(thefile);
      with nam do begin
         length:=0;
         repeat
            length:=succ(length);
            read(thefile,c);
            letters[length] := c
```

- 173 -

```
        until (eoln(thefile)) or
              (length>=namelength) or
              (letters[length]=' ');
        if letters[length]=' ' then length:=length-1;
        if length<namelength
           then for i:=length+1 to namelength do
letters[i]:=' '
      end;
      readln(thefile)
end; (* brname *)
(* end module book.brname version = 'delmod 6.54 86 nov 12
tds/gds' *)

(* begin module book.brline *)
procedure brline(var thefile: text; var l: lineptr);
(* read a line from the file *)
```

- 174 -

```
var
      i,j: integer;
      acharacter: char;
begin
      skipstar(thefile);
      i:=0;
      while (not eoln(thefile)) do begin
         i:=succ(i);
         read(thefile,acharacter);
         l^.letters[i]:=acharacter
      end;
      if i<l^.length then for j:=i+1 to l^.length do
l^.letters[j]:=' ';
      l^.length:=i;
      l^.next:=nil;
      readln(thefile)
end;
(* end module book.brline version = 'delmod 6.54 86 nov 12
tds/gds' *)

(* begin module book.brdirect *)
procedure brdirect(var thefile: text; var direct:
direction);
(* read a direction *)
var   ch: char;
begin
      skipstar(thefile);
      readln(thefile,ch);
      if ch='+' then direct:=plus
                else direct:=minus
end;
(* end module book.brdirect version = 'delmod 6.54 86 nov
12 tds/gds' *)

(* begin module book.brconfig *)
procedure brconfig(var thefile: text; var config:
configuration);
```

- 175 -

```
(* read a configuration *)
var   ch: char;
begin
      skipstar(thefile);
      readln(thefile,ch);
      if ch='l' then config:=linear
                else config:=circular
end;
```
(* end module book.brconfig version = 'delmod 6.54 86 nov 12 tds/gds' *)

(* begin module book.brnotenumber *)
procedure brnotenumber(var thefile: text; var note: lineptr);
(* book note reading to obtain the number of the object. the procedure returns the value of the number as a global. (this is not such a good practice, but we are stuck with it for now.) *)

- 176 -

```
begin (* brnotenumber *)
      note:=nil;
      numbered := false;
      number := 0; (* force number to zero if there
          is no number at all *)
      (* the next character is n or * depending on whether
there are notes *)
      if thefile^ = 'n' then begin
          readln(thefile);
          if thefile^ <> 'n' then begin
              skipstar(thefile);
              if not eoln(thefile) then begin
                  if thefile^ = '#' then begin
                      numbered := true;
                      get(thefile); (* move past the number
symbol *)
                      read(thefile,number);
                  end
              end;
              repeat
                  readln(thefile)
              until thefile^ = 'n';
              readln(thefile)
          end
          else readln(thefile)
      end
end; (* brnotenumber *)
(* end module book.brnotenumber version = 'delmod 6.54 86
nov 12 tds/gds' *)

(* begin module book.brnote *)
procedure brnote(var thefile: text; var note: lineptr);
(* read note key *)
var
      newnote: lineptr; (* the new note *)
      previousnote: lineptr; (* the last line of the notes
*)
```

- 177 -

```
begin (* brnote *)
      note:=nil;
      if thefile^ = 'n' then begin (* enter note *)
         readln(thefile);
         if thefile^ <> 'n' then begin (* abort null note
(n/n) *)
            getline(note);
            newnote:=note;
            while thefile^ <> 'n' do begin (* wait until
end of note *)
               brline(thefile,newnote);
               previousnote:=newnote;
               (* get next note *)
               getline(newnote^.next);
               newnote:=newnote^.next;
            end;
            (* last note was not used, so: *)
```

- 178 -

```
            clearline(newnote);
            previousnote^.next:=nil;
            readln(thefile)
         end
         else readln(thefile)
      end
end; (* brnote *)
(* end module book.brnote version = 'delmod 6.54 86 nov 12
tds/gds' *)

(* begin module book.brheader *)
procedure brheader(var thefile: text; var hea: header);
(* read the header of a key. *)
begin
      with hea do begin
         (* read key name *)
         brname(thefile,keynam);

(* read full name *)
         getline(fulnam);
         brline(thefile,fulnam);

(* read note key *)
         if readnumber then brnotenumber(thefile,note)
                       else brnote(thefile,note)
      end
end;
(* end module book.brheader version = 'delmod 6.54 86 nov
12 tds/gds' *)

(* begin module book.brpiekey *)
procedure brpiekey(var thefile: text; var pie: piekey);
(* read piece key *)
begin
      with pie do begin
         brheader(thefile,hea);
         brreanum(thefile,mapbeg);
```

- 179 -

```
        brconfig(thefile,coocon);
        brdirect(thefile,coodir);
        brnumber(thefile,coobeg);
        brnumber(thefile,cooend);
        brconfig(thefile,piecon);
        brdirect(thefile,piedir);
        brnumber(thefile,piebeg);
        brnumber(thefile,pieend);
    end
end;
(* end module book.brpiekey version = !delmod 6.54 86 nov
12 tds/gds' *)

(* begin module book.brdna *)
procedure brdna(var thefile: text; var dna: dnaptr);
```

- 180 -

```
(* read in dna from thefile *)
(* note: if the dna were circularized, by linking the last dnastring
to the first, then the cleardna routine could not clear properly,
and would loop forever... there is no reason to do that, since a simple
mod function will allow one to access the circle. *)
var
      ch: char;
      workdna: dnaptr;
begin
      getdna(dna);
      workdna:=dna;
      ch:=getto(thefile,['d']);
      read(thefile,ch); (* skipstar *)
      while (ch = '*') do
      begin
         read(thefile,ch); (* skip blank *)
         repeat
            read(thefile,ch);
            if ch in ['a','c','g','t'] then begin
               if workdna^.length=dnamax then begin
                  getdna(workdna^.next);
                  workdna:=workdna^.next
               end;
               workdna^.length:=succ(workdna^.length);
               workdna^.part[workdna^.length]:=chartobase(ch)
            end
         until eoln(thefile);
         readln(thefile); (* go to next line *)
         read(thefile,ch); (* ch is either '*' or 'd' *)
      end;
      readln(thefile)
end;
(* end module book.brdna version = 'delmod 6.54 86 nov 12
```

```
tds/gds' *)

(* begin module book.brpiece *)
procedure brpiece(var thefile: text; var pie: pieceptr);
(* read in a piece *)
begin
      brpiekey(thefile,pie^.key);
      if numbered or (not skipunnum)
          then brdna(thefile,pie^.dna)
end;
(* end module book.brpiece version = 'delmod 6.54 86 nov
12 tds/gds' *)

(* begin module book.brinit *)
procedure brinit(var book: text);
(* check that the book is ok to read, and
   set up the global variables for br routines *)
```

- 182 -

```
begin (* brinit *)
      (* halt if the book is bad (first word is 'halt') or
the first
         character is not * *)
      reset(book);
      if not eof(book) then begin
         (* check for the date line *)
         if book^ <> '*' then begin
            if book^ <> 'h'
            then writeln(output, ' this is not the first
line of a book:')
            else writeln(output, ' bad book:');
            write(output, ' ');

while not (eoln(book) or eof(book)) do begin
               write(output, book^);
               get(book)
            end;
            writeln(output);
            halt
         end
      end
      else begin
         writeln(output, ' book is empty');
         halt
      end;

(* initialize free storage *)
      freeline:=nil;
      freedna:=nil;

readnumber:=true; (* usually we read in numbers for
items *)
      number:=0; (* arbitrary value *)
      numbered:=false; (* the piece has no number (none
yet read in) *)
      skipunnum:=false;
```

- 183 -

```
end; (* brinit *)
(* end module book.brinit version = 'delmod 6.54 86 nov 12
tds/gds' *)

(*
*************************************************************
************** *)
(* end module package.brpiece version = 'delmod 6.54 86
nov 12 tds/gds' *)

(* begin module book.getpiece *)
procedure getpiece(var thefile: text; var pie: pieceptr);
(* move to and read in the next piece in the book *)
var   ch: char;
begin
```

- 184 -

```
      ch:=getto(thefile,['p']); (* get to the next p(iece)
in the book *)
      if ch<>' ' then begin
         brpiece(thefile,pie);
         ch:=getto(thefile,['p']); (* read past closing p
*)
      end
end;
(* end module book.getpiece version = 'delmod 6.54 86 nov
12 tds/gds' *)

(*
************************************************************
************** *)
(* end module package.getpiece version = 'delmod 6.54 86
nov 12 tds/gds' *)

(* begin module book.getbase *)
function getbase(position: integer; pie: pieceptr):base;
(* get a base from the nth position (internal coordinates)
of the
   piece.  no protection is made against positions outside
the piece *)
var
      workdna: dnaptr;
      p: integer; (* the last base of the dna part *)
begin
      workdna:=pie^.dna;
      p:=dnamax;
      while position>p do begin
         p:=p+dnamax;
         workdna:=workdna^.next
      end;
      getbase:=workdna^.part[position-(p-dnamax)]
end;
(* end module book.getbase version = 2.11; (@ of ri.p 1995
May 24 *)
```

- 185 -

```
(* begin module scan.readparameters *)
procedure readparameters(var scanp: text;
                         var todo: integer;
                         var cutoffRi: real;
                         var cutoffP: real;
                         var fromwanted, towanted: integer;
                         var ways: integer);
(* read from the scanp file the parameters *)
begin
   reset(scanp);

todo := maxint; (* do all sequences *)
   cutoffRi := -maxint; (* do all sequences *)
   cutoffP := 0; (* do all sequences *)
   fromwanted := -maxint;
   towanted := +maxint;
```

- 186 -

```
   ways := 2;

if not eof(scanp) then begin
      readln(scanp,todo);
      if todo < 0 then todo := maxint;

readln(scanp, cutoffRi);
      readln(scanp, cutoffP);
      readln(scanp, fromwanted, towanted);
      readln(scanp, ways)
   end;

end;
(* end module scan.readparameters *)

(* begin module scan.getmatrix *)
procedure getmatrix(var afile: text; var matrix: rblarray;
                    var frombase, tobase: integer;
                    var fromwanted, towanted: integer;
                    var mean, stdev: real);
(* get the matrix from a file, with the defining
coordinate limits,
followed by the mean and standard deviation *)
var
   b: base; (* a base in the matrix *).
   l: integer; (* a coordinate in the matrix *)
begin
   reset(afile);
   while afile^='*' do readln(afile); (* skip the header
*)
   readln(afile,frombase,tobase);

if fromwanted < frombase then begin
      writeln(output,'Warning: from region is reset from
',fromwanted:1,
                     ' to the edge of the matrix at ',
frombase:1);
```

- 187 -

```
    fromwanted := frombase;
  end;

if towanted > tobase then begin
    writeln(output,'Warning: to region is reset from
',towanted:1,
                   ' to the edge of the matrix at ',
tobase:1);
    towanted := tobase;
  end;

if towanted-fromwanted+1 > maxribl then begin
    writeln(output,'The matrix is too big:');
    writeln(output,'increase constant maxribl');
    writeln(output,'or reduce the requested from - to
range in scanp');
    halt
```

- 188 -

```
end;

(* skip unneeded matrix material *)
for l := frombase to fromwanted - 1 do readln(afile);

for l := 1 to towanted-fromwanted+1 do begin
   for b := a to t do read(afile,matrix[b,l]);
   readln(afile)
end;

(* skip unneeded matrix material *)
for l := towanted + 1 to tobase do readln(afile);

while afile^='*' do readln(afile);
readln(afile,mean);
while afile^='*' do readln(afile);
readln(afile,stdev);
{
writeln(output,'values read:');
writeln(output,mean:10:2);
writeln(output,stdev:10:2);
} end;
(* end module scan.getmatrix *)

(* begin module scan.matrixsymmetry *)
function matrixsymmetry(matrix: rblarray;
                        fromwanted, towanted: integer):
boolean;
(* determine if the matrix has a dyad axis of symmetry *)
var
   b: base; (* a base in the matrix *)
   l: integer; (* a coordinate in the matrix *)
   length: integer; (* length of the used part of the
matrix *)
   symmetric: boolean; (* true if no violation of matrix
```

- 189 -

```
      symmetry has been found yet *)
begin
   symmetric := true;
   length := towanted-fromwanted+1;
   for l := 1 to length do begin
      for b := a to t do begin
         if matrix[b,l] <> matrix[complement(b),length - l
+ 1]
         then symmetric := false;
{
write(output, matrix[b,l]:5:2,' ');
write(output, matrix[complement(b),length - l + 1]:5:2,'
');
writeln(output,symmetric)
}
      end;
   end;
   matrixsymmetry := symmetric
end;
```

- 190 -

```
(* end module scan.matrixsymmetry *)

(* begin module simpson *)
procedure simpson(upper : real; var answer,tol : real);
(* Perform a numerical integration of the Gaussian
distribution using Simpson's
   rule.  The variable upper is the z value, the number of
standard deviations
   from the mean.  Written by Mark Shaner, 1992   *)
var
  i  (* a counter *): integer;
  x,x1,x2, (* the independent variables for calculating
the value of functions
          *)

pi, (* the value of pi *)
  val, (* the value of 1/sqrt(2*pi), it is used in
calculating the value of the
       gaussian for any x value, and is defined as a
variable in order to
       speed calculations. *)
  deltax, (* the distance between every x value and the
subsequent one *)
  evensum, (* the sum of the area under each of the even
numbered parabolas *)
  oddsum, (* the sum of the area under each of the odd
numbered parabolas *)
  endsum, (* the sum of the area under the first and last
parabolas *)
  endcor, (* the value of the end correction, it is
determined using dgauss *)
  sum1 : real; (* a place to store the previous sum so
that it can be compared
          with the subsequent sum to determine if the
tolerance level has
          been reached *)
  pieces : integer; (* the number of parabolas under the
```

- 191 -

```
curve *)
  lower, (* the lower bound of the integration *)
  sum :real; (* the value of the area under the curve *)

begin
  pi := 4.0*arctan(1.0);
  val := 1/sqrt (2*pi);
  (* activate both files to be used *)
  lower := 0;
  upper := abs(upper);
  tol := 1/maxint;
  pieces := 2;
  deltax := (upper-lower)/pieces;
  x := lower + deltax;
  oddsum := val*exp(-0.5*x*x);
  evensum := 0.0;
```

- 192 -

```
  x1 := lower;
  x2 := upper;
  endsum := val*exp(-0.5*x1*x1) + val*exp(-0.5*x2*x2);
  endcor := -(x1*val)*exp(-0.5*x1*x1) -
(-(x2*val)*exp(-0.5*x2*x2));
  sum := (endsum + 4.0*oddsum)*deltax/3.0;

repeat
    pieces := pieces*2;
    sum1 := sum;
    deltax := (upper - lower)/pieces;
    evensum := evensum + oddsum;
    oddsum := 0.0;
    for i := 1 to (pieces div 2) do
    begin
      x := lower + deltax*(2.0*i-1.0);
      oddsum := oddsum + val*exp(-0.5*x*x)
    end;
    sum := (7.0*endsum + 14.0*evensum + 16.0*oddsum +
endcor*deltax)
          *deltax/15.0;
  until abs(sum-sum1) <= abs(tol*sum);
  answer := (0.5 - sum);
  if answer < 0.0 then answer := 0.0; (* safety for
roundoff errors *)
(*
  writeln (upper:7:5,'       ',answer:7:5,'+/-',tol)
*)
end;
(* end module simpson *)

(* begin module scan.scansequence *)
procedure scansequence(var list: text;
                          riblmatrix: rblarray;
                          frombase,tobase: integer;
                          apiece: pieceptr;
                          cutoffRi: real;
```

- 193 -

```
                                cutoffP: real;
                      var sites, positionsevaluated: integer;
                                bothways: boolean;
                                mean, stdev: real);
(* scan the sequence apiece with the riblmatrix (which runs from frombase to
tobase) and put the results to list.  Don't report sites below the cutoff Ri or
cuttoff probability P.  Report the number of sites and the number of positions
evaluated.  Scan the complementary strand at the same time if bothways is
true.  The routine is written to be reasonably fast, so it uses several
'parameters' which are precalculated. *)
```

- 194 -

```
var
   b: base; (* the base at position 1 *)
   i: integer; (* internal coodinates for a piece *)
   l: integer; (* standard coordinate of the base around
aligned point *)
   p: real; (* probability of result *)
   parameter1: integer; (* for calculating coordinate of
the base
                                in the matrix *)
   parameter2: integer; (* for calculating coordinate of
the base
                                in the matrix *)
   parameter3: integer; (* for calculating coordinate
shift of the zero base
       upon matrix inversion.  Recall that -from <> +to, so
when the matrix is
       reversed, the point being evaluated shifts by this
amount. *)
   Ri: real; (* the value of the riblmatrix applied to the
sequence at i *)
   Ric: real; (* Same as Ri, but for the complementary
orientation *)
   tol: real; (* tolerance in the resulting p *)
   z: real; (* z value of Ri with respect to mean and st.
dev. *)

procedure writeitout(Ri: real; i: integer; orientation:
integer);
(* write an Ri evalutation at coordinate i out if it
passes the criterion.
specify the orientation *)
begin (* Z - take absolute value now before the if statement
for simplicity *)
   z := (Ri-mean)/stdev;
```

- 195 -

```
    (* probability *)
    if (abs(z) > 0) and (abs(z) < 9) then simpson(abs(z),
p, tol)
                                       else p := 0.0;

if (Ri >= cutoffRi) and (p >= cutoffP)   then begin
       sites := sites + 1;

if numbered
       then write(list, ' ', number:nfield, ' ')
       else write(list, ' (no.#) ');

(* length of the sequence *)
       write(list, ' ', piecelength(apiece):nfield);

(* name of the piece *)
       write(list, ' ',apiece^.key.hea.keynam.letters);

(* coordinate of the evaluation *)
       write(list,' ',inttopie(i, apiece):nfield);
```

- 196 -

```
      (* orientation of the matrix *)
      write(list,' ',orientation:nfield);

(* the evaluation *)
      write(list,' ',Ri:infofield:infodecim);

write(list,' ',z:infofield:infodecim);

write(list,' ',p:infofield:infodecim);

writeln(list);
   end;
end;
begin (* scansequence *)
   sites := 0;
   parameter1 := 1-frombase;
   parameter2 := tobase+1;
   parameter3 := frombase+tobase;
   for i := -frombase+1 to piecelength(apiece)-tobase do
begin
      Ri := 0.0;
      if bothways then Ric := 0.0;
      for l := frombase to tobase do begin
         (* do the sequence *)
         b := getbase(i + l, apiece);
         Ri := Ri + riblmatrix[b, l + parameter1];

(* do the complement *)
         if bothways
         then Ric := Ric + riblmatrix[complement(b),
parameter2 - l];
      end;
      writeitout(Ri,i,+1);
      if bothways then writeitout(Ric,i+parameter3,-1);
   end;

(* To calculate the positions evaluated, we find the
```

- 197 -

```
region of the sequence
      which is used:
         positionsevaluated :=
(piecelength(apiece)-tobase) - (-frombase+1) + 1;
      but this can be simplified: *)
   positionsevaluated := piecelength(apiece) - tobase +
frombase;
   if positionsevaluated < 0 then positionsevaluated := 0;
end; (* scansequence *)
(* end module scan.scansequence *)

(* begin module scan.themain *)
procedure themain(var book, wmatrix, scanp, data: text);
(* the main procedure *)
var
   apiece: pieceptr; (* a piece of DNA *)
   count: integer; (* number of sequences done so far *)
```

- 198 -

```
    cutoffRi: real; (* lowest Ri value to print to data
file *)
    cutoffP: real; (* lowest probability print to data file
*)
    frombase, tobase: integer; (* the coordinates of w *)
    fromwanted, towanted: integer; (* region of w to use
for the scan *)
    mean: real; (* mean of Ri *)
    oneway: boolean; (* scan the sequences and not there
complements *)
    positionsevaluated: integer; (* positions evaluated in
the piece *)
    sites: integer; (* number of sites found in the piece
*)
    stdev: real; (* standard deviation of Ri *)
    todo: integer; (* number of sequences to do *)
    totalpositionsevaluated: integer; (* positions
evaluated in the book *)
    totalsites: integer; (* number of sites found in the
book *)
    riblmatrix: rblarray; (* the weight matrix, Ri(b,l) *)
    ways: integer; (* 0 = program figures it out, 1 = scan
sequence as is, 2 =
        scan sequence and complement *)
procedure tellsymmetry(var f: text; oneway: boolean; ways:
integer);
(* tell the directions of the scan to file f *)
begin
    if oneway
    then begin
        writeln(f,'* The sequences in the book will be
scanned one way');
        if ways = 0
        then writeln(f,'* since the matrix is symmetric')
        else writeln(f,'* because you asked me to!');
    end
    else begin
```

- 199 -

```
      writeln(f,'* Scanning Both the sequences and their',
                 ' complements in the book');
      if ways = 0
      then writeln(f,'* since the matrix is asymmetric')
      else writeln(f,'* because you asked me to!');
   end;
   writeln(f,'*');
end;
begin
   writeln(output, 'scan ',version:4:2);

readparameters(scanp,todo,cutoffRi,cutoffP,fromwanted,towanted,ways);

(* initialize the variables *)
   reset(wmatrix);
   getmatrix(wmatrix, riblmatrix, frombase, tobase, fromwanted, towanted,
```

- 200 -

```
         mean, stdev);

rewrite(data);
   writeln(data, '* scan ',version:4:2);
   writeln(data, '* with matrix from:');
   writeln(data,
'**********************************************************
**');
   reset(wmatrix);
   while wmatrix^='*' do copyaline(wmatrix,data); (* copy
the header *)
   writeln(data,
'**********************************************************
**');
   writeln(data,'* scan matrix is FROM = ',frombase:1,',
TO = ',tobase:1);
   writeln(data,'* region used for the scan is FROM = ',
                 fromwanted:1,', TO = ',towanted:1);

writeln(data, '* Scan of book:');
   reset(book);
   copyaline(book,data);

writeln(data,'*  mean = ',mean:infofield:infodecim);
   writeln(data,'* stdev = ',stdev:infofield:infodecim);
   writeln(output,'*  mean = ',mean:infofield:infodecim);
   writeln(output,'* stdev = ',stdev:infofield:infodecim);

brinit(book);
   new(apiece);

writeln(output,'count of the sequences scanned (every
',countmark:1,'):');
   count := 0;

writeln(data,'*');
   writeln(data,'* lowest   Ri cutoff =
```

- 201 -

```
',cutoffRi:infofield:infodecim);
   writeln(data,'* lowest probability = ',cutoffP
:infofield:infodecim);

case ways of
      0: oneway := matrixsymmetry(riblmatrix, fromwanted,
towanted);
      1: oneway := true;
      2: oneway := false;
   end;
   tellsymmetry(output,oneway,ways);
   tellsymmetry(data,oneway,ways);

writeln(data,'* DEFINITION OF THE DATA COLUMNS:');
   writeln(data,'* 1 piece number');
   writeln(data,'* 2 piece length');
   writeln(data,'* 3 piece name');
```

- 202 -

```
   writeln(data,'* 4 piece coordinate');
   writeln(data,'* 5 matrix orientation (+1 = as in book,
-1 = complement)');
   writeln(data,'* 6 Ri evaluation (bits per site)');
   writeln(data,'* 7 Z');
   writeln(data,'* 8 probability');
   writeln(data,'*');

totalsites := 0;
   totalpositionsevaluated := 0;
   while (not eof(book)) and (count < todo) do begin
      getpiece(book, apiece);
      if not eof(book) then begin
         count := count + 1;
         if (count mod countmark) = 0 then
writeln(output,count:1);
      scansequence(data, riblmatrix, fromwanted, towanted, apiece,cutoffRi,cutoffP,sites,positionsevaluated,
                    not oneway, mean, stdev);

totalsites := totalsites + sites;
         totalpositionsevaluated :=
totalpositionsevaluated
                                   + positionsevaluated;
         writeln(data,'* ',sites:1,' sites found in
piece',
                 ' ',apiece^.key.hea.keynam.letters);
         writeln(data,'* ',positionsevaluated:1,'
positions evaluated');
         clearpiece(apiece); (* clear the piece for reuse
*)
      end
   end;
   writeln(data,'*');
   writeln(data,'* ',totalsites:1,' sites found in this
book in');
```

- 203 -

```
   writeln(data,'* ',totalpositionsevaluated:1,' total
positions evaluated');
   if totalsites > 0 then
    writeln(data,'* ', ln(totalpositionsevaluated/totalsites)/ln(2):infodecim:inf
ofield,
                    ' effective Rfrequency (bits per site)');
end;
(* end module scan.themain *)
begin
   themain(book,ribl,scanp,data);
1: end.
```

APPENDIX D

-1      number of seqs to scan 0 = none, positive = that number; negative = all
-500    information content at or above which to report in the data file.
0       probability at or above which to report in the data file.
-10 +10 desired region of the rib1 weight matrix to use
0       0: program figures it out; 1: one way scan; 2: two way scan.
    scanp: parameters to control the program.

- 205 -

APPENDIX E

```
program dnaplot(dnain, dnaout, dnaplotp, positions,
dnasymbols, output);
(* dnaplot: plot values of a large DNA sequence
   modules: prgmod, dops *)

label 1; (* end of program *)

const
(* begin module version *)
   version = 3.19; (* of dnaplot.p 1995 June 10
origin before 1993 August 11 *)
(* end module version *)

(* begin module describe.dnaplot *)
(*
name
   dnaplot: plot values of a large DNA sequence synopsis
   dnaplot(dnain: in, dnaout: out, dnaplotp: in,
           positions: in, dnasymbols: in, output: out)

files
   dnain: An data input file created by scan.  It
contains header lines that
       begin with asterisks ('*') that are copied to
dnaout.  Remaining lines
       are the data in columns, ending with end of file.

dnaout: output in PostScript format dnaplotp: Parameter file for dnaplot, which is
configured as followed:

frompos topos       These two integers are the
```

- 206 -

```
positions on the
                        sequence which the graph will
represent.  If,
                        instead, the first character
on the line is 'r',
                        then these numbers are read
from the positions
                        file for each sequence.

sCol cCol vCol  columns to read from the
dnain file numperpg        number of graphs per page
        numperln        number of base pairs per line
        bitlower bitupper   lower and upper bounds of
bits to display orix oriy       x, y origin of plot (in cm)
```

- 207 -

```
     xaxlength yaxlength   length of the x and y axes in
cm
     showaxis              t=true means show coordinate
axis to dnaout
     xinterval yinterval   size of intervals on axes to
plot
     xsubint   ysubint     x and y sub intervals to mark
     xwidth    ywidth      width of numbers in
characters                 .
     xdecimal  ydecimal    number of decimal places
     xticlength xticdx xticdy  length of tic mark and
shift of number (cm)
     yticlength yticdx yticdy  length of tic mark and
shift of number (cm)
     sequencelabel         t=true means print sequence
number on graphs
     xaxislabel            the label for the x axis
     yaxislabel            the label for the y axis
     plottype              How to draw the plot:
                           z = lines from zero to value
                           b = lines from bottom of
graph to value
     dodash                Whether to put vertical
dashed lines around        .
                           segments of continuous
sequence.  This is
                           important for distinguishing
between the absence
                           of sequence and low Ri
values, but this often gets
                           in the way, so it can be
turned off:
                           d = do dashes
                           n = no dashes positions:  If the first character on the first line of
the parameter file
```

- 208 - is an 'r' then this file will be read to determine the positions to graph
for each sequence.  The file consists of pairs of integers, one pair per
line, representing the first (frompos) and last (topos) coordinates to be
plotted.

dnasymbols: If the file is not empty, then it contains information on how
and where to plot special symbols to make marks on the graph.  Each line
has 5 values:
    symbol (first character): the type of symbol to draw:
        c = circle
        s = square
        t = triangle
    symboltype (second character): the way to draw the symbol:

- 209 -

```
        s = stroked as a solid line
        f = filled
        d = dotted line
     symbolplacement (third character): where to put
the symbol on the graph:
        a = use absolute location (given by
symbolbits) on graph
        r = use relative location (given by
symbolbits) from current Ri value
     symbolbits (real): the distance in bits
     symbolsize (real): radius of a circle or side of
square and triangle
        relative to the spacing between graph lines.
A value of 1 fits
        between the lines.
     piece number (integer):  The number of the
fragment to mark,
        as given in the dnain file
     piece coordinate (integer):  the coordinate on
the piece to mark
        as given in the dnain file
```

```
***********************************************************
**********
     * The symbols MUST be in increasing order of
position in the plot! *

***********************************************************
**********
```

Lines that are empty or begin with "*" are
ignored.

output: messages to the user description

- 210 - dnaplot creates a PostScript graph of information content (or
  other values) versus position on a DNA sequence.

examples dnasymbols
The line:
csa 15 0.5 1 100
means place a circle, stroked, at absolute 15 bits, 0.5 size,
for sequence 1 at coordinate 100.

documentation see also
  scan.p, xyplo.p, dbbk.p

- 211 - author
    Stacy L. Bartram, modified by Tom Schneider bugs

The program cannot handle negatively numbered base systems because the axis
    cannot give decreasing numbers (yet or ever). These simply come out as
    blank (or the program will halt, depending on the version).

technical notes

```
*)
(* end module describe.dnaplot *)

(* constants continued *)
(* begin module dnaplot.const *)
   infofield = 12; (* size of field for printing information in bits *)
   infodecim = 6; (* number of decimal places for printing information *)
       (* these are used for conlist only *)
   nfield = 4; (* size of field for printing n, the number of sites *)
(* end module dnaplot.const *)

(* begin module pic.const *)
   pi = 3.14159265354; (* circumference divided by diameter of circle *)
   picwidth = 8; (* width of numbers printed to the file
*)
   picdecim = 5; (* number of decimal places for numbers
*)
   charwidth = 0.0625; (* the width of characters in inches (ie, inches/char)
```

- 212 -

```
                        this allows centering of strings.
*)
   (* note: for the Times-Roman  font, 0.0625 is a good value.
            for the Courier-Bold font, 0.08   is a good value. *)
   dotfactor = 0.00625; (* the size of dots *)
   defscale = 28.35; (* default scale factor.  coordinate units per cm *)
(* end module pic.const version = 2.66; (@ of dops.p 1994 Oct 6 *)

(* begin module interact.const *)
     maxstring = 150; (* the maximum string *)
(* end module interact.const version = 4.13; (@ of prgmod.p 1994 sep 5 *)

type
(* begin module interact.type *)
     string = record (* a string of characters *)
```

- 213 -

```
        letters: array[1..maxstring] of char; (* the
letters in the string *)
        length: integer; (* the number of characters in
the string *)
        current: integer; (* the letter we are working on
*)
     end;
(* end module interact.type version = 4.13; (@ of prgmod.p
1994 sep 5 *)

(* begin module dnaplot.type *)
   params = record
     frompos, topos: integer; (* positions on sequence
graph will represent *)
     readpositions: boolean; (* if true, obtain frompos
and topos from
                              the positions file *)

(* columns of the dnain file:
        sequence number (integer), coordinate number
(integer), value (real) *)
     sCol: integer; (* sequence number *)
     cCol: integer; (* coordinate number *)
     vCol: integer; (* value *)

numperpg: integer; (* number of horizontal lines per
page *)
     numperln: integer; (* number of base pairs per line
*)
     bitspercm: real;   (* height of vertical lines for
information content *)
     bitlower, bitupper: real;  (* lower and upper bounds
of bits to display *)

orix, oriy: real;    (* x, y origin of plot (in cm)
*)
     xaxlength, yaxlength: real; (* length of the x and y
```

- 214 -

```
axes in cm *)
     showaxis: boolean;    (* show coordinate axis *)
     xinterval, yinterval, (* number of intervals on axes
to plot *)
     xsubint, ysubint,     (* number of sub intervals on
axes to mark *)
     xwidth, ywidth,       (* width of numbers in
characters *)
     xdecimal, ydecimal: integer; (* number of decimal
places *)
     xticlength, xticdx, xticdy, (* length of tic mark,
shift of number (cm) *)
     yticlength, yticdx, yticdy: (* length of tic mark,
shift of number (cm) *)
         real;
     sequencelabel: boolean; (* true means print sequence
number on graphs *)
     xaxislabel, (* label for x axis *)
     yaxislabel: (* label for y axis *)
         string;
     plottype: char; (* type of plot to produce *)
```

- 215 -

```
     dodash: char;  (* do dashes or not *)
  end;
(* end module dnaplot.type *)

{ junk this silly code eventually:
     infonum: real;       (* information above which to
report to dnaout *)
     MagicNumber: real;   (* print Ri even if it is below
infonum *)
from parameters:
* the next two are not valid in this version and must not
be included
     infonum              information above which to
report to dnaout
     MagicNumber          print Ri even if it is below
infonum
from technical notes
  In Kenn Rudd's database, there are unknown sections of
the E. coli genome.
  Delila was designed with the idea that unknown sequence
would always be
  determined.  So the program dbbk which converts to
Delila format substitutes
  an A at every unknown base.  When a string of A's is
evaluated by an Ri1
  matrix, it gives a unique value, called the
"MagicNumber" that can therefore
  be used to detect the regions of unknown sequence.
This program is set up
  so that when it comes across the MagicNumber, it
assumes the sequence is
  missing.  If the user requests that values below zero
not be plotted, the
  positions with the MagicNumber will be plotted anyway,
to indicate the
  regions where there is no sequence.
in writing loop:
```

- 216 -
```
        if (vVal = MagicNumber) then vVal := 0;
} var
(* begin module dnaplot.var *)
   dnain, (* input data from scan *)
   dnaout, (* output - PostScript graph instructions *)
   dnaplotp, (* file from which to read the parameters *)
   positions, (* file from which to read the positions to
plot *)
   dnasymbols: text; (* file from which to read the plot
symbols *)
(* end module dnaplot.var *)

(* begin module pic.var *)
   inpicture: boolean; (* true if we are drawing the
picture,
                             ie, startpic has been called *)
```

- 217 -

```
   picxglobal, picyglobal: real; (* absolute location in
the graph *)
   pictolerance: real; (* 10 raised to the picwidth,
      to detect values close to zero *)

scale: real; (* scale factor.  graphic coordinate units
per inch *)

(* NONSTANDARD for efficient use of postscript, keep track
of
whether there is a current path *)
   inpath: boolean;

(* NONSTANDARD keep track of number of segments drawn so
that
they can be stroked.  This (probably) solves the problem
of the
Apple printer dying because it can't handle the data. *)
   segments: integer;

xsideold, ysideold: real; (* current size of a
rectangle.  see rectsize *)
(* end module pic.var version = 2.66; (@ of dops.p 1994
Oct 6 *)

(* begin module halt *)
procedure halt;
(* stop the program.  the procedure performs a goto to the
end of the
   program.  you must have a label:
      label 1;
   declared, and also the end of the program must have
this label:
      1: end.
   examples are in the module libraries.
   this is the only goto in the delila system. *)
begin
```

- 218 -

```
      writeln(output,' program halt.');
      goto 1
end;
(* end module halt version = 4.13; (@ of prgmod.p 1994 sep
5 *)

(* begin module interact.clearstring *)
procedure clearstring(var ribbon: string);
(* empty the string *)
var    index: integer; (* to the ribbon *)
begin (* clearstring *)
      with ribbon do begin
          for index := 1 to maxstring do letters[index] :=
' ';
          length := 0;
          current := 0;
      end
end; (* clearstring *)
(* end module interact.clearstring version = 4.13; (@ of
prgmod.p 1994 sep 5 *)
```

- 219 -

```
(* begin module interact.getstring *) .
procedure getstring(var afile: text; var buffer: string;
                    var gotten: boolean);
(* get a string from a file not using string calls.  this lets one
obtain lines from a file without interactive prompts *)
var  index: integer; (* of buffer *)
begin (* getstring *)
     clearstring(buffer);
     if eof(afile)
     then gotten := false
     else begin
         index := 0;
         while (not eoln(afile)) and (index < maxstring) do begin
             index := succ(index);
             read(afile, buffer.letters[index])
         end;

if not eoln(afile) then begin
         writeln(output, ' getstring: a line exceeds maximum string size (',
                         maxstring:1,')');
             halt
         end;

buffer.length := index;
         buffer.current := 1;
         readln(afile);
         gotten := true
     end
end; (* getstring *)
(* end module interact.getstring version = 4.13; (@ of prgmod.p 1994 sep 5 *)

(* begin module interact.writestring *)
procedure writestring(var tofile: text; var s: string);
```

- 220 -

```pascal
(* write the string s to file tofile, no writeln *)
var   i: integer; (* index to s *)
begin (* writestring *)
      with s do for i := 1 to length do write(tofile,
letters[i])
end; (* writestring *)
(* end module interact.writestring version = 4.13; (@ of
prgmod.p 1994 sep 5 *)

(* begin module skipblanks *)
procedure skipblanks(var thefile: text);
(* skip over blanks until a non-blank, or end of line, is
found *)
begin
      while (thefile^ = ' ') and not eoln(thefile) do
get(thefile);
end;
```

- 221 -

```
procedure skipnonblanks(var thefile: text);
(* skip over nonblanks until a blank, or end of line, is
found *)
begin
      while (thefile^ <> ' ') and not eoln(thefile) do
get(thefile);
end;

procedure skipcolumn(var thefile: text);
(* skip over a data column *)
begin
   skipblanks(thefile); skipnonblanks(thefile)
end;
(* end module skipblanks version = 4.13; (@ of prgmod.p
1994 sep 5 *)

(* begin module copyaline *)
procedure copyaline(var fin, fout: text);
(* copy a line from file fin to file fout *)
begin (* copyaline *)
      while not eoln(fin) do begin
         fout^ := fin^;
         put(fout);
         get(fin)
      end;
      readln(fin);
      writeln(fout);
end; (* copyaline *)
(* end module copyaline version = 4.13; (@ of prgmod.p
1994 sep 5 *)

(*
***********************************************************
******** *)
(* graphics for axes *)

(* begin module dnaplot.startpic *)
```

- 222 -

```pascal
procedure startpic(var afile:text; setscale,x,y: real;
thefont: char);
(* open the graphics field, with the given scale, and at
(x,y)
in that scale.  scale is in device coordinates per inch.
The font is chosen with thefont; t = Times-Roman, c =
Courier-Bold *)
(* start pic output to file afile, set the globals *)
(* NONSTANDARD *)
(* this is the actual "world" coordinates used: *)
(*                         xmin,  xmax,  ymin, ymax *)
(*    ns; if (setwindow(-5.0/scale, +5.0/scale,
-5.0/scale, +5.0/scale)*)
begin
   scale := setscale; (* set the global scale *)

case thefont of
```

- 223 -

```
      'c': begin
            writeln(afile,'/Courier-Bold findfont'); (*
locate the font *)
            writeln(afile,10:1,' scalefont'); (* set the
font size in points*)
        end;
       't': begin
            writeln(afile,'/Times-Roman findfont'); (*
locate the font *)
            writeln(afile,12:1,' scalefont'); (* set the
font size in points*)
        end;
    end;

writeln(afile,'setfont'); (* put the font into the
current font *)

(* set the scale to inches
    writeln(afile,
                scale:picwidth:picdecim,' ',
                scale:picwidth:picdecim,' scale'); *)

(* define some things in postscript *)
    (* doline allows less stuff to be put in the output
file.
       it takes two numbers off the stack, copies them,
draws a line
       to them as coordinates. *)
(* replaced by 'currentpoint translate'
    writeln(afile,'/doline { 2 copy lineto } def');
*)
    (* define a function that makes inches out of a number
*)
(* do this all internally here, it's faster
    writeln(afile,'/i { ',scale:picwidth:picdecim,' mul}
def');
*)
```

- 224 -

```
(* move to the start point on the page *)
writeln(afile,
                 (x*scale):picwidth:picdecim,
              ' ',(y*scale):picwidth:picdecim,
              ' translate');

writeln(afile);
   writeln(afile,'% Define functions so the text produced
is smaller');
   writeln(afile,'/a {stroke newpath 0 0} def     %
special for arc');
   writeln(afile,'/c {stroke 0 0 moveto} def     %
current point');
   writeln(afile,'/f {findfont 10 scalefont setfont}
def');
   writeln(afile,'    % to set fonts simply use the f
function.  Example:');
```

- 225 -

```
    writeln(afile,'   %/Symbol f (\142) /Courier-Bold f
(-galactosidase');
    writeln(afile,'/l {lineto} def');
    writeln(afile,'/m {moveto} def');
    writeln(afile,'/n {stroke newpath 0 0 moveto} def');
(* new segment *)
    writeln(afile,'/rl {rlineto} def');
    writeln(afile,'/rm {rmoveto} def');
    writeln(afile,'/s {newpath 0 0 moveto} def     % Start
path ');
    writeln(afile,'/t {currentpoint translate} def %
translate ');
    writeln(afile,'/x {show} def                   % show
teXt ');
    writeln(afile);

(* start out the pathway *)
    inpath := false;
    (* start the number of segments written: *)
    segments := 0;

(* now for the normal pic stuff: *)
    inpicture := true;
    picxglobal := 0.0;
    picyglobal := 0.0;
    pictolerance := trunc(exp(picwidth*ln(10))+0.5)
(*;writeln(output,'pictolerance =
',pictolerance:picwidth:picdecim);*)
end;

(* MODIFIED from pic.startpic version = 2.66; (@ of dops.p
1994 Oct 6 *)
(* end module dnaplot.startpic *)

(* begin module pic.drawr *)
procedure drawr(var afile: text; dx,dy: real; visibility:
char;
```

- 226 -
```
        spacing: real);
(* make a line to file afile by relative draw of dx,dy
with visibility
  i invisible
  - dashed
  . dotted
  l line
with the dashes or dots separated by the spacing given
(this has no effect with invisible and line). *)
(* NONSTANDARD *)
var
    ddx,ddy: real; (* changes in dx and dy for dots and
dashes *)
    dr: real; (* the hypotenuse, the distance actually
drawn *)
    on: boolean; (* draw linesegment if true *)
    y: real; (* the variable for tracking dots and dashes
*)
    r: integer; (* number of times to cycle for dots and
dashes *)
```

- 227 -

```
   ss: real; (* precalculated value to make things a bit
faster *)
   theta: real; (* angle of the line *)
procedure checkseg(var afile: text);
(* NONSTANDARD checks how many segments have been written,
if
more than 'buffer', stroke them to the postscript page *)
const buffer = 10;
begin
   if segments >= buffer
   then begin
   (* New segment: writeln(afile,'stroke newpath 0 0
moveto'); *)
      writeln(afile,'n');
      segments := 0
   end
   else segments := segments + 1;
end;
begin (* drawr *)
   if not inpath then begin
      (* starts from current coordinates *)
      (* Start path: writeln(afile,'newpath 0 0 moveto');
*)
      writeln(afile,'s');
      inpath := true
   end
   else checkseg(afile);
(* checks
if not (visibility in ['l','i','.','-'])
then writeln(afile,'%YELLLLLL!!!',visibility,'!');
writeln(afile,'% ',visibility,' line');*)

(* put these on the stack, they will always be used *)
   write(afile,    (dx*scale):picwidth:picdecim,
                ' ',(dy*scale):picwidth:picdecim);
   case visibility of
   'l','i': begin
```

```
                         - 228 -
              case visibility of
                 'i': write(afile,' m');
                 'l': write(afile,' l');
              end
           end;
 '.','-': begin (* make up our own dots and dashes *)
             writeln(afile); (* move away from the
(dx,dy) on the stack *)
             if spacing <= 0.0 then begin
                writeln(output,'drawr: spacing zero with
. or - line');
                halt
             end;
             if dx = 0.0
             then begin
                ddx := 0.0; (* avoid division by zero *)
                ddy := scale*spacing;
```

- 229 -

```
              if dy < 0 then ddy := - ddy; (* this
makes sure that
              we draw lines straight down if that
was the request *)
           end
           else begin
              (* find out the angle of the slope,
intentionally
                 lose the sign *)
              theta := arctan(abs(dy/dx));

ddx := scale*spacing*cos(theta);
              ddy := scale*spacing*sin(theta);

(* return the sign to the little buggers
*)
              if dx < 0 then ddx := -ddx;
              if dy < 0 then ddy := -ddy;
           end;
           y := 0;
           case visibility of
              '.': ss := scale*dotfactor;
              '-': on := true;
           end;

dr := sqrt(dx*dx+dy*dy);
           for r := 1 to round(dr/spacing) do begin
              case visibility of
              '-': begin
                    write(afile,
(ddx):picwidth:picdecim,
',(ddy):picwidth:picdecim);
                    if on
                    then writeln(afile,' rl')
                    else writeln(afile,' rm');
                    on := not on
```

- 230 -
```
                    end;
            '.': begin
                    (* put out a dot like in dotr *)
                    write(afile,
+ss:picwidth:picdecim,' 0 rl');
                    write(afile,' ',
-ss:picwidth:picdecim,' 0 rl');
                    write(afile,'
',(ddx):picwidth:picdecim,
                                        '
',(ddy):picwidth:picdecim);
                    writeln(afile,' rm');
                 end;
              end
         end;
         (* let's make really sure we got there!! *)
```

- 231 -

```
            writeln(afile,' m'); (* pulled from the
stack *)
         end;
    end;

(* an elegant way to make postscript keep a global
record is
    to translate the coordinates! *)
    (* writeln(afile,' currentpoint translate'); *)
    writeln(afile,' t');

picxglobal := picxglobal + dx;
    picyglobal := picyglobal + dy;
end;
(* end module pic.drawr version = 2.66; (@ of dops.p 1994
Oct 6 *)

(* begin module pic.mover *)
procedure mover(var afile: text; dx,dy: real);
(* move relative the amount (dx, dy). *)
begin
    drawr(afile,dx,dy,'i',0.0);
end;
(* end module pic.mover version = 2.66; (@ of dops.p 1994
Oct 6 *)

(* begin module pic.liner *)
procedure liner(var afile: text; dx,dy: real);
(* draw a line the relative amount (dx, dy). *)
begin
    drawr(afile,dx,dy,'l',0.0);
end;
(* end module pic.liner version = 2.66; (@ of dops.p 1994
Oct 6 *)

(* begin module pic.drawa *)
```

- 232 -

```
procedure drawa(var afile: text; x,y: real; visibility:
char;
              spacing: real);
(* make a line to file afile to absolute coordinate x,y
with visibility
  i invisible
  - dashed
  . dotted
  l line
with the dashes or dots separated by the spacing given
(this has no effect with invisible and line). *)
var
   dx, dy: real; (* differences between current and
desired
                  locations *)
begin
   dx := x - picxglobal;
   dy := y - picyglobal;
```

- 233 -

```
   drawr(afile,dx,dy,visibility,spacing)
end;
(* end module pic.drawa version = 2.66; (@ of dops.p 1994
Oct 6 *)

(* begin module pic.movea *)
procedure movea(var afile: text; x,y: real);
(* move to absolute x and y *)
begin
   drawa(afile,x,y,'i',0.0);
end;
(* end module pic.movea version = 2.66; (@ of dops.p 1994
Oct 6 *)

(* begin module pic.linea *)
procedure linea(var afile: text; x,y: real);
(* draw a line from current position to absolute x and y
*)
begin
   drawa(afile,x,y,'l',0.0);
end;
(* end module pic.linea version = 2.66; (@ of dops.p 1994
Oct 6 *)

(* begin module pic.graphstring *)
procedure graphstring(var tofile: text; var s: string;
justification: char);
(* graph the string s.  If it is recognized as a quoted
string (surrounded
by double quotes), graph it without the quotes and center
it.
Otherwise justify it based on the justification character:
'l' left, 'c' centered, 'r' right.
For right and centered justification, the drawing point is
the same
as before the string was done.  For left justification it
is at the
```

- 234 -

```
right of the string to allow more to be added on there.
If not in picture (global variable inpicture), there is no
output *)
(* NONSTANDARD: PostScript dependent code.  Since
different fonts
have different sized characters, one must rely on the
PostScript
to handle the justification of the string. *)
var i: integer; (* index to s, and temporary storage *)
    quoted: boolean; (* true if the string is quoted *)
    skipping: boolean; (* true if skipping leading blanks
*)
begin
   if (inpicture and (s.length > 0))
   then with s do begin
      if length > 2
      then if (letters[1]='"') and (letters[length]='"')
           then quoted := true
           else quoted := false          .
      else quoted := false;
```

- 235 -

```
    (* override so quoted strings are always centered *)
    if quoted then justification := 'c';

(* do the non-standard postscript: *)
    if justification <> 'l' then write(tofile,'gsave ');

(* do postscript to complete pervious path *)
    (* set current point: writeln(tofile,'stroke 0 0
moveto'); *)
    writeln(tofile,'c');

if justification = 'c' then begin
        (* when centering, skip leading blanks *)
        if letters[1] = ' ' then skipping := true
                            else skipping := false;
    end
    else skipping := false;

write(tofile,'('); (* begin postscript literal *)
    if quoted (* take it literally *)
    then for i := 2 to length-1 do
write(tofile,letters[i])
    else for i := 1 to length
        do if skipping then begin (* skip leading
blanks *)
                if letters[i] <> ' '
                then begin
                    skipping := false;
                    write(tofile,letters[i])
                end
            (* else skip the blank by not writing it *)
            end
            else write(tofile,letters[i]);
    write(tofile,')'); (* end postscript literal *)

if justification = 'c' (* center the string *)
    then write(tofile,' dup stringwidth pop neg 2 div 0
```

- 236 -

```
rmoveto')
      else if justification = 'r' (* rigth justify the
string *)
      then write(tofile,' dup stringwidth pop neg 0
rmoveto');

writeln(tofile,' x'); (* show the literal *)
      inpath := false; (* force new path from here *)

if justification <> 'l' then write(tofile,'grestore
');
   end
(* There is no output if not in picture
   else begin
      writestring(tofile,s);
      writeln(tofile)
   end
 *)
end;
```

- 237 -

```
(* end module pic.graphstring version = 2.66; (@ of dops.p
1994 Oct 6 *)

(* begin module pic.stringinteger *)
procedure stringinteger(number: integer; var name: string;
                        width: integer; leadingzeros:
boolean);
(* make the string from the number, start putting
characters in
after the current length point. use width characters.
if leadingzeros is true, trail zeros before the number. *)
var
   bigdigit: integer; (* the location of the biggest digit
*)
   dig: integer; (* number of digits in the number *)
   place: integer; (* place to write the next digit of the
number *)
   sign: integer; (* the sign of the number *)
begin
   with name do begin
      if number < 0
      then begin
         sign := -1;
         length := length + 1; (* provide room for the
sign!! *)
         number := -number;
         if leadingzeros then begin
            writeln(output,'WARNING: stringinteger: the
sign of a negative',
                           ' number with leading zeros is
lost');
         end
      end
      else sign := +1;

(* log 10 of the number plus 1 is the number of
digits in the number.
```

- 238 -

```
      On this sun computer ln(1000)/ln(10) is 2.9999,
which when
      truncated gives 2, rather than the desired 3.  To
avoid this
      kind of problem, 0.1 is added. *)
      if number > 9
      then dig := trunc(ln(number+0.1)/ln(10))+1
      else dig := 1;

if dig > width then begin
          writeln(output,'stringinteger: number width too
small');
          writeln(output,dig:1,' digit number
(',number:1,')');
          writeln(output,'does not fit in ',width:1,'
characters');
          halt
      end;
      if leadingzeros
      then bigdigit := length + 1 (* no sign if leading
zeros *)
      else begin
          bigdigit := length + width - dig + 1;
```

- 239 -

```
        if (bigdigit <= length) and (sign < 0) then begin
            writeln(output,'stringinteger: no room for
sign');
            halt
        end;
    end;
    if sign < 0 then letters[bigdigit-1] := '-';

for place := length + width downto bigdigit do begin
        case (number mod 10) of
            0: letters[place] := '0';
            1: letters[place] := '1';
            2: letters[place] := '2';
            3: letters[place] := '3';
            4: letters[place] := '4';
            5: letters[place] := '5';
            6: letters[place] := '6';
            7: letters[place] := '7';
            8: letters[place] := '8';
            9: letters[place] := '9';
        end;
        number := number div 10;
    end;
    length := length + width;
    end
end;
(* end module pic.stringinteger version = 2.66; (@ of
dops.p 1994 Oct 6 *)

(* begin module pic.stringreal *)
procedure stringreal(number: real; var name: string;
                     width, decimal: integer);
(* make the string from the real number, start putting
characters in
at the start point. use width characters and decimal
characters
after the decimal place *)
```

- 240 -

```
(* note that the rounding operation to get the digits
below zero
     must be done first.  then the digits above zero can
be lopped off.
     this makes 99.99 come out correctly to 100.0 (to 1
decimal place)
     otherwise, 99.99 -> 0.99 -> 1.0 (rounded) -> 10
(print with 1 decimal
     place), and stringinteger won't be happy about that.
*)
var
   abovezero: integer; (* the number shifted above the
decimal place, to
      'decimal' positions (and rounded) *)
   shift: integer; (* power of ten used to shift a number
around
      relative to the decimal point *)
   sign: integer; (* the sign of the number *)
```

- 241 -

```
   thedecimal: integer; (* integer version of the decimal
part of the number *)
   theupper: integer; (* integer version of the upper part
of the number *)
begin
   if number < 0 then sign := -1
                 else sign := +1;

number := abs(number); (* make positive *)

(* the amount to shift the number above zero *)
   shift := round(exp(decimal*ln(10))); (* amount to move
above zero *)
   abovezero := round(number*shift); (* move above zero,
round off *)
   theupper := trunc(abovezero/shift);
   thedecimal := abovezero - shift*theupper;

(* create the actual real number *)
   (* before decimal point *)

stringinteger(sign*theupper,name,width-decimal-1,false);
   with name do begin (* put in the decimal point *)
      length := length + 1;
      letters[length] := '.';
   end;
   stringinteger(thedecimal,name,decimal,true); (* after
decimal point *)
end;
(* end module pic.stringreal version = 2.66; (@ of dops.p
1994 Oct 6 *)

(* begin module pic.picnumber *)
procedure picnumber(var afile: text;
                    dx, dy, number: real; width, decimal:
integer;
                    justification: char);
```

- 242 -

```
(* Supply graphic commands for a 'number' whose center is
at the relative point
(dx, dy) from the current point, 'width' characters wide
and 'decimal'
characters beyond the decimal point.
If the width is zero, no number is produced.
procedure stringnumber(number: integer; start: integer;
var name: string);
the location after the call is the same as before the
call.
The string is optionally justified: left, centered or
right: lcr. *)
var
   name: string; (* the string to pack the number into for
shipping out *)
begin
   if width > 0 then begin
```

- 243 -

```
      mover(afile,dx,dy);

clearstring(name);

if decimal>0
      then stringreal(number,name,width,decimal)
      else stringinteger(round(number),name,width,false);

graphstring(afile, name, justification);
      mover(afile,-dx,-dy);
   end
end;
(* end module pic.picnumber version = 2.66; (@ of dops.p
1994 Oct 6 *)

(* begin module pic.xtic *)
procedure xtic(var afile: text; length, dx, dy, number:
real;
               width, decimal: integer;
               logxnormal: boolean;
               logxbase: real);
(* produce a tic mark for the x axis of "length" long.
Supply a number whose center is at the relative point (dx,
dy)
from the end to the tick, 'width' characters wide and
'decimal'
characters beyond the decimal point.
If the width is zero, no number is produced.
the location after the call is the same as before the
call.
If logxnormal is true, then raise the number
to logxbase. *)
begin
   liner(afile,0.0,-length);
   if logxnormal
   then
picnumber(afile,dx,dy,exp(number*logxbase),width,decimal,'
```

- 244 -

```
c')
   else picnumber(afile,dx,dy,number,width,decimal,'c');
   mover(afile,0.0,length);
end;
(* end module pic.xtic version = 2.66; (@ of dops.p 1994
Oct 6 *)

(* begin module pic.ytic *)
procedure ytic(var afile: text; length, dx, dy: real;
               number: real;
               width, decimal: integer;
               logynormal: boolean;
               logybase: real);
(* produce a tic mark for the y axis of "length" long.
```

Supply a number whose right side is started at the relative point (dx, dy)
from the end to the tick, 'width' characters wide and 'decimal'
characters beyond the decimal point.
If the width is zero, no number is produced.
the location after the call is the same as before the call.
If logynormal is true, then raise the number

- 245 -

```
to logybase. *)
begin
   liner(afile,-length,0.0);

(* convert the number if we are doing logynormal: *)
   if logynormal then number := exp(number*logybase);

picnumber(afile,dx,dy,number,width,decimal,'r');
   mover(afile,length,0.0);
end;
(* end module pic.ytic version = 2.66; (@ of dops.p 1994
Oct 6 *)

(* begin module pic.doaxis *)
procedure doaxis(var afile: text;
         theaxis: char;
         alength,fromtic,interval,totic: real;
         subintervals: real;
         length, dx, dy: real;
         width, decimal: integer;
         logscale, lognormal: boolean;
         logbase: real);
(* draw an axis starting from the current position.
Which axis it is is defined by theaxis, 'x' (horizontal)
or 'y' (vertical).
Combining the code for both axes into one procedure is a
little
slower, but drawing the axis does note ever take
significant time,
and this allows improvements to be made on both axes
simultaneously.
The length of the axis is alength.
The axis is labeled with numbers starting with fromtic
at intervals given up to totic.
The remaining variables describe the form of the tic marks
as in ytic.
If the width is zero, no number is produced.
```

- 246 -

```
the location after the call is the same as before the
call.
If logscale and lognormal is true, then raise the tic
numbers to logbase.
 *)
var
   half: real; (* half the jump interval.  By adding this
to the while loops,
                we assure that the very last tic gets
done, and isn't lost
                due to roundoff *)
   jump: real; (* the space to move on the graph between
tic marks *)
   jumpdistance: real; (* the total jumps made.  this may
not be
      a simple function of the input variables since they
may
      not work out to an exact number of jumps *)
   tic: real; (* the numerical value of the tic label *)
```

- 247 -

```
   dosubtics: boolean; (* do sub tics *)
   subtic: real; (* the numerical value of the (unlabeled)
subtic *)
   subinterval: real; (* the numerical interval between
subtics *)
   subjump: real; (* the space to move on the graph
between subtic marks *)
   halfsubinterval: real; (* half a subjump, see half *)

currentspot: real; (* current graphing spot *)
   oldspot: real; (* previous graphing spot *)
   axisscale: real; (* axis scaling factor *)

begin

{
writeln(output,'In doaxis');
writeln(output,'interval=',interval:10:4);
writeln(output,'subintervals=',subintervals:10:4);
writeln(output,'logbase=',logbase:10:4);
} if theaxis = 'x' then begin
      liner(afile,+alength,0.0);
      mover(afile,-alength,0.0);
   end
   else begin
      liner(afile,0.0,+alength);
      mover(afile,0.0,-alength);
   end;

if totic = fromtic then begin
      writeln(output,'doaxis: ',theaxis,' axis fromtic and
totic',
                      ' cannot be equal');
      halt;
   end;
```

- 248 -

```
  if (alength = 0.0) or (interval = 0.0) then begin
     writeln(output,'doaxis: neither ',
                     theaxis,' axis length nor interval
can be zero');

halt;
  end;

axisscale := alength / (totic - fromtic);
  jump := axisscale * interval;
  jumpdistance := 0;
  half := interval / 2.0;

if subintervals > 1 then begin
```

- 249 -

```
      dosubtics := true;
      subinterval := interval/subintervals;
      halfsubinterval := subinterval / 2.0;
      subjump := jump/subintervals;
   end
   else begin
      dosubtics := false;
      subinterval := 0;
      halfsubinterval := 0;
      subjump := 0;
   end;

tic := fromtic;
   if interval > 0.0 then while tic <= totic+half do begin
      if theaxis = 'x'
      then
xtic(afile,length,dx,dy,tic,width,decimal,lognormal,logbas
e)
      else
ytic(afile,length,dx,dy,tic,width,decimal,lognormal,logbas
e);

tic := tic + interval;
      if tic <= totic+half then begin .
{
writeln(output,'TIC=',tic:10:4);
writeln(afile,'% tic=',tic:10:4);
mover(afile,0.05,0.0);
}
         if dosubtics then begin (* do subtic marks *)
            if logscale then begin (* do subtic marks on
log scale *)
            (* subtic starts as a "normal" number (ie, no
log taken) at tic: *)
{
writeln(output,'2^tic=',exp(tic*logbase):10:4);
writeln(output,'2^(tic+interval)=',exp((tic+interval)*logb
```

- 250 -

```
ase):10:4);
}
                subtic := exp(tic*logbase);
                (* subtic will proceed to the same but at
tic+interval.
                We divide that into the subintervals. *)
{
writeln(output,'halfsubinterval=',halfsubinterval:10:4,'
original');
}
                subinterval := (exp((tic+interval)*logbase)
- subtic)/subintervals;
                halfsubinterval := subinterval/2.0;

{
writeln(output,'subtic=          ',subtic:10:4);
writeln(output,'subinterval=     ',subinterval:10:4);
```

- 251 -

```
writeln(output,'halfsubinterval=',halfsubinterval:10:4);
} oldspot := axisscale * tic;
                while subtic < exp(logbase*(tic+interval))
- halfsubinterval
                do begin (* although tic is on a log scale,
                            we have to have subtic on the regular
scale
                            to alter the positions of the subtics
*)

(* if subinterval is constant,
                            the following makes linearly spaced
marks: *)
                        subtic := subtic + subinterval;

(* the actual jumps have to be in the
log form: *)
                        currentspot :=
axisscale*ln(subtic)/logbase;
                        subjump := currentspot - oldspot;
{
writeln(output,'        SUBTIC=',subtic:10:4);
writeln(output,'
ln(SUBTIC)/logbase=',ln(subtic)/logbase:10:4);
writeln(output,'        currentspot=',currentspot:10:4);
writeln(output,'        subjump=',subjump:10:4);
writeln(output,'        oldspot=',oldspot:10:4);
writeln(afile,'% subtic=',subtic:10:4);
}
                        oldspot := currentspot;

if theaxis = 'x' then begin
```

- 252 -

```
xtic(afile,length/2,dx,dy,0,0,0,lognormal,logbase);
                mover(afile,subjump,0.0);
            end
            else begin ytic(afile,length/2,dx,dy,0,0,0,lognormal,logbase);
                mover(afile,0.0,subjump);
            end;

jumpdistance := jumpdistance + subjump;
            end
        end
        else begin (* do subtic marks on regular scale
*)
            subtic := tic;
            while subtic < tic+interval-halfsubinterval
do begin
                subtic := subtic + subinterval;
```

- 253 -
```
              if theaxis = 'x' then begin
                  mover(afile,subjump,0.0);

xtic(afile,length/2,dx,dy,0,0,0,lognormal,logbase);
                  end
                  else begin
                      mover(afile,0.0,subjump);

ytic(afile,length/2,dx,dy,0,0,0,lognormal,logbase);
                  end;

jumpdistance := jumpdistance + subjump;
                end
              end
          end
          else begin (* do regular tic marks *)
              if theaxis = 'x' then mover(afile,jump,0.0)
                               else mover(afile,0.0,jump);
              jumpdistance := jumpdistance + jump
          end
      end
   end
   else if interval < 0.0 then while tic >= totic-half do
begin
      if dosubtics then writeln(output,'Sorry, no subtics
with negative scales');

if theaxis = 'x'
      then
xtic(afile,length,dx,dy,tic,width,decimal,lognormal,logbas
e)
      else
ytic(afile,length,dx,dy,tic,width,decimal,lognormal,logbas
e);

tic := tic + interval;
      if tic >= totic-half then begin
```

- 254 -

```
        if theaxis = 'x' then mover(afile,jump,0.0)
                          else mover(afile,0.0,jump);
        jumpdistance := jumpdistance + jump
      end
  end;

if theaxis = 'x' then mover(afile,-jumpdistance,0.0)
                    else mover(afile,0.0,-jumpdistance)
end;
(* end module pic.doaxis version = 2.66; (@ of dops.p 1994
Oct 6 *)

(* begin module pic.xaxis *)
procedure xaxis(var afile: text;
         axlength,fromtic,interval,totic: real;
         xsubintervals: real;
         length, dx, dy: real;
         width, decimal: integer;
```

- 255 -

```
          logxscale, logxnormal: boolean;
          logxbase: real);
(* draw an x axis starting from the current position. *)
begin
   doaxis(afile,
          'x',
          axlength,fromtic,interval,totic,
          xsubintervals,
          length, dx, dy,
          width, decimal,
          logxscale, logxnormal,
          logxbase)
end;
(* end module pic.xaxis version = 2.66; (@ of dops.p 1994
Oct 6 *)

(* begin module pic.yaxis *)
procedure yaxis(var afile: text;
          aylength,fromtic,interval,totic: real;
          ysubintervals: real;
          length, dx, dy: real;
          width, decimal: integer;
          logyscale, logynormal: boolean;
          logybase: real);
(* draw an y axis starting from the current position. *)
begin
   doaxis(afile,
          'y',
          aylength,fromtic,interval,totic,
          ysubintervals,
          length, dx, dy,
          width, decimal,
          logyscale, logynormal,
          logybase)
end;
(* end module pic.yaxis version = 2.66; (@ of dops.p 1994
Oct 6 *)
```

- 256 -

```
(*
**************************************************************
******** *)

(* begin module dnaplot.ReadColumns *)
procedure ReadColumns(var fin: text;
                      xCol, yCol: integer;
                      var xVal: integer;
                      var yVal: real);
(* reads data xVal (integer) and yVal (real)
from columns xCol and yCol in fin *)
var
  col: integer; (* current column being read *)
  done: boolean; (* done skipping lines *)
```

- 257 -

```pascal
begin(* ReadColumns *)
  (* skip data lines *)
  done := false;
  while not done do begin
    if eof(fin)
    then done := true
    else if fin^ = '*'
         then readln(fin)
         else done := true
  end;
  if not eof(fin) then begin
    if xCol < yCol then begin
      for col := 1 to xCol-1 do skipcolumn(fin);
      read(fin, xVal);
      for col := xCol+1 to yCol-1 do skipcolumn(fin);
      read(fin, yVal);
    end
    else if yCol < xCol then begin
      for col := 1 to yCol-1 do skipcolumn(fin);
      read(fin, yVal);
      for col := yCol+1 to xCol-1 do skipcolumn(fin);
      read(fin, xVal);
    end;
    readln(fin);
  end;
end;
(* end module dnaplot.ReadColumns *)

(* begin module dnaplot.skipdata *)
procedure skipdata(var fin: text);
(* skip data lines in fin that begin with asterisk *)
var
  done: boolean; (* done skipping lines *)
begin
  (* skip data lines *)
  done := false;
  while not done do begin
```

```
                    - 258 -
    if eof(fin)
    then done := true
    else if fin^ = '*'
         then readln(fin)
         else done := true
  end;
end;
(* end module dnaplot.skipdata *)

(* begin module dnaplot.grabcolumns *)
procedure grabcolumns(var fin: text;
                      xCol, yCol, zCol: integer;
                      var xVal: integer;
                      var yVal: integer;
                      var zVal: real);
```

- 259 -

```
(* read data fromfin:
    xVal (integer) yVal (integer) and zVal (real)
from columns
    xCol yCol zCol
The columns must be in order.
The procedure skips blank data columns after reading
so that the end of file is reached after reading the
last piece of data. *)
var
  col: integer; (* current column being read *)
begin
  if not eof(fin) then begin
    for col := 1 to xCol-1 do skipcolumn(fin);
    read(fin, xVal);
    for col := xCol+1 to yCol-1 do skipcolumn(fin);
    read(fin, yVal);
    for col := yCol+1 to zCol-1 do skipcolumn(fin);
    read(fin, zVal);
    readln(fin);
  end;
  skipdata(fin);
end;
(* end module dnaplot.grabcolumns *)

(* begin module dnaplot.readparam *)
procedure readparam(var finp: text; var parameters:
params);
(* reads the parameters from finp *)
var
    gotten: boolean; (* true if a label string was read *)
begin(* readparam *)
  with parameters do begin
    reset(finp);

if finp^='r'
    then begin
        readpositions := true;
```

- 260 -

```
      readln(finp);
   end
   else begin
      readpositions := false;
      readln(finp, frompos, topos);
   end;

(*
   readln(finp, infonum);
   readln(finp, MagicNumber);
*)
   readln(finp, sCol, cCol, vCol);

readln(finp, numperpg);
   readln(finp, numperln);
```

- 261 -

```
    readln(finp, bitlower, bitupper);

readln(finp, orix, oriy);
    readln(finp, xaxlength, yaxlength);
    if finp^ = 't' then showaxis := true
                   else showaxis := false;
    readln(finp);

readln(finp, xinterval, yinterval);
    readln(finp, xsubint, ysubint);
    readln(finp, xwidth, ywidth);
    readln(finp, xdecimal, ydecimal);
    readln(finp, xticlength, xticdx, xticdy);
    readln(finp, yticlength, yticdx, yticdy);

if yaxlength <= 0.0 then begin
       writeln(output, 'ERROR: yaxislength cannot be less
than 0');
       halt;
    end;

bitspercm := (bitupper - bitlower)/yaxlength;

if (sCol = cCol) or
       (cCol = vCol) or
       (vCol = sCol)
    then begin
       writeln(output, 'ERROR: sCol cCol and vCol columns
read',
                       ' cannot be equal');
       halt;
    end;

if (sCol > cCol) or
       (cCol > vCol) or
       (vCol < sCol)
    then begin
```

- 262 -

```
    writeln(output, 'ERROR: sCol cCol and vCol columns
read',
                     ' must be in increasing order');
      halt;
    end;

if sCol <= 0 then begin
      writeln(output, 'ERROR: sCol cannot be less than
0');
      halt;
    end;

if cCol <= 0 then begin
      writeln(output, 'ERROR: cCol cannot be less than
0');
      halt;
    end;

if vCol <= 0 then begin
```

- 263 -

```
      writeln(output, 'ERROR: vCol cannot be less than
0');
      halt;
    end;

if finp^ = 't' then sequencelabel := true
                   else sequencelabel := false;
    readln(finp);

getstring(finp,xaxislabel,gotten);
    if not gotten then writeln(output,'no xaxislabel');
    getstring(finp,yaxislabel,gotten);.
    if not gotten then writeln(output,'no yaxislabel');

readln(finp,plottype);
    if not (plottype in ['z','b']) then begin
      writeln(output, 'plottype must be z or b');
      halt;
    end;

if eof(finp) then begin
       writeln(output, 'missing dodash parameter');
       halt
    end;

readln(finp,dodash);
    if not (dodash in ['d','n']) then begin
      writeln(output, 'dodash must be d or n');
      halt;
    end;

end;
end;
(* end module dnaplot.readparam *)

(* begin module dnaplot.writeparam *)
(* write the finp parameters to output *)
```

- 264 -

```
procedure writeparam(var fout: text; parameters: params);
begin(* writeparam *)
with parameters do begin
  writeln(fout, '%
*****************************************************');
  writeln(fout, '% User Specified Parameters:');

if readpositions then begin
  writeln(fout, '% reading frompos and topos from the
positions file');
  end
  else begin
  writeln(fout, '     /frompos ', frompos:infofield,'
def');
  writeln(fout, '       /topos ', topos:infofield,' def');
  end;
```

- 265 -

```
(*
  writeln(fout, '     /infonum ',
infonum:infofield:infodecim,' def');
  writeln(fout, ' /MagicNumber ',
MagicNumber:infofield:infodecim,' def');
*)
  writeln(fout, '         /sCol ', sCol:infofield,' def');
  writeln(fout, '         /cCol ', cCol:infofield,' def');
  writeln(fout, '         /vCol ', vCol:infofield,' def');

writeln(fout, '     /numperpg ', numperpg:infofield,'
def');
  writeln(fout, '     /numperln ', numperln:infofield,'
def');
  writeln(fout, '     /bitlower ',
bitlower:infofield:infodecim,' def');
  writeln(fout, '     /bitupper ',
bitupper:infofield:infodecim,' def');

writeln(fout, '         /orix ',
orix:infofield:infodecim,' def');
  writeln(fout, '         /oriy ',
oriy:infofield:infodecim,' def');
  writeln(fout, '     /xaxlength ',
xaxlength:infofield:infodecim,' def');
  writeln(fout, '     /yaxlength ',
yaxlength:infofield:infodecim,' def');

write   (fout, '     /showaxis ');
  if showaxis then write(fout,'true') else
write(fout,'false');
  writeln(fout, ' def');

writeln(fout, '    /xinterval ', xinterval:infofield,'
def');
  writeln(fout, '    /yinterval ', yinterval:infofield,'
def');
```

- 266 -

```
  writeln(fout, '    /xsubint    ', xsubint:infofield,'
def');
  writeln(fout, '    /ysubint    ', ysubint:infofield,'
def');
  writeln(fout, '     /xwidth ', xwidth:infofield,'
def');
  writeln(fout, '     /ywidth ', ywidth:infofield,'
def');
  writeln(fout, '    /xdecimal ', xdecimal:infofield,'
def');
  writeln(fout, '    /ydecimal ', ydecimal:infofield,'
def');

writeln(fout, '  /xticlength ',
xticlength:infofield:infodecim,' def');
  writeln(fout, '      /xticdx ',
xticdx:infofield:infodecim,' def');
  writeln(fout, '      /xticdy ',
xticdy:infofield:infodecim,' def');

writeln(fout, '  /yticlength ',
yticlength:infofield:infodecim,' def');
  writeln(fout, '      /yticdx ',
yticdx:infofield:infodecim,' def');
  writeln(fout, '      /yticdy ',
yticdy:infofield:infodecim,' def');
```

- 267 -

```
  writeln(fout, '    /bitspercm ',
bitspercm:infofield:infodecim,' def');
write(fout, '/xaxislabel: (');
writestring(fout,xaxislabel); writeln(fout,') def');
write(fout, '/yaxislabel: (');
writestring(fout,yaxislabel); writeln(fout,') def');
  writeln(fout, '    /plottype (', plottype, ') def');

(*  writeln(fout, '      /dodash (', dodash, ') def'); *)

write(fout, '/dodash ');
  if dodash = 'd' then write(fout,'true')
                  else write(fout,'false');
  writeln(fout, ' def');

writeln(fout, '%
*****************************************************');
  writeln(fout, '%');
end;
end;
(* end module dnaplot.writeparam *)

(* begin module dnaplot.rightjustifynumber *)
procedure rightjustifynumber(var fout: text; var anumber:
integer);
(* number the axis by right justifying the number *)
begin
  (* right justify the string, with a one space gap on the
right: *)
  writeln(fout, '(',anumber:1,' )');
  writeln(fout,' dup stringwidth pop neg 0 rmoveto');
  writeln(fout, '(',anumber:1,') show');
  writeln(fout, '0 0 moveto');
end;
(* end module dnaplot.rightjustifynumber *)

(* begin module makelogo.marktype *)
```

- 268 -

```
procedure makemarktype(var f: text; marktype: char);
(* make the mark type to the file f *)
begin
   case marktype of
      'f': writeln(f,' fill');
      's': writeln(f,' stroke');
      'd': writeln(f,' [3] 0 setdash stroke');
   end;
end;
(* end module makelogo.marktype *)

(* begin module dnaplot.getsymbol *)
procedure getsymbol(var dnasymbols: text;
                    var symbol, symboltype,
symbolplacement: char;
```

- 269 -

```
                    var symbolbits, symbolsize: real;
                    var symbolpiece, symbolcoordinate:
integer);
(* get the symbol information from dnasymbols.  Skip
comments
that begin with "*". *)
begin
   if not eof(dnasymbols)
   then while (dnasymbols^ = '*') or eoln(dnasymbols) do
readln(dnasymbols);

if eof(dnasymbols) then begin
      symbol := ' ';
   end
   else begin
      read(dnasymbols, symbol);
      read(dnasymbols, symboltype);
      read(dnasymbols, symbolplacement);
      read(dnasymbols, symbolbits);
      read(dnasymbols, symbolsize);
      read(dnasymbols, symbolpiece);
      read(dnasymbols, symbolcoordinate);
      readln(dnasymbols);
   end;
end;
(* end module dnaplot.getsymbol *)

(* begin module dnaplot.writepostscript *)
procedure writepostscript(var fin, fout: text; parameters:
params;
                          var positions, dnasymbols:
text);
(* read data from the fin file and write PostScript to the
fout file.
Use positions to determine the range to plot if parameter
readpositions
is true.  Use the dnasymbols to put marks on the graph *)
```

- 270 -

```
var
   currentpos: integer; (* the currently plotted position
*)
   cVal: integer; (* the coordinate column in fin *)
   graphsperpage: integer; (* current count of graphs on
this page *)
   inout: char; (* i = inside data, o = outside.  This
allows the program
      to mark the edges of where the data lies. *)
   newsequence: boolean; (* true just after we start a new
sequence.
      This is used to trigger making a new set of axes *)
   pagenumber: integer; (* the current page *)
   sVal: integer; (* the sequence number column in fin *)
   vVal: real;    (* the value column in fin *)
   seqnum: integer; (* the current sequence number *)
   symbol: char; (* the current symbol: c(ircle), s(quare),
t(riangle)
      and blank meaning that there are no further symbols
*)
```

- 271 -

```
  symboltype: char; (* how to mark the current symbol, see
makemarktype *)
  symbolplacement: char; (* how to place the current
symbol, a(bsolute)
      on the graph or r(elative) to the current Ri value *)
  symbolbits: real; (* where to place the current symbol
on the absolute
      or relative scale *)
  symbolsize: real; (* size of symbols relative to graph
spacing *)
  symbolpiece: integer; (* the piece number on which to
plot the next symbol *)
  symbolcoordinate: integer; (* the coordinate to plot the
next symbol *)
  ygraphsize: real; (* the size into which the graphs fit
vertically *)

procedure drawxaxis;
(* draw the x axis *)
begin with parameters do begin
  writeln(fout);
  writeln(fout,'% draw x axis');
  writeln(fout,'gsave % [ xaxis');
  writeln(fout,'0 ',bitlower/bitspercm
*defscale:infofield:infodecim,
            ' translate');
  writeln(fout,'0 0 moveto');
  xaxis(fout, xaxlength*defscale,currentpos,xinterval,currentpos+numperl
n,
      xsubint,
      xticlength*defscale, xticdx*defscale,
xticdy*defscale,
      xwidth, xdecimal,
      false, false, 2.0);
  (* now put the label out *)
```

- 272 -

```
  writeln(fout,(xaxlength /2.0 *
defscale):infofield:infodecim, ((xticlength+3*xticdy)*defscale):infofield:infodecim,
                ' moveto');
  write(fout,'(');
  if sequencelabel then writeln(fout,'sequence:
',seqnum:1,', ');
  writestring(fout,xaxislabel); writeln(fout,')');
  writeln(fout,' dup stringwidth pop neg 2 div 0 rmoveto %
center');
  writeln(fout,'show');
  writeln(fout,'grestore % ] xaxis');
  if plottype = 'b' then begin
     writeln(fout, '0 0 moveto');
     writeln(fout, xaxlength:infofield:infodecim, ' cm  0
cm lineto');
     writeln(fout, 'stroke');
  end;
```

- 273 -

```
end; end;

procedure drawyaxis;
(* since tic marks are drawn individually, the total
length is larger than the stack can handle and one gets
a limit check in ghostscript.  So put them out each
time... *)
begin with parameters do begin
  (* begin plotting the axes *)
{
  writeln(fout, '0 0 moveto');
  writeln(fout, '0 cm yaxlength cm lineto');
  writeln(fout, 'stroke');
}
  (* move to zero of y axis then draw *)
  writeln(fout);
  writeln(fout,'% draw y axis');
  writeln(fout,'gsave % [ yaxis');
  writeln(fout,'0 ',bitlower/bitspercm
*defscale:infofield:infodecim,
              ' translate');
  writeln(fout,'0 0 moveto');
  yaxis(fout,
        yaxlength*defscale,bitlower,yinterval,bitupper,
        ysubint,
        yticlength*defscale, yticdx*defscale,
yticdy*defscale,
        ywidth, ydecimal,
        false, false, 2.0);
  (* now put the label out *)
  writeln(fout,((0)*defscale):infofield:infodecim,
              ((yaxlength+xticlength) *
defscale):infofield:infodecim,
              ' moveto');
  write  (fout, '('); writestring(fout,yaxislabel);
writeln(fout,') show');
  writeln(fout,'grestore % ] yaxis');
```

- 274 -

```
  writeln(fout);
(* end plotting the axes *)
end; end; (* drawyaxis *)

procedure stepcurrent;
(* step one position and
do a page or axes depending on the value of currentpos and
graphsperpage *)
var
   dopage: boolean; (* if true, start a page *)
   doaxes: boolean; (* if true, draw the axes *)
begin with parameters do begin currentpos := succ(currentpos);
{
writeln(output,'stepcurrent currentpos=',currentpos:1);
}
```

- 275 -

```
(* The last part of the logic below is that the very
last base was done on
    the previous graph or page, so don't it do again *)

doaxes := ((((currentpos-frompos) mod numperln) = 0)
             and (currentpos <> topos))
            or newsequence;

(* only when we have completed a graph do we count it!
*)
  if doaxes then graphsperpage := succ(graphsperpage);

dopage := (graphsperpage >= numperpg) or (pagenumber =
0);

{
writeln(output,'graphsperpage = ',graphsperpage:1);
writeln(output,'pagenumber = ',pagenumber:1);
writeln(output,'currentpos=frompos =
',(currentpos=frompos):1);
writeln(output,'dopage = ',dopage);
writeln(output,'doaxes = ',doaxes);
writeln(output,'newsequence = ',newsequence);
}

(* note: one cannot put the grestore and gsave inside
the startpage and
    endpage functions:  for some reason they are ignored!
*)
  if dopage then begin (* finish the last data segment *)
      if inout = 'i' then begin
         writeln(fout,'dodash {segmentmark} if');
         inout := 'o';
      end;
```

- 276 -

```
    pagenumber := succ(pagenumber);
    graphsperpage := 0;
    writeln(output, 'starting page ',pagenumber:1);
    if pagenumber > 1 then begin
        writeln(fout, 'grestore % ] end page )
',(pagenumber-1):1);
        writeln(fout, 'showpage');
    end;
    writeln(fout);
    writeln(fout, '%%Page: ',pagenumber:1,'
',pagenumber:1);
    writeln(fout, 'gsave startpage % [ start page (
',(pagenumber):1);
    doaxes := true; (* new axes are needed on the new
page *)
  end;

if doaxes then begin (* finish the last data segment *)
    if inout = 'i' then begin
```

- 277 -

```
      writeln(fout,'dodash {segmentmark} if');
      inout := 'o';
   end;

writeln(output, 'drawing axis @ ', currentpos:1);
   writeln(fout,' 0 ',-ygraphsize:infofield:infodecim,'
cm translate');
   if showaxis then begin
      drawxaxis;
      drawyaxis;
   end;

case plottype of (* start out at the right place *)
      'b': writeln(fout,'0              .
',bitlower:infofield:infodecim,' bits moveto');
      'z': writeln(fout,'0 0 moveto');
   end;
   newsequence := false;
 end;

end; end; (* stepcurrent *)

procedure drawsymbols;
(* select the symbol, the way to draw it, its size, its
position *)
begin
  if symboltype <> ' ' then begin
    if (currentpos = symbolcoordinate) and
       (sVal = symbolpiece) then begin·
      writeln(fout);
      writeln(fout,'gsave % symbol @ ',currentpos:nfield);
      writeln(fout,'  currentpoint pop % x position');
(* This is a method to put the symbol BETWEEN lines by
modifying x:
  writeln(fout,'spaceperbase 2 div neg add');
*)
```

- 278 -

```
case symbolplacement of
    'a': write(fout, symbolbits:infofield:infodecim,'
bits');
    'r': write(fout,
(vVal+symbolbits):infofield:infodecim,' bits');
end;
writeln(fout, ' % y position');

(* size is based on spacing between lines *)
writeln(fout,symbolsize:infofield:infodecim,
            ' spaceperbase mul % size');

case symbol of
  'c': write(fout,'  circlesymbol');
  't': write(fout,'  trianglesymbol');
  's': write(fout,'  squaresymbol');
```

- 279 -

```
     end;

makemarktype(fout, symboltype);

writeln(fout,'grestore');

(* move to next symbol *)
     getsymbol(dnasymbols, symbol, symboltype,
symbolplacement,
               symbolbits, symbolsize, symbolpiece,
symbolcoordinate);
    end;
  end;
end;

begin(* writepostscript *)
with parameters do begin writeln(fout, 'gsave % { % writepostscript');
  writeln(fout, 'clear');
  writeln(fout, '/Times-Roman findfont');
  writeln(fout, '12 scalefont');
  writeln(fout, 'setfont');
  writeln(fout);
  startpic(fout, 1.0, 0.0, 0.0,'t');

(* begin setting scale factors *)
  writeln(fout, '/cmfactor 72 2.54 div def % defines
points -> centimeters');
  writeln(fout, '/cm {cmfactor mul} def % defines
centimeters');
  writeln(fout, '/bits {', bitspercm:infofield:infodecim,
' div cm } def',
               '  % defines bits');
  writeln(fout, '/totalseq ', topos:infofield,
frompos:infofield, ' sub def',
               '  % the length of the total sequence');
```

- 280 -

```
  writeln(fout, '/spacing ',
yaxlength:infofield:infodecim, numperpg:infofield,
                ' div cm def  % the space between lines');
  writeln(fout, '/spaceperbase ',
xaxlength:infofield:infodecim, ' cm ',
                numperln:infofield, ' div def % determines
the space',
                ' between base pairs');
  writeln(fout);

(* set up a page *)
  ygraphsize := yaxlength;
  (* + xticlength + 3*xticdy + 3*yticdy;*)
  if xticlength < 0 then ygraphsize := ygraphsize -
3*xticlength;
  if xticdy < 0 then ygraphsize := ygraphsize - 3*xticdy;
  if yticdy < 0 then ygraphsize := ygraphsize - 3*yticdy;
```

- 281 -

```
  writeln(fout, '/startpage {');
  writeln(fout,    orix:infofield:infodecim, ' cm',
                ' ',(oriy +
numperpg*ygraphsize):infofield:infodecim,
                ' cm translate');
  writeln(fout, 'erasepage');
  writeln(fout,'0 0 moveto');
  writeln(fout, '} def');
  writeln(fout);

(* The function d is named with a single character
     to save space and increase speed in the final
PostScript file *)
  writeln(fout);
  case plottype of
      'z': begin
         writeln(fout, '/d {bits currentpoint exch dup %
drawmarks zero');
         writeln(fout, '4 1 roll exch');
         writeln(fout, '4 2 roll lineto');
         writeln(fout, 'stroke');
         writeln(fout, 'pop spaceperbase add 0 cm moveto}
def');
     end;
     'b': begin
         writeln(fout, '/d {bits currentpoint exch dup %
drawmarks bottom');
         writeln(fout, '4 1 roll exch');
         writeln(fout, '4 2 roll lineto');
         writeln(fout, 'stroke');
         writeln(fout, 'pop spaceperbase add ',
bitlower/bitspercm:infofield:infodecim,
                      ' cm moveto} def');
     end;
  end;
  writeln(fout);
```

- 282 -

```
  writeln(fout,'/segmentmark { % mark at the contiguous
segment of plot');
  writeln(fout,'gsave % [');
{ writeln(fout,'1 0 0 setrgbcolor '); mark red for
testing}
  writeln(fout,'currentpoint pop 0 translate % use x
position but not y');
  writeln(fout,'0
',bitlower/bitspercm:infofield:infodecim, ' cm moveto');
  writeln(fout,'0
',bitupper/bitspercm:infofield:infodecim, ' cm lineto');
  writeln(fout,'[2 4] 0 setdash % DO DASH'); (* turn dash
on *)
  writeln(fout,'stroke % DO DASH');
  writeln(fout,'[] 0 setdash % DO DASH'); (* turn dash off
*)
  writeln(fout,'grestore % ]');
  writeln(fout,'} bind def');
  writeln(fout);
```

- 283 -

```
writeln(fout,'/presegmentmark { % mark before the
contiguous segment of plot');
  writeln(fout,'gsave % [');
  writeln(fout,'  currentpoint pop % x position');
  writeln(fout,'  spaceperbase sub % new x position');
  writeln(fout,'  dup 0 gt { % don''t mark left of axis');
  writeln(fout,'    0 translate');
  writeln(fout,'    0 0 moveto');
  writeln(fout,'    segmentmark');
  writeln(fout,'  } if');
  writeln(fout,'grestore % ]');
  writeln(fout,'} bind def');
  writeln(fout);

(* define symbols and their use.  Code taken from
makelogo 8.07 *)
  writeln(fout,'/circlesymbol { % x y radius circlesymbol
- (path)');
  writeln(fout,'newpath 0 360 arc closepath} bind def');
  writeln(fout);

writeln(fout,'/sqrt3 3 sqrt def');
  writeln(fout,'/trianglesymbol { % x y radius
trianglesymbol - (path)');
  writeln(fout,'/r exch def');
  writeln(fout,'/sqrt3r sqrt3 r mul def');
  writeln(fout,'translate');
  writeln(fout,'% firstaxis');
  writeln(fout,'120 rotate');
  writeln(fout,'% secondaxis');
  writeln(fout,'0 r translate');
  writeln(fout,'-120 rotate');
  writeln(fout,'newpath');
  writeln(fout,'0 0 moveto');
  writeln(fout,'sqrt3r 0 lineto');
  writeln(fout,'-300 rotate');
  writeln(fout,'% thirdaxis');
```

- 284 -

```
writeln(fout,'sqrt3r 0 lineto');
writeln(fout,'closepath} bind def');
writeln(fout);

writeln(fout,'/squaresymbol { % x y side squaresymbol -
(path)');
writeln(fout,'/side exch def');
writeln(fout,'translate');
writeln(fout,'side 2 div neg dup translate');
writeln(fout,'newpath');
writeln(fout,'0 0 moveto');
writeln(fout,'0 side lineto');
writeln(fout,'side side lineto');
writeln(fout,'side 0 lineto');
writeln(fout,'closepath} bind def');.
```

- 285 -

```
  writeln(fout);

writeln(fout, '%%EndProlog');

writeln(fout);
  (**** Start the main loop through the data, making the
graph ************)

reset(positions);

reset(dnasymbols);
  getsymbol(dnasymbols, symbol, symboltype,
symbolplacement, symbolbits,
            symbolsize, symbolpiece, symbolcoordinate);

pagenumber := 0;
  graphsperpage := 0;
  seqnum := -maxint; (* force new sequence function in
main loop *)
  currentpos := frompos-1;
  newsequence := false;

skipdata(fin);
  repeat
     grabcolumns(fin, sCol, cCol, vCol, sVal, cVal, vVal);
{
writeln(output,'grabbed:',
' sVal=',sVal:1,
' cVal=',cVal:1,
' vVal=',vVal:1);
} if seqnum <> sVal then begin
          newsequence := true;
          if readpositions then readln(positions, frompos,
topos);
          seqnum := sVal;
```

- 286 -

```
      writeln(output);
      write(output,'SEQUENCE ',seqnum:1);
      writeln(output,', positions: ', frompos:1, ' to
',topos:1);
      currentpos := frompos-1;
      stepcurrent;
      inout := 'o';   (* we start outside the data *)
    end;

if (cVal >= frompos) and (cVal <= topos) then begin
      (* skip over blanks and catch up to cVal *)
      (* If curpos is GREATER than cVal, then the
sequence
         numbering is DECREASING and the direction of
plotting
         geez... can this be handled?  Well, the graph
coordinates
```

- 287 -

```
          cannot go negative!  Looks like this is a bug
for now. *)
       if currentpos > cVal then begin
          writeln(output);
          writeln(output,'The current position',
                         ' currentpos = ', currentpos:1,
                         ' exceeds',
                         ' cVal = ', cVal:1,
                         ' at sequence ',seqnum:1,'.');
          write(output,'This program cannot handle
negative');
          writeln(output,' coordinate systems because');
          writeln(output,'the axes can only be drawn
positively.');
          write  (output,'This error may also have occured
because');
          writeln(output,' the program cannot handle
scans');
          writeln(output,'in both directions.');
          halt
       end;

while currentpos < cVal do begin
          (* if inside the data, finish it with out mark
*)
          if inout = 'i' then begin
             writeln(fout,'dodash {segmentmark} if');
             inout := 'o';
          end;

drawsymbols;
          (* draw the data line here *)
          case plottype of
             'b': write(fout,bitlower:infofield:infodecim,'
d'); (* drawmarks *)
             'z': write(fout,'0 d'); (* drawmarks *)
          end;
```

- 288 -

```
            writeln(fout, ' % @ ', currentpos:nfield);
            stepcurrent;
        end;

if (currentpos <> cVal) then begin
            if not eof(fin) then begin
                writeln(output,'ERROR:',
                                ' currentpos = ',
currentpos:1,
                                ' <> ',
                                ' cVal =', cVal:1,
                                ' at sequence ',seqnum:1);
                halt
            end
            else begin (* else we just hit end of data *)
                (* if inside the data, finish it with out
mark *)
                if inout = 'i' then begin.
                    writeln(fout,'dodash {segmentmark} if');
                    inout := 'o';
```

- 289 -

```
              end;
           end
        end
        else begin
           if (vVal < bitlower) then vVal := bitlower;

(* if outside the data, start it with going in
mark *)
           if inout = 'o' then begin
              writeln(fout,'dodash {presegmentmark} if');
              inout := 'i';
           end;

drawsymbols;
           write(fout, vVal:infofield:infodecim,' d'); (*
drawmarks *)
           writeln(fout, ' % @ ', cVal:nfield);
           stepcurrent;
        end;
     end;
  until eof(fin);

(* final mark of all if needed *)
  if inout = 'i' then begin
     writeln(fout,'dodash {segmentmark} if');
     inout := 'o';
  end;

writeln(fout, 'grestore % end page ] ',pagenumber:1);
  writeln(fout, '%%Page: ',pagenumber:1,' ',pagenumber:1);
  writeln(fout);

writeln(fout, '%%Trailer');
  writeln(fout, '%%Pages: ',pagenumber:1);
  writeln(fout);
  writeln(fout, 'showpage');
  writeln(fout, 'grestore % } writepostscript end graphics
```

- 290 -

```
) ');
  writeln(fout);

if symbol <> ' ' then begin
      writeln(output,'WARNING: There are unused
dnasymbols:');
      while symbol <> ' ' do begin
          writeln(output);
          writeln(output,'symbol:
',symbol:infofield);
          writeln(output,'symboltype:
',symboltype:infofield);
          writeln(output,'symbolplacement:
',symbolplacement:infofield);
          writeln(output,'symbolbits:
',symbolbits:infofield:infodecim);
          writeln(output,'symbolsize:
',symbolsize:infofield:infodecim);
          writeln(output,'symbolpiece:
',symbolpiece:infofield);
```

- 291 -

```
writeln(output,'symbolcoordinate:',symbolcoordinate:infofi
eld);
        getsymbol(dnasymbols, symbol, symboltype,
symbolplacement,
                  symbolbits, symbolsize, symbolpiece,
symbolcoordinate);
      end;
  end;

end;
end;
(* end module dnaplot.writepostscript *)

(* begin module dnaplot.makeheader *)
procedure makeheader(var fin: text; parameters: params;
var fout: text);
(* Reads the header lines from fin and writes them to
fout. *)
var
  totalnumpages: integer; (* total number of pages that
will be produced *)
begin (* makeheader *)

with parameters do begin
    if not readpositions then begin
      (* determine how many pages the process will
produce *)
      totalnumpages :=
round((((topos-frompos)/numperln)/numperpg));
      write(output, 'For each sequence, dnaplot will
produce ',
                    totalnumpages:1,' page');
      if totalnumpages <> 1 then write(output,'s');
      writeln(output,' of graphs.');
    end;

(* do our PostScript duty *)
```

- 292 -

```
    rewrite(fout);
    writeln(fout, '%!PS-ADOBE-2.0');
    writeln(fout, '%%DocumentFonts: Times-Roman');
    writeln(fout, '%%Title: dnaplot ',version:4:2);
    writeln(fout, '%%Creator: Thomas D. Schneider');
    writeln(fout, '%%CreationDate: -');
    writeln(fout, '%%For: -');
    writeln(fout, '%%Pages: (atend)');
    writeln(fout, '%%PageOrder: Ascend');
{   writeln(fout, '%%BoundingBox: 40 40.33 571.7 752');}
    writeln(fout, '%%EndComments');
    writeln(fout);
  end;

reset(fin);
  repeat
    write(fout, '% ');
```

- 293 -

```
    copyaline(fin, fout); (* copy commented lines of fin
to fout *)
    until fin^ <> '*';

writeln(fout);
end;
(* end module dnaplot.makeheader *)

(* begin module dnaplot.themain *)
procedure themain(var fin, fout, finp, positions,
dnasymbols: text);
(* the main procedure of the program *)
var
    parameters: params; (* parameters read from finp *)

begin(* themain *)
  writeln(output, 'dnaplot ', version:4:2);
  readparam(finp, parameters);
  makeheader(fin, parameters, fout);
  writeparam(fout, parameters);
  writepostscript(fin, fout, parameters, positions,
dnasymbols);
end;
(* end module dnaplot.themain *)

begin
    themain(dnain, dnaout, dnaplotp, positions,
dnasymbols);
1: end.
```

- 294 -
APPENDIX F

| | | |
|---|---|---|
| 0 500 | frompos topos | positions on sequence graph will represent |
| 1 4 6 | sCol cCol vCol | columns to read from the dnain file |
| 2 | numperpg | number of graphs per page |
| 201 | numperln | number of base pairs per line |
| -30 +20 | bitlower bitupper | lower and upper bounds of bits to display |
| 2.54 10.54 | orix oriy | x, y origin of plot (in cm) |
| 15.24 8.00 | xaxlength yaxlength | length of the x and y axes in cm |
| true | showaxis | show axes to dnaout |
| 100  5 | xinterval yinterval | size of intervals on axes to plot |
| 2 5 | xsubint ysubint | number of sub intervals on axes to mark |
| 5 6 | xwidth    ywidth | width of numbers in characters |
| 0 0 | xdecimal ydecimal | number of decimal places |
| 0.2  0.0  -0.4 | xticlength xticdx xticdy | length of tic mark and sh |
| 0.2 -0.15 -0.15 | yticlength yticdx yticdy | length of tic mark and sh |
| t | sequencelabel | t=true means print sequence number on graphs |
| Position (bases) | | |
| Ri (bits) | | |
| b | plottype | z=from zero, b=from bottom of graph to value |
| d | dodash | d=do dashes, n=no dashes |

- 295 -

- 296 -

APPENDIX G

```
* dnasymbols: example file for the dnaplot program
* the values on each line are:
*
* symbol: c(ircle) s(quare) t(riangle)
* symboltype: s(troke) f(ill) d(ash)
* symbolplacement: a(bsolute) r(elative)
* symbolbits; the shift from symbolplacement in bits
* symbolsize: size in line separations
* symbolpiece: sequence number to mark
* symbolcoordinate: coordinate to mark
* eg:
* csa 15 0.5 1 100
* This means place a circle, stroked, at absolute 15 bits,
0.5 size,
* for sequence 1 at coordinate 100.
*
* Lines that start with "*" are comments.
* Completely blank lines are allowed.

csa 15 0.5 1 100
tsa 16 0.5 1 101
tfa 17 1 1 102

* put squares at each data point
ssr 0 0.2 1 103
sfr 0 0.2 1 104
sdr 0 0.2 1 105
ssr 0 0.2 1 106
sfr 0 0.2 1 107
sdr 0 0.2 1 108
ssr 0 0.2 1 109

* "float" triangles 5 bits above each data point
tsr 5 0.2 1 110
tfr 5 0.2 1 111
```

- 297 -

```
tdr 5 0.2 1 112
tsr 5 0.2 1 113
tfr 5 0.2 1 114
tdr 5 0.2 1 115
tsr 5 0.2 1 116

* put a circle below
cfr -5 0.2 1 117

* mark on the x axis:
csa 0 0.2 1 119
csa 0 0.2 1 120
```

- 298 -

APPENDIX H

```
program walker(book, ribl, colors, walkerp, walk, output);
(* walker: walk an information weight matrix across a
sequence Tom Schneider
  NCI/FCRDC Bldg 469. Room 144
  P.O. Box B
  Frederick, MD  21702-1201
  (301) 846-5581 (-5532 for messages)
  network address: toms@ncifcrf.gov National Cancer Institute
  Laboratory of Mathematical Biology

1995
*)

label 1; (* end of program *)

const
(* begin module version *)
version = 3.10; (* of walker.p 1995 June 23
origin 1994 November 1 *)
(* end module version *)

(* begin module describe.walker *)
(*
name
   walker: walk an information weight matrix across a
sequence synopsis
   walker(book: in, ribl: in, colors: in, walkerp: in,
          walk: out, output: out)
```

- 299 - files
    book: a book from the Delila system ribl: a weight matrix from the Ri program colors: definitions of how to color letters.  See
makelogo.p for details.

walkerp:  parameters to control this program rangefrom: integer, FROM of the ribl matrix to use.
        rangeto: integer, TO of the ribl matrix to use.

basesperline: integer, number of bases per line to
display.

linesperpage: integer, number of lines per page to
display.

basenumber: integer, the base on the line to place
the zero of the walker
        at initially on the page.  It must be between 0 and
basesperline - 1.
        Counting begins at zero on the left side of the
page.

linenumber: integer, the line number to place the
zero of the walker at
        initially on the page.  It must be between 0 and
linesperpage - 1.
        Counting begins at zero on the bottom of the page.

coornumber: integer, the coordinate number to place
the zero of the
        walker at initially.  If this number is not found in
the piece
        coordinate system, the walker will be placed at the

- 300 - beginning of the
    sequence when coornumber's value is zero or negative
and placed at the
    end of the sequence when coornumber's value is
positive.

pagewidth: real, the width of the lines of sequence
in cm.
    pageheight: real, the height of the lines of
sequence in cm.
    pagex: real, the x coordinate of the page lower left
corner in cm.
    pagey: real, the y coordinate of the page lower left
corner in cm.

lowerbound: real < 0, the lowest Ri(b,1) value in
bits that can be fully
    displayed (bases with lower values are clipped and
have a red line on
    the bottom).

boxes: charcter: if 'b' then the walker characters
are surrounded by
    character-boxes as defined below.  Otherwise the
boxes are invisible.

outofsequence: charcter: if 'o' then the walker is
set next to the
    sequence.  Otherwise the walker is in line with the
sequence.  Thanks
    to Seth Taylor for suggesting this option on 1994
November 22.

ALL LINES FOLLOWING THIS POINT:  These are inserted
into the walk
        as commands before the initial display.

- 301 -

```
walk: A postscript program that implements the walk.
    It is to be run with ghostscript:
        gs -q walk
    Ghostscript then pops up a graphics window and the
user types commands to
    control the display.  (The -q just makes ghostscript
quiet on startup.)
    The program reports information to the user that
include the position,
    the individual information for the current position
(Ri, bits) and the Z
    score for this Ri given the mean (Rsequence) and
standard deviation of
    the original population of sequences used to create
the ribl matrix.
    When the absolute value of the Z score is less than
or equal to 2, an
    arrow (<---) indicates that the position is likely
to be a site.
    Likewise, when the Ri value is positive, this is
indicated by plus signs
    (++++).  (The actual test can be set by the user.)
The user can type '?'
    or 'help' to get a list of commands.  These commands
are discussed in
    further detail below.

NOTE: the Ri evaluation is ONLY for the portion of
the walker displayed
        on the screen.

output:  Messages to the user.

description
    This program creates a PostScript program, called the
"walk", by
    reformatting the DNA sequences in a Delila book and
```

- 302 - joining them to the ribl
   matrix.  The user then runs the "walk" using the interactive PostScript
   interpreter ghostscript.  Within the ghostscript graphic page appears part
   or all of the sequence(s) in the book.  The majority of the letters are
   black, but a portion are in color.  These letters correspond to the
   evaluation of those bases by the Ri(b,l) matrix read from the ribl file.
   The height of each letter is proportional to its weight in the matrix.  Thus
   the user can immediately see the components of the weight matrix as applied
   to the particular sequence.  The user may then type commands to move the
   evaluated region around.  The user literally walks the evaluation across the
   sequence, and thereby gains a sense of the reaction each part of the
   recognizer to each part of the sequence.

GENERAL SCHEME OF A WALKER PAGE

A walker page consists of a rectangular array of character boxes:

```
        <------------- basesperline ------------>   (10 in this case)
         0    1    2    3    4    5    6    7    8    9

^  ------------------------------------------                ^
   p  |  |152|153|154|155|156|157|158|159|1   |2   |               |
   a  |  |   |   |   |   |   |   |   |   |    |    | 2             |
   g  |  |   |   |   |   |   |   |   |   |    |    |               |
   e  |  |   |   |   |   |   |   |   |   |    |    |               |
```

```
                          - 303 -
h    |  ------------------------------------                |
e    |  |3  |4  |5  |6  |7  |8  |9  |10 |11 |12 |           |
i    |  |   |   |   |   |   |   |   |   |   |   | 1
linesperpage
g    |  |   |   |   |   |   |   | ! |   |   |   |          (3 in
this case)
h    |  |   |   |   |   |   |   |   |   |   |   |           |
t    |  ------------------------------------                |
     |  |13 |14 |15 |16 |17 |18 |19 |20 |21 |22 |           |
(    |  |   |   |   |   |   |   |   |   |   |   | 0         |
c    |  |   |   |   |   |   |   |   |   |   |   |           |
m    |  |   |   |   |   |   |   |   |   |   |   |           |
)  v *------------------------------------                  v
     *
      * <----------- pagewidth (cm) ------------>
     *
```

**** lower left hand corner is at pagex horizontal (cm) and pagey vertical (cm) on the page, starting from the PostScript default zero coordinate.

The "!" is at basenumber = 5, linenumber = 1, coornumber = 8

All the parameters: basenumber, linenumber, coornumber, basesperline, linesperpage, pageheight, pagex and pagey are defined independently. The physical positioning parameters pagex, pagey, pagewidth and pageheight determine where the entire set of character boxes is placed on the page.

Each character box size is determined by the basesperline and linesperpage so that the required number fit the defined area of the page. The zerobase of the walker is set initially at the coordinate given

- 304 - by basenumber and linenumber.  The coordinates of the bases for the rest
of the sequence are determined by the coordinate of the zerobase of the
walker.

Note that the coordinate system in the example above
represents a fragment of a circular DNA, with coordinates running from 152 up
to 159, followed by a jump to the start of numbering at 1 and then
proceeding up to 22.  (These kinds of coordinates can be generated and handled by
Delila programs.)

GENERAL SCHEME OF A WALKER CHARACTER BOX

```
+---+ <-- 2 bits per base
|   |
|---| <-- 0 bits per base
|   |
|   |
|   |
|   |
+---+ <-- lowerbound bits per base
```

The box has a part above zero in which letters appear
upright and a part below zero in which the letters appear rotated 180
degrees if they are within the evaluated region or black and upright if
they outside.

If the walker is out of the sequence, then a gap of
height 1 bit is created just above the 2 bits mark.  The sequence is

- 305 - put there.
  The rest of the characterbox is scaled accordingly.

Bases which have positive Ri(b,l) values run upward
from 0 to 2 bits, those
  that have a negative value run downward. If a base
evaluates to a number of
  bits lower than lowerbound, it will be drawn down but
any amount below
  lowerbound is cutoff. To indicate this situation, the
background becomes
  purple. If the base has a value less than -500 bits,
it is considered to be
  negative infinity, and the background becomes black.
(The convention is to
  represent negative infinity by -1000 in the Ri(b,l)
matrix.)

COMMANDS

When the walk program is run in GhostView, the user can
control the display
  by means of typed commands. These commands are built
from PostScript
  procedures. This means that any arguments must be
given before the command
  itself. This may feel a little strange at first, bit
it is easy to get used
  to. For example, to go to location 132, the user
types:
       132 goto<cr>
     where <cr> is a carriage return.

means that the command is proceeded by a number.
  * means not implemented yet Movement Commands: These commands affect the direction

- 306 - that the walker or
    the sequence moves. Which moves depends on the w
command. The commands are
    the same as those of the Unix editor vi.

h: move left on the page (# is optional)
    # j: move down on the page (# is optional)
    # k: move up on the page (# is optional)
    # l: move right on the page (# is optional)

Move commands may have an integer in front which says
how many times to
    move. The program will repeat the command.

*   n: next sequence
*   p: previous sequence w: A toggle between two states:
        the walker  moves along the stationary sequence,
            or
        the sequence moves along the stationary walker.

q: quit
    ?: help message r: Refresh the page.
    R: restore or restart ghostscript on the current walk
file. This allows one
        to start over or to modify the walk and restart
without quitting
        ghostscript. The modification could be done by the
walker program, by
        hand-editing or by another program.

a,c,g,t: Mutate the given absolute location to the
desired base. For
        example, to set base 100 to be an "a", type "100 a".

- 307 -

A,C,G,T: Mutate the given relative location to the desired base. The
    location is relative to the current position of the walker. For example,
    to set the base 10 to the left of the walker zero to be an "a", type "-10
    A".

setwait: set the wait time in seconds after display (starts at zero)
isasecond: set the number of {1 pop} cycles per second. This depends
    on how fast your computer is and should be adjusted.

goto: Type a coordinate and then "goto". For example, to get to coordinate
    100 type "100 goto". The zero base of the walker will be set to the
    coordinate.

jump: Like goto except one gives the relative number of bases to move. For
    example, to move 5 bases in the 5' direction, type "-5 jump". The zero
    base of the walker will be set to the new coordinate.

boxes: toggle between having boxes and not. These are mostly helpful
    for seeing where things are on the page.
lines: Set the number of lines per page, eg type "3 lines".
bases: Set the number of bases per page, eg type "30 bases".
    ("wide" can also be used)
left, right, up, down: move the graphic on the page in units of cm.

- 308 - example: "0.5 right" moves the graphic right half a cm.

height, width: set the page height or width in cm.

in: Put the walker into the sequence.
  out: Put the walker out of the sequence.

wave: define base at which the low point of the cosine wave is set.
    example: "5 wave" puts the low point at base +5.

waveon: Turns on drawing the wave.
  waveoff: Turns off drawing the wave.

toggleprinting or tp: a toggle that turns on and off printing. This allows
    one to give several commands without seeing the display change. Turning
    printing on automatically causes a display.

toggleerase or te: a toggle that turns on and off eraseing the page. In
    conjunction with the toggleprinting command this allows one to display
    several walkers on a page for making a figure.

from: change FROM range of the matrix to use
  # to: change TO range of the matrix to use help: help message setri: set minimum Ri for searching and display
  # setz: set minimum Z for searching and display
  # f: search forward to next site which fits search criteria
  # b: search backward to next site which fits search criteria

- 309 -

TO MAKE PRINTOUTS

The walker is interactive, which means that the PostScript showpage function
is not called since it would pause the screen and then wipe out the display
at every command.  However, printers require showpage and if it is not
inculded they won't print anything.  If you do this they will spend a few
minutes rendering the page and then nothing will come out!  To make
printouts, attach:

gsave showpage grestore to the end of the walk file.  The gsave/grestore assure that the graphics
state is not lost during the showpage.  You can put any commands you like in
front of the showpage:

180 goto boxes out showpage

This allows one to set up the page as desired.

TO IMBED IN FIGURES

In addition to the note above about showpage, the walk file contains
commands that translate the image.  To prevent these from affecting the
surrounding PostScript, they must be enclosed in a gsave-grestore pair.  The
gsave is provided at the start of the walk file.  The grestore is provided
by the q command.

- 310 -

Commands can be put at the end of the parameter (walkerp) file. The command
 toggleprint is called before and after these commands, so the commands are
 normally not seen. If you surround your commands with calls to toggleprint,
 you will see a movie of the actions taken.

The command toggleerase allows one to draw several walkers on a page, merely
 by preventing the previously drawn one from being erased.

ACKNOWLEDGMENTS

I thank Seth Taylor for suggesting the mode for the walker being outside the
 sequence, Paul Hengen for suggesting the cosine wave applied to the letters
 and Denise Rubens for suggesting the mutation function.

examples

```
-10     rangefrom: integer, FROM of the ribl matrix to use
+10     rangeto: integer, TO of the ribl matrix to use
50      basesperline: integer, number of bases per line to display.
3       linesperpage: integer, number of lines per page to display.
20      basenumber: integer, the base on the line to place the zero of the walker
1 0     linenumber: integer, the line number to place the zero of the walker
132     coornumber: integer, the coordinate number to place the zero of the walker
18.5    pagewidth: real, the width of the lines of sequence in cm.
```

- 311 -

24.9   pageheight: real, the height of the lines of sequence in cm.
1.5    pagex: real, the x coordinate of the page lower left corner in cm.
1.5    pagey: real, the y coordinate of the page lower left corner in cm.
-4     lowerbound: real < 0, the lowest Ri(b,1) value in bits displayed
nb     boxes: b: boxes around each character
io     insequence: i: in the sequence, else out
% all lines from this point on are PostScript commands
% The "%" makes a comment
% walkerp: parameters for walker 3.03 and higher
% The following commands make a picture of 2 walkers
% waveoff        % turn off waves
1 lines          % display only one line
10 up            % move 10 cm up
5 height         % make the line only 5 high
44 wide          % show 44 characters across
w 5 h w          % move the sequence 5 positions left
132 goto         % put the walker in a new spot
toggleprinting toggleprinting % force printing
toggleerase      % prevent erasing during the next steps
6 down           % jump 6 cm down
143 goto         % put the walker in a new spot
toggleprinting toggleprinting % force printing
% gsave showpage grestore % unearth the command if you send this to a printer!

documentation
    Ghostscript documentation can be found from:
    http://www.cs.wisc.edu/~ghost/index.html
    Here are other World Wide Web links if that one isn't available:
<a href=http://ilios.eng.monash.edu.au/~rjl/ghost/index.html>
 Australian copy of the Ghostscript WWW pages</a>

- 312 -

```
<LI>
<a
href=http://godel.ph.utexas.edu/Members/timg/gs/gs.html>
 Atari Ghostscript WWW page</a>
<LI>
<a href=ftp://smallo.ruhr.de/pub/ghost/gs.faq>Frequently
Asked Questions</a>
(the official text version)
<LI>
<a href=http://www.adobe.com/> Adobe WWW home page</a>
</UL>
<HR>
Corrections to the Ghostscript WWW pages should be mailed
to
rjl@monu1.cc.monash.edu.au see also
    delila.p, makelogo.p, ri.p, scan.p, dnaplot.p author
    Thomas Dana Schneider bugs Known Bughs:

Only one sequence is loaded from the book.

With parameter for 3 lines, reset to 1 line puts the
entire display too
    low.  Yet starting with 1 line it's ok.  Some global
parmaeter is not being
    set in definepageparameters.  (Same thing: When there
is one line per page
    the position is too low, one needs to use (eg) "5 up".)

180 goto 1 goto - it doesn't erase old stuff to left!
```

- 313 -

Something uses up virtual memory every time the walker takes a step.

Eventually this causes an error and GhostScript dies:

Error: /VMerror in --charpath--
VM status: 0 16061098 16168018
Current file position is 5
XIO:  fatal IO error 12 (Not enough memory) on X server ":0.0"
      after 47675 requests (45252 known processed) with 2497 events remaining.

Why?

When number of lines per page is changed, the cosine wave height does not
   change correctly, often being too small.  (Apparently fixed.)

The display glitches sometimes by leaving behind pieces that should get
   erased.  This occurs when numbers are being are displayed that don't fit
   into the available area and get clipped.  A relevant location in the code is
   in the routine displaywalker at: "white 0 0 charbox fill" A replacement
   replacement:  "0 0 charbox clip erasepage initclip" does not help.  Perhaps
   this is the wrong part of the code.  It is also possible that the problem is
   in ghostscript.  The effect sometimes occurs as one is moveing the walker
   around.  Letters that are drawn that go below the lower bound don't get
   cleared properly.

- 314 -

Range checking does not work properly. If the ribl has a range
from -100 to +99, then a request for -99 to +100 bombs. This
should be caught in walker.

Perhaps there should be a function that automatically defines the
lower bound in bits so that the user does not need to figure thisout.

Resetting lower bound messes up the display!

f (and probably b) searches don't work when the display is toggled
off. Fortunately this is easy to get around: just determine the
locations and use goto.

technical notes

Note: encapsulation of the figure requires a gsave and a grestore to
surround the walk code to undo the translation to the basenumber = 0,
linenumber = 0 coordinate and any other translations done by commands.

No showpage is provided, since this does not help during interactive
graphics. Worse, ghostscript pauses at every showpage or copypage, saying:

">>copypage, press <return> to continue<<"

So the user would be forced to type extra carriage returns for every

- 315 - command.  If a showpage is needed for making a
printout, it must be added
   later.

isasecond is a global constant that·defines the number
of {1 pop} operations
   that the display can run through in 1 second.  This
must be determined for
   each computer.

*)
(* end module describe.walker *)

(* begin module walker.const *)
   infofield = 12; (* size of field for printing
information in bits *)
   infodecim = 6; (* number of decimal places for printing
information *)
       (* these are used for conlist only *)
   isasecond = 100000; (* this number of {1 pop}
operations should take 1 second *)
   maxribl = 401; (* largest matrix allowed *)
   negativeinfinity = -500;  (* negative infinity for a
base *)
   nfield = 4; (* size of field for printing n, the number
of sites *)
   gooddisplay = false;  (* see technical notes in
makelogo.p for explanation. *)
   outline = false;  (* don't use outline characters in
walker *)
   showingbox = false;  (* show the box around the
character when debugging *)
   shrinking = false;  (* shrink the character inside its
box *)
(* end module walker.const *)

(* begin module book.const *)

- 316 -

```
(* constants needed for book manipulations *)

dnamax = 3000;  (* length of dna arrays *)
      namelength = 20; (* maximum key name length *)
      linelength = 80; (* maximum line readable in book *)

(* end module book.const version = 1.96; (@ of scan.p 1995
April 22 *)

(* begin module postscript.constants *)
   pwid = 8; (* width in character places to print
PostScript numbers *)
   pdec = 5; (* decimal places to print PostScript numbers
*)
   pdecolor = 4; (* decimal places for color descriptions
(5 WILL CAUSE
                    NeWS 1.1 TO BOMB) *)
(* end module postscript.constants *)

type (* begin module walker.type *)
   parameters = record (* parameters to control this
program *)
      (* all definitions are given in the walkerp
parameter definition *)
      rangefrom: integer;
      rangeto: integer;

basesperline: integer;
      linesperpage: integer;

basenumber: integer;
      linenumber: integer;
      coornumber: integer;

pagewidth: real;
```

- 317 -

```
    pageheight: real;
    pagex: real;
    pagey: real;

lowerbound: real;

fractionofline: real;
(* fractionofline is not necessary so is not user settable
anymore.

walkerp:
1    fractionofline: real 0 to 1, line fraction that
bases fit into vertically walkerp definition:
*    fractionofline: real 0 to 1, the fraction of 0 to 2
bits that
        the bases outside the site fit into vertically.

description:
*   Outside the walker, the letters are shrunken vertically
by a factor of
    fractionofline so that they won't bump into the next
line.  Normally this
    should be set to 1.
*)

boxes: char;
    outofsequence: char;
  end;
(* end module walker.type *)

(* begin module book.type *)
(* types needed for book manipulations *)

chset = set of 'a'..'z';
```

- 318 -

```
(* types defined in book definition *)

alpha = packed array[1..namelength] of char; (* this
is not alfa *)

(* name is a left justified string with blanks
following the
          characters *)
     name = record
          letters: alpha;
          length: 0..namelength (* zero means an
unspecified structure *)
     end;

lineptr = ^line;
     line = record (* a line of characters *)
          letters: packed array [1..linelength] of char;
          length: 0..linelength;
          next: lineptr
     end;

direction = (plus, minus, dircomplement,
dirhomologous);
     configuration = (linear, circular);
     state = (on, off);

header = record (* header of key *)
          keynam: name; (* key name of structure *)
          fulnam: lineptr; (* full name of structure *)
          note:   lineptr (* note key *)
     end;

(* base types *)
     base = (a,c,g,t);
     dnaptr = ^dnastring;
```

- 319 -

```
dnarange = 0..dnamax;
seq = packed array[1..dnamax] of base;
dnastring = record
   part: seq;
   length: dnarange;
   next: dnaptr
end;

orgkey = record (* organism key *)
   hea: header;
   mapunit: lineptr (* genetic map units *)
end;

chrkey = record (* chromosome key *)
   hea: header;
   mapbeg: real; (* number of genetic map beginning
*)
   mapend: real (* number of genetic map ending *)
end;

pieceptr = ^piece;
piekey = record (* piece key *)
   hea: header;
   mapbeg: real; (* genetic map beginning *)
   coocon: configuration; (* configruation
(circular/linear) *)
   coodir: direction; (* direction (+/-) relative to
genetic map *)
   coobeg: integer; (* beginning nucleotide *)
   cooend: integer; (* ending nucleotide *)
   piecon: configuration; (* configruation
(circular/linear) *)
   piedir: direction; (* direction (+/-) relative to
coordinates *)
   piebeg: integer; (* beginning nucleotide *)
   pieend: integer; (* ending nucleotide *)
```

- 320 -

```
    end;

piece = record
       key: piekey;
       dna: dnaptr
    end;

reference = record
       pienam : name;   (* name of piece referred to *)
       mapbeg : real;   (* genetic map beginning *)
       refdir : direction;   (* direction relative to
coordinates *)
       refbeg : integer;   (* beginning nucleotide *)
       refend : integer;   (* ending nucleotide *)
    end;

genkey = record   (* gene key *)
       hea : header;
       ref : reference;
    end;

trakey = record   (* transcript key *)
       hea : header;
       ref : reference;
    end;

markerptr = ^marker;
    markey = record (* marker key *)
       hea : header;
       ref : reference;
       sta : state;
       phenotype : lineptr;
       next : markerptr;
    end;

marker = record
```

- 321 -

```
        key : markey;
        dna : dnaptr;
    end;

(* end module book.type version = 2.11; (@ of ri.p 1995
May 24 *)

(* begin module scan.type *)
    rblarray = array[a..t, 0..maxribl] of real; (*
real(B,L) *)
(* end module scan.type version = 2.11; (@ of ri.p 1995
May 24 *)

var
    book, ribl, colors, walkerp, walk: text; (* files used
by this program *)

(* begin module book.var *)
(*
**************************************************************
************** *)
(* global variables needed for book manipulations *)

(* free storage: *)
        freeline: lineptr; (* unused lines *)
        freedna: dnaptr; (* unused dnas *)

readnumber: boolean; (* whether to read a number
from the notes, or
                                to read in the notes *)
        number: integer; (* the number of the item just read
*)
        numbered: boolean; (* true when the item just read
is numbered *)
        skipunnum: boolean; (* a control variable to allow
skipping of
                                un-numbered items in the book
```

- 322 -

```
*)

(*
***************************************************************
************** *)
(* end module book.var version = 2.11;  (@ of ri.p 1995 May
24 *)

(* begin module halt *)
procedure halt;
(* stop the program.  the procedure performs a goto to the
end of the
   program.  you must have a label:
      label 1;
   declared, and also the end of the program must have
this label:
      1: end.
   examples are in the module libraries.
   this is the only goto in the delila system. *)
begin
     writeln(output,' program halt.');
     goto 1
end;
(* end module halt version = 2.11; (@ of ri.p 1995 May 24
*)

(* begin module copyaline *)
procedure copyaline(var fin, fout: text);
(* copy a line from file fin to file fout *)
begin (* copyaline *)
     while not eoln(fin) do begin
         fout^ := fin^;
         put(fout);
         get(fin)
     end;
     readln(fin);
     writeln(fout);
```

- 323 -

```
end; (* copyaline *)
(* end module copyaline version = 2.11; (@ of ri.p 1995
May 24 *)

(* begin module package.getpiece *)
(*
***************************************************************
************** *)
(* begin module package.brpiece *)
(*
***************************************************************
************** *)
(* begin module book.basis *)
(* procedures needed for book manipulations *)

(* get procedures should be used for all linked lists of
records *)

procedure getline(var l: lineptr);
(* obtain a line from the free line list or by making a
new one *)
begin
      if freeline<>nil
         then begin
            l:=freeline;
            freeline:=freeline^.next
         end
         else new(l);
      l^.length:=0;
      l^.next:=nil
end;

procedure getdna(var l: dnaptr);
begin
      if freedna<>nil
         then begin
            l:=freedna;
```

- 324 -

```
            freedna:=freedna^.next
        end
        else new(l);
    l^.length:=0;
    l^.next:=nil
end;

(* clear procedures should be called each time the records
are no longer needed
        failure to do this may result in a stack
overflow. *)

procedure clearline(var l: lineptr);
(* return a line to the free line list *)
var    lptr: lineptr;
begin
    if l<>nil then begin
        lptr:=l;
        l:=l^.next;
        lptr^.next:=freeline;
        freeline:=lptr
    end
end;

procedure cleardna(var l: dnaptr);
var    lptr: dnaptr;
begin
    if l<>nil then begin
        lptr:=l;
        l:=l^.next;
        lptr^.next:=freedna;
        freedna:=lptr
    end
end;

procedure clearheader(var h: header);
(* clear the header h (remove lines to free storage) *)
```

- 325 -

```
begin
      with h do begin
          clearline(fulnam);
          while note<>nil do clearline(note)
      end
end;

procedure clearpiece(var p: pieceptr);
(* clear the dna of the piece *)
begin
      while p^.dna<>nil do cleardna(p^.dna);
      clearheader(p^.key.hea)
end;

function chartobase(ch:char):base;
(* convert a character into a base *)
begin
      case ch of
          'a': chartobase:=a;
          'c': chartobase:=c;
          'g': chartobase:=g;
          't': chartobase:=t
      end
end;

function basetochar(ba:base):char;
(* convert a base into a character *)
begin
      case ba of
          a: basetochar:='a';
          c: basetochar:='c';
          g: basetochar:='g';
          t: basetochar:='t';
      end
end;

function complement(ba:base):base;
```

- 326 -

```
(* take the complement of ba *)
begin
      case ba of
          a: complement:=t;
          c: complement:=g;
          g: complement:=c;
          t: complement:=a;
      end
end;

function pietoint(p: integer; pie: pieceptr): integer;
(* p is a coordinate on the piece.
   we want to transform p into a number
   from 1 to n: an internal coordinate system for
   easy manipulation of piece coordinates *)
var   i: integer; (* an intermediate value *)
begin
      with pie^.key do begin
          case piedir of
              plus:  if p>=piebeg
                     then i:=p-piebeg+1
                     else i:=(p-coobeg)+(cooend-piebeg)+2;
              minus: if p<=piebeg
                     then i:=piebeg-p+1
                     else i:=(cooend-p)+(piebeg-coobeg)+2
          end;
          pietoint:=i
      end
end;

function inttopie(i: integer; pie: pieceptr):integer;
(* i is in the range 1 to some maximum.  it is an internal
coordinate
   system for the program.  we want to do a
   coordinate transformation to obtain
   a value in the range of the piece called pie:
   i=1 corresponds to piebeg and
```

- 327 -

```
   i=its maximum corresponds to pieend *)
var   p: integer; (* an intermediate value *)
begin
     with pie^.key do begin
        case piedir of
           plus: begin
              p:=piebeg+(i-1);
              if p>cooend
                 then if coocon=circular
                    then p:=p-(cooend-coobeg+1)
           end;
           minus: begin
              p:=piebeg-(i-1);
              if p<coobeg
                 then if coocon=circular
                    then p:=p+(cooend-coobeg+1)
           end
        end;
        inttopie:=p
     end
end;

function piecelength(pie: pieceptr): integer;
(* return the length of the dna in pie *)
begin
     piecelength:=pietoint(pie^.key.pieend,pie)
end;

(* end module book.basis version = 'delmod 6.54 86 nov 12
tds/gds' *)

(* begin module book.getto *)
function getto(var thefile: text; ch: chset): char;
(* search the file for a character in the first line which
is a
   member of the set ch. *)
var achar: char;
```

- 328 -

```
begin
    achar:=' ';
    while (not(achar in ch)) and (not eof(thefile))
        do readln(thefile,achar);
    if (achar in ch) then getto:=achar
                     else getto:=' '
end;
(* end module book.getto version = 'delmod 6.54 86 nov 12
tds/gds' *)

(* begin module book.skipstar *)
procedure skipstar(var thefile:text);
(* skip start of line (or star = '*'). *)
begin (* skipstar *)
    if thefile^ <> '*' then begin
        writeln(output,' procedure skipstar: bad book');
        writeln(output,' "*" expected as first character
on the line, but "',
                        thefile^,'" was found');
        halt
    end;
    get(thefile); (* skip the star *)

if thefile^ <> ' ' then begin
        writeln(output,' procedure skipstar: bad book');
        writeln(output,' "* " expected on a line but "*',
                        thefile^,'" was found');
        halt
    end;
    get(thefile) (* skip the blank *)
end; (* skipstar *)
(* end module book.skipstar version = 'delmod 6.54 86 nov
12 tds/gds' *)

(* begin module book.brreanum *)
procedure brreanum(var thefile: text; var reanum: real);
(* read a real number from the file *)
```

- 329 -

```
begin
      skipstar(thefile);
      readln(thefile,reanum);
end;
(* end module book.brreanum version = 'delmod 6.54 86 nov
12 tds/gds' *)

(* begin module book.brnumber *)
procedure brnumber(var thefile: text; var num: integer);
(* read a number from the file *)
begin
      skipstar(thefile);
      readln(thefile,num)
end;
(* end module book.brnumber version = 'delmod 6.54 86 nov
12 tds/gds' *)

(* begin module book.brname *)
procedure brname(var thefile: text; var nam: name);
(* read a name from the file *)
var   i: integer; (* an index to the name *)
      c: char;  (* a character read *)
begin (* brname *)
      skipstar(thefile);
      with nam do begin
         length:=0;
         repeat
            length:=succ(length);
            read(thefile,c);
            letters[length] := c
         until (eoln(thefile)) or
               (length>=namelength) or
               (letters[length]=' ');
         if letters[length]=' ' then length:=length-1;
         if length<namelength
            then for i:=length+1 to namelength do
letters[i]:=' '
```

- 330 -

```
      end;
      readln(thefile)
end; (* brname *)
(* end module book.brname version = 'delmod 6.54 86 nov 12
tds/gds' *)

(* begin module book.brline *)
procedure brline(var thefile: text; var l: lineptr);
(* read a line from the file *)
var
      i,j: integer;
      acharacter: char;
begin
      skipstar(thefile);
      i:=0;
      while (not eoln(thefile)) do begin
         i:=succ(i);
         read(thefile,acharacter);
         l^.letters[i]:=acharacter
      end;
      if i<l^.length then for j:=i+1 to l^.length do
l^.letters[j]:=' ';
      l^.length:=i;
      l^.next:=nil;
      readln(thefile)
end;
(* end module book.brline version = 'delmod 6.54 86 nov 12
tds/gds' *)

(* begin module book.brdirect *)
procedure brdirect(var thefile: text; var direct:
direction);
(* read a direction *)
var   ch: char;
begin
      skipstar(thefile);
      readln(thefile,ch);
```

- 331 -

```
      if ch='+' then direct:=plus
              else direct:=minus
end;
(* end module book.brdirect version = 'delmod 6.54 86 nov
12 tds/gds' *)

(* begin module book.brconfig *)
procedure brconfig(var thefile: text; var config:
configuration);
(* read a configuration *)
var   ch: char;
begin
      skipstar(thefile);
      readln(thefile,ch);
      if ch='l' then config:=linear
              else config:=circular
end;
(* end module book.brconfig version = 'delmod 6.54 86 nov
12 tds/gds' *)

(* begin module book.brnotenumber *)
procedure brnotenumber(var thefile: text; var note:
lineptr);
(* book note reading to obtain the number of the object.
the procedure returns the value of the number as a global.
(this is not such a good practice, but we are stuck with
it for now.) *)
begin (* brnotenumber *)
      note:=nil;
      numbered := false;
      number := 0; (* force number to zero if there
          is no number at all *)
      (* the next character is n or * depending on whether
there are notes *)
      if thefile^ = 'n' then begin
          readln(thefile);
          if thefile^ <> 'n' then begin
```

- 332 -

```
              skipstar(thefile);
              if not eoln(thefile) then begin
                 if thefile^ = '#' then begin
                    numbered := true;
                    get(thefile); (* move past the number
symbol *)
                    read(thefile,number);
                 end
              end;
              repeat
                 readln(thefile)
              until thefile^ = 'n';
              readln(thefile)
           end
           else readln(thefile)
        end
end; (* brnotenumber *)
(* end module book.brnotenumber version = 'delmod 6.54 86
nov 12 tds/gds' *)

(* begin module book.brnote *)
procedure brnote(var thefile: text; var note: lineptr);
(* read note key *)
var
      newnote: lineptr; (* the new note *)
      previousnote: lineptr; (* the last line of the notes
*)
begin (* brnote *)
      note:=nil;
      if thefile^ = 'n' then begin (* enter note *)
         readln(thefile);
         if thefile^ <> 'n' then begin (* abort null note
(n/n) *)
            getline(note);
            newnote:=note;
            while thefile^ <> 'n' do begin (* wait until
end of note *)
```

- 333 -

```
                brline(thefile,newnote);
                previousnote:=newnote;
                (* get next note *)
                getline(newnote^.next);
                newnote:=newnote^.next;
            end;
            (* last note was not used, so: *)
            clearline(newnote);
            previousnote^.next:=nil;
            readln(thefile)
         end
         else readln(thefile)
      end
end; (* brnote *)
(* end module book.brnote version = 'delmod 6.54 86 nov 12
tds/gds' *)

(* begin module book.brheader *)
procedure brheader(var thefile: text; var hea: header);
(* read the header of a key. *)
begin
      with hea do begin
          (* read key name *)
          brname(thefile,keynam);

(* read full name *)
          getline(fulnam);
          brline(thefile,fulnam);

(* read note key *)
          if readnumber then brnotenumber(thefile,note)
                        else brnote(thefile,note)
      end
end;
(* end module book.brheader version = 'delmod 6.54 86 nov
12 tds/gds' *)
```

- 334 -

```
(* begin module book.brpiekey *)
procedure brpiekey(var thefile: text; var pie: piekey);
(* read piece key *)
begin
      with pie do begin
           brheader(thefile,hea);
           brreanum(thefile,mapbeg);
           brconfig(thefile,coocon);
           brdirect(thefile,coodir);
           brnumber(thefile,coobeg);
           brnumber(thefile,cooend);
           brconfig(thefile,piecon);
           brdirect(thefile,piedir);
           brnumber(thefile,piebeg);
           brnumber(thefile,pieend);
      end
end;
(* end module book.brpiekey version = 'delmod 6.54 86 nov
12 tds/gds' *)

(* begin module book.brdna *)
procedure brdna(var thefile: text; var dna: dnaptr);
(* read in dna from thefile *)
(* note: if the dna were circularized, by linking the last
dnastring
to the first, then the cleardna routine could not clear
properly,
and would loop forever... there is no reason to do that,
since a simple
mod function will allow one to access the circle. *)
var
      ch: char;
      workdna: dnaptr;
begin
      getdna(dna);
      workdna:=dna;
      ch:=getto(thefile,['d']);
```

- 335 -

```
    read(thefile,ch); (* skipstar *)
    while (ch = '*') do
    begin
        read(thefile,ch); (* skip blank *)
        repeat
            read(thefile,ch);
            if ch in ['a','c','g','t'] then begin
                if workdna^.length=dnamax then begin
                    getdna(workdna^.next);
                    workdna:=workdna^.next
                end;
                workdna^.length:=succ(workdna^.length);

workdna^.part[workdna^.length]:=chartobase(ch)
            end
        until eoln(thefile);
        readln(thefile); (* go to next line *)
        read(thefile,ch); (* ch is either '*' or 'd' *)
    end;
    readln(thefile)
end;
(* end module book.brdna version = 'delmod 6.54 86 nov 12
tds/gds' *)

(* begin module book.brpiece *)
procedure brpiece(var thefile: text; var pie: pieceptr);
(* read in a piece *)
begin
    brpiekey(thefile,pie^.key);
    if numbered or (not skipunnum)
        then brdna(thefile,pie^.dna)
end;
(* end module book.brpiece version = 'delmod 6.54 86 nov
12 tds/gds' *)

(* begin module book.brinit *)
procedure brinit(var book: text);
```

- 336 -

```
(* check that the book is ok to read, and
   set up the global variables for br routines *)
begin (* brinit *)
      (* halt if the book is bad (first word is 'halt') or
the first
         character is not * *)
      reset(book);
      if not eof(book) then begin
         (* check for the date line *)
         if book^ <> '*' then begin
            if book^ <> 'h'
            then writeln(output, ' this is not the first
line of a book:')
            else writeln(output, ' bad book:');
            write(output, ' ');

while not (eoln(book) or eof(book)) do begin
               write(output, book^);
               get(book)
            end;
            writeln(output);
            halt
         end
      end
      else begin
         writeln(output, ' book is empty');
         halt
      end;

(* initialize free storage *)
      freeline:=nil;
      freedna:=nil;

readnumber:=true; (* usually we read in numbers for
items *)
      number:=0; (* arbitrary value *)
      numbered:=false; (* the piece has no number (none
```

- 337 -

```
yet read in) *)
      skipunnum:=false;
end; (* brinit *)
(* end module book.brinit version = 'delmod 6.54 86 nov 12
tds/gds' *)

(*
**************************************************************
************** *)
(* end module package.brpiece version = 'delmod 6.54 86
nov 12 tds/gds' *)

(* begin module book.getpiece *)
procedure getpiece(var thefile: text; var pie: pieceptr);
(* move to and read in the next piece in the book *)
var   ch: char;
begin
      ch:=getto(thefile,['p']); (* get to the next p(iece)
in the book *)
      if ch<>' ' then begin
         brpiece(thefile,pie);
         ch:=getto(thefile,['p']); (* read past closing p
*)
      end
end;
(* end module book.getpiece version = 'delmod 6.54 86 nov
12 tds/gds' *)

(*
**************************************************************
************** *)
(* end module package.getpiece version = 1.96; (@ of
scan.p 1995 April 22 *)

(* begin module book.getbase *)
function getbase(position: integer; pie: pieceptr):base;
(* get a base from the nth position (internal coordinates)
```

- 338 -

```
of the
   piece.  no protection is made against positions outside
the piece *)
var
      workdna: dnaptr;
      p: integer; (* the last base of the dna part *)
begin
      workdna:=pie^.dna;
      p:=dnamax;
      while position>p do begin
         p:=p+dnamax;
         workdna:=workdna^.next
      end;
      getbase:=workdna^.part[position-(p-dnamax)]
end;
(* end module book.getbase version = 2.11; (@ of ri.p 1995
May 24 *)

(* begin module package.numbar *)
(*
*************************************************************
************** *)
(* begin module numberdigit *)
function numberdigit(number, logplace:integer): char;
(* return the digit at the place value ('logplace')
position of number.
example:
      numberdigit(13625, 3) = 3
      numberdigit(13625, 4) = 1
*)
var
      place: integer; (* the exponent of logplace *)
      count: integer; (* used to make place *)
      absolute: integer; (* the absolute value of number
*)
      acharacter: char; (* the character to be returned *)
procedure digit;
```

- 339 -
```
(* extract a digit at the place position *)
var
      tenplace: integer; (* ten times place *)
      z: integer; (* an intermediate value *)
      d: integer; (* the digit extracted *)
begin (* digit *)
      tenplace:=10*place;
      z:=absolute-((absolute div tenplace)*tenplace);
      if place = 1
         then d:=z
         else d:= z div place;
      case d of
         0: acharacter:='0';
         1: acharacter:='1';
         2: acharacter:='2';
         3: acharacter:='3';
         4: acharacter:='4';
         5: acharacter:='5';
         6: acharacter:='6';
         7: acharacter:='7';
         8: acharacter:='8';
         9: acharacter:='9';
      end
end; (* digit *)
procedure sign;
(* put a negative sign out or a positive sign *)
begin (* sign *)
      if number <0 then acharacter:='-'
                   else acharacter:='+'
end; (* sign *)
begin (* numberdigit *)
      place:=1;
      for count:=1 to logplace do place:=10*place;

if number=0 then begin
         if place=1 then acharacter:='0'
                    else acharacter:=' '
```

- 340 -

```
    end
    else begin
        absolute:=abs(number);
        if absolute < (place div 10)
            then acharacter:=' '
            else if absolute >= place
                    then digit
                    else sign
    end;
    numberdigit:=acharacter
end; (* numberdigit *)
(* end module numberdigit version = 'prgmod 3.96   85 mar
18 tds'; *)

(* begin module numbersize *)
function numbersize(n: integer):integer;
(* calculate amount of space to be reserved for the
integer n *)
const ln10 = 2.30259; (* natural log of 10 - for
conversion to log base 10 *)
      epsilon = 0.00001; (* a small number to correct log
base 10 errors *)
begin (* numbersize *)
      if n = 0
          then numbersize:=1
          else numbersize:=trunc(ln(abs(n))/ln10 + epsilon)
+ 2;
(* the epsilon assures that we do not lose a place due to
   roundoff.  eg, sometimes log base 10 of 10 would be
   0.9999 instead of 1, and we would not do it right...
   note: this will fail for very large numbers on the
order of 1/epsilon. *)
(* the 2 is for the sign and last digit *)
end; (* numbersize *)
(* end module numbersize version = 'prgmod 3.96   85 mar 18
tds'; *)
```

- 341 -

```
(* begin module numberbar *)
procedure numberbar(var afile: text; spaces, firstnumber,
lastnumber: integer;
                    var linesused: integer);
(* write a bar of numbers to a file, with several spaces
before.
   the number of lines used is returned *)
var
     logplace: integer; (* the log of the digit being
looked at *)
     spacecount: integer; (* count of spaces *)
     number: integer; (* the current number being written
*)
begin
     if abs(firstnumber) > abs(lastnumber)
         then linesused:= numbersize(firstnumber)
         else linesused:= numbersize(lastnumber);

for logplace:=linesused-1 downto 0 do begin
         for spacecount:=1 to spaces do write(afile,' ');
         for number:=firstnumber to lastnumber
             do write(afile,numberdigit(number,logplace));
         writeln(afile)
     end
end;
(* end module numberbar version = 'prgmod 3.96   85 mar 18
tds'; *)
(*
**************************************************************
************** *)
(* end module package.numbar version = 'prgmod 3.96   85
mar 18 tds'; *)

(* begin module book.stepbase *)
function stepbase(startdna: dnaptr; var dna: dnaptr; var
d: dnarange): base;
(* advance d by one base in dna and then return the base
```

- 342 - at the new d.
   (this means that one should initialize d to zero)
   if we go past the last base, we restart at startdna.
   note: d is not the number of the base... it is used as a
   record for stepbase.  do not mess with it, and do not use it to find
   out what base you are on.  use a separate counter.  *)
begin
      if (d=dnamax) or (d=dna^.length) then begin
         d:=1;
         dna:=dna^.next;
         if dna=nil then dna:=startdna
      end
      else d:=succ(d);
      stepbase:=dna^.part[d]
end;
(* end module book.stepbase version = 'delmod 6.65 94 sep 5 tds/gds' *)

(* begin module nextbase *)
procedure initnextbase(var book: text; var pie: pieceptr;
                       var lastbase, endofbook: boolean);
(* initialize variables for function nextbase.
   book is the book to be read,
   pie is the piece,
   lastbase is the flag that is true when we are at the
   last base of a piece,
   and endofbook is true if we are at the end of the book
(see nextbase). *)
begin
      brinit(book);

new(pie);
      with pie^ do begin
         with key.hea do begin
            fulnam:=nil;

- 343 -

```
            note:=nil
        end;
        dna:=nil
    end;

lastbase:=true; (* this will trigger reading of the
next piece *)
    if eof(book) then endofbook:=true
                 else endofbook:=false
end;

function nextbase(var book: text;   (* the book being read
*)
(* the next variables can be ignored *)
                var pie: pieceptr; (* the piece *)
                var dnalink: dnaptr; (* the current link
we are on *)
                var dnalinkspot: dnarange; (* the spot
in the dnalink *)
(* these are useful to the general user: *)
                var dnaspot, (* integer in 1 to length,
which base this is *)
                    length: integer; (* length of this
piece *)
                var lastbase, (* true if the base was
the last one on
                                    the piece. *)
                    endofbook: boolean) (* true when we
have reached
                                           the end of
the book *)
                : base;
(* the user simply declares variables for
   book, pie, dnalink, dnalinkspot (of the appropriate
type)
note: you can convert the valuespot to published
coordinates by
```

- 344 -

```
      pubcoords:= inttopie(dnaspot,pie);

warning: if the end of the book has been reached, then
endofbook
is true, but the value returned by the function has no
meaning.
*)
begin
      if not lastbase then begin
          nextbase:=stepbase(pie^.dna,dnalink,dnalinkspot);
          dnaspot:=succ(dnaspot);
          if dnaspot = length then lastbase:=true
      end
      else begin (* we are at the last base of the
previous piece *)
          clearpiece(pie);
          getpiece(book,pie);
          if not eof(book) then begin
              dnalink:=pie^.dna;
              dnalinkspot:=0;
              dnaspot:=0;
              length:=piecelength(pie);
              lastbase:=false;
              endofbook:=false;

nextbase:=nextbase(book,pie,dnalink,dnalinkspot, dnaspot,length,lastbase,endofbook)
          end
          else begin
              endofbook:=true; (* we have reached the end of
the book *)
              lastbase:=false; (* we are no longer at the
last base *)
              nextbase:=a (* a fake value *)
          end
      end
```

- 345 -

```
end;
(* end module nextbase version = 'delmod 6.65 94 sep 5
tds/gds' *)

(************************************************************
******************)

(* begin module scan.getmatrix *)
procedure getmatrix(var afile: text; var matrix: rblarray;
                    var frombase, tobase: integer;
                    var fromwanted, towanted: integer;
                    var mean, stdev: real);
(* get the matrix from a file, with the defining
coordinate limits,
followed by the mean and standard deviation *)
var
   b: base; (* a base in the matrix *)
   l: integer; (* a coordinate in the matrix *)
begin
   reset(afile);
   while afile^='*' do readln(afile); (* skip the header
*)
   readln(afile,frombase,tobase);

if fromwanted < frombase then begin
       writeln(output,'Warning: from region is reset from
',fromwanted:1,
                    ' to the edge of the matrix at ',
frombase:1);
       fromwanted := frombase;
   end;

if towanted > tobase then begin
       writeln(output,'Warning: to region is reset from
',towanted:1,
                    ' to the edge of the matrix at ',
tobase:1);
```

- 346 -

```
      towanted := tobase;
   end;

if towanted-fromwanted+1 > maxribl then begin
      writeln(output,'The matrix is too big:');
      writeln(output,'increase constant maxribl');
      writeln(output,'or reduce the requested from - to
range in scanp');
      halt
   end;

(* skip unneeded matrix material *)
   for l := frombase to fromwanted - 1 do readln(afile);

for l := 1 to towanted-fromwanted+1 do begin
      for b := a to t do read(afile,matrix[b,l]);
      readln(afile)
   end;

(* skip unneeded matrix material *)
   for l := towanted + 1 to tobase do readln(afile);

while afile^='*' do readln(afile);
   readln(afile,mean);
   while afile^='*' do readln(afile);
   readln(afile,stdev);
{
writeln(output,'values read:');
writeln(output,mean:10:2);
writeln(output,stdev:10:2);
} end;
(* end module scan.getmatrix version = 1.96; (@ of scan.p
1995 April 22 *)

(***********************************************************
```

- 347 -

```
*******************)

(* begin module readparameters *)
procedure readparameters(var walkerp: text; var p:
parameters);
(* read parameters p from walkerp *)
begin
   reset(walkerp);

with p do begin
      readln(walkerp, rangefrom);
      readln(walkerp, rangeto);

readln(walkerp, basesperline);
      readln(walkerp, linesperpage);

readln(walkerp, basenumber);
      if basenumber > basesperline - 1.then begin
         writeln(output,'basenumber cannot be >
basesperline - 1 =',
                              basesperline:1);
         halt
      end;
      if basenumber < 0 then begin
         writeln(output,'basenumber cannot be < 0');
         halt
      end;

readln(walkerp, linenumber);
      if linenumber > linesperpage -1 then begin
         writeln(output,'linenumber cannot be >
linesperpage - 1 =',
                              linesperpage:1);
         halt
      end;
      if linenumber < 0 then begin
         writeln(output,'linenumber cannot be < 0');
```

- 348 -

```
    halt
end;

readln(walkerp, coornumber);

readln(walkerp, pagewidth);
readln(walkerp, pageheight);
readln(walkerp, pagex);
readln(walkerp, pagey);

readln(walkerp, lowerbound);
if lowerbound > 0.0 then begin
    writeln(output,'lowerbound cannot be > 0.0');
    halt
end;

(*
readln(walkerp, fractionofline);
if fractionofline > 1.0 then begin
    writeln(output,'fractionofline cannot be > 1.0');
    halt
end;
if fractionofline <= 0.0 then begin
    writeln(output,'fractionofline cannot be <=
0.0');
    halt
end;
*)
fractionofline := 1.0;

readln(walkerp, boxes);

readln(walkerp, outofsequence);
if not (outofsequence in ['i','o']) then begin
    writeln(output,'outofsequence must be either "i"
or "o"');
    halt
```

- 349 -

```
    end;

end
end;
(* end module readparameters *)

(* begin module writeparameters *)
procedure writeparameters(var w: text; p: parameters);
(* write parameters p to w *)
begin
   with p do begin
      writeln(w);
      writeln(w, '% user defined parameters');
      writeln(w, '/rangefrom ', rangefrom:1,' def');
      writeln(w, '/rangeto ', rangeto:1,' def');

writeln(w, '/basesperline ', basesperline:1,' def');
      writeln(w, '/linesperpage ', linesperpage:1,' def');
      writeln(w, '/basenumber ', basenumber:1,' def');
      writeln(w, '/linenumber ', linenumber:1,' def');
      writeln(w, '/coornumber ', coornumber:1,' def');

writeln(w, '/pagewidth ', pagewidth:pwid:pdec,' cm
def');
      writeln(w, '/pageheight ', pageheight:pwid:pdec,' cm
def');
      writeln(w, '/pagex ', pagex:pwid:pdec,' cm def');
      writeln(w, '/pagey ', pagey:pwid:pdec,' cm def');

writeln(w, '/lowerbound ', lowerbound:pwid:pdec,'
def');
      writeln(w, '/fractionofline ',
fractionofline:pwid:pdec,' def');

write(w, '/boxstate ');
      if boxes = 'b'
         then write(w,'true')
```

- 350 -

```
      else write(w,'false');
   writeln(w, ' def');

write(w, '/outofsequence ');
   if outofsequence = 'o'
      then write(w,'true')
      else write(w,'false');
   writeln(w, ' def');

end
end;
(* end module writeparameters *)

(* begin module createheader *)
procedure createheader(var w: text);
(* create the header of the w file *)
begin
rewrite(w);
writeln(w,'%! walker ',version:4:2);
writeln(w,'/version {(version = ',version:4:2,' of
walker.p)} def');
writeln(w,'version =');
writeln(w,'(Documentation for this program is in walker.p)
=');
writeln(w);
writeln(w,'/cmfactor 72 2.54 div def % defines points ->
centimeters');
writeln(w,'/cm { cmfactor mul} def % defines
centimeters');
writeln(w);
writeln(w,'/zbound 3 def % defines upper Z score for
reporting sites');
writeln(w,'/ribound 0 def % defines lower ribltotal for
reporting sites');
writeln(w,'/ribltotal 0 def');
writeln(w,'/Z 0 def');
writeln(w,'% note: the wave phase is not changed when page
```

- 351 -

```
is redrawn');
writeln(w,'/wavephase 0 def % initial value of phase of
cosine wave');
writeln(w,'/doingwave true def % whether or not the wave
is drawn');
writeln(w,'/printing true def % whether to print all the
time or not');
writeln(w,'/forcedisplay true def');
writeln(w,'/doerasepage true def % whether to erase the
page');
writeln(w);
writeln(w,'gsave');
end;
(* end module createheader *)

(* begin module createender *)
procedure createender(var w: text);
(* create the ender of the w file *)
begin
writeln(w);
writeln(w,'displayentirepage');
writeln(w,'% showpage % unearth this for printing');
writeln(w);
end;
(* end module createender *)

(* begin module makelogo.protectpostscript *)
procedure protectpostscript(var afile: text; c: char);
(* Special characters must be protected against!  Put out
a protective
backslash for character c which would otherwise destroy
the PostScript
interpreter.  The parenthesis is used in PostScript to
indicate the bounds of a
string, while the percent is the comment character.  The
backslash also needs
protection, since it is the escape to indicate that the
```

- 352 -

```
next character is part
of the string. *)
begin
   if c in ['(',')','%','\'] then write(afile,'\');
end;
(* end module makelogo.protectpostscript *)

(* begin module makecolors *)
procedure makecolors(var colors, l: text);
(* make color definitions.  The code is taken from
makelogo *)
var
  symbol: char; (* a symbol to which to assign a color *)
  red, green, blue: real; (* color definitions *)
begin
   (* set up the color statements *)
   reset(colors);
   writeln(l);
   writeln(l,'/setcolor { % char setcolor -, define
colors');
   writeln(l,'/char exch def');
   while not eof(colors) do begin
      if colors^ <> '*' then begin (* skip comment lines
*)
         (* implement the backslash protection scheme: *)
         if colors^ = '\' then get(colors);
         readln(colors,symbol,red,green,blue);
         write(l,'char (');
         protectpostscript(l,symbol);
         write(l,symbol,') eq {');
         if (red = 1.0) or (red = 0.0) then
write(l,round(red):1)
                                          else
write(l,red:pwid:pdecolor);
         write(l,' ');
         if (green = 1.0) or (green = 0.0) then
write(l,round(green):1)
```

- 353 -

```
                                        else
write(1,green:pwid:pdecolor);
        write(1,' ');
        if (blue = 1.0) or (blue = 0.0) then
write(1,round(blue):1)
                                        else
write(1,blue:pwid:pdecolor);
        writeln(1,' setrgbcolor} if');
      end
      else readln(colors);
   end;
   writeln(1,'} bind def');
end;
(* end module makecolors *)

(* begin module makesequencearray *)
procedure makesequencearray(var book, fout: text);
(* Use the nextbase routines to create postscript code
that will generate a postscript array containing the
bases and their coordinates.
This procedure was created by starting from the
demonextbase
routine in the delmod.p module library. *)
const
   basesperline = 5; (* number of bases to pack on a line
*)
var
   (* these variables are all defined in nextbase *)
   pie: pieceptr;
   dnalink: dnaptr;
   dnalinkspot: dnarange;
   dnaspot, length: integer;
   lastbase, endofbook: boolean;

(* this variable is needed to catch the value of
nextbase,
      so that we can check that we have not reached the
```

- 354 -
```
end of the book. *)
   character: char;
   basecount: integer; (* number of bases counted so far
*)
begin
   initnextbase(book,pie,lastbase,endofbook);

writeln(fout);
   writeln(walk,'% Define the sequence and associated
variables');
   writeln(fout,'/storeseq{ % coord base storeseq -');
   writeln(fout,'% store the base # at the internal
coordinate in the sequence');
   writeln(fout,'/base exch def');
   writeln(fout,'/coord exch def');
   writeln(fout,'sequence place [base coord] put');
   writeln(fout,'/place place 1 add def');
   writeln(fout,'} bind def');

writeln(fout,'/a {0 storeseq} def');
   writeln(fout,'/c {1 storeseq} def');
   writeln(fout,'/g {2 storeseq} def');
   writeln(fout,'/t {3 storeseq} def');
(*    writeln(fout,'/symbols [(A) (C) (G) (T)] def');*)
   writeln(fout,'/symbols [(a) (c) (g) (t)] def');

writeln(fout,'/place 0 def');

writeln(fout,'% The sequence is expressed as:');
   writeln(fout,'% the published coordinate of the base');
(* writeln(fout,'% the internal coordinate of the base');
*)
   writeln(fout,'% the base at that coordinate');
   basecount := 0;
{
the following code allows multiple sequences to be read,
but
```

- 355 -

```
there is no way to handle this quite yet
zzz
   while not endofbook do begin
}
   repeat
      character:=basetochar(
         nextbase(book,pie,dnalink,dnalinkspot,
                  dnaspot,length,lastbase,endofbook));
      if not endofbook then begin if dnaspot = 1 then begin
            writeln(fout,'/sequencelength
',piecelength(pie):1,' def');
            writeln(fout,'% sequencelength is the number
of bases in the sequence');
            writeln(fout,'/sequence sequencelength array
def');
            writeln(fout,'% upperseq is the highest
internal coordinate');
            writeln(fout,'/upperseq sequencelength 1 sub
def');
         end;

(* note: internal coordinates start with zero in
postscript
            since postscript arrays start at zero.  So we
report
            that the base is at position dnaspot-1 *)
         (* Now the program has been modified so that the
spot
            is not reported.  This reduces the size of
the walker file.*)

if (basecount mod basesperline) <> 0 then
write(fout,' ');
         basecount := succ(basecount);
         write(fout,    inttopie(dnaspot,pie):1,
```

- 356 -

```
                    (* ' ',(dnaspot-1):1, *)
                    ' ',character);
         if (basecount mod basesperline) = 0 then
writeln(fout);
      end;
      if lastbase then begin
         writeln(fout);
         writeln(fout,'% end of a piece ',length:1,' bp')
      end;
   until lastbase;
{
   end
}
end;
(* end module makesequencearray *)

(* begin module makeribl *)
procedure makeribl(var ribl, walk: text; var fromwanted,
towanted: integer);
(* Make the ribl matrix in PostScript in the walk file.
The matrix ranges from
frombase to tobase.  The part to write out is fromwanted
to towanted.  Define
the mean and standard deviation of the Ri distribution as
variables. *)
var
   l: integer; (* position in the from-to coordinates *)
   position: integer; (* position in the riblmatrix
corresponding to l *)

frombase, tobase: integer; (* the coordinates of w *)
{
   fromwanted, towanted: integer; (* region of w to use
for the scan *)
}
   mean: real; (* mean of Ri *)
   riblmatrix: rblarray; (* the weight matrix, Ri(b,l) *)
```

- 357 -

```
   stdev: real; (* standard deviation of Ri *)
begin
{ this should not be done here at all!.z zzz
   (* find out the size of the matrix *)
   reset(ribl);
   while ribl^ = '*' do readln(ribl);
   readln(ribl,fromwanted, towanted);
} getmatrix(ribl, riblmatrix, frombase, tobase,
fromwanted, towanted,
             mean, stdev);
(*
writeln(output,'ribl[a,1]=',riblmatrix[a,1]:10:5);
*)

writeln(walk);
   writeln(walk,'% Define the Ribl matrix and associated
variables');
   writeln(walk,'/frombase ',frombase:1,' def');
   writeln(walk,'/tobase ',tobase:1,' def');
   writeln(walk,'/fromwanted ',fromwanted:1,' def');
   writeln(walk,'/towanted ',towanted:1,' def');
   writeln(walk,'/mean ',mean:infofield:infodecim,' def');
   writeln(walk,'/stdev ',stdev:infofield:infodecim,'
def');
   writeln(walk);
   writeln(walk,'/maxribl towanted fromwanted sub 1 add
def');
   writeln(walk,'/ribl maxribl array def');
   writeln(walk);
   writeln(walk,'/storeribl{ % avalue cvalue gvalue tvalue
storeribl -');
   writeln(walk,'% store the four values at place in the
ribl');
   writeln(walk,'/tvalue exch def');
   writeln(walk,'/gvalue exch def');
```

- 358 -

```
   writeln(walk,'/cvalue exch def');
   writeln(walk,'/avalue exch def');
   writeln(walk,'ribl place [avalue cvalue gvalue tvalue]
put');
   writeln(walk,'/place place 1 add def');
   writeln(walk,'} bind def');

writeln(walk,'/place 0 def');

for l := frombase to tobase do begin
       position := l - frombase+1;
       write(walk,'
',riblmatrix[a,position]:infofield:infodecim);
       write(walk,'
',riblmatrix[c,position]:infofield:infodecim);
       write(walk,'
',riblmatrix[g,position]:infofield:infodecim);
       write(walk,'
',riblmatrix[t,position]:infofield:infodecim);
       writeln(walk,'  storeribl % ',l:1);
   end;
   writeln(walk,'/riblzero frombase neg def');
end;
(* end module makeribl *)

(* begin module makelogo.truth *)
procedure truth(var f: text; b: boolean);
(* write the true-false value of b to file f *)
begin
  if b then write(f,'true')
       else write(f,'false');
end;
(* end module makelogo.truth *)

{zzz: destroy makecolors ... this superceeds it}
(* or keep make colors?  There is that fade thing that may
be
```

- 359 -

```
useful, which fades the entire set based on total
evaluation *)
(* begin module varchardefs *)
procedure varchardefs(var l, colors: text;
                      showingbox, outline, shrinking:
boolean);
(* write the PostScript procedures for making variable
character
sizes to the file l.  Show the box around the character or
make the character
in outline if these booleans are true.  These routines
come from makelogo. *)
var
   symbol: char; (* a symbol to which to assign a color *)
   red, green, blue: real; (* color definitions *)
begin writeln(l);
writeln(l,'% Make the variable character size definition
functions');
write   (l,'/showingbox '); truth(l,showingbox);
writeln(l,' def');
write   (l,'/outline '); truth(l,outline); writeln(l,'
def');
write   (l,'/shrinking '); truth(l,shrinking); writeln(l,'
def');

writeln(l);
if outline then begin
   writeln(l,'% Since outlining goes around the inner edge
of the character');
   writeln(l,'% make the thickness of the character bigger
to compensate.');
   writeln(l,'/setthelinewidth {2 setlinewidth} def')
end
else begin
   writeln(l,'/setthelinewidth {1 setlinewidth} def')
```

- 360 -

```
end;
writeln(l,'setthelinewidth % set to normal linewidth');

(* note:  this is redundant ... *)
writeln(l);
writeln(l,'% Set up the font size for the graphics');
writeln(l,'/fontsize charwidth def');
writeln(l);

writeln(l);
writeln(l,'/charparams { % char charparams => uy ux ly
lx');
writeln(l,'% takes a single character and returns the
coordinates that');
writeln(l,'% defines the outer bounds of where the ink
goes');
writeln(l,'  gsave');
writeln(l,'    newpath');
writeln(l,'    0 0 moveto');
writeln(l,'    % take the character off the stack and use
it here:');
writeln(l,'    true charpath ');
writeln(l,'    flattenpath ');
writeln(l,'    pathbbox % compute bounding box of 1 pt.
char => lx ly ux uy');
writeln(l,'    % the path is here, but toss it away ...');
writeln(l,'  grestore');
writeln(l,'  /uy exch def');
writeln(l,'  /ux exch def');
writeln(l,'  /ly exch def');
writeln(l,'  /lx exch def');
(*
writeln(l,'%     % print the parameters to the user:');
writeln(l,'%     (lx) lx (ly) ly (ux) ux (uy) uy pstack');
writeln(l,'%     clear % clean up the stack, having
printed all that');
*)
```

- 361 -

```
writeln(l,'} bind def');
writeln(l);

writeln(l,'/dashbox { % xsize ysize dashbox -');
writeln(l,'% draw a dashed box of xsize by ysize (in
points)');
writeln(l,'  /ysize exch def % the y size of the box');
writeln(l,'  /xsize exch def % the x size of the box');
writeln(l,'  1 setlinewidth');
writeln(l,'  gsave');
writeln(l,'    % Define the width of the dashed lines for
boxes:');
writeln(l,'    newpath');
writeln(l,'    0 0 moveto');
writeln(l,'    xsize 0 lineto');
writeln(l,'    xsize ysize lineto');
writeln(l,'    0 ysize lineto');
writeln(l,'    0 0 lineto');
writeln(l,'    [3] 0 setdash');
writeln(l,'    stroke');
writeln(l,'  grestore');
writeln(l,'  setthelinewidth');
writeln(l,'} bind def');
writeln(l);

writeln(l,'/boxshow { % xsize ysize char boxshow');
writeln(l,'% show the character with a box around it,
sizes in points');
writeln(l,'gsave');
writeln(l,'  /tc exch def % define the character');
writeln(l,'  /ysize exch def % the y size of the
character');
writeln(l,'  /xsize exch def % the x size of the
character');
writeln(l,'  /xmulfactor 1 def /ymulfactor 1 def');
writeln(l);
```

- 362 -

```
writeln(1,' % if ysize is negative, make everything upside down!');
writeln(1,'  ysize 0 lt {');
writeln(1,'    % put ysize normal in this orientation');
writeln(1,'    /ysize ysize abs def');
writeln(1,'    xsize ysize translate');
writeln(1,'    180 rotate');
writeln(1,'  } if');
writeln(1);

writeln(1,'  showingbox {dashbox} if');
(* hold these out of walker since they slow down things:
writeln(1,'  % Don''t show the box if it is a vertical bar, otherwise do.');
writeln(1,'  showingbox {tc (|) ne {xsize ysize dashbox} if} if');
writeln(1);
writeln(1,'  shrinking {tc (|) ne {');
writeln(1,'    xsize knirhs mul ysize knirhs mul translate');
writeln(1,'    shrink shrink scale');
writeln(1,'  } if} if');
writeln(1);
*)

writeln(1,'  2 {');
writeln(1,'    gsave');
writeln(1,'    xmulfactor ymulfactor scale');
writeln(1,'    tc charparams');
writeln(1,'    grestore');
writeln(1);
```

(* NOTE: The following if statements in the next two sections make sure that
the size of the character has not gone to zero. This apparently can happen
under OpenWindows, but not NeWS the Apple laserwriter or

- 363 -

Freedom of the Press
Tektronix colorquick conversion. *)

writeln(l,'    ysize % desired size of character in points');
writeln(l,'    uy ly sub % height of character in points');
writeln(l,'    dup 0.0 ne {'');
writeln(l,'       div % factor by which to scale up the character');
writeln(l,'       /ymulfactor exch def');
writeln(l,'    } % end if');
writeln(l,'    {pop pop}');   (* remove the stuff from the stack and go on *)
writeln(l,'    ifelse');
writeln(l);
writeln(l,'    xsize % desired size of character in points');
writeln(l,'    ux lx sub % width of character in points');
writeln(l,'    dup 0.0 ne {'');
writeln(l,'       div % factor by which to scale up the character');
writeln(l,'       /xmulfactor exch def');
writeln(l,'    } % end if');
writeln(l,'    {pop pop}');
writeln(l,'    ifelse');
writeln(l,'  } repeat');
writeln(l);

(* The letter I must be specially centered in the Helvetica-Bold font.
We also account for the width of the character itself, so it should be centered
perfectly. *)
writeln(l,' % Adjust horizontal position if the symbol is an I');
writeln(l,'    tc (I) eq {charwidth 2 div % half of

- 364 -

```
requested character width');
writeln(l,'          ux lx sub 2 div % half of the
actual character');
writeln(l,'             sub    0 translate} if');
writeln(l,'  % Avoid x scaling for I');
writeln(l,'  tc (I) eq {/xmulfactor 1 def} if');
writeln(l);

writeln(l,'  /xmove xmulfactor lx mul neg def');
writeln(l,'  /ymove ymulfactor ly mul neg def');
writeln(l);

writeln(l,'  newpath');
writeln(l,'  xmove ymove moveto');
writeln(l,'  xmulfactor ymulfactor scale');
writeln(l);

if outline
then begin
    writeln(l,'  % Outline characters:');
    (* get the character's path: *)
    writeln(l,'  tc true charpath');
    (* erase the center of the character (seems necessary
to do!) *)
    writeln(l,'  gsave 1 setgray fill grestore');
    (* clip everything outside the character to prevent
characters
      from overlapping each other (!) and then stroke the
edge.
      Thus only the part of the stroke that reaches into
the CENTER
      of the character becomes black and so the character
size does
      not change even though it is an outline. *)
    writeln(l,'  clip stroke');
    writeln(output);
    writeln(output,'WARNING: Outlined characters will',
```

- 365 -
```
                     ' not display at all under NeWS');
   writeln(output,'but will print fine on an Apple
LaserWriter IIntx');
   writeln(output);
end
else writeln(l,'   tc show');

writeln(l,'grestore');
writeln(l,'} bind def');
writeln(l);

writeln(l,'/numchar{ % charheight character numchar');
writeln(l,'% Make a character of given height in cm,');
{writeln(l,'% then move vertically by that amount'); NOT
NEEDED FOR WALKER}
writeln(l,'  gsave');
writeln(l,'    /char exch def');
writeln(l,'    /charheight exch cm def');

(* set up the color statements *)
reset(colors);
while not eof(colors) do begin
   if colors^ <> '*' then begin (* skip comment lines *)
      (* implement the backslash protection scheme: *)
      if colors^ = '\' then get(colors);
      readln(colors,symbol,red,green,blue);
      write(l,'   char (');
      protectpostscript(l,symbol);
      write(l,symbol,') eq {');
      if (red = 1.0) or (red = 0.0) then
write(l,round(red):1)
                                          else
write(l,red:pwid:pdecolor);
      write(l,' ');
      if (green = 1.0) or (green = 0.0) then
write(l,round(green):1)
                                          else
```

- 366 -

```
write(1,green:pwid:pdecolor);
      write(1,' ');
      if (blue = 1.0) or (blue = 0.0) then
write(1,round(blue):1)
                                              else
write(1,blue:pwid:pdecolor);
      writeln(1,' setrgbcolor} if');
   end
   else readln(colors);
end;

(* note: adding the following text is sufficient to cause
the converter to C to bomb with a segmentation fault!
writeln(1,'    % note: charwidth and charheight');
writeln(1,'    %  have already been converted to points');
*)

writeln(1,'    charwidth charheight char boxshow');
writeln(1,'  grestore');

(*
writeln(1,'  % the abs in the translation function below',
          ' handles negative heights');
*)

(* The if statements ask if the character height is
greater than
one point.  If it is, the display should be ok.  If not,
some
displays mess up, notably OpenWindows (!).  Force the
character
to be 1 point high just to be safe.  I hate bad
implementations
of PostScript! *)

if gooddisplay
then writeln(1,'   0 charheight abs translate')
```

- 367 -

```
else writeln(l,'  charheight abs 1 gt {0 charheight abs
translate} if');

writeln(l,'} bind def'); (* numchar *)
writeln(l);
end;

(* end module varchardefs *)

(* begin module definecosine *)
procedure definecosine(var w: text);
(* define the cosine routine.
example test:
% amplitude  phase  wavelength  base:
 -2.50000 cm  6.40000 cm  8.48000 cm  7.50000 cm
% xmin ymin xmax ymax step:
 -4.80000 cm  0.00000 cm 17.60000 cm 50.50000 cm 1
  0.5 cm 0.1 cosine
*)
begin
writeln(w);
writeln(w,'/degpercycle 360 def');
writeln(w,' ');
writeln(w,'/cosine {%    amplitude   phase   wavelength
base');
writeln(w,'%            xmin ymin xmax ymax step dash
thickness');
writeln(w,'%            cosine -');
writeln(w,'% draws a cosine wave with the given
parameters:');
writeln(w,'% amplitude (points): height of the wave');
writeln(w,'% phase (points): starting point of the wave');
writeln(w,'% wavelength (points): length from crest to
crest');
writeln(w,'% base (points): lowest point of the curve');
writeln(w,'% xmin ymin xmax ymax (points): region in which
to draw');
```

- 368 -

```
writeln(w,'% step steps for drawing a cosine wave');
writeln(w,'% dash if greater than zero, size of dashes of
the wave (points)');
writeln(w,'% thickness if greater than zero, thickness of
wave (points)');
writeln(w);
writeln(w,'   /thickness exch def');
writeln(w,'   /dash exch def');
writeln(w,'   /step exch def');
writeln(w,'   /ymax exch def');
writeln(w,'   /xmax exch def');
writeln(w,'   /ymin exch def');
writeln(w,'   /xmin exch def');
writeln(w,'   /base exch def');
writeln(w,'   /wavelength exch def');
writeln(w,'   /phase exch def');
writeln(w,'   /amplitude exch def');
writeln(w,'   % fun := amplitude*cos(
((-y-phase)/wavelength)*360) + base');
writeln(w,'   /fun {phase sub wavelength div degpercycle
mul cos');
writeln(w,'            amplitude mul base add} def');
writeln(w);
writeln(w,'   gsave');
writeln(w,'    /originallinewidth currentlinewidth def');
writeln(w,'    thickness 0 gt {thickness setlinewidth}
if');
writeln(w,'    /c currentlinewidth def');
writeln(w,'%   Make the curve fit into the region
specified');
writeln(w,'    newpath');
writeln(w,'    xmin ymin c sub moveto');
writeln(w,'    xmax ymin c sub lineto');
writeln(w,'    xmax ymax c add lineto');
writeln(w,'    xmin ymax c add lineto');
writeln(w,'    closepath');
writeln(w,'    clip'); (* stroke'); *)
```

```
- 369 -
writeln(w);
writeln(w,'    newpath');
writeln(w,'    xmin dup fun moveto');
writeln(w,'    xmin step xmax { % loop from xmin by step to xmax');
writeln(w,'      dup fun lineto } for');
writeln(w,'    dash 0 gt {[dash cvi] 0 setdash} if % turn dash on');
writeln(w,'    stroke');
writeln(w);
writeln(w,'    originallinewidth setlinewidth');
writeln(w,'  grestore');
writeln(w,'} bind def');
writeln(w);
end;
(* end module definecosine *)

(* begin module definewait *)
procedure definewait(var w: text);
(* define the wait procedures and variables *)
begin
writeln(w);
writeln(w,'/isasecond { % set the number of {1 pop} cycles per second');
writeln(w,'/second exch def');
writeln(w,'(a second is now defined as this many loops:) =');
writeln(w,'second =');
writeln(w,'} def');

writeln(w,'/wait {% n wait -; wait n seconds');
(* writeln(w,'(wait start) ='); *)
writeln(w,'second mul round cvi {1 pop} repeat');
(* writeln(w,'(wait stop) ='); *)
writeln(w,'} def');

writeln(w,'/setwait {% set the wait time after display');
```

- 370 -

```
writeln(w,'/waittime exch def');
writeln(w,'(waiting between moves is now (seconds):) =');
writeln(w,'waittime =');
writeln(w,'} def');

(* writeln(w,isasecond:1,' isasecond');  This is
unnecessary - see the help command *)
(* writeln(w,'0 setwait');  This is unnecessary - see the
help command *)
writeln(w,'/second ',isasecond:1,' def');
writeln(w,'/waittime 0 def');
end;
(* end module definewait *)

(* begin module def1 *)
procedure def1(var w: text);
(* part 1 of the definitions *)
begin (* [ *)

writeln(w);
writeln(w,'/definepageparameters { % wrap these
definitions together');
writeln(w,'% define characters');
writeln(w,'/charwidth pagewidth basesperline div def %
character width');
writeln(w,'/ncharwidth charwidth neg def % negative of
charwidth');
writeln(w,'/charshift charwidth 6 div def');
writeln(w,'/upperbound 2 def % upper bound, bits');
writeln(w,'outofsequence');
writeln(w,'{/gapbits upperbound fractionofline mul def} %
gap size in bits');
writeln(w,'{/gapbits 0 def}');
writeln(w,'ifelse');
writeln(w,'/bitspercm');
writeln(w,'   upperbound lowerbound sub gapbits add %
bits');
```

- 371 -

```
writeln(w,'    pageheight linesperpage div % cm');
writeln(w,'    div def % bits per cm');
writeln(w,'/cmperbit 1 bitspercm div def');
writeln(w,'/gapcm gapbits bitspercm div def % the gap size
in cm');
writeln(w,'/charupper upperbound bitspercm div def % upper
bound of characters');
writeln(w,'/charlower lowerbound bitspercm div def % lower
bound of characters');
writeln(w,'/charrange charupper charlower sub def',
         ' % total height of character box');

writeln(w,'/charbox { % character box');
writeln(w,'moveto');
writeln(w,'charwidth 0 rlineto');
writeln(w,'ncharwidth 0 rlineto');
writeln(w,'0 charlower rlineto');
writeln(w,'charwidth 0 rlineto');
writeln(w,'0 charrange rlineto');
writeln(w,'ncharwidth 0 rlineto');
writeln(w,'closepath} bind def');

writeln(w,'% convert bits to cm fitting the size');
writeln(w,'/bittocm charupper 2 div cmfactor div def');
writeln(w,'/bittocm2 charupper cmfactor div def');

writeln(w,'% oh boy here we go with the sine!!!
YOWWW!!!');
writeln(w,'/wavelength 10.6 def % bases per 360 degrees');
writeln(w,'/wavefactor 360 wavelength div def');

writeln(w,'/makesine {% scale the y axis by the cosine
of');
writeln(w,'% the distance from the internalcoordinate');
writeln(w,'ic internalcoordinate sub wavephase sub
wavefactor mul');
writeln(w,'cos 1 sub -4 div 0.5 add');
```

- 372 -

```
writeln(w,'gapbits 0 eq {bittocm2} {gapbits} ifelse mul');
writeln(w,'} bind def');

writeln(w);
writeln(w,'% define fonts and characters');
writeln(w,'% Set up the font size for the graphics');
writeln(w,'/fontsize charwidth def');
writeln(w,'% set the font');
(*writeln(w,'/Helvetica-Bold findfont fontsize scalefont
setfont');*)
writeln(w,'/Times-Bold findfont fontsize scalefont
setfont');

writeln(w);
writeln(w,'} bind def % end of definepageparameters');
writeln(w,'definepageparameters % make these definitions
available now!');

writeln(w);
writeln(w,'% define colors ');
writeln(w,'/red    {1 0 0 setrgbcolor} def');
writeln(w,'/green  {0 1 0 setrgbcolor} def');
writeln(w,'/blue   {0 0 1 setrgbcolor} def');
writeln(w,'/purple {1 0 1 setrgbcolor} def');
writeln(w,'/yellow {1 1 0 setrgbcolor} def');
writeln(w,'/orange {1 0.7 0 setrgbcolor} def');
writeln(w,'/black  {0 0 0 setrgbcolor} def');
writeln(w,'/white  {1 1 1 setrgbcolor} def');
writeln(w,'/grey   {0.5 0.5 0.5 setrgbcolor} def');

writeln(w);
writeln(w,'% store the current color as a background
color');
writeln(w,'/setbackcolor {/backcolorstore currentrgbcolor
3 array astore def} def');
writeln(w,'% backcolor retrieves the color');
writeln(w,'/backcolor {backcolorstore aload pop
```

- 373 -

```
setrgbcolor} def');
writeln(w,'% initial setting');
writeln(w,'white setbackcolor');

writeln(w);
writeln(w,'/rectangle { % height width x y rectangle
(path)');
writeln(w,'moveto');
writeln(w,'/height exch def');
writeln(w,'/width exch def');
writeln(w,'0 width rlineto');
writeln(w,'height 0 rlineto');
writeln(w,'0 width neg rlineto');
writeln(w,'closepath');
writeln(w,'} bind def');

definewait(w);
(* A smooth cosine is not used in this.version of walker.
It
is hard to implement and would be slow.
definecosine(w);
*)

writeln(w);
writeln(w,'/tochar {x charwidth mul y charrange');
writeln(w,'outofsequence {gapcm add charshift add} if');
writeln(w,'mul} def ');

writeln(w);
writeln(w,'/stepto { % x y stepto -  stepto the place');
writeln(w,'/y exch def');
writeln(w,'/x exch def');
writeln(w,'tochar charbox fill');
writeln(w,'gsave tochar charbox black stroke grestore}
def');

writeln(w);
```

- 374 -

```
writeln(w,'/tointernal { % ec tointernal ic boolean');
writeln(w,'% convert external coordinate (ec)');
writeln(w,'% to internal coordinate (ic)');
writeln(w,'% if found, the boolean is true and ic is
returned.');
writeln(w,'% otherwise the boolean is false and no
coordinate is returned.');
writeln(w,'/ec exch def');
writeln(w,'/ic 0 def');
writeln(w,'count /stacksize exch def');
writeln(w,'sequence {');
writeln(w,'   1 get');
writeln(w,'   ec eq');
writeln(w,'   {ic exit}');
writeln(w,'   if');
writeln(w,'   /ic ic 1 add def');
writeln(w,'} forall');
writeln(w,'count stacksize 1 add eq % element was found
and returned?');
writeln(w,'} bind def');

writeln(w);
writeln(w,'/setinternal { % externalcoordinate setinternal
internalcoordinate');
writeln(w,'% convert external coordinate
(externalcoordinate)');
writeln(w,'% to internal coordinate (internalcoordinate) 0
to upperseq');
writeln(w,'% if found, the internalcoordinate is set.');
writeln(w,'% If not found, internalcoordinate is set
to:');
writeln(w,'%    0 if externalcoordinate <= 0');
writeln(w,'%    upperseq if externalcoordinate > 0');
writeln(w,'/externalcoordinate exch def');
writeln(w,'/internalcoordinate 0 def');
writeln(w,'externalcoordinate tointernal');
writeln(w,'not { externalcoordinate 0 le');
```

- 375 -

```
writeln(w,'   {0} {upperseq} ifelse');
writeln(w,'} if');
writeln(w,'dup /internalcoordinate exch def');
writeln(w,'} bind def');

writeln(w);
writeln(w,'coornumber setinternal pop % set initial
internalcoordinate');

end; (* ] *)
(* end module def1 *)

(* begin module def2 *)
procedure def2(var w: text);
(* part 2 of the definitions *)
begin (* [ *)

writeln(w);
writeln(w,'/grabbasenumber { % internalcoordinate grabbase
n found');
writeln(w,'% if found, found is true and the element n is
next');
writeln(w,'% otherwise found is false and there is no
element n.');
writeln(w,'% n is the number equivalent of the base');
writeln(w,'/ic exch def');
writeln(w,'  ic 0 ge');
writeln(w,'  ic upperseq le');
writeln(w,'  and');
writeln(w,'   {sequence ic get');
writeln(w,'     0 get true} % extract the numerical
equivalent of a letter');
writeln(w,'   {false}');
writeln(w,'ifelse');
writeln(w,'} bind def');

writeln(w);
```

- 376 -

```
writeln(w,'/grabbase { % internalcoordinate grabbase c found');
writeln(w,'% if found, found is true and the element c is next');
writeln(w,'% otherwise found is false and there is no element c.');
writeln(w,'% c is the base as a character');
writeln(w,'/ic exch def');
writeln(w,'  ic 0 ge');
writeln(w,'  ic upperseq le');
writeln(w,'  and');
writeln(w,'   {sequence ic get');
writeln(w,'    0 get % extract the numerical equivalent of a letter');
writeln(w,'    symbols exch get true} % convert to a letter ');
writeln(w,'   {false}');
writeln(w,'ifelse');
writeln(w,'} bind def');

writeln(w);
writeln(w,'/setxy { % ic setxy boolean');
writeln(w,'% setxy takes an internal coordinate ic,');
writeln(w,'% and sees if a move to that position on the page is possible.');
writeln(w,'% if so, it sets x and y,');
writeln(w,'% and the boolean is true, otherwise false.');
writeln(w,'/ic exch def');
writeln(w,'ic 0 ge ic upperseq le and');
writeln(w,'{ % inside the sequence');
writeln(w,'   % PostScript mod is not a true modulo function!');
writeln(w,'   % So we make our own:');
writeln(w,'   /xtemp ic internalcoordinate sub basenumber add def');
writeln(w,'   /ytemp linenumber def');
writeln(w,'   { xtemp basesperline lt');
```

- 377 -

```
writeln(w,'    {exit}');
writeln(w,'    {/xtemp xtemp basesperline sub def');
writeln(w,'     /ytemp ytemp 1 sub def}');
writeln(w,'    ifelse');
writeln(w,'  } loop');
writeln(w,'  { xtemp 0 ge');
writeln(w,'    {exit}');
writeln(w,'    {/xtemp xtemp basesperline add def');
writeln(w,'     /ytemp ytemp 1 add def}');
writeln(w,'    ifelse');
writeln(w,'  } loop');
writeln(w,'  ytemp 0 ge');
writeln(w,'  ytemp linesperpage lt');
writeln(w,'  and');
writeln(w,'  dup {');
writeln(w,'      /x xtemp def');
writeln(w,'      /y ytemp def');
writeln(w,'  } if');
writeln(w,'}');
writeln(w,'{ % not inside the sequence');
writeln(w,'  false');
writeln(w,'}');
writeln(w,'ifelse');
writeln(w,'} bind def');

writeln(w);
writeln(w,'/gettoxy { % ic gettoxy boolean');
writeln(w,'% gettoxy takes an internal coordinate ic,');
writeln(w,'% attempts to move the zero base of the
walker');
writeln(w,'% to that position on the page');
writeln(w,'% and if it succeeds it sets x, y, basenumber
and linenumber.');
writeln(w,'% Then it moves there and');
writeln(w,'% the variable internalcoordinate is set to
ic.');
writeln(w,'% If it succeeds the boolean is true, otherwise
```

```
false.');
writeln(w,'% If true, the zerobase will be at (basenumber,
linenumber).');
writeln(w,'setxy dup');
writeln(w,'{  tochar moveto');
writeln(w,'   /basenumber x def');
writeln(w,'   /linenumber y def');
writeln(w,'} if');
writeln(w,'} bind def');

writeln(w);
writeln(w,'/displaywalker { % show the walker');
writeln(w,'% at internalcoordinate, basenumber,
linenumber');
writeln(w,'gsave');
writeln(w,'% print the zero base');
writeln(w,'/x basenumber def ');
writeln(w,'/y linenumber def');
writeln(w,'tochar moveto');
writeln(w,'currentpoint translate');
writeln(w,'% this should be the same as: ');
writeln(w,'% 0 getoxy pop');
writeln(w,'% zap previous symbol there');
writeln(w,'white 0 0 charbox fill gsave 0 0 charbox black
stroke grestore');
writeln(w,'/thebase internalcoordinate grabbase not {exit}
if def');
writeln(w,'/cmhigh charupper cmfactor div def ');
writeln(w,'cmhigh thebase numchar');
writeln(w,'grestore');
writeln(w,'% here do the rest of the walker');
writeln(w,'} bind def');

writeln(w);
writeln(w,'/anycolornumchar{ % charheight character
numchar');
writeln(w,'% Make a character of given height in cm,');
```

- 379 -

```
writeln(w,'  gsave');
writeln(w,'    /char exch def');
writeln(w,'    /charheight exch cm def');
writeln(w,'    charwidth charheight char boxshow');
writeln(w,'  grestore');
writeln(w,'  charheight abs 1 gt {0 charheight abs translate} if');
writeln(w,'} bind def');

writeln(w);
writeln(w,'/anycolorletter { % ic colorletter');
writeln(w,'% evaluate and print the base at ic in anycolor');
writeln(w,'/ic exch def');
writeln(w,'gsave');
writeln(w,'ic setxy pop');
writeln(w,'tochar moveto');
writeln(w,'currentpoint translate');
writeln(w,'currentrgbcolor % save current color on the stack');
writeln(w,'% zap previous symbol there');
writeln(w,'backcolor 0 0 charbox fill gsave');
writeln(w,'boxstate {0 0 charbox black stroke} if grestore');
writeln(w,'setrgbcolor % restore current color from the stack');
writeln(w,'/thebase ic grabbase not {exit} if def');

writeln(w,'outofsequence');
writeln(w,'{');
writeln(w,'gsave');
writeln(w,'   0 2 bitspercm div translate');
writeln(w,'   0 0 moveto');
writeln(w,'   charwidth 0 rlineto');
writeln(w,'   0 gapcm rlineto');
writeln(w,'   ncharwidth 0 rlineto');
writeln(w,'   closepath');
```

- 380 -

```
writeln(w,'   white fill');
writeln(w,'   grey');
writeln(w,'   0 charshift translate');

writeln(w,'   doingwave');
writeln(w,'    {makesine thebase anycolornumchar}');
writeln(w,'    {bittocm thebase anycolornumchar}');
writeln(w,'   ifelse');
writeln(w,'grestore');
writeln(w,'}');
writeln(w,'{');
writeln(w,'gsave');
writeln(w,'   doingwave');
writeln(w,'    {makesine thebase anycolornumchar}');
writeln(w,'    {bittocm thebase anycolornumchar}');
writeln(w,'   ifelse');
writeln(w,'grestore');
writeln(w,'}');
writeln(w,'ifelse');

writeln(w,'grestore');
writeln(w,'} bind def');

writeln(w);
writeln(w,'/evaluate { % ic evaluate bits');
writeln(w,'% give the bits at position ic');
writeln(w,'/ic exch def');
writeln(w,'ribl');
writeln(w,'ic internalcoordinate sub riblzero add get');
writeln(w,'ic grabbasenumber pop get} bind def');

end; (* ] *)
(* end module def2 *)

(* begin module def3 *)
procedure def3(var w: text);
(* part 3 of the definitions *)
```

- 381 -

```
const
  linestrlength = 60; (* length of an output line *)
var
  blanks: integer; (* for writing blanks *)
  atspot: integer; (* location of at on output display *)
  rispot: integer; (* location of Ri on output display *)
  zspot:  integer; (* location of Z on output display *)
begin (* [ *)

writeln(w);
writeln(w,'/colorletter { % ic colorletter');
writeln(w,'% evaluate and print the base at ic in color');
writeln(w,'/ic exch def');
writeln(w,'gsave');
writeln(w,'ic setxy pop');
writeln(w,'tochar moveto');
writeln(w,'currentpoint translate');
writeln(w,'% zap previous symbol there');
writeln(w,'backcolor 0 0 charbox fill gsave');
writeln(w,'boxstate {0 0 charbox black stroke} if
grestore');
writeln(w,'/thebase ic grabbase not {(colorletter error) =
exit} if def');

writeln(w,'gsave');
writeln(w,'outofsequence');
writeln(w,'{');
writeln(w,'   0 2 bitspercm div translate');
writeln(w,'   0 0 moveto');
writeln(w,'   charwidth 0 rlineto');
writeln(w,'   0 gapcm rlineto');
writeln(w,'   ncharwidth 0 rlineto');
writeln(w,'   closepath');
writeln(w,'   white fill');
writeln(w,'   blue');
writeln(w,'   0 charshift translate');
writeln(w,'   doingwave');
```

- 382 -

```
writeln(w,'    {makesine thebase anycolornumchar}');
writeln(w,'    {1 thebase anycolornumchar}');
writeln(w,'    ifelse');
writeln(w,'}');
writeln(w,'{');
writeln(w,'    doingwave');
writeln(w,'    { % draw line at wave');
writeln(w,'        0 makesine cm currentlinewidth sub moveto');
writeln(w,'        charwidth 0 rlineto');
writeln(w,'        grey stroke');
writeln(w,'    } if');
writeln(w,'}');
writeln(w,'ifelse');
writeln(w,'grestore');

writeln(w,'/bits ic evaluate def');
writeln(w,'/cmhigh bits bittocm mul def');
writeln(w,'bits 0 lt {');
writeln(w,'    bits lowerbound lt');
writeln(w,'    {');
writeln(w,'        newpath');
writeln(w,'        0 0 moveto');
writeln(w,'        0 charlower rlineto');
writeln(w,'        charwidth 0 rlineto');
writeln(w,'        0 charlower neg rlineto');
writeln(w,'        closepath');
writeln(w,'        clip');
writeln(w,'        bits ',negativeinfinity,' lt');
writeln(w,'        {black}');
writeln(w,'        {purple}');
writeln(w,'        ifelse');
writeln(w,'        fill');
writeln(w,'        0 cmhigh cm translate');
writeln(w,'        cmhigh thebase numchar');
writeln(w,'        initclip');
(*
```

- 383 -

```
writeln(w,'      bits =');
*)
writeln(w,'   } ');
writeln(w,'   {');
writeln(w,'      0 cmhigh cm translate');
writeln(w,'      cmhigh thebase numchar');
writeln(w,'   }');
writeln(w,'   ifelse');
writeln(w,'   }');
writeln(w,'   {cmhigh thebase numchar}');
writeln(w,'ifelse');
writeln(w,'grestore');
writeln(w,'} bind def');

writeln(w);
writeln(w,'% mechanism for finding the total Ri value
evaluated');
writeln(w,'/sumribl {/ribltotal ribltotal bits add def}
def');

writeln(w);
writeln(w,'% string for numbers');
writeln(w,'/str 10 string def');
writeln(w,'/linestr ',linestrlength:1,' string def');
writeln(w,'/onedecimal {10 mul round 10 div} def % 1
decimal');

writeln(w,'/fourdecimal {% number location fourdecimal');
writeln(w,'% put the number at the location in linestr.');
writeln(w,'% use 4 decimal places, and put a blank for the
positive sign');
writeln(w,'/numberlocation exch def');
writeln(w,'/numbervalue exch def');
writeln(w,'linestr');
writeln(w,'numberlocation');
writeln(w,'  numbervalue -100 gt');
writeln(w,'  {');
```

- 384 -

```
writeln(w,'  numbervalue 0 gt {1 add} if');
writeln(w,'  % numbervalue abs 9 gt { numbervalue abs log
cvi sub } if');
writeln(w,'  numbervalue abs 9 gt { numbervalue abs log
cvi sub } if');
writeln(w,'  numbervalue 10000 mul round 10000 div');
writeln(w,'  str cvs putinterval');
writeln(w,'  }');
writeln(w,'  {');
writeln(w,'  1 sub');
writeln(w,'  (-Infinity) putinterval');
writeln(w,'  }');
writeln(w,'ifelse');
writeln(w,'} bind def');

writeln(w);
writeln(w,'/displaydata {');
writeln(w,'% Display the ribltotal');
writeln(w,'/Z ribltotal mean sub stdev div def');
writeln(w,'ribltotal ribound gt Z abs zbound le and');
writeln(w,'{0.4 0.2 1 sethsbcolor setbackcolor} % pink');
writeln(w,'{1 0.2 1 sethsbcolor setbackcolor} %
greenish');
writeln(w,'ifelse');
writeln(w,'gsave');
writeln(w,'   internalcoordinate colorletter');
writeln(w,'   internalcoordinate setxy pop');
writeln(w,'   tochar charbox clip');
writeln(w,'   tochar translate');
writeln(w,'   0 0 moveto');
writeln(w,'      internalcoordinate evaluate 0 le');
writeln(w,'       { black charwidth 0 translate 0 0 moveto
90 }');
writeln(w,'       { black 0 0 moveto -90 }');
writeln(w,'   ifelse');
writeln(w,'   rotate 0 charshift moveto');
```

- 385 -

```
writeln(w,'   /externalcoordinate sequence
internalcoordinate get 1 get def');

writeln(w,'   externalcoordinate str cvs show');
writeln(w,'   ( ) show');
writeln(w,'   ribltotal onedecimal');
writeln(w,'   str cvs show');
writeln(w,'   ( ) show');
writeln(w,'   Z onedecimal');
writeln(w,'   str cvs show');
writeln(w,'   initclip');
writeln(w,'grestore');

writeln(w,'white setbackcolor');

(* The following code combines all the display data into
one line *)
write  (w,'linestr 0 (');
for blanks := 1 to linestrlength do write(w,' ');
writeln(w,') putinterval');
atspot := 0;
writeln(w,'linestr ',atspot:1,' (at ) putinterval');
writeln(w,'linestr ',atspot+3:1,' externalcoordinate str
cvs putinterval');
rispot := 11;
writeln(w,'linestr ',rispot:1,' ( Ri =) putinterval');
writeln(w,'ribltotal ',rispot+6:1,' fourdecimal');
writeln(w,'linestr ',rispot+15:1,' (bits) putinterval');
zspot := 33;
writeln(w,'linestr ',zspot:1,' ( Z =) putinterval');
writeln(w,'Z ',zspot+4:1,' fourdecimal');
writeln(w,'ribltotal ribound gt {linestr ',zspot+12:1,'
(++++) putinterval} if');
writeln(w,'Z abs zbound le {linestr ',zspot+17:1,' (<---)
putinterval} if');
writeln(w,'linestr = flush'); (* force it out for
immediate viewing *)
```

- 386 -

```
writeln(w,'} bind def');

writeln(w);
writeln(w,'/movesequence { % - movesequence -');
writeln(w,'% keep the walker steady, move the sequence to
internalcoordinate');

writeln(w,'/oldlocation internalcoordinate def');
writeln(w,'/internalcoordinate newlocation def');

writeln(w,'printing { % print suppression');

writeln(w,'grey setbackcolor');
writeln(w,'internalcoordinate colorletter');
writeln(w,'white setbackcolor');

(* initialize the value at the zero coordinate! *)
writeln(w,'/ribltotal internalcoordinate evaluate def');

(* loop to display the walker *)
writeln(w,'/fromout false def');
writeln(w,'/toout false def');
writeln(w,'/dfzb 1 def % distance from zero base');

writeln(w,'{ % loop to display the walker');
writeln(w,' fromout not');
writeln(w,' { /below internalcoordinate dfzb sub def');
writeln(w,'   below setxy');
writeln(w,'   dfzb rangefrom neg le');
writeln(w,'   and');
writeln(w,'   { tochar moveto');
writeln(w,'     below colorletter sumribl');
writeln(w,'   }');
writeln(w,'   {/fromout true def');
writeln(w,'   }');
writeln(w,'   ifelse');
writeln(w,' } if');
```

- 387 -

```
writeln(w,' toout not');
writeln(w,' { /above internalcoordinate dfzb add def');
writeln(w,'   above setxy');
writeln(w,'   dfzb rangeto le');
writeln(w,'   and');
writeln(w,'   {  tochar moveto');
writeln(w,'      above colorletter sumribl');
writeln(w,'   }');
writeln(w,'   {/toout true def');
writeln(w,'   }');
writeln(w,'   ifelse');
writeln(w,' } if');
writeln(w,' fromout toout and {exit} if');
writeln(w,' /dfzb dfzb 1 add def');
writeln(w,'} loop % for walker');

writeln(w,'displaydata');
```

(* If the walker is steady and there is no wave, then we don't need to display
the rest of the sequence. This speeds up the display. *)

```
writeln(w,'/fromout false def');
writeln(w,'/toout false def');
writeln(w,' /below below 1 add def % reset');
writeln(w,' /above above 1 sub def % reset');
writeln(w,'doingwave sequencemoves forcedisplay or or {');
writeln(w,' { % loop to display the reset of the page');
writeln(w,'  fromout not');
writeln(w,'  { /below below 1 sub def');
writeln(w,'    below setxy');
writeln(w,'    { tochar moveto');
writeln(w,'      grey below anycolorletter');
writeln(w,'    }');
writeln(w,'    {/fromout true def');
writeln(w,'    }');
writeln(w,'    ifelse');
```

- 388 -

```
writeln(w,'  } if');
writeln(w,'  toout not');
writeln(w,'  { /above above 1 add def');
writeln(w,'    above setxy');
writeln(w,'    {  tochar moveto');
writeln(w,'       grey above anycolorletter');
writeln(w,'    }');
writeln(w,'    {/toout true def');
writeln(w,'    }');
writeln(w,'    ifelse');
writeln(w,'  } if');
writeln(w,'  fromout toout and {exit} if');
writeln(w,'  /dfzb dfzb 1 add def');
writeln(w,' } loop % for page');
writeln(w,'}');

writeln(w,'{ % cleanup behind walker');
writeln(w,'  /dfzb 0 def');
writeln(w,'/oldbelow oldlocation rangefrom add def');
writeln(w,'/oldabove oldlocation rangeto add def');
writeln(w,'{ % loop for clearing walker');
writeln(w,' fromout not');
writeln(w,'  { /ic oldlocation dfzb sub def');
writeln(w,'    ic setxy');
writeln(w,'    ic oldbelow ge');
writeln(w,'    and   ');
writeln(w,'    {%  tochar moveto');
writeln(w,'     ic below lt ic above gt or');
writeln(w,'   {grey ic anycolorletter');
writeln(w,'} if');
writeln(w,'    }');
writeln(w,'    {/fromout true def');
writeln(w,'    }');
writeln(w,'    ifelse');
writeln(w,' } if   ');
writeln(w,' toout not');
writeln(w,'  { /ic oldlocation dfzb add def');
```

- 389 -

```
writeln(w,'   ic setxy');
writeln(w,'   ic oldabove le');
writeln(w,'   and');
writeln(w,'   {%  tochar moveto');
writeln(w,'    ic below lt ic above gt or');
writeln(w,'    {grey ic anycolorletter');
writeln(w,'} if');
writeln(w,'    }');
writeln(w,'   {/toout true def');
writeln(w,'    }');
writeln(w,'    ifelse');
writeln(w,' } if');
writeln(w,'  fromout toout and {exit} if');
writeln(w,'  /dfzb dfzb 1 add def');
writeln(w,'} loop % for removing old walker');
writeln(w,'}');

writeln(w,'ifelse');

writeln(w,'waittime wait');
writeln(w,'} if % print suppression');
writeln(w,'} bind def');

writeln(w);
writeln(w,'/movewalker { % - movewalker -');
writeln(w,'% keep the sequence steady, move the walker to internalcoordinate');
writeln(w,'% change the position on the page also!');
writeln(w,'newlocation setxy');
writeln(w,'{% we can move there');
writeln(w,'/basenumber x def');
writeln(w,'/linenumber y def');
writeln(w,'movesequence');
writeln(w,'} % we can move there');
writeln(w,'{ (It''s not possible to move there because ) =');
writeln(w,'  newlocation 0 lt newlocation upperseq gt
```

- 390 -

```
or');
writeln(w,'  {(it''s off the sequence) =}');
writeln(w,'  {(it''s off the page - perhaps switch to
sequence move mode?) =}');
writeln(w,'  ifelse');
writeln(w,'}');
writeln(w,'ifelse');
writeln(w,'} def');

writeln(w);
writeln(w,'/takestep { % value takestep - ; take a step');
writeln(w,'% the value is the new internalcoordinate');
writeln(w,'/newlocation exch def');
writeln(w,'newlocation grabbase');
writeln(w,'  {pop % the new location is ok');
writeln(w,'   % depending on the toggle we might move
sequence or walker');
writeln(w,'   sequencemoves');
writeln(w,'     {movesequence}');
writeln(w,'     {movewalker}');
writeln(w,'   ifelse');
writeln(w,'  }');
writeln(w,'  {/newlocation internalcoordinate def %
refuse to move');
writeln(w,'   (There Is No Sequence In That Direction!)
=}');
writeln(w,'ifelse');
writeln(w,'} bind def');

writeln(w);
writeln(w,'% ERROR HANDLING');

writeln(w);
writeln(w,'errordict /undefined',
         ' {= (Sorry, I don''t know that command) =}
put');
```

- 391 -

```
writeln(w);
writeln(w,'% The following can only be done ONCE');
writeln(w,'pagex pagey translate % done ONCE');
writeln(w,'0 charlower neg translate % move to zero of the
character box');
writeln(w);

end; (* ] *)
(* end module def3 *)

(* begin module def4 *)
procedure def4(var w: text);
(* part 4 of the definitions *)
begin (* [ *)
writeln(w,'/searchtest {% test if the search should end');
writeln(w,'ribltotal ribound gt Z abs zbound le and');
writeln(w,'{(^GFound one!)= exit} if');
writeln(w,'} bind def');
end; (* ] *)
(* end module def4 *)

(* begin module definitions *)
procedure definitions(var w: text);
(* define functions and initial values.  This has to be
broken into several
parts because the compiler runs out of memory otherwise.
This happens because
these are routines heavy in the use of literals, and those
take lots of memory.
*)
begin
  def1(w);
  def2(w);
  def3(w);
  def4(w);
end;
(* end module definitions *)
```

- 392 -

```
(* begin module displayentirepage *)
procedure displayentirepage(var w: text);
(* display the entire page *)
begin
writeln(w,'/displayentirepage {% display the entire
page');
(*
pageheight pagewidth 0 0 rectangle white fill
0 charlower neg translate % move to zero of the character
box
*)
writeln(w,'printing {');
writeln(w,'   doerasepage {erasepage} if');
writeln(w,'   definepageparameters');
writeln(w,'   boxstate {');
writeln(w,'      0 1 linesperpage 1 sub');
{zzzqqq}
writeln(w,'      { /y exch def');
writeln(w,'          0 1 basesperline 1 sub');
writeln(w,'          { /x exch def');
writeln(w,'             tochar charbox blue stroke');
writeln(w,'          } for');
writeln(w,'      } for');
writeln(w,'   } if');
writeln(w,'   /forcedisplay true def');
writeln(w,'   internalcoordinate takestep');
writeln(w,'   /forcedisplay false def');
writeln(w,'} if');
writeln(w,'} bind def');
end;
(* end module displayentirepage *)

(* begin module defineusercommands *)
procedure defineusercommands(var w: text);
(* define the user commands and their consequences *)
begin
```

- 393 -

```
writeln(w);
writeln(w);
writeln(w,'% USER DEFINITIONS');

writeln(w);
writeln(w,'/r { % redisplay the page');
writeln(w,' displayentirepage ');
writeln(w,'} bind def');

writeln(w);
writeln(w,'/R { % reset everything');
writeln(w,'clear');
writeln(w,'(clearing stack, graphics state and restarting
program) =');
writeln(w,'clear');
writeln(w,'initgraphics');
writeln(w,'erasepage');
writeln(w,'(walk) run');
writeln(w,'} bind def');

writeln(w);
writeln(w,'% Movement Commands, as in vi');

writeln(w,'/h { % move left');
writeln(w,'count 0 le {1} if');
writeln(w,'dup 0 lt');
writeln(w,'   {abs 1}'); (* a subtle trick: call the other
if it's negative! *)
writeln(w,'   {{internalcoordinate 1');
writeln(w,'    sequencemoves {add} {sub} ifelse takestep}
repeat}');
writeln(w,'ifelse');
writeln(w,'} def');

writeln(w,'/l { % move right');
writeln(w,'count 0 le {1} if');
writeln(w,'dup 0 lt');
```

- 394 -

```
writeln(w,'    {abs h}'); (* a subtle trick: call the other
if it's negative! *)
writeln(w,'    {{internalcoordinate 1');
writeln(w,'     sequencemoves {sub} {add} ifelse takestep}
repeat}');
writeln(w,'ifelse');
writeln(w,'} def');

writeln(w,'/j { % move down');
writeln(w,'count 0 le {1} if');
writeln(w,'dup 0 lt');
writeln(w,'    {abs k}'); (* a subtle trick: call the other
if it's negative! *)
writeln(w,'    {{internalcoordinate basesperline');
writeln(w,'     sequencemoves {sub} {add} ifelse takestep}
repeat}');
writeln(w,'ifelse');
writeln(w,'} def');

writeln(w,'/k { % move up');
writeln(w,'count 0 le {1} if');
writeln(w,'dup 0 lt');
writeln(w,'    {abs j}'); (* a subtle trick: call the other
if it's negative! *)
writeln(w,'    {{internalcoordinate basesperline');
writeln(w,'   sequencemoves {add} {sub} ifelse takestep}
repeat}');
writeln(w,'ifelse');
writeln(w,'} def');

writeln(w);
writeln(w,'% Toggle to define whether the sequence moves
or the walker moves');
writeln(w,'/sequencemoves false def');
writeln(w,'/w {/sequencemoves sequencemoves not def');
writeln(w,'sequencemoves {(Sequence Moves)} {(Walker
Moves)} ifelse =');
```

- 395 -

```
writeln(w,'} bind def');

writeln(w);
writeln(w,'/boxes {/boxstate boxstate not def
displayentirepage} def');

writeln(w);
writeln(w,'/q {grestore quit} def');

writeln(w);
writeln(w,'/? {help} def');

writeln(w);
writeln(w,'/help {(Detailed instructions for Walker
',version:4:2,
                 ' are given in) =');
writeln(w,'(the source code file walker.p.) =');

writeln(w,'(# means you must supply a number BEFORE you
type the command name.)=');
writeln(w,'(# h: move left [# is optional])=');
writeln(w,'(# j: move down [# is optional])=');
writeln(w,'(# k: move up [# is optional])=');
writeln(w,'(# l: move right [# is optional])=');
writeln(w,'(w: toggle between walker and sequence
moving)=');
writeln(w,'(q: quit)=');
writeln(w,'(?: help message)=');
writeln(w,'(r: Refresh the page)=');
writeln(w,'(R: restart ghostscript on the current walk
file)=');
writeln(w,'(# a,c,g,t: Mutate the given absolute location
to the desired base)=');
writeln(w,'(# A,C,G,T: Mutate the given relative location
to the desired base)=');
writeln(w,'(# goto: go to the given coordinate)=');
writeln(w,'(# jump: jump a relative number of bases)=');
```

```
                          - 396 -
writeln(w,'(boxes: toggle between having boxes and
not)=');
writeln(w,'(# lines (line): Set the number of lines per
page)=');
writeln(w,'(# bases (base, wide): Set the number of bases
per page)=');
writeln(w,'(# left, right, up, down: move the graphic on
the page',
           ' in units of cm)=');
(* writeln(w,'(   [no # means 1 cm])='); not worth the text
of coding *)
writeln(w,'(# height, width: set the page height or width
in cm)=');
writeln(w,'(# lower: set the lower bound in bits)=');
writeln(w,'(in: put the walker into the sequence)=');
writeln(w,'(out: take the walker out of the sequence)=');
writeln(w,'(# wave: define base at which the low point of
the',
           ' cosine wave is set)=');
writeln(w,'(waveon: turns on drawing the wave.)=');
writeln(w,'(waveoff: turns off drawing the wave)=');
writeln(w,'(toggleprinting or tp: a toggle that turns on
and off printing)=');
writeln(w,'(toggleerase or te: a toggle that turns on and
off page erase)=');
writeln(w,'(# from: change FROM range of the matrix to
use)=');
writeln(w,'(# to: change TO range of the matrix to
use)=');
writeln(w,'(help: help message)=');
writeln(w,'(# setwait: set the wait time in seconds after
display)=');
writeln(w,'(      waittime is currently:)= waittime =');
writeln(w,'(# isasecond: set the number of {1 pop} cycles
per second)=');
writeln(w,'(      seconds is currently:)= second =');
writeln(w,'(# setri: set minimum Ri for searching and
```

- 397 -

```
display)=');
writeln(w,'(      ribound is currently:)= ribound =');
writeln(w,'(# setz: set minimum Z for searching and
display)=');
writeln(w,'(      zbound is currently:)= zbound =');
writeln(w,'(# f: search forward to next site which fits
search criteria)=');
writeln(w,'(# b: search backward to next site which fits
search criteria)=');

writeln(w,'} def');

writeln(w);
writeln(w,'/in { % make the walker be in the sequence');
writeln(w,'/outofsequence false def');
writeln(w,'displayentirepage');
writeln(w,'} bind def');

writeln(w);
writeln(w,'/out { % make the walker be out of the
sequence');
writeln(w,'/outofsequence true def');
writeln(w,'displayentirepage');
writeln(w,'} bind def');

writeln(w);
writeln(w,'/goto {');
writeln(w,'count 0 le');
writeln(w,'{(To use the "goto" command to go to coordinate
180 type "180 goto") =}');
writeln(w,'{cvi tointernal');
writeln(w,'  {takestep}');
writeln(w,'  {(that base is not on the sequence) =}');
writeln(w,'  ifelse');
writeln(w,'}');
writeln(w,'ifelse');
writeln(w,'} bind def');
```

- 398 -

```
writeln(w);
writeln(w,'/jump {');
writeln(w,'count 0 le');
writeln(w,'{(To use the "jump" command to move 5 bases
5'', type "-5 jump") =}');
writeln(w,'{cvi internalcoordinate add takestep}');
writeln(w,'ifelse');
writeln(w,'} bind def');

writeln(w);
writeln(w,'/to { % set the rangeto');
writeln(w,'count 0 le');
writeln(w,'{(To use the "to" command to set rangeto to -5,
type "-5 to") =}');
writeln(w,'{dup tobase gt');
writeln(w,'  {pop (rangeto must be smaller than tobase) =
tobase =}');
writeln(w,'  { dup frombase lt');
writeln(w,'    {pop (rangeto must be greater than or equal
to rangefrom)',
                '  = rangefrom =}');
writeln(w,'    {/rangeto exch def');
writeln(w,'     displayentirepage}');
writeln(w,'    ifelse');
writeln(w,'  } ifelse');
writeln(w,'} ifelse');
writeln(w,'} bind def');

writeln(w);
writeln(w,'/from { % set the rangefrom');
writeln(w,'count 0 le');
writeln(w,'{(To use the "from" command to set rangefrom to
-5, type "-5 from") =}');
writeln(w,'{dup frombase lt');
writeln(w,' {pop (rangefrom must be larger than frombase)
= frombase =}');
writeln(w,' { dup tobase gt');
```

- 399 -

```
writeln(w,'    {pop (rangefrom must be less than or equal
to rangeto)',
              ' = rangeto =}');
writeln(w,'    {/rangefrom exch def');
writeln(w,'     displayentirepage}');
writeln(w,'   ifelse');
writeln(w,'  } ifelse');
writeln(w,'} ifelse');
writeln(w,'} bind def');

writeln(w);
writeln(w,'/bases { % set the basesperline');
writeln(w,'count 0 le');
writeln(w,'{(To use the "bases" command to set
basesperline to 5,',
          ' type "5 bases") =}');
writeln(w,'{dup 1 lt');
writeln(w,' {pop (basesperline must be larger than 0)
=}');
writeln(w,' {/basesperline exch def');
writeln(w,'    /basenumber basesperline 2 idiv def');
writeln(w,'    displayentirepage}');
writeln(w,' ifelse');
writeln(w,'} ifelse');
writeln(w,'} bind def');
writeln(w,'/base {bases} def');
writeln(w,'/wide {bases} def');

writeln(w);
writeln(w,'/lines { % set the linesperpage');
writeln(w,'count 0 le');
writeln(w,'{(To use the "lines" command to set
linesperpage to 5,',
          ' type "5 lines") =}');
writeln(w,'{dup 1 lt');
writeln(w,' {pop (linesperpage must be larger than 0)
=}');
```

- 400 -

```
writeln(w,' {/linesperpage exch def');
writeln(w,'   /linenumber linesperpage 2 idiv def');
writeln(w,'    displayentirepage}');
writeln(w,' ifelse');
writeln(w,'} ifelse');
writeln(w,'} bind def');
writeln(w,'/line {lines} def');

writeln(w);
writeln(w,'/left { % move the page left');
writeln(w,'count 0 le');
writeln(w,'{(to move left 2 cm type "2 left") =}');
writeln(w,'{neg cm 0 cm translate');
writeln(w,' displayentirepage');
writeln(w,'} ifelse');
writeln(w,'} bind def');

writeln(w);
writeln(w,'/right { % move the page right');
writeln(w,'count 0 le');
writeln(w,'{(to move right 2 cm type "2 right") =}');
writeln(w,'{cm 0 cm translate');
writeln(w,' displayentirepage');
writeln(w,'} ifelse');
writeln(w,'} bind def');

writeln(w);
writeln(w,'/down { % move the page down');
writeln(w,'count 0 le');
writeln(w,'{(to move down 2 cm type "2 down") =}');
writeln(w,'{0 exch neg cm translate');
writeln(w,' displayentirepage');
writeln(w,'} ifelse');
writeln(w,'} bind def');

writeln(w);
writeln(w,'/up { % move the page up');
```

- 401 -

```
writeln(w,'count 0 le');
writeln(w,'{(to move up 2 cm type "2 up") =}');
writeln(w,'{0 exch cm translate');
writeln(w,' displayentirepage');
writeln(w,'} ifelse');
writeln(w,'} bind def');

writeln(w);
writeln(w,'/height { % define the page height');
writeln(w,'count 0 le');
writeln(w,'{(page height is in cm and must be positive, eg
"3 height") =}');
writeln(w,'{/pageheight exch cm def');
writeln(w,' displayentirepage');
writeln(w,'} ifelse');
writeln(w,'} bind def');

writeln(w);
writeln(w,'/width { % define the page width');
writeln(w,'count 0 le');
writeln(w,'{(page width is in cm and must be positive, eg
"3 width") =}');
writeln(w,'{/pagewidth exch cm def');
writeln(w,' displayentirepage');
writeln(w,'} ifelse');
writeln(w,'} bind def');

writeln(w);
writeln(w,'/lower { % lower bound');
writeln(w,'/lowerbound exch def');
writeln(w,'displayentirepage');
writeln(w,'} bind def');

writeln(w);
writeln(w,'/wave { % set the wave phase');
writeln(w,'count 0 le');
writeln(w,'{(to put the wave low point at base -3, type
```

- 402 -

```
"-3 wave") =}');
writeln(w,'{/wavephase exch def');
writeln(w,' displayentirepage');
writeln(w,'} ifelse');
writeln(w,'} bind def');

writeln(w);
writeln(w,'/waveon { % set the wave state on');
writeln(w,'/doingwave true def');
writeln(w,'displayentirepage');
writeln(w,'} bind def');

writeln(w);
writeln(w,'/waveoff { % set the wave state off');
writeln(w,'/doingwave false def');
writeln(w,'displayentirepage');
writeln(w,'} bind def');

writeln(w);
writeln(w,'/toggleprinting { % turn on or off printing');
writeln(w,'/printing printing not def');
writeln(w,'printing');
writeln(w,'{(Printing is on.) =}');
writeln(w,'{(Printing is suppressed.) =}');
writeln(w,'ifelse');
writeln(w,'displayentirepage');
writeln(w,'} bind def');
writeln(w,'/tp {toggleprinting} bind def');

writeln(w);
writeln(w,'/toggleerase { % turn on or off erase');
writeln(w,'/doerasepage doerasepage not def');
writeln(w,'doerasepage');
writeln(w,'{(page erase is on.) =}');
writeln(w,'{(page erase is suppressed.) =}');
writeln(w,'ifelse');
writeln(w,'displayentirepage');
```

- 403 -

```
writeln(w,'} bind def');
writeln(w,'/te {toggleerase} bind def');

writeln(w);
writeln(w,'% mutation controls:');

writeln(w,'/m {sequence exch get pstack pop} def');

writeln(w,'/mutate{ % ic base# mutate -');
writeln(w,'% store the base # at the internal coordinate
ic in the sequence');
writeln(w,'/base exch def');
writeln(w,'/ic exch def');
writeln(w,'/ec sequence ic get 1 get def % external
coordinate');
writeln(w,'sequence ic [base ec] put ');
writeln(w,'} bind def');

writeln(w);
writeln(w,'/a { % external coordinate a - % set external
coordinate to a');
writeln(w,'count 0 le');
writeln(w,'{(To use the "a" command to mutate base 10,
type "10 a") =}');
writeln(w,'{ tointernal');
writeln(w,'  {0 mutate displayentirepage}');
writeln(w,'  {(That coordinate is not on this sequence)
=}');
writeln(w,' ifelse');
writeln(w,'} ifelse');
writeln(w,'} bind def');

writeln(w);
writeln(w,'/c { % external coordinate a - % set external
coordinate to c');
writeln(w,'count 0 le');
writeln(w,'{(To use the "c" command to mutate base 10,
```

- 404 -

```
type "10 c") =}');
writeln(w,'{ tointernal');
writeln(w,'  {1 mutate displayentirepage}');
writeln(w,'  {(That coordinate is not on this sequence)
=}');
writeln(w,'  ifelse');
writeln(w,'} ifelse');
writeln(w,'} bind def');

writeln(w);
writeln(w,'/g { % external coordinate a - % set external
coordinate to g');
writeln(w,'count 0 le');
writeln(w,'{(To use the "g" command to mutate base 10,
type "10 g") =}');
writeln(w,'{ tointernal');
writeln(w,'  {2 mutate displayentirepage}');
writeln(w,'  {(That coordinate is not on this sequence)
=}');
writeln(w,'  ifelse');
writeln(w,'} ifelse');
writeln(w,'} bind def');

writeln(w);
writeln(w,'/t { % external coordinate a - % set external
coordinate to t');
writeln(w,'count 0 le');
writeln(w,'{(To use the "t" command to mutate base 10,
type "10 t") =}');
writeln(w,'{ tointernal');
writeln(w,'  {3 mutate displayentirepage}');
writeln(w,'  {(That coordinate is not on this sequence)
=}');
writeln(w,'  ifelse');
writeln(w,'} ifelse');
writeln(w,'} bind def');
```

- 405 -

```
writeln(w);
writeln(w,'%%%%%%%%%%%%%%%%%%%%%%%%%');

writeln(w);
writeln(w,'/A { % relative coordinate a - % set relative
coordinate to a');
writeln(w,'count 0 le');
writeln(w,'{(To use the "A" command to mutate relative
base +10, type "10 A") =}');
writeln(w,'{ coornumber add tointernal');
writeln(w,'   {0 mutate displayentirepage}');
writeln(w,'   {(That coordinate is not on this sequence)
=}');
writeln(w,'  ifelse');
writeln(w,'} ifelse');
writeln(w,'} bind def');

writeln(w);
writeln(w,'/C { % relative coordinate a - % set relative
coordinate to c');
writeln(w,'count 0 le');
writeln(w,'{(To use the "C" command to mutate relative
base +10, type "10 C") =}');
writeln(w,'{ coornumber add tointernal');
writeln(w,'   {1 mutate displayentirepage}');
writeln(w,'   {(That coordinate is not on this sequence)
=}');
writeln(w,'  ifelse');
writeln(w,'} ifelse');
writeln(w,'} bind def');

writeln(w);
writeln(w,'/G { % relative coordinate a - % set relative
coordinate to g');
writeln(w,'count 0 le');
writeln(w,'{(To use the "G" command to mutate relative
base +10, type "10 G") =}');
```

- 406 -

```
writeln(w,'{ coornumber add tointernal');
writeln(w,'  {2 mutate displayentirepage}');
writeln(w,'  {(That coordinate is not on this sequence)
=}');
writeln(w,'  ifelse');
writeln(w,'} ifelse');
writeln(w,'} bind def');

writeln(w);
writeln(w,'/T { % relative coordinate a - % set relative
coordinate to t');
writeln(w,'count 0 le');
writeln(w,'{(To use the "T" command to mutate relative
base +10, type "10 T") =}');
writeln(w,'{ coornumber add tointernal');
writeln(w,'  {3 mutate displayentirepage}');
writeln(w,'  {(That coordinate is not on this sequence)
=}');
writeln(w,'  ifelse');
writeln(w,'} ifelse');
writeln(w,'} bind def');

writeln(w);
writeln(w,'%%%%%%%%%%%%%%%%%%%%%%%%%');

writeln(w);
writeln(w,'/setri { % set the ri bound');
writeln(w,'count 0 le');
writeln(w,'{(use setri to set the Ri bound; it needs a
number in bits) =');
writeln(w,' (current value:) = ribound =}');
writeln(w,'{/ribound exch def');
writeln(w,'} ifelse');
writeln(w,'} bind def');

writeln(w);
writeln(w,'/setz { % set the z bound');
```

```
writeln(w,'count 0 le');
writeln(w,'{(setz to set the z bound needs a number) =');
writeln(w,'  (current value:) = zbound ≐}');
writeln(w,'{/zbound exch abs def');
writeln(w,'} ifelse');
writeln(w,'} bind def');

{zzz}
writeln(w,'/f { % search forward');
writeln(w,'count 0 le {1} if');
writeln(w,'dup 0 lt');
writeln(w,'  {abs b}'); (* a subtle trick: call the other
if it's negative! *)
writeln(w,'  {{internalcoordinate 1');
writeln(w,'    sequencemoves {sub} {add} ifelse takestep
searchtest} repeat}');
writeln(w,'ifelse');
writeln(w,'} def');

writeln(w,'/b { % search backward');
writeln(w,'count 0 le {1} if');
writeln(w,'dup 0 lt');
writeln(w,'  {abs f}'); (* a subtle trick: call the other
if it's negative! *)
writeln(w,'  {{internalcoordinate 1');
writeln(w,'    sequencemoves {add} {sub} ifelse takestep
searchtest} repeat}');
writeln(w,'ifelse');
writeln(w,'} def');

end;
(* end module defineusercommands *)

(* begin module walker.themain *)
procedure themain(var book, ribl, colors, walkerp, walk:
text);
(* the main procedure of the program *)
```

- 408 -

```
var
    p: parameters; (* the parameters to control the program *)

begin
    writeln(output,'walker ',version:4:2);

createheader(walk);

readparameters(walkerp,p);

(* read in the colors and define the colors in the walk
*)
{   makecolors(colors, walk);}

(* read in the book and define the sequences in the
walk *)
    makesequencearray(book, walk);

(* read in the ribl and define the ribl array in the
walk *)
    makeribl(ribl, walk, p.rangefrom, p.rangeto);

(* write the actual parameters out.  This allows
makeribl
        to adjust the rangefrom and rangeto if necessary. *)
    writeparameters(walk,p);

definitions(walk);
    varchardefs(walk, colors, showingbox, outline,
shrinking);
    defineusercommands(walk);

displayentirepage(walk);

(* obtain any other user commands from the walkerp
file: *)
```

- 409 -

```
   if not eof(walkerp) then begin
      writeln(output,'Commands are being read from the end
of walkerp');
      writeln(walk,'toggleprinting');
      while not eof(walkerp) do copyaline(walkerp, walk);
      writeln(walk,'toggleprinting');
{zzz}
{     writeln(w,'/forcedisplay true def');}
   end
   else createender(walk);

end;
(* end module walker.themain *)

begin
   themain(book, ribl, colors, walkerp, walk);
1: end.
```

- 410 -

APPENDIX I

```
-10     rangefrom: integer, FROM of the ribl matrix to use
+10     rangeto: integer, TO of the ribl matrix to use
50      basesperline: integer, number of bases per line to
display.
3       linesperpage: integer, number of lines per page to
display.
20      basenumber: integer, the base on the line to place
the zero of the walker
1 0     linenumber: integer, the line number to place the
zero of the walker
132     coornumber: integer, the coordinate number to place
the zero of the walker
18.5    pagewidth: real, the width of the lines of sequence
in cm.
24.9    pageheight: real, the height of the lines of
sequence in cm.
1.5     pagex: real, the x coordinate of the page lower
left corner in cm.
1.5     pagey: real, the y coordinate of the page lower
left corner in cm.
-4      lowerbound: real < 0, the lowest Ri(b,l) value in
bits displayed
nb      boxes: b: boxes around each character
io      insequence: i: in the sequence, else out
% all lines from this point on are PostScript commands
% The "%" makes a comment
% walkerp: parameters for walker 3.03 and higher
% The following commands make a picture of 2 walkers
% waveoff       % turn off waves
1 lines         % display only one line
15 up           % move 15 cm up
5 height        % make the line only 5 cm high
44 wide         % show 44 characters across
w 5 h w         % move the sequence 5 positions left
132 goto        % put the walker in a new spot
```

- 411 -

```
toggleprinting toggleprinting % force printing
toggleerase    % prevent erasing during the next steps
6 down         % jump 6 cm down
138 goto       % put the walker in a new spot
toggleprinting toggleprinting % force printing
6 down         % jump 6 cm down
143 goto       % put the walker in a new spot
toggleprinting toggleprinting % force printing
copypage % cause printing on a printer but don't wipe the
page like showpage
```

- 412 -

APPENDIX J

```
%! walker 3.10
/version {(version = 3.10 of walker.p)} def
version =
(Documentation for this program is in walker.p) =

/cmfactor 72 2.54 div def % defines points -> centimeters
/cm { cmfactor mul} def % defines centimeters /zbound 3 def % defines upper Z score for reporting sites
/ribound 0 def % defines lower ribltotal for reporting
sites
/ribltotal 0 def
/Z 0 def
% note: the wave phase is not changed when page is redrawn
/wavephase 0 def % initial value of phase of cosine wave
/doingwave true def % whether or not the wave is drawn
/printing true def % whether to print all the time or not
/forcedisplay true def
/doerasepage true def % whether to erase the page gsave % Define the sequence and associated variables
/storeseq{ % coord base storeseq -
% store the base # at the internal coordinate in the
sequence
/base exch def
/coord exch def
sequence place [base coord] put
/place place 1 add def
} bind def
/a {0 storeseq} def
/c {1 storeseq} def
/g {2 storeseq} def
/t {3 storeseq} def
```

- 413 -

```
/symbols [(a) (c) (g) (t)] def
/place 0 def
% The sequence is expressed as:
% the published coordinate of the base
% the base at that coordinate
/sequencelength 1149 def
% sequencelength is the number of bases in the sequence
/sequence sequencelength array def
% upperseq is the highest internal coordinate
/upperseq sequencelength 1 sub def
1 a 2 c 3 g 4 a 5 t
6 t 7 t 8 a 9 t 10 t
11 g 12 g 13 t 14 t 15 c
16 t 17 t 18 g 19 a 20 a
21 a 22 a 23 c 24 c 25 a
26 a 27 g 28 g 29 t 30 t
31 t 32 t 33 t 34 g 35 a
36 t 37 a 38 a 39 a 40 g
41 c 42 a 43 a 44 t 45 c
46 c 47 t 48 c 49 c 50 a
51 t 52 g 53 a 54 g 55 a
56 a 57 a 58 a 59 g 60 c
61 g 62 a 63 c 64 t 65 a
66 a 67 a 68 a 69 t 70 t
71 c 72 t 73 t 74 c 75 c
76 t 77 t 78 a 79 t 80 c
81 t 82 g 83 a 84 t 85 g
86 t 87 a 88 a 89 a 90 g
91 g 92 a 93 g 94 a 95 a
96 a 97 a 98 t 99 c 100 a
101 t 102 g 103 g 104 c 105 t
106 a 107 c 108 t 109 a 110 t
111 t 112 g 113 g 114 g 115 t
116 a 117 t 118 a 119 t 120 t
121 c 122 g 123 g 124 g 125 t
126 g 127 t 128 c 129 a 130 a
131 c 132 a 133 a 134 t 135 t
```

- 414 -

```
136 g 137 a 138 c 139 c 140 a
141 a 142 a 143 a 144 t 145 a
146 t 147 c 148 g 149 a 150 t
151 t 152 t 153 a 154 c 155 a
156 g 157 c 158 g 159 t 160 a
161 a 162 t 163 g 164 c 165 g
166 c 167 t 168 t 169 a 170 c
171 t 172 a 173 g 174 t 175 g
176 c 177 a 178 a 179 a 180 t
181 t 182 g 183 t 184 g 185 a
186 c 187 c 188 g 189 c 190 a
191 t 192 t 193 t 194 t 195 t
196 g 197 a 198 a 199 g 200 a
201 c 202 c 203 g 204 t 205 a
206 t 207 c 208 a 209 g 210 t
211 g 212 g 213 c 214 a 215 a
216 g 217 a 218 t 219 t 220 g
221 c 222 a 223 a 224 a 225 c
226 c 227 g 228 c 229 c 230 c
231 c 232 g 233 g 234 c 235 c
236 t 237 g 238 a 239 a 240 a
241 c 242 g 243 g 244 g 245 c
246 g 247 t 248 t 249 a 250 a
251 a 252 g 253 t 254 a 255 t
256 g 257 t 258 a 259 a 260 a
261 t 262 a 263 a 264 a 265 g
266 g 267 c 268 g 269 a 270 t
271 a 272 c 273 t 274 c 275 t
276 t 277 g 278 t 279 c 280 g
281 t 282 c 283 t 284 g 285 g
286 a 287 a 288 a 289 t 290 t
291 a 292 g 293 a 294 c 295 a
296 g 297 a 298 c 299 t 300 g
301 g 302 g 303 c 304 c 305 g
306 t 307 a 308 g 309 c 310 g
311 t 312 g 313 a 314 a 315 a
316 a 317 a 318 t 319 c 320 t
```

- 415 -

321 g 322 g 323 t 324 g 325 g
326 c 327 g 328 t 329 t 330 a
331 a 332 t 333 a 334 t 335 c
336 a 337 g 338 a 339 a 340 t
341 t 342 a 343 c 344 a 345 t
346 g 347 a 348 a 349 c 350 g
351 t 352 g 353 g 354 a 355 g
356 c 357 t 358 c 359 a 360 c
361 t 362 t 363 c 364 c 365 a
366 t 367 t 368 c 369 t 370 t
371 t 372 a 373 a 374 c 375 c
376 g 377 a 378 t 379 a 380 g
381 t 382 a 383 t 384 t 385 g
386 a 387 t 388 a 389 c 390 c
391 a 392 g 393 t 394 a 395 g
396 c 397 g 398 c 399 g 400 a
401 t 402 g 403 g 404 g 405 g
406 c 407 g 408 a 409 t 410 t
411 c 412 t 413 t 414 t 415 t
416 t 417 t 418 c 419 a 420 t
421 g 422 t 423 a 424 a 425 t
426 g 427 t 428 c 429 a 430 g
431 c 432 a 433 c 434 t 435 g
436 g 437 c 438 c 439 g 440 a
441 g 442 a 443 t 444 g 445 g
446 a 447 g 448 c 449 g 450 a
451 g 452 a 453 a 454 t 455 t
456 a 457 a 458 t 459 c 460 g
461 t 462 c 463 g 464 a 465 g
466 c 467 g 468 a 469 a 470 c
471 c 472 c 473 t 474 t 475 g
476 c 477 c 478 g 479 g 480 a
481 c 482 t 483 g 484 g 485 c
486 t 487 g 488 c 489 c 490 g
491 c 492 c 493 a 494 g 495 a
496 g 497 c 498 g 499 c 500 a
501 a 502 g 503 g 504 a 505 c

- 416 -

```
506 g 507 a 508 c 509 t 510 g
511 g 512 g 513 a 514 g 515 g
516 g 517 c 518 g 519 c 520 c
521 c 522 t 523 c 524 g 525 g
526 g 527 c 528 g 529 a 530 t
531 c 532 a 533 a 534 c 535 a
536 a 537 a 538 c 539 a 540 t
541 g 542 a 543 a 544 c 545 a
546 g 547 g 548 a 549 a 550 c
551 a 552 g 553 a 554 t 555 t
556 a 557 g 558 t 559 c 560 g
561 g 562 c 563 t 564 a 565 t
566 t 567 a 568 g 569 a 570 g
571 a 572 a 573 a 574 g 575 g
576 c 577 c 578 a 579 t 580 c
581 c 582 t 583 c 584 g 585 g
586 c 587 a 588 g 589 c 590 a
591 a 592 t 593 t 594 a 595 g
596 c 597 t 598 a 599 t 600 t
601 a 602 t 603 t 604 t 605 t
606 t 607 g 608 g 609 t 610 a
611 t 612 t 613 g 614 g 615 c
616 g 617 t 618 a 619 t 620 c
621 c 622 a 623 c 624 c 625 t
626 t 627 a 628 t 629 a 630 c
631 a 632 g 633 a 634 t 635 a
636 c 637 t 638 t 639 t 640 c
641 c 642 g 643 g 644 c 645 a
646 a 647 g 648 c 649 a 650 g
651 t 652 a 653 t 654 a 655 a
656 a 657 a 658 a 659 a 660 a
661 c 662 g 663 a 664 a 665 t
666 g 667 a 668 a 669 t 670 t
671 a 672 a 673 a 674 a 675 t
676 a 677 a 678 a 679 a 680 a
681 t 682 c 683 a 684 c 685 a
686 a 687 c 688 a 689 g 690 g
```

- 417 -

```
691  a  692  t  693  g  694  g  695  a
696  t  697  a  698  t  699  a  700  a
701  c  702  a  703  t  704  t  705  t
706  t  707  t  708  g  709  t  710  a
711  a  712  t  713  a  714  c  715  a
716  g  717  g  718  c  719  g  720  t
721  a  722  t  723  g  724  g  725  c
726  a  727  t  728  a  729  a  730  a
731  t  732  a  733  a  734  a  735  c
736  c  737  g  738  a  739  a  740  a
741  g  742  g  743  g  744  t  745  a
746  t  747  a  748  c  749  a  750  a
751  a  752  a  753  a  754  a  755  g
756  a  757  c  758  a  759  g  760  c
761  a  762  t  763  c  764  t  765  a
766  a  767  t  768  t  769  a  770  a
771  a  772  a  773  a  774  g  775  a
776  g  777  a  778  a  779  a  780  a
781  a  782  a  783  t  784  t  785  c
786  a  787  a  788  c  789  g  790  t
791  a  792  t  793  t  794  a  795  a
796  c  797  a  798  t  799  a  800  t
801  a  802  t  803  a  804  g  805  t
806  g  807  t  808  a  809  a  810  c
811  g  812  c  813  g  814  c  815  t
816  c  817  a  818  c  819  g  820  a
821  t  822  a  823  a  824  g  825  g
826  c  827  c  828  t  829  a  830  t
831  g  832  t  833  t  834  a  835  c
836  a  837  t  838  c  839  c  840  a
841  g  842  c  843  t  844  a  845  t
846  a  847  g  848  a  849  c  850  g
851  a  852  c  853  a  854  t  855  c
856  g  857  c  858  t  859  c  860  a
861  a  862  a  863  a  864  c  865  a
866  c  867  t  868  a  869  c  870  c
871  a  872  g  873  a  874  c  875  a
```

- 418 -

```
 876 c  877 a  878 g  879 t  880 a
 881 t  882 t  883 c  884 a  885 c
 886 c  887 t  888 g  889 g  890 a
 891 a  892 a  893 g  894 g  895 c
 896 t  897 t  898 t  899 t  900 t
 901 a  902 a  903 t  904 c  905 a
 906 a  907 a  908 a  909 t  910 g
 911 t  912 t  913 a  914 g  915 a
 916 t  917 g  918 t  919 a  920 a
 921 g  922 c  923 a  924 a  925 t
 926 t  927 a  928 c  929 g  930 g
 931 a  932 c  933 a  934 g  935 a
 936 a  937 a  938 a  939 a  940 a
 941 t  942 a  943 g  944 t  945 a
 946 a  947 a  948 g  949 t  950 t
 951 t  952 a  953 t  954 g  955 c
 956 c  957 t  958 c  959 a  960 a
 961 g  962 t  963 g  964 t  965 c
 966 g  967 a  968 t  969 a  970 a
 971 c  972 c  973 t  974 g  975 g
 976 a  977 t  978 g  979 a  980 c
 981 a  982 c  983 a  984 g  985 g
 986 t  987 a  988 a  989 g  990 c
 991 c  992 t  993 g  994 g  995 c
 996 a  997 t  998 a  999 a 1000 c
1001 a 1002 t 1003 t 1004 g 1005 g
1006 t 1007 t 1008 a 1009 t 1010 c
1011 a 1012 a 1013 a 1014 a 1015 a
1016 c 1017 c 1018 t 1019 t 1020 c
1021 c 1022 a 1023 a 1024 a 1025 a
1026 g 1027 g 1028 a 1029 a 1030 a
1031 a 1032 t 1033 t 1034 t 1035 t
1036 a 1037 t 1038 g 1039 g 1040 c
1041 a 1042 c 1043 a 1044 a 1045 g
1046 t 1047 a 1048 a 1049 t 1050 c
1051 a 1052 a 1053 c 1054 a 1055 c
1056 t 1057 a 1058 a 1059 c 1060 a
```

- 419 -

```
1061 g 1062 t 1063 c 1064 t 1065 g
1066 t 1067 c 1068 g 1069 c 1070 t
1071 g 1072 c 1073 t 1074 g 1075 a
1076 c 1077 c 1078 c 1079 a 1080 g
1081 a 1082 a 1083 t 1084 a 1085 a
1086 c 1087 c 1088 t 1089 g 1090 a
1091 a 1092 c 1093 a 1094 a 1095 a
1096 t 1097 c 1098 c 1099 c 1100 a
1101 g 1102 t 1103 c 1104 c 1105 g
1106 c 1107 a 1108 c 1109 t 1110 g
1111 g 1112 g 1113 c 1114 a 1115 c
1116 c 1117 g 1118 c 1119 t 1120 a
1121 t 1122 c 1123 g 1124 a 1125 g
1126 c 1127 g 1128 t 1129 c 1130 t
1131 g 1132 t 1133 c 1134 t 1135 t
1136 c 1137 t 1138 g 1139 g 1140 t
1141 c 1142 t 1143 g 1144 c 1145 g
1146 t 1147 t 1148 c 1149 c
% end of a piece 1149 bp % Define the Rib1 matrix and associated variables
/frombase -10 def
/tobase 10 def
/fromwanted -10 def
/towanted 10 def
/mean     8.240408 def
/stdev    2.671146 def /maxribl towanted fromwanted sub 1 add def
/ribl maxribl array def /storeribl{ % avalue cvalue gvalue tvalue storeribl -
% store the four values at place in the ribl
/tvalue exch def
/gvalue exch def
/cvalue exch def
/avalue exch def
```

- 420 -

```
ribl place [avalue cvalue gvalue tvalue] put
/place place 1 add def
} bind def
/place 0 def
     0.530957    -1.469043    -0.106473     0.247164
storeribl % -10
    -0.028470    -0.469043    -0.816966     0.723602
storeribl % -9
    -0.276398     0.045531    -0.816966     0.581583
storeribl % -8
    -3.276398    -6.266787     1.852886    -2.276398
storeribl % -7
     0.115920    -0.188935     0.045531    -0.106473
storeribl % -6
    -0.106473    -0.575958    -0.691435     0.767997
storeribl % -5
    -2.691435     0.852886    -1.469043     0.677799
storeribl % -4
     1.581583    -3.276398    -0.469043    -3.276398
storeribl % -3
     1.183034    -1.106473    -1.276398    -0.369507
storeribl % -2
     0.852886    -1.691435    -1.106473     0.424042
storeribl % -1
     0.852886    -2.691435    -2.691435     0.852886
storeribl % 0
     0.424042    -1.106473    -1.691435     0.852886
storeribl % 1
    -0.369507    -1.276398    -1.106473     1.183034
storeribl % 2
    -3.276398    -0.469043    -3.276398     1.581583
storeribl % 3
     0.677799    -1.469043     0.852886    -2.691435
storeribl % 4
     0.767997    -0.691435    -0.575958    -0.106473
storeribl % 5
    -0.106473     0.045531    -0.188935     0.115920
```

- 421 -

```
storeribl % 6
    -2.276398       1.852886      -6.266787     -3.276398
storeribl % 7
     0.581583      -0.816966       0.045531     -0.276398
storeribl % 8
     0.723602      -0.816966      -0.469043     -0.028470
storeribl % 9
     0.247164      -0.106473      -1.469043      0.530957
storeribl % 10
/riblzero frombase neg def % user defined parameters
/rangefrom -10 def
/rangeto 10 def
/basesperline 50 def
/linesperpage 3 def
/basenumber 20 def
/linenumber 1 def
/coornumber 132 def
/pagewidth 18.50000 cm def
/pageheight 24.90000 cm def
/pagex   1.50000 cm def
/pagey   1.50000 cm def
/lowerbound -4.00000 def
/fractionofline  1.00000 def
/boxstate false def
/outofsequence false def /definepageparameters { % wrap these definitions together
% define characters
/charwidth pagewidth basesperline div def % character
width
/ncharwidth charwidth neg def % negative of charwidth
/charshift charwidth 6 div def
/upperbound 2 def % upper bound, bits
outofsequence
{/gapbits upperbound fractionofline mul def} % gap size in
```

- 422 -

```
bits
{/gapbits 0 def}
ifelse
/bitspercm
    upperbound lowerbound sub gapbits add % bits
    pageheight linesperpage div % cm
    div def % bits per cm
/cmperbit 1 bitspercm div def
/gapcm gapbits bitspercm div def % the gap size in cm
/charupper upperbound bitspercm div def % upper bound of
characters
/charlower lowerbound bitspercm div def % lower bound of
characters
/charrange charupper charlower sub def % total height of
character box
/charbox { % character box
moveto
charwidth 0 rlineto
ncharwidth 0 rlineto
0 charlower rlineto
charwidth 0 rlineto
0 charrange rlineto
ncharwidth 0 rlineto
closepath} bind def
% convert bits to cm fitting the size
/bittocm charupper 2 div cmfactor div def
/bittocm2 charupper cmfactor div def
% oh boy here we go with the sine!!!   YOWWW!!!
/wavelength 10.6 def % bases per 360 degrees
/wavefactor 360 wavelength div def
/makesine {% scale the y axis by the cosine of
% the distance from the internalcoordinate
ic internalcoordinate sub wavephase sub wavefactor mul
cos 1 sub -4 div 0.5 add
gapbits 0 eq {bittocm2} {gapbits} ifelse mul
} bind def
```

- 423 -

```
% define fonts and characters
% Set up the font size for the graphics
/fontsize charwidth def
% set the font
/Times-Bold findfont fontsize scalefont setfont } bind def % end of definepageparameters
definepageparameters % make these definitions available
now!

% define colors
/red     {1 0 0 setrgbcolor} def
/green   {0 1 0 setrgbcolor} def
/blue    {0 0 1 setrgbcolor} def
/purple  {1 0 1 setrgbcolor} def
/yellow  {1 1 0 setrgbcolor} def
/orange  {1 0.7 0 setrgbcolor} def
/black   {0 0 0 setrgbcolor} def
/white   {1 1 1 setrgbcolor} def
/grey    {0.5 0.5 0.5 setrgbcolor} def % store the current color as a background color
/setbackcolor {/backcolorstore currentrgbcolor 3 array
astore def} def
% backcolor retrieves the color
/backcolor {backcolorstore aload pop setrgbcolor} def
% initial setting
white setbackcolor /rectangle { % height width x y rectangle (path)
moveto
/height exch def
/width exch def
0 width rlineto
height 0 rlineto
0 width neg rlineto
closepath
```

- 424 -

```
} bind def

/isasecond { %`set the number of {1 pop} cycles per second
/second exch def
(a second is now defined as this many loops:) =
second =
} def
/wait {% n wait -; wait n seconds
second mul round cvi {1 pop} repeat
} def
/setwait {% set the wait time after display
/waittime exch def
(waiting between moves is now (seconds):) =
waittime =
} def
/second 100000 def
/waittime 0 def /tochar {x charwidth mul y charrange
outofsequence {gapcm add charshift add} if
mul} def /stepto { % x y stepto -   stepto the place
/y exch def
/x exch def
tochar charbox fill
gsave tochar charbox black stroke grestore} def /tointernal { % ec tointernal ic boolean
% convert external coordinate (ec)
% to internal coordinate (ic)
% if found, the boolean is true and ic is returned.
% otherwise the boolean is false and no coordinate is
returned.
/ec exch def
/ic 0 def
count /stacksize exch def
```

- 425 -

```
sequence {
    1 get
    ec eq
    {ic exit}
    if
    /ic ic 1 add def
  } forall
  count stacksize 1 add eq % element was found and returned?
} bind def /setinternal { % externalcoordinate setinternal
internalcoordinate
% convert external coordinate (externalcoordinate)
% to internal coordinate (internalcoordinate) 0 to
upperseq
% if found, the internalcoordinate is set.
% If not found, internalcoordinate is set to:
%    0 if externalcoordinate <= 0
%    upperseq if externalcoordinate > 0
/externalcoordinate exch def
/internalcoordinate 0 def
externalcoordinate tointernal
not { externalcoordinate 0 le
    {0} {upperseq} ifelse
} if
dup /internalcoordinate exch def
} bind def coornumber setinternal pop % set initial
internalcoordinate /grabbasenumber { % internalcoordinate grabbase n found
% if found, found is true and the element n is next
% otherwise found is false and there is no element n.
% n is the number equivalent of the base
/ic exch def
  ic 0 ge
```

- 426 -

```postscript
 ic upperseq le
 and
   {sequence ic get
     0 get true} % extract the numerical equivalent of a
letter
   {false}
 ifelse
} bind def /grabbase { % internalcoordinate grabbase c found
% if found, found is true and the element c is next
% otherwise found is false and there is no element c.
% c is the base as a character
/ic exch def
 ic 0 ge
 ic upperseq le
 and
   {sequence ic get
     0 get % extract the numerical equivalent of a letter
     symbols exch get true} % convert to a letter
   {false}
 ifelse
} bind def /setxy { % ic setxy boolean
% setxy takes an internal coordinate ic,
% and sees if a move to that position on the page is
possible.
% if so, it sets x and y,
% and the boolean is true, otherwise false.
/ic exch def
ic 0 ge ic upperseq le and
{ % inside the sequence
   % PostScript mod is not a true modulo function!
   % So we make our own:
   /xtemp ic internalcoordinate sub basenumber add def
   /ytemp linenumber def
```

- 427 -

```
    { xtemp basesperline lt
      {exit}
      {/xtemp xtemp basesperline sub def
       /ytemp ytemp 1 sub def}
      ifelse
    } loop
    { xtemp 0 ge
      {exit}
      {/xtemp xtemp basesperline add def
       /ytemp ytemp 1 add def}
      ifelse
    } loop
    ytemp 0 ge
    ytemp linesperpage lt
    and
    dup {
         /x xtemp def
         /y ytemp def
    } if
  }
  { % not inside the sequence
    false
  }
  ifelse
} bind def /gettoxy { % ic gettoxy boolean
% gettoxy takes an internal coordinate ic,
% attempts to move the zero base of the walker
% to that position on the page
% and if it succeeds it sets x, y, basenumber and
linenumber.
% Then it moves there and
% the variable internalcoordinate is set to ic.
% If it succeeds the boolean is true, otherwise false.
% If true, the zerobase will be at (basenumber,
linenumber).
```

- 428 -

```
setxy dup
{  tochar moveto
   /basenumber x def
   /linenumber y def
} if
} bind def /displaywalker { % show the walker
% at internalcoordinate, basenumber, linenumber
gsave
% print the zero base
/x basenumber def
/y linenumber def
tochar moveto
currentpoint translate
% this should be the same as:
% 0 getoxy pop
% zap previous symbol there
white 0 0 charbox fill gsave 0 0 charbox black stroke
grestore
/thebase internalcoordinate grabbase not {exit} if def
/cmhigh charupper cmfactor div def
cmhigh thebase numchar
grestore
% here do the rest of the walker
} bind def /anycolornumchar{ % charheight character numchar
% Make a character of given height in cm,
  gsave
    /char exch def
    /charheight exch cm def
    charwidth charheight char boxshow
  grestore
  charheight abs 1 gt {0 charheight abs translate} if
} bind def
```

- 429 -

```
/anycolorletter { % ic colorletter
% evaluate and print the base at ic in anycolor
/ic exch def
gsave
ic setxy pop
tochar moveto
currentpoint translate
currentrgbcolor % save current color on the stack
% zap previous symbol there
backcolor 0 0 charbox fill gsave
boxstate {0 0 charbox black stroke} if grestore
setrgbcolor % restore current color from the stack
/thebase ic grabbase not {exit} if def
outofsequence
{
gsave
    0 2 bitspercm div translate
    0 0 moveto
    charwidth 0 rlineto
    0 gapcm rlineto
    ncharwidth 0 rlineto
    closepath
    white fill
    grey
    0 charshift translate
    doingwave
    {makesine thebase anycolornumchar}
    {bittocm thebase anycolornumchar}
    ifelse
grestore
}
{
gsave
    doingwave
    {makesine thebase anycolornumchar}
    {bittocm thebase anycolornumchar}
    ifelse
```

- 430 -

```
grestore
}
ifelse
grestore
} bind def

/evaluate { % ic evaluate bits
% give the bits at position ic
/ic exch def
ribl
ic internalcoordinate sub riblzero add get
ic grabbasenumber pop get} bind def /colorletter { % ic colorletter
% evaluate and print the base at ic in color
/ic exch def
gsave
ic setxy pop
tochar moveto
currentpoint translate
% zap previous symbol there
backcolor 0 0 charbox fill gsave
boxstate {0 0 charbox black stroke} if grestore
/thebase ic grabbase not {(colorletter error) = exit} if
def
gsave
outofsequence
{
    0 2 bitspercm div translate
    0 0 moveto
    charwidth 0 rlineto
    0 gapcm rlineto
    ncharwidth 0 rlineto
    closepath
    white fill
    blue
    0 charshift translate
```

- 431 -

```
    doingwave
    {makesine thebase anycolornumchar}
    {1 thebase anycolornumchar}
    ifelse
}
{
    doingwave
    {   % draw line at wave
        0 makesine cm currentlinewidth sub moveto
        charwidth 0 rlineto
        grey stroke
    } if
}
ifelse
grestore
/bits ic evaluate def
/cmhigh bits bittocm mul def
bits 0 lt {
    bits lowerbound lt
    {
        newpath
        0 0 moveto
        0 charlower rlineto
        charwidth 0 rlineto
        0 charlower neg rlineto
        closepath
        clip
        bits       -500 lt
        {black}
        {purple}
        ifelse
        fill
        0 cmhigh cm translate
        cmhigh thebase numchar
        initclip
    }
    {
```

- 432 -

```
    0 cmhigh cm translate
    cmhigh thebase numchar
  }
  ifelse
  }
  {cmhigh thebase numchar}
ifelse
grestore
} bind def % mechanism for finding the total Ri value evaluated
/sumribl {/ribltotal ribltotal bits add def} def % string for numbers
/str 10 string def
/linestr 60 string def
/onedecimal {10 mul round 10 div} def % 1 decimal
/fourdecimal {% number location fourdecimal
% put the number at the location in linestr.
% use 4 decimal places, and put a blank for the positive
sign
/numberlocation exch def
/numbervalue exch def
linestr
numberlocation
  numbervalue -100 gt
  {
  numbervalue 0 gt {1 add} if
  % numbervalue abs 9 gt { numbervalue abs log cvi sub }
if
  numbervalue abs 9 gt { numbervalue abs log cvi sub } if
  numbervalue 10000 mul round 10000 div
  str cvs putinterval
  }
  {
  1 sub
  (-Infinity) putinterval
```

- 433 -

```
  }
ifelse
} bind def

/displaydata {
% Display the ribltotal
/Z ribltotal mean sub stdev div def
ribltotal ribound gt Z abs zbound le and
{0.4 0.2 1 sethsbcolor setbackcolor} % pink
{1 0.2 1 sethsbcolor setbackcolor} % greenish
ifelse
gsave
    internalcoordinate colorletter
    internalcoordinate setxy pop
    tochar charbox clip
    tochar translate
    0 0 moveto
        internalcoordinate evaluate 0 le
        { black charwidth 0 translate 0 0 moveto 90 }
        { black 0 0 moveto -90 }
    ifelse
    rotate 0 charshift moveto
    /externalcoordinate sequence internalcoordinate get 1
get def
    externalcoordinate str cvs show
    ( ) show
    ribltotal onedecimal
    str cvs show
    ( ) show
    Z onedecimal
    str cvs show
    initclip
grestore
white setbackcolor
linestr 0 (
            ) putinterval
linestr 0 (at ) putinterval
```

- 434 -

```
linestr 3 externalcoordinate str cvs putinterval
linestr 11 ( Ri =) putinterval
ribltotal 17 fourdecimal
linestr 26 (bits) putinterval
linestr 33 ( Z =) putinterval
Z 37 fourdecimal
ribltotal ribound gt {linestr 45 (++++) putinterval} if
Z abs zbound le {linestr 50 (<---) putinterval} if
linestr = flush
} bind def /movesequence { % - movesequence -
% keep the walker steady, move the sequence to
internalcoordinate
/oldlocation internalcoordinate def
/internalcoordinate newlocation def
printing { % print suppression
grey setbackcolor
internalcoordinate colorletter
white setbackcolor
/ribltotal internalcoordinate evaluate def
/fromout false def
/toout false def
/dfzb 1 def % distance from zero base
{ % loop to display the walker
 fromout not
 { /below internalcoordinate dfzb sub def
   below setxy
   dfzb rangefrom neg le
   and
   {  tochar moveto
      below colorletter sumribl
   }
   {/fromout true def
   }
   ifelse
 } if
```

- 435 -

```
toout not
{ /above internalcoordinate dfzb add def
  above setxy
  dfzb rangeto le
  and
  {  tochar moveto
     above colorletter sumribl
  }
  {/toout true def
  }
  ifelse
} if
  fromout toout and {exit} if
  /dfzb dfzb 1 add def
} loop % for walker
displaydata
/fromout false def
/toout false def
 /below below 1 add def % reset
 /above above 1 sub def % reset
doingwave sequencemoves forcedisplay or or {
 { % loop to display the reset of the page
  fromout not
  { /below below 1 sub def
    below setxy
    {  tochar moveto
       grey below anycolorletter
    }
    {/fromout true def
    }
    ifelse
  } if
  toout not
  { /above above 1 add def
    above setxy
    {  tochar moveto
       grey above anycolorletter
```

```
                        - 436 -
      }
      {/toout true def
      }
      ifelse
   } if
   fromout toout and {exit} if
   /dfzb dfzb 1 add def
 } loop % for page
}
{ % cleanup behind walker
   /dfzb 0 def
/oldbelow oldlocation rangefrom add def
/oldabove oldlocation rangeto add def
{ % loop for clearing walker
 fromout not
 { /ic oldlocation dfzb sub def
   ic setxy
   ic oldbelow ge
   and
   {% tochar moveto
    ic below lt ic above gt or
  {grey ic anycolorletter
 } if
     }
     {/fromout true def
     }
   ifelse
 } if
 toout not
 { /ic oldlocation dfzb add def
   ic setxy
   ic oldabove le
   and
   {% tochar moveto
    ic below lt ic above gt or
    {grey ic anycolorletter
 } if
```

- 437 -

```
       }
      {/toout true def
       }
      ifelse
   } if
    fromout toout and {exit} if
    /dfzb dfzb 1 add def
 } loop % for removing old walker
 }
 ifelse
 waittime wait
 } if % print suppression
 } bind def /movewalker { % - movewalker -
% keep the sequence steady, move the walker to
internalcoordinate
% change the position on the page also!
newlocation setxy
{% we can move there
/basenumber x def
/linenumber y def
movesequence
} % we can move there
{ (It's not possible to move there because ) =
   newlocation 0 lt newlocation upperseq gt or
   {(it's off the sequence) =}
   {(it's off the page - perhaps switch to sequence move
mode?) =}
   ifelse
}
ifelse
} def /takestep { % value takestep - ; take a step
% the value is the new internalcoordinate
/newlocation exch def
```

- 438 -

```
newlocation grabbase
    {pop % the new location is ok
    % depending on the toggle we might move sequence or
walker
    sequencemoves
       {movesequence}
       {movewalker}
    ifelse
    }
    {/newlocation internalcoordinate def % refuse to move
      (There Is No Sequence In That Direction!) =}
ifelse
} bind def

% ERROR HANDLING errordict /undefined {= (Sorry, I don't know that command)
=} put % The following can only be done ONCE
pagex pagey translate % done ONCE
0 charlower neg translate % move to zero of the character
box /searchtest {% test if the search should end
ribltotal ribound gt Z abs zbound le and
{(^GFound one!)= exit} if
} bind def % Make the variable character size definition functions
/showingbox false def
/outline false def
/shrinking false def /setthelinewidth {1 setlinewidth} def
setthelinewidth % set to normal linewidth
```

- 439 -

```
% Set up the font size for the graphics
/fontsize charwidth def

/charparams { % char charparams => uy ux ly lx
% takes a single character and returns the coordinates that
% defines the outer bounds of where the ink goes
  gsave
    newpath
    0 0 moveto
    % take the character off the stack and use it here:
    true charpath
    flattenpath
    pathbbox % compute bounding box of 1 pt. char => lx ly ux uy
    % the path is here, but toss it away ...
  grestore
  /uy exch def
  /ux exch def
  /ly exch def
  /lx exch def
} bind def /dashbox { % xsize ysize dashbox -
% draw a dashed box of xsize by ysize (in points)
  /ysize exch def % the y size of the box
  /xsize exch def % the x size of the box
  1 setlinewidth
  gsave
    % Define the width of the dashed lines for boxes:
    newpath
    0 0 moveto
    xsize 0 lineto
    xsize ysize lineto
    0 ysize lineto
    0 0 lineto
```

- 440 -

```
    [3] 0 setdash
    stroke
  grestore
  setthelinewidth
} bind def

/boxshow { % xsize ysize char boxshow
% show the character with a box around it, sizes in points
gsave
  /tc exch def % define the character
  /ysize exch def % the y size of the character
  /xsize exch def % the x size of the character
  /xmulfactor 1 def /ymulfactor 1 def % if ysize is negative, make everything upside down!
  ysize 0 lt {
    % put ysize normal in this orientation
    /ysize ysize abs def
    xsize ysize translate
    180 rotate
  } if showingbox {dashbox} if
  2 {
    gsave
    xmulfactor ymulfactor scale
    tc charparams
    grestore ysize % desired size of character in points
    uy ly sub % height of character in points
    dup 0.0 ne {
      div % factor by which to scale up the character
      /ymulfactor exch def
    } % end if
    {pop pop}
    ifelse
```

- 441 -

```
  xsize % desired size of character in points
  ux lx sub % width of character in points
  dup 0.0 ne {
    div % factor by which to scale up the character
    /xmulfactor exch def
  } % end if
  {pop pop}
  ifelse
} repeat % Adjust horizontal position if the symbol is an I
tc (I) eq {charwidth 2 div % half of requested character
width
          ux lx sub 2 div % half of the actual
character
          sub     0 translate} if
% Avoid x scaling for I
tc (I) eq {/xmulfactor 1 def} if /xmove xmulfactor lx mul neg def
/ymove ymulfactor ly mul neg def newpath
xmove ymove moveto
xmulfactor ymulfactor scale tc show
grestore
} bind def /numchar{ % charheight character numchar
% Make a character of given height in cm,
  gsave
    /char exch def
    /charheight exch cm def
    char (A) eq {  0.1821 1   0.1819 setrgbcolor} if
    char (a) eq {  0.1821 1   0.1819 setrgbcolor} if
```

- 442 -

```
    char (C) eq {0   0.9372 1 setrgbcolor} if
    char (c) eq {0   0.9372 1 setrgbcolor} if
    char (T) eq {1 0 0 setrgbcolor} if
    char (t) eq {1 0 0 setrgbcolor} if
    char (U) eq {1 0 0 setrgbcolor} if
    char (u) eq {1 0 0 setrgbcolor} if
    char (G) eq {1   0.7000 0 setrgbcolor} if
    char (g) eq {1   0.7000 0 setrgbcolor} if
    charwidth charheight char boxshow
  grestore
  charheight abs 1 gt {0 charheight abs translate} if
} bind def

% USER DEFINITIONS

/r { % redisplay the page
 displayentirepage
} bind def

/R { % reset everything
clear
(clearing stack, graphics state and restarting program) =
clear
initgraphics
erasepage
(walk) run
} bind def % Movement Commands, as in vi
/h { % move left
count 0 le {1} if
dup 0 lt
  {abs 1}
  {{internalcoordinate 1
    sequencemoves {add} {sub} ifelse takestep} repeat}
```

- 443 -

```
ifelse
} def
/l { % move right
count 0 le {1} if
dup 0 lt
  {abs h}
  {{internalcoordinate 1
    sequencemoves {sub} {add} ifelse takestep} repeat}
ifelse
} def
/j { % move down
count 0 le {1} if
dup 0 lt
  {abs k}
  {{internalcoordinate basesperline
    sequencemoves {sub} {add} ifelse takestep} repeat}
ifelse
} def
/k { % move up
count 0 le {1} if
dup 0 lt
  {abs j}
  {{internalcoordinate basesperline
    sequencemoves {add} {sub} ifelse takestep} repeat}
ifelse
} def % Toggle to define whether the sequence moves or the
walker moves
/sequencemoves false def
/w {/sequencemoves sequencemoves not def
sequencemoves {(Sequence Moves)} {(Walker Moves)} ifelse =
} bind def /boxes {/boxstate boxstate not def displayentirepage} def /q {grestore quit} def
```

- 444 -

```
/? {help} def

/help {(Detailed instructions for Walker 3.10 are given
in) =
(the source code file walker.p.) =
(# means you must supply a number BEFORE you type the
command name.) =
(# h: move left [# is optional]) =
(# j: move down [# is optional]) =
(# k: move up [# is optional]) =
(# l: move right [# is optional]) =
(w: toggle between walker and sequence moving) =
(q: quit) =
(?: help message) =
(r: Refresh the page) =
(R: restart ghostscript on the current walk file) =
(# a,c,g,t: Mutate the given absolute location to the
desired base) =
(# A,C,G,T: Mutate the given relative location to the
desired base) =
(# goto: go to the given coordinate) =
(# jump: jump a relative number of bases) =
(boxes: toggle between having boxes and not) =
(# lines (line): Set the number of lines per page) =
(# bases (base, wide): Set the number of bases per page) =
(# left, right, up, down: move the graphic on the page in
units of cm) =
(# height, width: set the page height or width in cm) =
(# lower: set the lower bound in bits) =
(in: put the walker into the sequence) =
(out: take the walker out of the sequence) =
(# wave: define base at which the low point of the cosine
wave is set) =
(waveon: turns on drawing the wave.) =
(waveoff: turns off drawing the wave) =.
(toggleprinting or tp: a toggle that turns on and off
printing) =
```

- 445 -

(toggleerase or te: a toggle that turns on and off page erase)=
(# from: change FROM range of the matrix to use)=
(# to: change TO range of the matrix to use)=
(help: help message)=
(# setwait: set the wait time in seconds after display)=
(        waittime is currently:)= waittime =
(# isasecond: set the number of {1 pop} cycles per second)=
(        seconds is currently:)= second =
(# setri: set minimum Ri for searching and display)=
(        ribound is currently:)= ribound =
(# setz: set minimum Z for searching and display)=
(        zbound is currently:)= zbound =
(# f: search forward to next site which fits search criteria)=
(# b: search backward to next site which fits search criteria)=
} def /in { % make the walker be in the sequence
/outofsequence false def
displayentirepage
} bind def /out { % make the walker be out of the sequence
/outofsequence true def
displayentirepage
} bind def /goto {
count 0 le
{(To use the "goto" command to go to coordinate 180 type "180 goto") =}
{cvi tointernal
  {takestep}
  {(that base is not on the sequence) =}

- 446 -

```
  ifelse
}
ifelse
} bind def

/jump {
count 0 le
{(To use the "jump" command to move 5 bases 5', type "-5
jump") =}
{cvi internalcoordinate add takestep}
ifelse
} bind def /to { % set the rangeto
count 0 le
{(To use the "to" command to set rangeto to -5, type "-5
to") =}
{dup tobase gt
 {pop (rangeto must be smaller than tobase) = tobase =}
 { dup frombase lt
   {pop (rangeto must be greater than or equal to
rangefrom) = rangefrom =}
   {/rangeto exch def
    displayentirepage}
   ifelse
 } ifelse
} ifelse
} bind def /from { % set the rangefrom
count 0 le
{(To use the "from" command to set rangefrom to -5, type
"-5 from") =}
{dup frombase lt
 {pop (rangefrom must be larger than frombase) = frombase
=}
 { dup tobase gt
```

```
    {pop (rangefrom must be less than or equal to rangeto)
= rangeto =}
   {/rangefrom exch def
    displayentirepage}
   ifelse
 } ifelse
} ifelse
} bind def /bases { % set the basesperline
count 0 le
{(To use the "bases" command to set basesperline to 5,
type "5 bases") =}
{dup 1 lt
 {pop (basesperline must be larger than 0)   =}
 {/basesperline exch def
   /basenumber basesperline 2 idiv def
   displayentirepage}
 ifelse
} ifelse
} bind def
/base {bases} def
/wide {bases} def /lines { % set the linesperpage
count 0 le
{(To use the "lines" command to set linesperpage to 5,
type "5 lines") =}
{dup 1 lt
 {pop (linesperpage must be larger than 0)   =}
 {/linesperpage exch def
   /linenumber linesperpage 2 idiv def
    displayentirepage}
 ifelse
} ifelse
} bind def
/line {lines} def
```

- 448 -

```
/left { % move the page left
count 0 le
{(to move left 2 cm type "2 left") =}
{neg cm 0 cm translate
 displayentirepage
} ifelse
} bind def /right { % move the page right
count 0 le
{(to move right 2 cm type "2 right") =}
{cm 0 cm translate
 displayentirepage
} ifelse
} bind def /down { % move the page down
count 0 le
{(to move down 2 cm type "2 down") =}
{0 exch neg cm translate
 displayentirepage
} ifelse
} bind def /up { % move the page up
count 0 le
{(to move up 2 cm type "2 up") =}
{0 exch cm translate
 displayentirepage
} ifelse
} bind def /height { % define the page height
count 0 le
{(page height is in cm and must be positive, eg "3
height") =}
{/pageheight exch cm def
```

- 449 -

```
displayentirepage
} ifelse
} bind def

/width { % define the page width
count 0 le
{(page width is in cm and must be positive, eg "3 width")
=}
{/pagewidth exch cm def
 displayentirepage
} ifelse
} bind def /lower { % lower bound
/lowerbound exch def
displayentirepage
} bind def /wave { % set the wave phase
count 0 le
{(to put the wave low point at base -3, type "-3 wave") =}
{/wavephase exch def
 displayentirepage
} ifelse
} bind def /waveon { % set the wave state on
/doingwave true def
displayentirepage
} bind def /waveoff { % set the wave state off
/doingwave false def
displayentirepage
} bind def /toggleprinting { % turn on or off printing
```

- 450 -

```
/printing printing not def
printing
{(Printing is on.) =}
{(Printing is suppressed.) =}
ifelse
displayentirepage
} bind def
/tp {toggleprinting} bind def /toggleerase { % turn on or off erase
/doerasepage doerasepage not def
doerasepage
{(page erase is on.) =}
{(page erase is suppressed.) =}
ifelse
displayentirepage
} bind def
/te {toggleerase} bind def % mutation controls:
/m {sequence exch get pstack pop} def
/mutate{ % ic base# mutate -
% store the base # at the internal coordinate ic in the
sequence
/base exch def
/ic exch def
/ec sequence ic get 1 get def % external coordinate
sequence ic [base ec] put
} bind def /a { % external coordinate a - % set external coordinate
to a
count 0 le
{(To use the "a" command to mutate base 10, type "10 a")
=}
{ tointernal
   {0 mutate displayentirepage}
```

- 451 -

```
    {(That coordinate is not on this sequence) =}
    ifelse
  } ifelse
} bind def /c { % external coordinate a - % set external coordinate
to c
count 0 le
{(To use the "c" command to mutate base 10, type "10 c")
=}
{ tointernal
    {1 mutate displayentirepage}
    {(That coordinate is not on this sequence) =}
    ifelse
  } ifelse
} bind def /g { % external coordinate a - % set external coordinate
to g
count 0 le
{(To use the "g" command to mutate base 10, type "10 g")
=}
{ tointernal
    {2 mutate displayentirepage}
    {(That coordinate is not on this sequence) =}
    ifelse
  } ifelse
} bind def /t { % external coordinate a - % set external coordinate
to t
count 0 le
{(To use the "t" command to mutate base 10, type "10 t")
=}
{ tointernal
    {3 mutate displayentirepage}
    {(That coordinate is not on this sequence) =}
```

- 452 -

```
    ifelse
  } ifelse
} bind def

%%%%%%%%%%%%%%%%%%%%%%%%%%

/A { % relative coordinate a - % set relative coordinate
to a
count 0 le
{(To use the "A" command to mutate relative base +10, type
"10 A") =}
{ coornumber add tointernal
  {0 mutate displayentirepage}
  {(That coordinate is not on this sequence) =}
  ifelse
} ifelse
} bind def /C { % relative coordinate a - % set relative coordinate
to c
count 0 le
{(To use the "C" command to mutate relative base +10, type
"10 C") =}
{ coornumber add tointernal
  {1 mutate displayentirepage}
  {(That coordinate is not on this sequence) =}
  ifelse
} ifelse
} bind def /G { % relative coordinate a - % set relative coordinate
to g
count 0 le
{(To use the "G" command to mutate relative base +10, type
"10 G") =}
{ coornumber add tointernal
  {2 mutate displayentirepage}
```

- 453 -

```
  {(That coordinate is not on this sequence) =}
  ifelse
} ifelse
} bind def /T { % relative coordinate a - % set relative coordinate
to t
count 0 le
{(To use the "T" command to mutate relative base +10, type
"10 T") =}
{ coornumber add tointernal
  {3 mutate displayentirepage}
  {(That coordinate is not on this sequence) =}
  ifelse
} ifelse
} bind def

%%%%%%%%%%%%%%%%%%%%%%%%%

/setri { % set the ri bound
count 0 le
{(use setri to set the Ri bound; it needs a number in
bits) =
 (current value:) = ribound =}
{/ribound exch def
} ifelse
} bind def /setz { % set the z bound
count 0 le
{(setz to set the z bound needs a number) =
 (current value:) = zbound =}
{/zbound exch abs def
} ifelse
} bind def
/f { % search forward
count 0 le {1} if
```

- 454 -

```
dup 0 lt
  {abs b}
  {{internalcoordinate 1
    sequencemoves {sub} {add} ifelse takestep searchtest}
repeat}
ifelse
} def
/b { % search backward
count 0 le {1} if
dup 0 lt
  {abs f}
  {{internalcoordinate 1
    sequencemoves {add} {sub} ifelse takestep searchtest}
repeat}
ifelse
} def
/displayentirepage {% display the entire page
printing {
  doerasepage {erasepage} if
  definepageparameters
  boxstate {
      0 1 linesperpage 1 sub
      { /y exch def
          0 1 basesperline 1 sub
          { /x exch def
              tochar charbox blue stroke
          } for
      } for
  } if
  /forcedisplay true def
  internalcoordinate takestep
  /forcedisplay false def
} if
} bind def
toggleprinting
% all lines from this point on are PostScript commands
% The "%" makes a comment
```

- 455 -

```
% walkerp: parameters for walker 3.03 and higher
% The following commands make a picture of 2 walkers
% waveoff        % turn off waves
%1 lines        % display only one line
%15 up          % move 15 cm up
%5 height       % make the line only 5 cm high
%44 wide        % show 44 characters across
%w 5 h w        % move the sequence 5 positions left
%132 goto       % put the walker in a new spot
%toggleprinting toggleprinting % force printing
%toggleerase    % prevent erasing during the next steps
%6 down         % jump 6 cm down
%138 goto       % put the walker in a new spot
%toggleprinting toggleprinting % force printing
%6 down         % jump 6 cm down
%143 goto       % put the walker in a new spot
%toggleprinting toggleprinting % force printing
%%% gsave showpage grestore % unearth the command if you
send this to a printer!
toggleprinting
```

We claim:

1. A method of determining sequence conservation of a binding site on a test nucleic acid sequence using a set of sequences, said set including nucleic acid base identity, base position and alignment information, comprising:
   (a) extracting base identity and alignment information to generate an aligned set of sequences corresponding to at least one pre-determined criterion;
   (b) generating in a computer an information weight matrix for said extracted information to provide an information model for said nucleic acid sequences, said matrix being calculated in accordance with the formula:
   $R_i(b,l)=2-(-\log_2 f(b,l)+e(n(l)))$, where $f(b,l)$ is the frequency of each base b at position l in the aligned sequences and $e(n(l))$ is a sample size correction factor for the n sequences in $f(b,l)$;
   (c) applying in a computer the individual information weight matrix $R_i$ to the test sequence, thereby assigning each position within the test sequence an information-based numerical value; and
   (d) determining the sequence conservation of the binding site on the test sequence by adding together the information-based numerical values.

2. The method of claim 1 further comprising the step of changing at least one base in said test sequence to be analyzed and repeating the steps (c)–(d).

3. The method of claim 2 wherein said model is a splice site donor sequence model.

4. The method of claim 2 wherein said model is a splice site acceptor sequence model.

5. The method of claim 1, further comprising outputting the evaluation of the matrix in at least one of the following:

(i) standard deviation of the individual base information from the wild-type n sequences, and (ii) the one tailed probability.

6. The method of claim 1, further comprising: outputting said matrix to a graphic interface.

7. The method of claim 6 wherein said sequence is DNA and the amplitude of the numerical value signal displays a sinosoidal wave having maximum values between 1 and 2 bits high having a period of 10.6 positions.

8. A method of claim 1, further comprising the step of displaying nucleic acid sequence information as a Walker, said information including base identity, base position, DNA helix angle and information weight matrix for said sequence, comprising displaying the sequence in a set of letters, wherein the amplitude of each letter at each base corresponds to the individual information weight of the letter at the base position.

9. The method of claim 8 wherein the display includes an indicia at one base position, a portion of said indicia defining the base position, individual information, and Z score of the Walker.

10. The method of claim 9 wherein a comparison between the individual information content signal for the region and a mean value signal of information is used to generate a Z score.

11. The method of claim 8 wherein the indicia include a letter representation of the base at that position.

12. The method of claim 8 wherein the Walker amplitude is positive for energetically-favored bases.

13. The method of claim 8 wherein the base position number of at least one base is displayed digitally.

14. The method of claim 13 wherein the individual information content of at least one base position is displayed.

15. The method of claim 14 wherein said display is digital.

16. The method of any claims 8, 9, 11–15 wherein said Walker is colorized.

17. A computer program product comprising: a computer usable medium embodying computer readable program code means for analyzing a test nucleic acid sequence using aligned nucleic acid sequences, the program code means comprising:

program code means for calculating the individual information weight matrix for said aligned sequences in accordance with the formula:

$R_i(b,l)=2-(-\log_2 f(b,l)+e(n(l))$, where $f(b,l)$ is the frequency of each base at position l in the aligned sequences and e(n(l) is a sample size correction factor for the n sequences in $f(b,l)$.

18. The computer program product of claim 17, wherein said medium is a tape medium.

19. The computer program product of claim 17, wherein said medium is a CD-Rom medium.

20. The computer program product of claim 17, wherein said medium is a random access memory.

21. The computer program product of claim 17, wherein said program code means is readable by a digital computer.

22. The computer program product of claim 17, wherein said program code means is in the PASCAL programming language.

23. A computer system having a central processing unit under the control of the program of claim 17.

24. A method for characterizing a binding site, utilizing a processor capable of generating an $R_i(b,l)$ information weight matrix signal and a display means capable of displaying screens associated with a plurality of functions comprising the steps of:

(a) applying said information weight matrix signal to a region of a sequence corresponding in size to the binding site;

(b) assigning each position within the region, an information-based numerical value signal based upon the information weight matrix signal;

(c) displaying said numerical value signal on said display means; and (d) characterizing the binding site by accumulating the information-based numerical value signal for each position within the region, producing an individual information content signal.

25. The method of claim 24 wherein said applying step is performed in multiple regions corresponding in size to the binding site.

26. The method of claims 1 or 24, wherein the binding site is characterized as having a polymorphism.

27. The method of claims 1 or 24, wherein the binding site is characterized as having a deleterious mutation.

28. A method of identifying binding sites utilizing a processor having a data entry means comprising the steps of:

(i) generating an information weight matrix signal based upon known binding site sequences;

(ii) applying a region corresponding in size to said binding sequence of an unknown sequence signal to the information weight matrix signal;

(iii) analyzing each position within the unknown sequence signal to determine information content signal at said position;

(iv) adding the information content signals together thereby generating an individual information content signal; and (v) identifying a binding site upon generation of a positive individual information content signal.

29. The method of claim 28 wherein the individual information weight matrix signal is applied step wise to each position within a sequence thereby generating a series of individual information content signals.

30. The method of claim 29 further comprising a display means wherein said series of individual information content signals are displayed in graphical form.

31. An article of manufacture for use in determining sequence conservation of a binding site on a test nucleic acid sequence using an aligned set of sequences comprising a computer readable medium, said medium containing individual information weight matrix generation signals for forming an information model corresponding to at least one predetermined criterion, said individual information weight matrix being defined by the formula:

$R_i(b,l)=2-(-\log_2 f(b,l)+e(n(l))$, where $f(b,l)$ is the frequency of each base b at position l in the aligned sequences and $e(n(l))$ is a sample size correction factor for the n sequences in $f(b,l)$;

said medium further comprising individual information weight matrix generating signals for generating an individual information weight matrix from the aligned sequences containing the binding site in accordance with said formula, thereby assigning each position within the aligned sequences an information-based numerical value; said medium further containing characterizing signals for determining the sequence conservation of the binding site in the test nucleic acid sequence based upon the individual information weight matrix.

32. The article of manufacture according to claim 31, wherein said model is a splice site donor sequence model.

33. The article of manufacture according to claim 31, wherein said model is a splice site acceptor sequence model.

34. The invention of claim 31, wherein said model is a promoter sequence model.

35. The invention of claim 31, wherein said model is a regulatory sequence model.

36. The article of manufacture of claim 31, wherein the binding site is characterized as having a polymorphism.

37. The article of manufacture of claim 31, wherein the binding site is characterized as having a deleterious mutation.

38. A method of displaying nucleic acid sequence information as a Walker, said information including base identity, base position, DNA helix angle and information based numerical values for said sequence, comprising: displaying the sequence in a set of letters, wherein the amplitude of the letter at each base corresponds to the individual information weight of each base at the base position.

39. The method of claim 38 wherein the Walker includes an indicia at a base position.

40. The method of claim 39 wherein the Walker includes the alpha letter indicia corresponding to the base.

41. The method of claim 38 wherein the Walker amplitude is positive for energetically-favored bases.

42. The method of claim 38 wherein the base position number of at least one base is displayed digitally.

43. The method of claim 42 wherein the information content of at least one base position is displayed.

44. The method of claim 42 wherein said display is digital.

45. The method of claim 38–44 wherein said Walker is colorized.

46. A computer program product comprising a computer usable medium embodying computer readable program code for displaying nucleic acid sequence information as a Walker, said information including base identity, base position, DNA helix angle and information weight matrix for said sequence, the program code means comprising: program code means for displaying the sequence as a Walker, wherein the amplitude of the Walker at each base corresponds to the individual information weight at the base position.

47. The computer program product according to claim 46, wherein said medium is a tape medium.

48. The computer program product according to claim 46, wherein said medium is a CD-Rom medium.

49. The computer program product according to claim 46, wherein said medium is a random access memory.

50. The computer program product according to claim 46, wherein said medium is an optical disk.

51. The computer program product according to claim 46, wherein said program code means is readable by a digital computer.

52. The program product of claim 46 further including program code means for displaying an indicia at a base position.

53. The program product of claim 46 further including program code means for displaying the alpha letter indicia corresponding to the base.

54. The program product of claim 46 further including program code means for displaying the Walker amplitude as positive for energetically-favored bases.

55. The program product of claim 46 further including program code means for displaying the base position number of at least one base is digital.

56. The program product of claim 46 further including program code means for displaying the information content of at least one base position.

57. The program product of claim 46 further including program code means for displaying said Walker in color.

* * * * *